(12) United States Patent
Ito et al.

(10) Patent No.: US 9,947,879 B2
(45) Date of Patent: Apr. 17, 2018

(54) ANTHRACENE DERIVATIVE AND ORGANIC ELECTROLUMINESCENCE ELEMENT USING SAME

(71) Applicant: Idemitsu Kosan Co., Ltd., Chiyoda-ku, Tokyo (JP)

(72) Inventors: Hirokatsu Ito, Sodegaura (JP); Hiroyuki Saito, Sodegaura (JP); Yumiko Mizuki, Sodegaura (JP); Masahiro Kawamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 299 days.

(21) Appl. No.: 14/650,488

(22) PCT Filed: Mar. 14, 2014

(86) PCT No.: PCT/JP2014/001481
§ 371 (c)(1),
(2) Date: Jun. 8, 2015

(87) PCT Pub. No.: WO2014/141725
PCT Pub. Date: Sep. 18, 2014

(65) Prior Publication Data
US 2015/0325800 A1     Nov. 12, 2015

(30) Foreign Application Priority Data

Mar. 15, 2013 (JP) ................................. 2013-053591
Apr. 12, 2013 (JP) ................................. 2013-084279

(51) Int. Cl.
*H01L 51/00* (2006.01)
*C07D 307/92* (2006.01)
(Continued)

(52) U.S. Cl.
CPC ........ *H01L 51/0073* (2013.01); *C07D 307/77* (2013.01); *C07D 307/91* (2013.01);
(Continued)

(58) Field of Classification Search
CPC ............. H01L 51/0073; H01L 51/0071; H01L 51/0074; H01L 51/5012; H01L 51/5206;
(Continued)

(56) References Cited

U.S. PATENT DOCUMENTS

2004/0137270 A1    7/2004 Seo et al.
2004/0209118 A1   10/2004 Seo et al.
(Continued)

FOREIGN PATENT DOCUMENTS

CN           103187531 A      7/2013
DE    10-2009-053-191 A1      5/2011
(Continued)

OTHER PUBLICATIONS

International Search Report dated Apr. 22, 2014 issued in Application PCT JP2014/001481.

*Primary Examiner* — Ruiyun Zhang
(74) *Attorney, Agent, or Firm* — Foley & Lardner LLP

(57) ABSTRACT

An anthracene derivative represented by the following formula (1): wherein in the formula (1), $L_1$ is selected from a single bond and a linking group, and the linking group is selected from a divalent arylene group, a divalent heterocyclic group, and a group formed by linking of 2 to 4 of divalent arylene groups and/or divalent heterocyclic groups. $Ar_1$ is selected from the following formulas (2) and (3). In the formulas (2) and (3), X is selected from an oxygen atom and a sulfur atom. In the formula (2), any one of $R_{11}$ to $R_{14}$ is used for bonding to $L_1$. In the formula (3), any one of $R_{21}$ to $R_{24}$ is used for bonding to $L_1$. $Ar_2$ is selected from a substituted or unsubstituted aryl group including 6 to 50 ring carbon atoms and a substituted or unsubstituted heterocyclic group including 5 to 50 ring atoms.

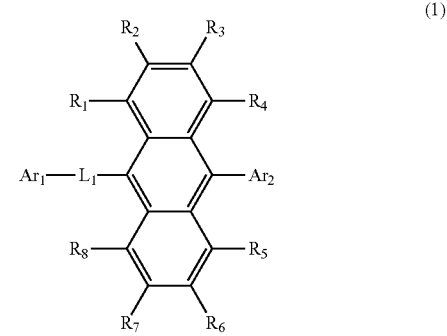

(1)

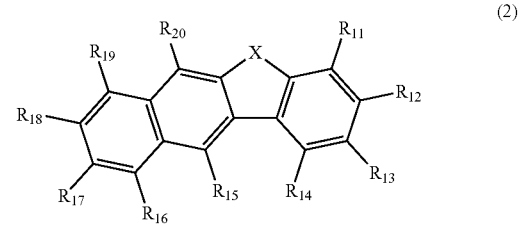

(2)

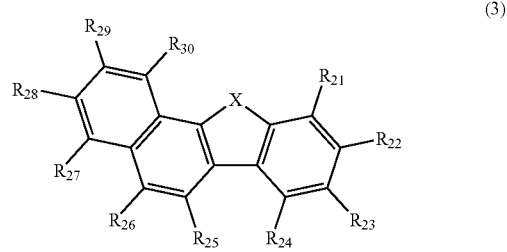

(3)

23 Claims, No Drawings

(51) Int. Cl.
*C09K 11/06* (2006.01)
*H01L 51/50* (2006.01)
*H05B 33/20* (2006.01)
*C07D 405/10* (2006.01)
*C07D 307/77* (2006.01)
*C07D 307/91* (2006.01)
*H01L 51/52* (2006.01)

(52) U.S. Cl.
CPC ......... *C07D 307/92* (2013.01); *C07D 405/10* (2013.01); *C09K 11/06* (2013.01); *H01L 51/0052* (2013.01); *H01L 51/0058* (2013.01); *H01L 51/0072* (2013.01); *H01L 51/5012* (2013.01); *H05B 33/20* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5206* (2013.01); *H01L 51/5221* (2013.01)

(58) Field of Classification Search
CPC ............ H01L 51/0052; H01L 51/0058; C07D 307/77; C07D 307/91; C07D 405/10; C09K 2211/1011; C09K 2211/1088; C09K 2211/1092
USPC ................... 428/690, 917; 257/40, E51.026; 549/456, 457, 41, 42; 548/440
See application file for complete search history.

(56) References Cited

U.S. PATENT DOCUMENTS

| | | |
|---|---|---|
| 2007/0072002 A1 | 3/2007 | Kim et al. |
| 2007/0247063 A1 | 10/2007 | Murase et al. |
| 2008/0107918 A1 | 5/2008 | Egawa et al. |
| 2008/0297037 A1 | 12/2008 | Vestweber et al. |
| 2008/0315754 A1 | 12/2008 | Kawamura et al. |
| 2009/0131673 A1 | 5/2009 | Tanabe et al. |
| 2009/0184313 A1 | 7/2009 | Buesing et al. |
| 2009/0230855 A1 | 9/2009 | Kim et al. |
| 2009/0247795 A1 | 10/2009 | Kawakami |
| 2009/0261717 A1 | 10/2009 | Buesing et al. |
| 2010/0032658 A1 | 2/2010 | Lee et al. |
| 2010/0033083 A1 | 2/2010 | Eum et al. |
| 2010/0045170 A1 | 2/2010 | Lee et al. |
| 2010/0253214 A1 | 10/2010 | Imai et al. |
| 2011/0108826 A1 | 5/2011 | Jang et al. |
| 2011/0121268 A1 | 5/2011 | Nagao et al. |
| 2011/0168992 A1 | 7/2011 | Bae et al. |
| 2011/0248247 A1 | 10/2011 | Matsumoto et al. |
| 2011/0297923 A1 | 12/2011 | Mizuki et al. |
| 2012/0013244 A1 | 1/2012 | Kawamura et al. |
| 2012/0037892 A1 | 2/2012 | Jang et al. |
| 2012/0056165 A1 | 3/2012 | Kawamura et al. |
| 2012/0080667 A1 | 4/2012 | Nowatari et al. |
| 2012/0112169 A1 | 5/2012 | Mizuki et al. |
| 2012/0138907 A1 | 6/2012 | Murase et al. |
| 2012/0138914 A1 | 6/2012 | Kawamura et al. |
| 2012/0165550 A1 | 6/2012 | Suzuki et al. |
| 2012/0165556 A1 | 6/2012 | Suzuki et al. |
| 2012/0181922 A1 | 7/2012 | Kawamura et al. |
| 2012/0217449 A1 | 8/2012 | Spreitzer et al. |
| 2012/0267615 A1 | 10/2012 | Fujita et al. |
| 2013/0087773 A1 | 4/2013 | Suzuki et al. |
| 2013/0187138 A1 | 7/2013 | Matsumoto et al. |
| 2013/0313538 A1 | 11/2013 | Kawamura et al. |
| 2014/0034943 A1 | 2/2014 | Mizuki et al. |
| 2014/0061622 A1 | 3/2014 | Ikeda et al. |
| 2014/0103319 A1 | 4/2014 | Kawamura et al. |
| 2014/0110686 A1 | 4/2014 | Fujita et al. |
| 2014/0159005 A1 | 6/2014 | Kawamura et al. |
| 2014/0197383 A1 | 7/2014 | Cho et al. |
| 2015/0005512 A1 | 1/2015 | Kawamura et al. |

FOREIGN PATENT DOCUMENTS

| | | |
|---|---|---|
| EP | 2-189-508 A2 | 5/2010 |
| EP | 2-256-176 A1 | 12/2010 |
| EP | 2 665 342 A1 | 11/2013 |
| EP | 2752907 A1 | 7/2014 |
| JP | H11111460 A | 4/1999 |
| JP | 2005314239 A | 11/2005 |
| JP | 2007-063501 A | 3/2007 |
| JP | 2007-077094 A | 3/2007 |
| JP | 2007063501 A | 3/2007 |
| JP | 2007-238500 A | 9/2007 |
| JP | 2010-034548 A | 2/2010 |
| JP | 2012503027 A | 2/2012 |
| JP | 2012-190863 A | 10/2012 |
| JP | 2013-258380 A | 12/2013 |
| JP | 2013-258381 A | 12/2013 |
| JP | 2014-165346 A | 9/2014 |
| KR | 2009086015 A | 8/2009 |
| KR | 2009131958 A | 12/2009 |
| KR | 10-2010-0002030 A | 1/2010 |
| KR | 2010002030 A | 1/2010 |
| KR | 2010021367 A | 2/2010 |
| KR | 2010066424 A | 6/2010 |
| KR | 2010094413 A | 8/2010 |
| KR | 10-2011-0018195 A | 2/2011 |
| KR | 10-2011-0099195 A | 2/2011 |
| KR | 10-2011-0024695 A | 3/2011 |
| KR | 2011024695 A | 3/2011 |
| KR | 20110049554 A | 5/2011 |
| KR | 2011099195 A | 9/2011 |
| KR | 10-2011-0123701 A | 11/2011 |
| KR | 2011123701 A | 11/2011 |
| KR | 2012104067 A | 9/2012 |
| KR | 20120122897 A | 11/2012 |
| KR | 2012135501 A | 12/2012 |
| KR | 10-2013-0075982 A | 7/2013 |
| KR | 10-2013-0083129 A | 7/2013 |
| KR | 2013075982 A | 7/2013 |
| KR | 10-2014-0068637 A | 6/2014 |
| KR | 10-2014-0076170 A | 6/2014 |
| KR | 10-2014-0076888 A | 6/2014 |
| KR | 2014068637 A | 6/2014 |
| KR | 2014074485 A | 6/2014 |
| KR | 2014076888 A | 6/2014 |
| KR | 2014083107 A | 7/2014 |
| KR | 2014090410 A | 7/2014 |
| KR | 2014095725 A | 8/2014 |
| KR | 2014095726 A | 8/2014 |
| KR | 2014095727 A | 8/2014 |
| KR | 2014095728 A | 8/2014 |
| KR | 2014095729 A | 8/2014 |
| KR | 10-1515814 B1 | 4/2015 |
| WO | WO2005113531 A1 | 12/2005 |
| WO | WO2006128800 A1 | 12/2006 |
| WO | WO2007140847 A1 | 12/2007 |
| WO | WO2008006449 A1 | 1/2008 |
| WO | WO2008143229 A1 | 11/2008 |
| WO | WO 2009/069537 A1 | 6/2009 |
| WO | WO-2010/010924 A1 | 1/2010 |
| WO | WO-2010/013675 A1 | 2/2010 |
| WO | WO2010052885 A1 | 5/2010 |
| WO | WO2010137285 A1 | 12/2010 |
| WO | WO 2011/074254 A1 | 6/2011 |
| WO | WO 2011/129096 A1 | 10/2011 |
| WO | WO2012045710 A1 | 4/2012 |
| WO | WO 2014/034691 A1 | 3/2014 |
| WO | WO2014035159 A1 | 3/2014 |
| WO | WO 2014/054914 A2 | 4/2014 |
| WO | WO2014054914 A2 | 4/2014 |
| WO | WO2014061963 A1 | 4/2014 |
| WO | WO2014088289 A1 | 6/2014 |

ANTHRACENE DERIVATIVE AND ORGANIC ELECTROLUMINESCENCE ELEMENT USING SAME

TECHNICAL FIELD

The invention relates to an anthracene derivative, an organic electroluminescence device using the same and an electronic appliance comprising the same.

BACKGROUND ART

An organic electroluminescence (EL) device is regarded as a promising solid-emitting large-area full color display device, and various developments have been conducted so far. In general, an organic EL device comprises an emitting layer and a pair of opposing electrodes that sandwich the emitting layer. When an electrical field is applied between the both electrodes, electrons are injected from the cathode and holes are injected from the anode. Further, these electrons are re-combined with the holes in the emitting layer, create an excited state, and energy is emitted as light when the excited state is returned to the ground state.

Conventional organic EL devices had a high driving voltage as compared with inorganic emitting diodes, and hence, the luminance and the luminous efficiency were low. In addition, conventional organic EL devices suffered significant deterioration in properties, and hence, practical application thereof has not been realized yet. Although gradual improvements have been attained in recent organic EL devices, there is an increasing demand for further improvements in luminous efficiency or the like.

With improvements in organic EL emitting materials, performance of an organic EL device has been gradually improved. Improvement in luminous efficiency in an organic EL device is an important subject that leads to lowering in consumption power or improvement in durability of a display. Although improvements have been attained by various researches so far, further improvements have been required.

In order to solve these problems, Patent Documents 1 to 6 disclose an organic EL device in which an anthracene derivative having dibenzofuran as a substituent is used as an emitting material.

Further, Patent Documents 4, 7 to 11 disclose an emitting material having a naphthobenzofuran structure or a naphthobenzothiophene structure. Although use of these materials leads to improvement in luminous efficiency, further improvement in efficiency has been required.

RELATED ART DOCUMENTS

Patent Documents

Patent Document 1: JP-A-H11-111460
Patent Document 2: JP-A-2005-314239
Patent Document 3: JP-A-2007-63501
Patent Document 4: WO06/128800
Patent Document 5: WO05/113531
Patent Document 6: WO08/143229
Patent Document 7: WO07/140847
Patent Document 8: WO08/6449
Patent Document 9: WO10/137285
Patent Document 10: JP-T-2012-503027
Patent Document 11: Korean Patent Publication No. 2012-0104067

SUMMARY OF THE INVENTION

An object of the invention is to provide a material capable of producing a low-voltage and high-efficient organic electroluminescence device.

According to one aspect of the invention, an anthracene derivative represented by the following formula (1) is provided.

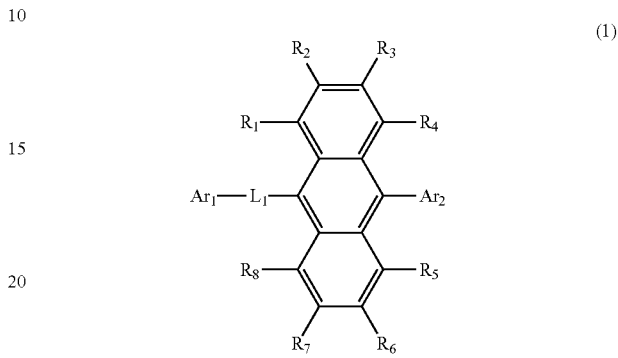

(1)

wherein in the formula (1), $R_1$ to $R_8$ are independently selected from a hydrogen atom, a halogen atom, a hydroxyl group, a cyano group, a substituted or unsubstituted amino group, a substituted or unsubstituted alkyl group including 1 to 20 carbon atoms, a substituted or unsubstituted alkoxy group including 1 to 20 carbon atoms, a substituted or unsubstituted aryloxy group including 6 to 30 carbon atoms that form a ring (hereinafter referred to as "ring carbon atoms"), a substituted or unsubstituted arylthio group including 6 to 30 ring carbon atoms, a substituted or unsubstituted alkylsilyl group including 3 to 60 carbon atoms, a substituted or unsubstituted arylsilyl group including 8 to 60 carbon atoms, a substituted or unsubstituted aryl group including 6 to 30 ring carbon atoms and a substituted or unsubstituted heterocyclic group including 5 to 30 atoms that form a ring (hereinafter referred to as "ring atoms").

$L_1$ is selected from a single bond and a linking group, and the linking group is selected from a divalent arylene group, a divalent heterocyclic group and a group formed by linking of 2 to 4 divalent arylene groups and/or divalent heterocyclic groups.

$Ar_1$ is selected from the following formulas (2) and (3).

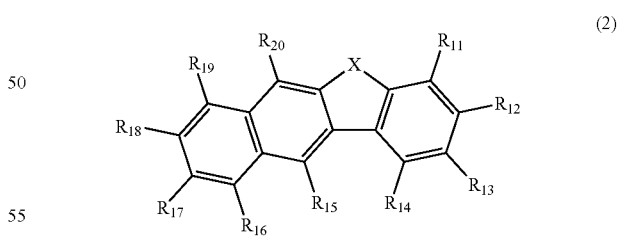

(2)

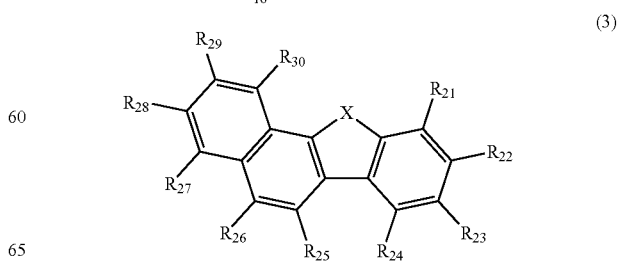

(3)

In the formulas (2) and (3), X is selected form an oxygen atom and a sulfur atom.

In the formula (2), any one of $R_{11}$ to $R_{14}$ is used for bonding to $L_1$. $R_{11}$ to $R_{14}$ that are not used for bonding to $L_1$ and $R_{15}$ to $R_{20}$ are the same as $R_1$ to $R_8$.

In the formula (3), any one of $R_{21}$ to $R_{24}$ is used for bonding to $L_1$. $R_{21}$ to $R_{24}$ that are not used for bonding to $L_1$ and $R_{25}$ to $R_{30}$ are the same as $R_1$ to $R_8$.

$Ar_2$ is selected from a substituted or unsubstituted aryl group including 6 to 50 ring carbon atoms and a substituted or unsubstituted heterocyclic group including 5 to 50 ring atoms.

Among $R_1$ to $R_8$, $R_{11}$ to $R_{20}$, $R_{21}$ to $R_{30}$, $L_1$ and $Ar_2$, adjacent groups may be bonded with each other to form a ring.

According to the invention, a material capable of producing a low-voltage and high-efficient organic electroluminescence device can be provided.

MODE FOR CARRYING OUT THE INVENTION

The anthracene derivative according to one aspect of the invention is represented by the following formula (1).

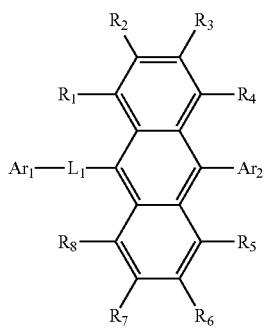

(1)

wherein in the formula (1), $R_1$ to $R_8$ are independently selected from a hydrogen atom, a halogen atom, a hydroxyl group, a cyano group, a substituted or unsubstituted amino group, a substituted or unsubstituted alkyl group including 1 to 20 carbon atoms, a substituted or unsubstituted alkoxy group including 1 to 20 carbon atoms, a substituted or unsubstituted aryloxy group including 6 to 30 ring carbon atoms, a substituted or unsubstituted arylthio group including 6 to 30 ring carbon atoms, a substituted or unsubstituted alkylsilyl group including 3 to 60 carbon atoms, a substituted or unsubstituted arylsilyl group including 8 to 60 carbon atoms, a substituted or unsubstituted aryl group including 6 to 30 ring carbon atoms and a substituted or unsubstituted heterocyclic group including 5 to 30 ring atoms.

$L_1$ is selected from a single bond and a linking group, and the linking group is selected from a divalent arylene group, a divalent heterocyclic group and a group formed by linking of 2 to 4 divalent arylene groups and/or divalent heterocyclic groups.

$Ar_1$ is selected from the following formulas (2) and (3).

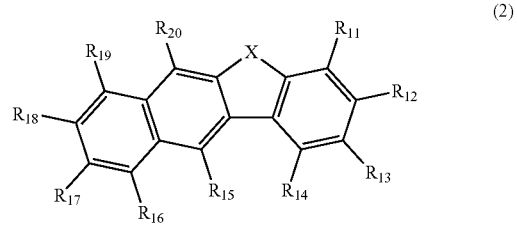

(2)

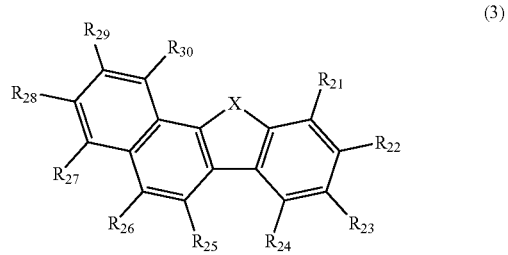

(3)

In the formulas (2) and (3), X is selected form an oxygen atom and a sulfur atom.

In the formula (2), any one of $R_{11}$ to $R_{14}$ is used for bonding to $L_1$. $R_{11}$ to $R_{14}$ that are not used for bonding to $L_1$ and $R_{15}$ to $R_{20}$ are the same as $R_1$ to $R_8$.

In the formula (3), any one of $R_{21}$ to $R_{24}$ is used for bonding to $L_1$. $R_{21}$ to $R_{24}$ that are not used for bonding to $L_1$ and $R_{25}$ to $R_{30}$ are the same as $R_1$ to $R_8$.

$Ar_2$ is selected from a substituted or unsubstituted aryl group including 6 to 50 ring carbon atoms and a substituted or unsubstituted heterocyclic group including 5 to 50 ring atoms.

Among $R_1$ to $R_8$, $R_{11}$ to $R_{20}$, $R_{21}$ to $R_{30}$, $L_1$ and $Ar_2$, adjacent groups may be bonded with each other to form a ring.

As stated in Patent Document 9, the substituents represented by the formulas (2) and (3) are substituents contributing to an increase in efficiency of an organic EL device. The invention has been completed based on a finding that, an organic EL device that can exhibit a luminous efficiency that is equivalent to or larger than that of Patent Document 9 can be driven at a lower voltage by specifying these substituents and the bonding position on the anthracene skeleton.

In the above-mentioned compound, by the bonding of the group represented by the formula (2) or (3) and an anthracene derivative at a specific position, intermolecular packing is improved due to the widening of the planarity of molecules, whereby electron-injecting/transporting performance is improved. Accordingly, when used in an organic EL device or the like, it can lower the driving voltage or improve the efficiency.

As the substituent represented by the formula (3), a substituent represented by the following formula (3') or the like can be given,

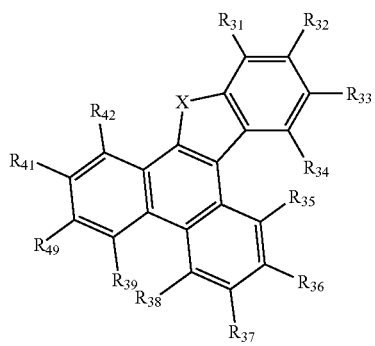

(3')

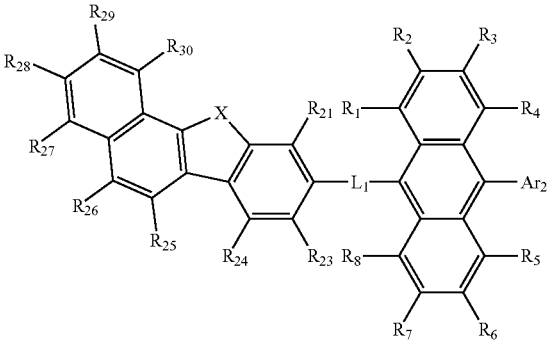

(6)

wherein in the formula (3'), any one of $R_{31}$ to $R_{34}$ is used for bonding to $L_1$. $R_{31}$ to $R_{34}$ that are not used for bonding to $L_1$ and $R_{35}$ to $R_{42}$ are the same as $R_1$ to $R_8$.

In the formula (2), $R_{12}$ or $R_{13}$ among $R_{11}$ to $R_{14}$ is preferably used for bonding to $L_1$. In the formula (3), $R_{22}$ or $R_{23}$ among $R_{21}$ to $R_{24}$ is preferably used for bonding to $L_1$.

That is, the above-mentioned anthracene derivative is preferably represented by any of the following formulas (4) to (7).

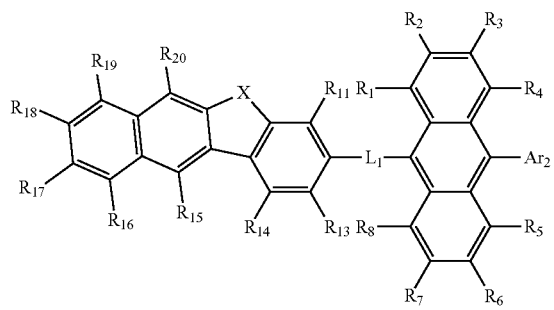

(4)

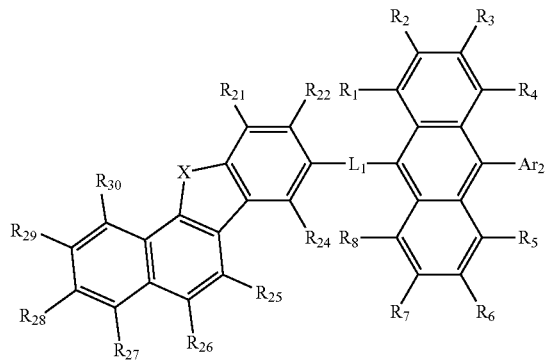

(7)

wherein in the formulas (4) to (7), $R_1$ to $R_8$, $L_1$, X, $R_{11}$ to $R_{20}$, $R_{21}$ to $R_{30}$ and $Ar_2$ are as defined in the formula (1).

In the formula (3'), $R_{32}$ or $R_{33}$ among $R_{31}$ to $R_{34}$ is preferably used for bonding to $L_1$. That is, the above-mentioned anthracene derivative is preferably represented by any of the following formula (6') or (7').

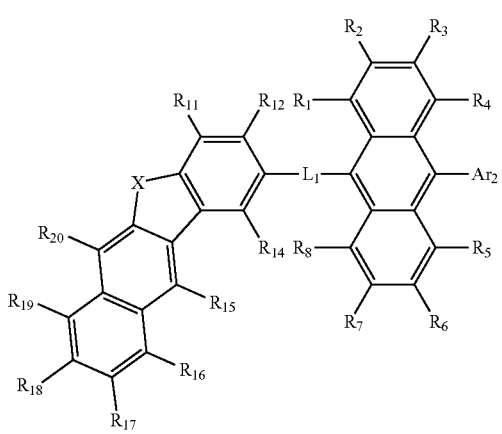

(5)

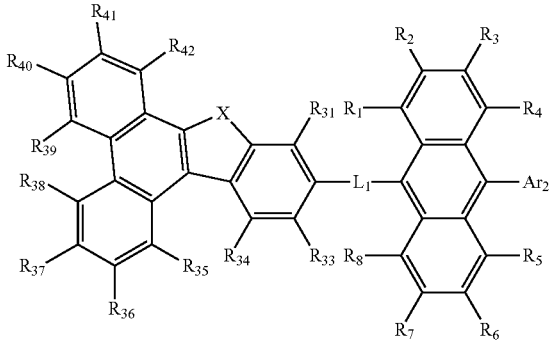

(6')

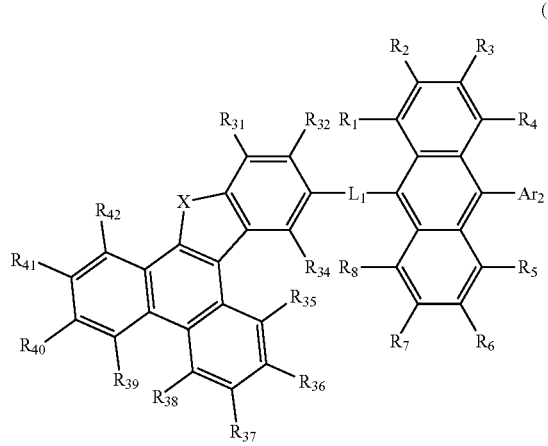

(7')

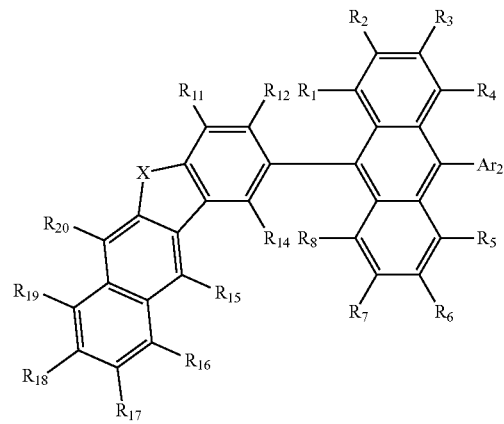

(9)

wherein in the formulas (6') and (7'), $R_1$ to $R_8$, $L_1$, X, $R_{31}$ to $R_{42}$ and $Ar_2$ are as defined in the formula (1).

In the formula (1), $Ar_2$ is preferably a substituted or unsubstituted aryl group.

$R_1$ to $R_8$ are preferably a hydrogen atom.

$L_1$ is preferably a single bond or a substituted or unsubstituted divalent arylene group.

In formulas (2), (3) and (3'), X is preferably an oxygen atom.

In the formula (2), $R_{11}$ to $R_{14}$ that are not used for bonding to $L_1$ and $R_{15}$ to $R_{20}$ are preferably independently a hydrogen atom.

In the formula (3), $R_{21}$ to $R_{24}$ that are not used for bonding to $L_1$ and $R_{25}$ to $R_{30}$ are preferably independently a hydrogen atom.

In the formula (3'), $R_{31}$ to $R_{34}$ that are not used for bonding to $L_1$ and $R_{35}$ to $R_{42}$ are preferably independently a hydrogen atom.

The above-mentioned anthracene derivative is preferably represented by any of the following formulas (8) to (11).

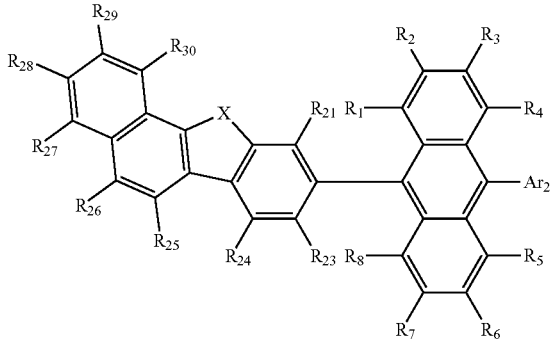

(10)

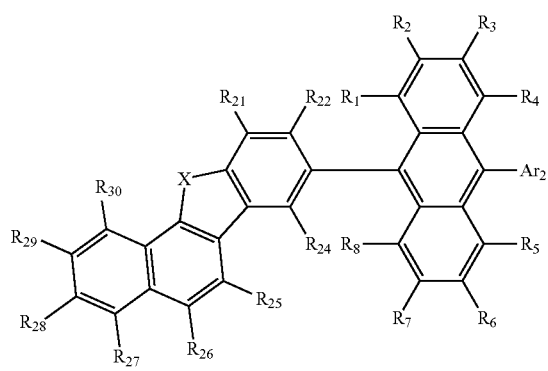

(11)

wherein in the formulas (8) to (11), $R_1$ to $R_8$, X, $R_{11}$ to $R_{20}$, $R_{21}$ to $R_{30}$ and $Ar_2$ are as defined in the formula (1).

The above-mentioned anthracene derivative is preferably represented by any of the following formulas (12) to (15).

(8)

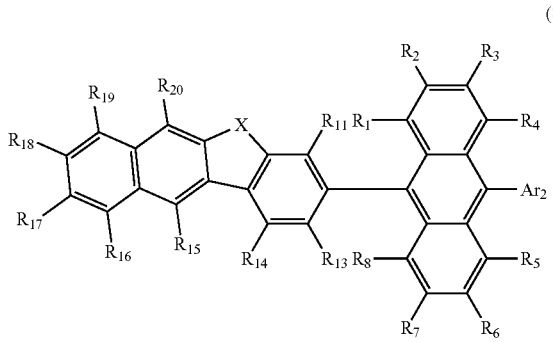

(12)

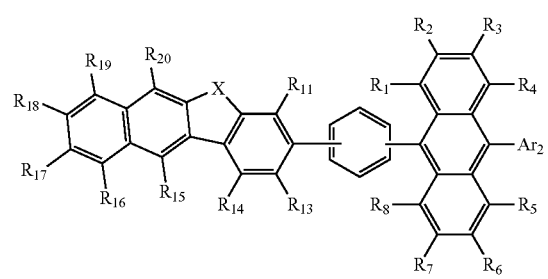

-continued (13)

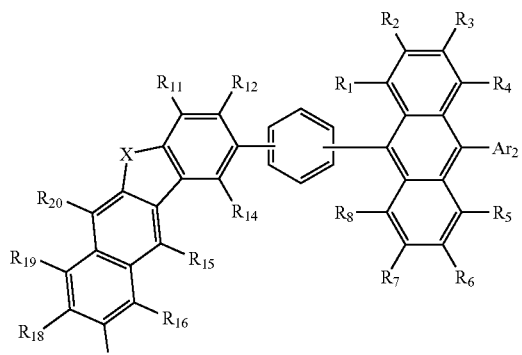

(14)

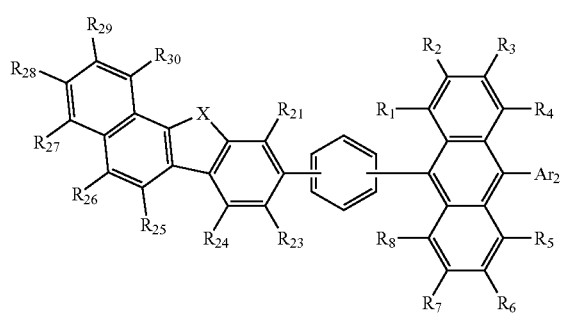

(15)

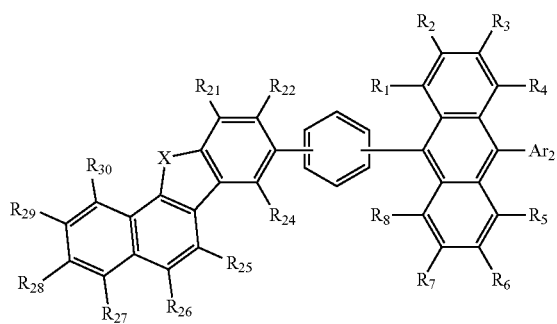

wherein in the formulas (12) to (15), $R_1$ to $R_3$, X, $R_{11}$ to $R_{20}$, $R_{21}$ to $R_{30}$ and $Ar_2$ are as defined in the formula (1).

The above-mentioned anthracene derivative is preferably represented by any of the following formulas (10'), (11'), (14') and (15').

(10')

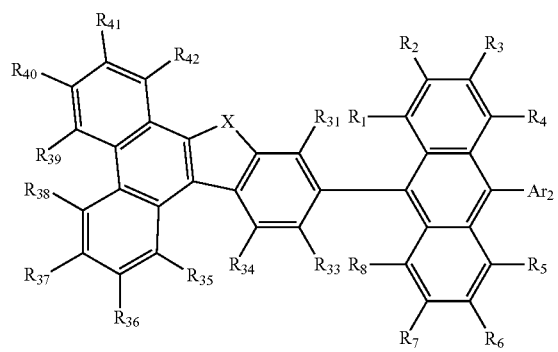

-continued (11')

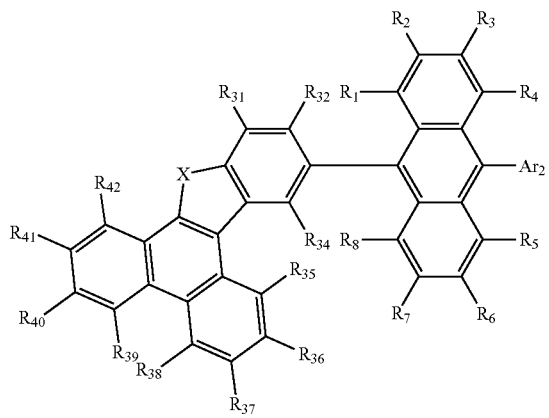

(14')

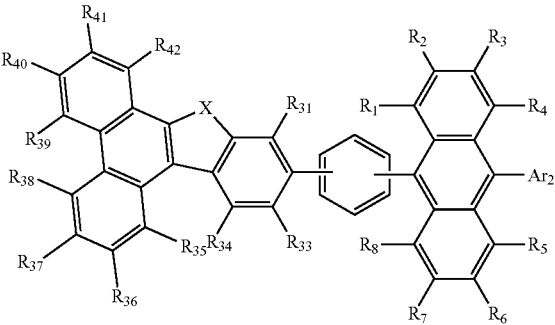

(15')

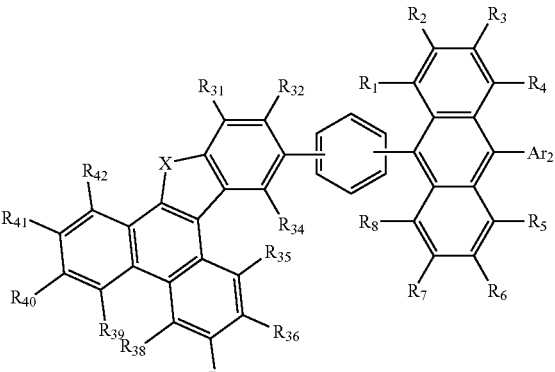

wherein in the formulas (10'), (11'), (14') and (15'), $R_1$ to $R_2$, X, $R_{31}$ to $R_{42}$, and $Ar_2$ are as defined in the formula (1).

In this specification, the "ring carbon atoms" means carbon atoms that constitute a saturated ring, an unsaturated ring or an aromatic ring. The "ring atoms" means carbon atoms and hetero atoms that constitute a hetero ring (including a saturated ring, an unsaturated ring and an aromatic ring).

In this specification, the "a to b carbon atoms" in the "substituted or unsubstituted XX group including a to b carbon atoms" mean the number of carbon atoms when the XX group is unsubstituted, and does not include the number of carbon atoms of the substituent when the XX group is substituted.

As the substituent of the "substituted or unsubstituted", unless otherwise indicated, a halogen atom, a cyano group, an alkyl group, a cycloalkyl group, a silyl group, a substituted silyl group, an alkoxy group, an aryloxy group, an arylthio group, an aryl group, a heterocyclic group, a halogenated alkyl group, a hydroxyl group, a nitro group, a carboxy group, an aralkyl group, or the like (mentioned later), can be given.

The "unsubstituted" in the "substituted or unsubstituted" means that the group is not substituted by the above-mentioned substituent and a hydrogen atom is bonded.

In the invention, the hydrogen atom includes isomers differing in the number of neutrons, i.e. protium, deuterium and tritium.

As for $R_1$ to $R_3$, $L_1$, $R_{11}$ to $R_{20}$, $R_{21}$ to $R_{30}$, $R_{31}$ to $R_{42}$, $Ar_2$ and each substituent in the "substituted or unsubstituted", a detailed explanation will be given below.

As the halogen atom, fluorine, chlorine, bromine, iodine or the like can be given, and fluorine is preferable. As the halogenated alkyl group, a fluoromethyl group, a difluoromethyl group, a trifluoromethyl group, a fluoroethyl group, a trifluoromethyl group or the like can be given.

As the amino group, one represented by —$NHR_w$ or —$N(R_w)_2$ can be given. As examples of the $R_w$, an aryl group including 6 to 30 ring carbon atoms (mentioned later) can be mentioned. In particular, a phenylamino group is preferable.

As the alkyl group including 1 to 20 (preferably 1 to 10, more preferably 1 to 8, and particularly preferably 1 to 4) carbon atoms, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group or the like can be mentioned. Further, the alkyl group may be an alkyl group substituted by an aryl group mentioned later, that is, a substituent obtained by combining an alkylene group and an aryl group (for example, a phenylmethyl group, a 2-phenylisopropyl group or the like).

The number of carbon atoms is preferably 1 to 10, with 1 to 6 being further preferable. Among these alkyl groups, a methyl group, an ethyl group, a propyl group, an isopropyl group, an n-butyl group, an s-butyl group, an isobutyl group, a t-butyl group, an n-pentyl group and an n-hexyl group are preferable.

As the cycloalkyl group, a cycloalkyl group including 3 to 20 (preferably 3 to 10, more preferably 3 to 8) ring carbon atoms can be given. For example, a cyclopropyl group, a cyclobutyl group, a cyclopentyl group, a cyclohexyl group, a 4-methylcyclohexyl group, an adamantyl group, a norbornyl group or the like can be given.

The alkoxy group including 1 to 20 (preferably 1 to 10, more preferably 1 to 8, and particularly preferably 1 to 4) carbon atoms is a group represented by —OY. As examples of Y, examples of the above-mentioned alkyl group can be given. The alkoxy group is a methoxy group or an ethoxy group, for example.

As the aryl group including 6 to 50 (preferably 6 to 30, more preferably 6 to 20, and particularly preferably 6 to 12) ring carbon atoms, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 6-chrycenyl group, a 1-benzo[c]phenanthryl group, a 2-benzo[c]phenanthryl group, a 3-benzo[c]phenanthryl group, a 4-benzo[c]phenanthryl group, a 5-benzo[c]phenanthryl group, a 6-benzo[c]phenanthryl group, a 1-benzo[g]chrycenyl group, a 2-benzo[g]chrycenyl group, a 3-benzo[g]chrycenyl group, a 4-benzo[g]chrycenyl group, a 5-benzo[g]chrycenyl group, a 6-benzo[g]chrycenyl group, a 7-benzo[g]chrycenyl group, a 8-benzo[g]chrycenyl group, a 9-benzo[g]chrycenyl group, a 10-benzo[g]chrycenyl group, a 11-benzo[g]chrycenyl group, a 12-benzo[g]chrycenyl group, a 13-benzo[g]chrycenyl group, a 14-benzo[g]chrycenyl group, a 1-benzo[a]anthryl group, a 2-benzo[a]anthryl group, a 3-benzo[a]anthryl group, a 4-benzo[a]anthryl group, a 5-benzo[a]anthryl group, a 6-benzo[a]anthryl group, a 7-benzo[a]anthryl group, a 8-benzo[a]anthryl group, a 9-benzo[a]anthryl group, a 10-benzo[a]anthryl group, a 11-benzo[a]anthryl group, a 12-benzo[a]anthryl group, a 13-benzo[a]anthryl group, a 14-benzo[a]anthryl group, a 1-triphenyl group, a 2-triphenyl group, a 1-fluorenyl group, a 2-fluorenyl group, a 3-fluorenyl group, a 4-fluorenyl group, a benzofluorenyl group, a dibenzofluorenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, or the like can be given.

A phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-fluorenyl group, a 2-fluorenyl group, a 3-fluorenyl group, a 4-fluorenyl group, a 5-benzo[c]phenanthryl group, a 4-benzo[a]anthryl group, a 7-benzo[a]anthryl group, a 1-triphenyl group and a 2-triphenyl group are preferable.

As for the 1-fluorenyl group, the 2-fluorenyl group, the 3-fluorenyl group and the 4-fluorenyl group, it is preferred that the carbon atom at the 9th position be substituted by the substituted or unsubstituted alkyl group including 1 to 20 carbon atoms or the substituted or unsubstituted aryl group including 6 to 18 carbon atoms.

In the specification, the aryl group (aromatic hydrocarbon) is a hydrocarbon composed of an aromatic single ring (non-fused aryl group) or a plurality of rings (fused aryl group).

The fused aryl group is, among the above-mentioned aryl groups, a group obtained by fusing of two or more ring structures. The non-fused aryl group is a group, among the above-mentioned aryl groups, other than the fused aryl groups.

As the fused aryl group, a fused aryl group including 10 to 50 (preferably 10 to 30, more preferably 10 to 20) ring carbon atoms can be given. Among the specific examples of the above-mentioned aryl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 6-chrysenyl group, a 5-benzo[c]phenanthryl group, a 4-benzo[a]anthryl group, a 7-benzo[a]anthryl group, a 1-triphenyl group, a 2-triphenyl group or the like can be given, for example.

Among these, a 1-naphthyl group, a 2-naphthyl group, a 1-phenanthryl group, a 2-phenanthryl group, a 3-phenanthryl group, a 4-phenanthryl group, a 9-phenanthryl group, a 5-benzo[c]phenanthryl group, a 4-benzo[a]anthryl group, a 7-benzo[a]anthryl group, a 1-triphenyl group and a 2-triphenyl group are preferable.

As the divalent arylene group, a group obtained by removing two hydrogen atoms from the above-mentioned aryl group can be mentioned.

The aryloxy group including 6 to 30 (preferably 6 to 20, more preferably 6 to 12) ring carbon atoms is a group represented by —OAr. As examples of Ar, the same aryl groups as those mentioned above can be given. The aryloxy group is a phenoxy group, for example.

The arylthio group including 6 to 30 (preferably 6 to 20, more preferably 6 to 12) ring carbon atoms is a group represented by —SAr. As examples of Ar, the same aryl groups as those mentioned above can be given.

As the heterocyclic group including 5 to 50 (preferably 5 to 30, more preferably 5 to 30, and particularly preferably 5 to 12) ring atoms, a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, 5-isoindolyl group, a 6-isoindolyl group, a 7-isoindoly group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 1-dibenzoisofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a quinolyl group, a 3-quinolyl group, a 4-quinolyl group, 5-quinolyl group, a 6-quinolyl group, a 7-quinolyl group, 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalynyl group, a 5-quinoxalynyl group, a 6-quinoxalynyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenathrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenathrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthoroin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indoyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-benzimidazolyl group, a 2-benzimidazolyl group, a 4-benzimidazolyl group, a 5-benzimidazolyl group, 6-benzimidazolyl group, a 7-benzimidazolyl group, a 2-imidazo[1,2-a]pyridinyl group, a 3-imidazo[1,2-a]pyridinyl group, a 5-imidazo[1,2-a]pyridinyl group, a 6-imidazo[1,2-a]pyridinyl group, a 7-imidazo[1,2-a]pyridinyl group, a 8-imidazo[1,2-a]pyridinyl group, a benzimidazol-2-one-1-yl group, a benzimidazol-2-one-3-yl group, a benzimidazol-2-one-4-yl group, a benzimidazol-2-one-5-yl group, a benzimidazol-2-one-6-yl group, a benzimidazol-2-one-7-yl group or the like can be given.

Among these, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-carbazolyl group, a 2-carbazolyl group, a 3-carbazolyl group, a 4-carbazolyl group, a 9-carbazolyl group, a 1-benzimidazolyl group, a 2-benzimidazolyl group, a 4-benzimidazolyl group, a 5-benzimidazolyl group, a 6-benzimidazolyl group, a 7-benzimidazolyl group, a 2-imidazo[1,2-a]pyridinyl group, a 3-imidazo[1,2-a]pyridinyl group, a 5-imidazo[1,2-a]pyridinyl group, a 6-imidazo[1,2-a]pyridinyl group, a 7-imidazo[1,2-a]pyridinyl group, a 8-imidazo[1,2-a]pyridinyl group, a 2-pyridinyl group, a 3-pyridinyl group, a 4-pyridinyl group, a 1,10-phenanthrolin-2-yl group, a 1,10-phenanthrolin-3-yl group, a 1,10-phenanthrolin-4-yl group, a 1,10-phenanthrolin-5-yl group, a benzoimidazol-2-one-1-yl group, a benzimidazol-2-one-3-yl group, a benzimidazol-2-one-4-yl group, a benzimidazol-2-one-5-yl group, a benzimidazol-2-one-6-yl group, a benzimidazol-2-one-7-yl group are preferable. A 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-carbazolyl group, a 2-carbazolyl group, a 3-carbazolyl group, a 4-carbazolyl group and a 9-carbazolyl group are particularly preferable.

The heterocyclic group includes a monocyclic heteroaromatic ring group, a heterofused aromatic ring group obtained by fusing of a plurality of heteroaromatic rings and a heterofused aromatic ring group obtained by fusing of an aromatic hydrocarbon ring and a heteroaromatic ring.

As the fused heterocyclic ring group including 8 to 30 (preferable 8 to 20) ring atoms, among the specific examples of the heterocyclic group given above, a dibenzofuranyl group, a dibenzothiophenyl group and a carbazolyl group can be mentioned, for example.

As the divalent heterocyclic group, a group obtained by removing two hydrogen atoms from the above-mentioned heterocyclic groups can be given.

The divalent arylene group and the divalent heterocyclic group forming the group formed by linking of 2 to 4 divalent arylene groups and/or divalent heterocyclic groups are respectively the same as those mentioned above. The arylene group is preferably selected from a substituted or unsubstituted phenylenyl group, a substituted or unsubstituted naphthalenyleny group, a substituted or unsubstituted phenanthrenylenyl group, a substituted or unsubstituted anthrylenyl group, a substituted or unsubstituted pyrenylenyl group and a substituted or unsubstituted fluorenylenyl group. The heterocyclic group is preferably selected from a substituted or unsubstituted pyridinylenyl group, a substituted or unsubstituted pyrimidinylenyl group, a substituted or unsubstituted pyrazinylenyl group, a substituted or unsubstituted pyridazinyleneyl group, a substituted or unsubstituted triazinylenyl group, a substituted or unsubstituted dibenzofuranylenyl group, a substituted or unsubstituted dibenzothiophenylenyl group, and a substituted or unsubstituted carbazolylenyl group.

The following structures are more preferable.

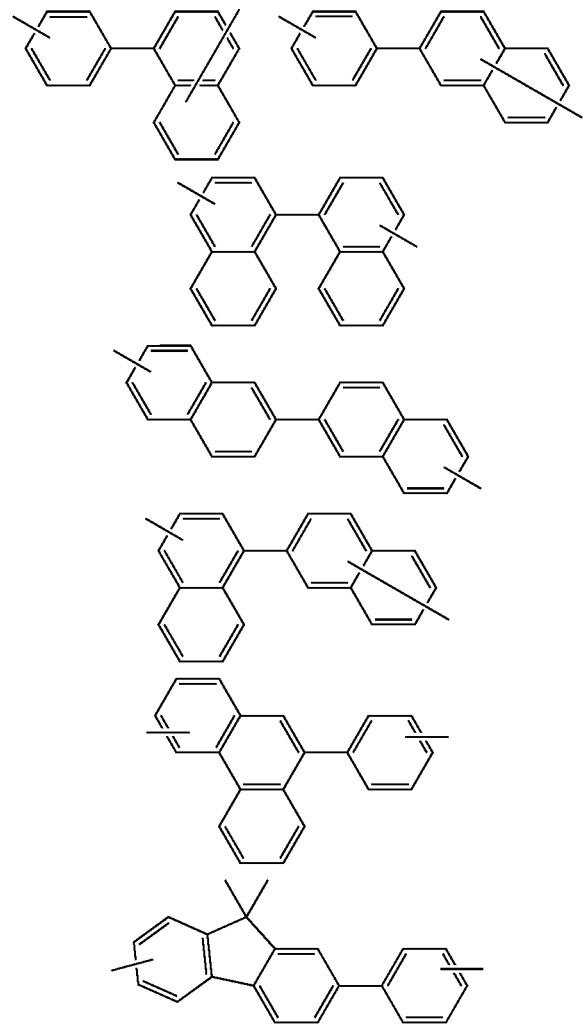

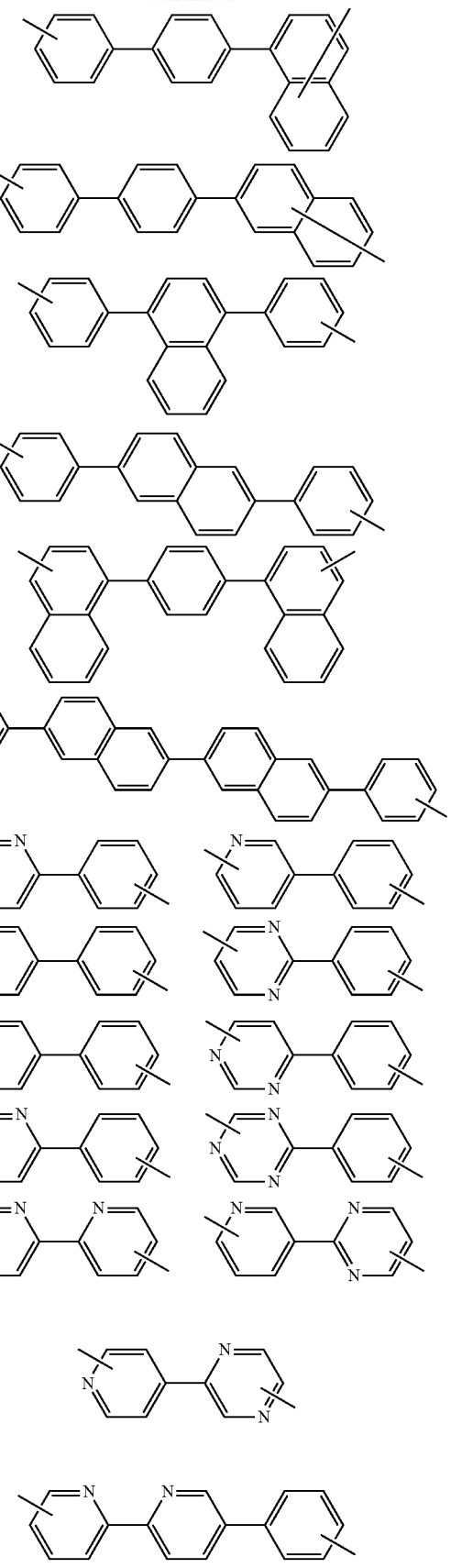

17
-continued
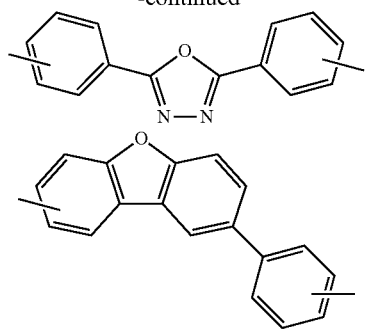
18
-continued
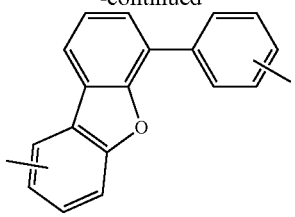
As for the preferable structure of the anthracene derivative formed by linking of 2 to 4 divalent arylene groups and/or divalent heterocyclic groups, the following can be given, for example.
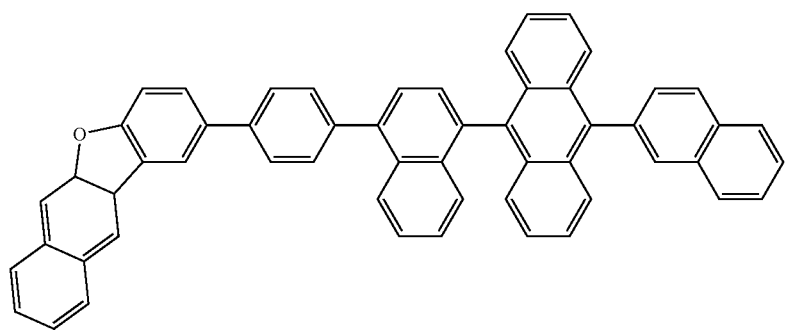
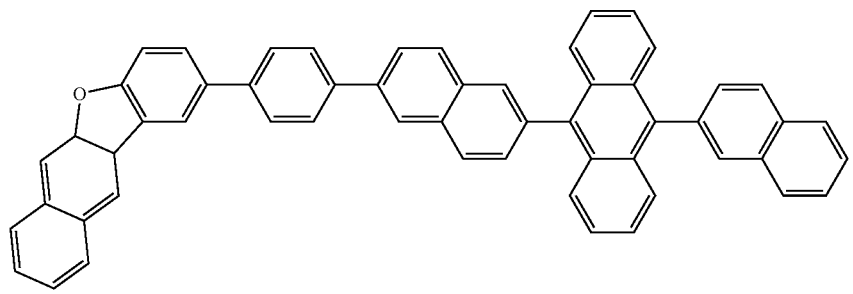
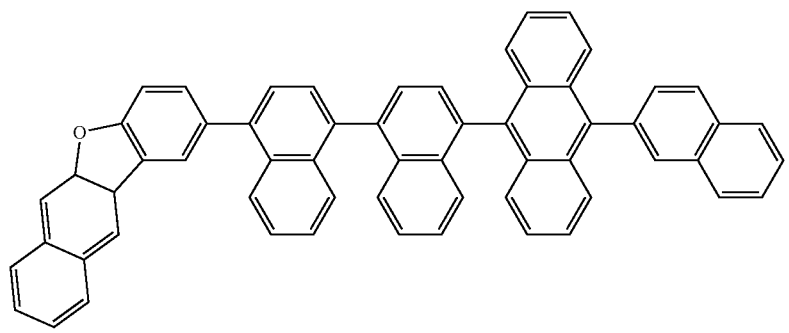
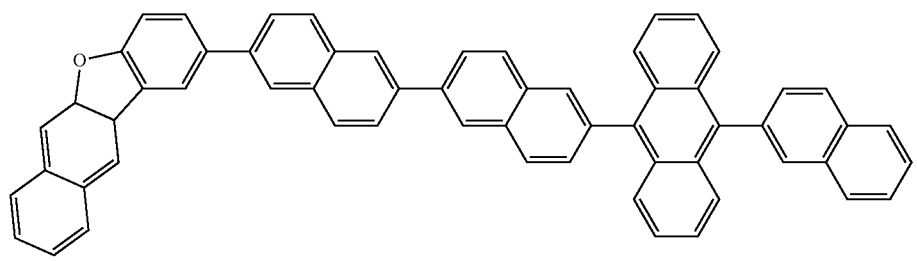

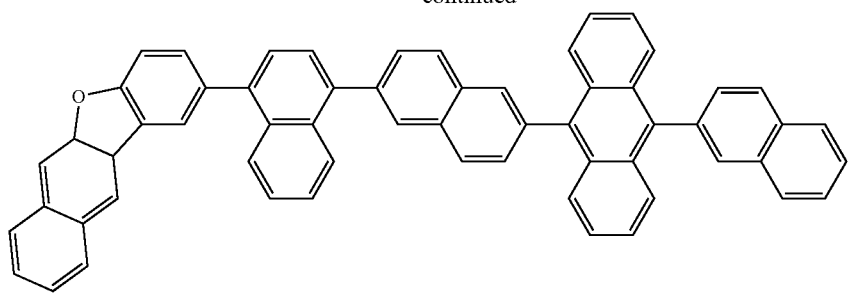
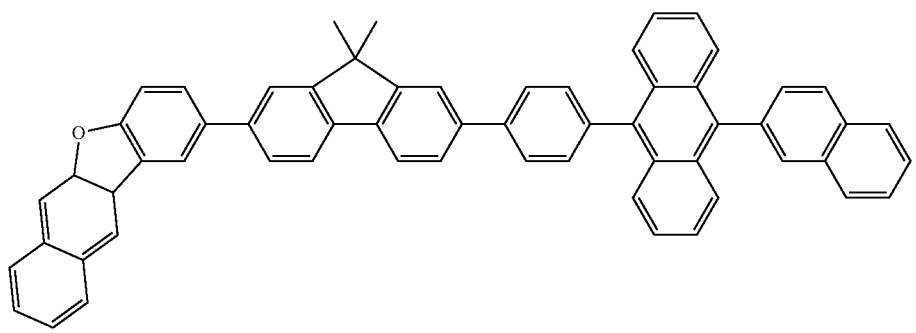
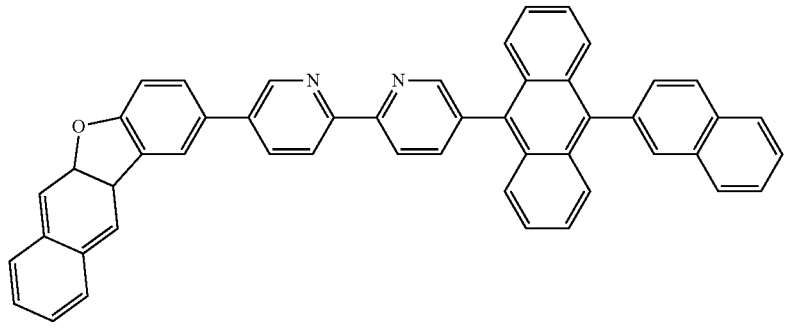
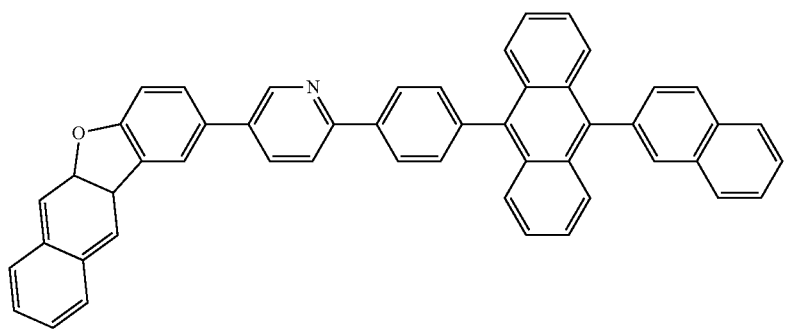
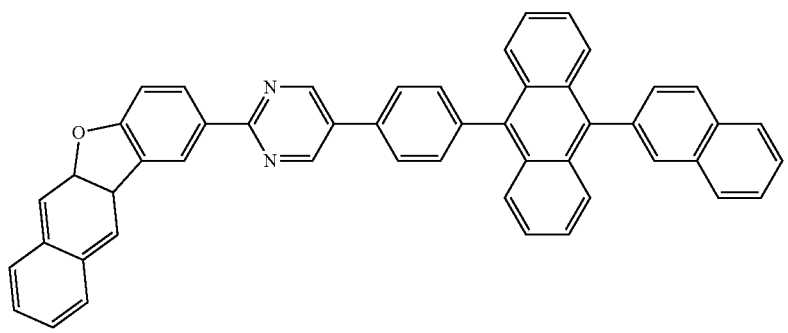

-continued

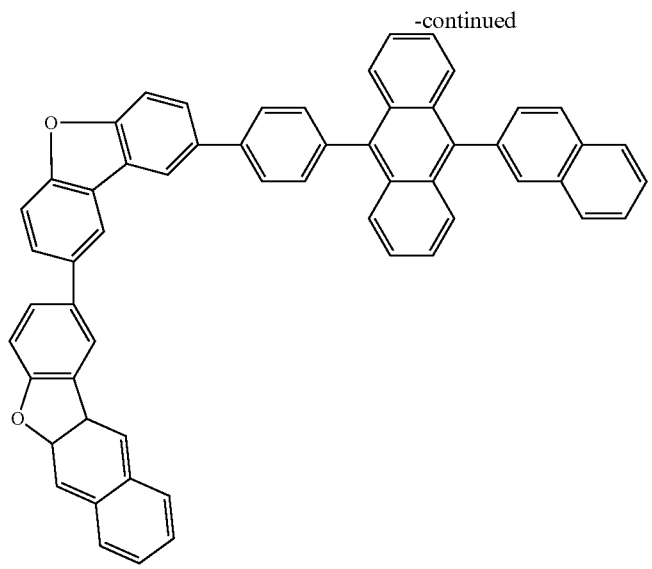

As the alkylsilyl group including 3 to 60 carbon atoms, a trialkylsilyl group including one of the alkyl groups given above as the examples of the alkyl group can be mentioned. Specific examples thereof include a trimethylsilyl group, a triethylsilyl group, a tri-n-butylsilyl group, a tri-n-octylsilyl group, a triisobutylsilyl group, a dimethylethylsilyl group, a dimethylisopropylsilyl group, a dimethyl-n-propylsilyl group, a dimethyl-n-butylsilyl group, a dimethyl-t-butylsilyl group, a diethylisopropylsilyl group, a vinyldimethylsilyl group, a propyldimethylsilyl group, a triisopropylsilyl group or the like can be given. The three alkyl groups may be the same or different.

As the arylsilyl group including 8 to 60 carbon atoms, an arylsilyl group, an alkylarylsilyl group, a dialkylarylsilyl group, a diarylsilyl group, an alkyldiarylsilyl group and a triarylsilyl group can be given. The plural aryl groups or the plural alkyl groups may be the same or different.

As the dialkylarylsilyl group, a dialkylarylsilyl group including two of the alkyl groups given above as the examples of the alkyl group and one of the aryl groups mentioned above can be mentioned, for example. It is preferred that the number of carbon atoms of the dialkylarylsilyl group be 8 to 30. The two alkyl groups may be the same or different.

As the alkyldiarylsilyl group, an alkyldiarylsilyl group including one of the alkyl groups given above as the examples of the alkyl group and two of the aryl groups mentioned above can be given, for example. It is preferred that the number of carbon atoms of the alkyldiarylsilyl group be 13 to 30. The two aryl groups may be the same or different.

As the triarylsilyl group, a triarylsilyl group including three of the aryl groups mentioned above can be given. It is preferred that the number of carbon atoms of the triarylsilyl group be 18 to 30. The three aryl groups may be the same or different.

As the arylsilyl group, a phenyldimethylsilyl group, a diphenylmethylsilyl group, a diphenyl-t-butylsilyl group and a triphenylsilyl group can be given, for example.

The aralkyl group is represented by —Y—Z. As examples of Y, the examples of alkylene corresponding to the examples of the alkyl can be given. As examples of Z, the examples of the aryl can be given. The aralkyl group is preferably an aralkyl group including 7 to 50 (the aryl part includes 6 to 49 (preferably 6 to 30, more preferably 6 to 20, particularly preferably 6 to 12) and the alkyl part includes 1 to 44 (preferably 1 to 30, more preferably 1 to 20, further preferably 1 to 10, and particularly preferably 1 to 6)) carbon atoms. The aralkyl group is preferably a benzyl group, a phenylethyl group and a 2-phenylpropane-2-yl group, for example.

The anthracene derivatives according to one aspect of the invention are exemplified below. The invention is not limited to these.

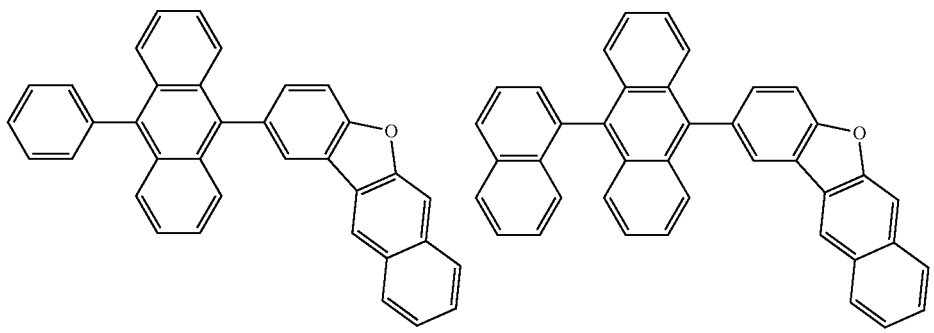

-continued
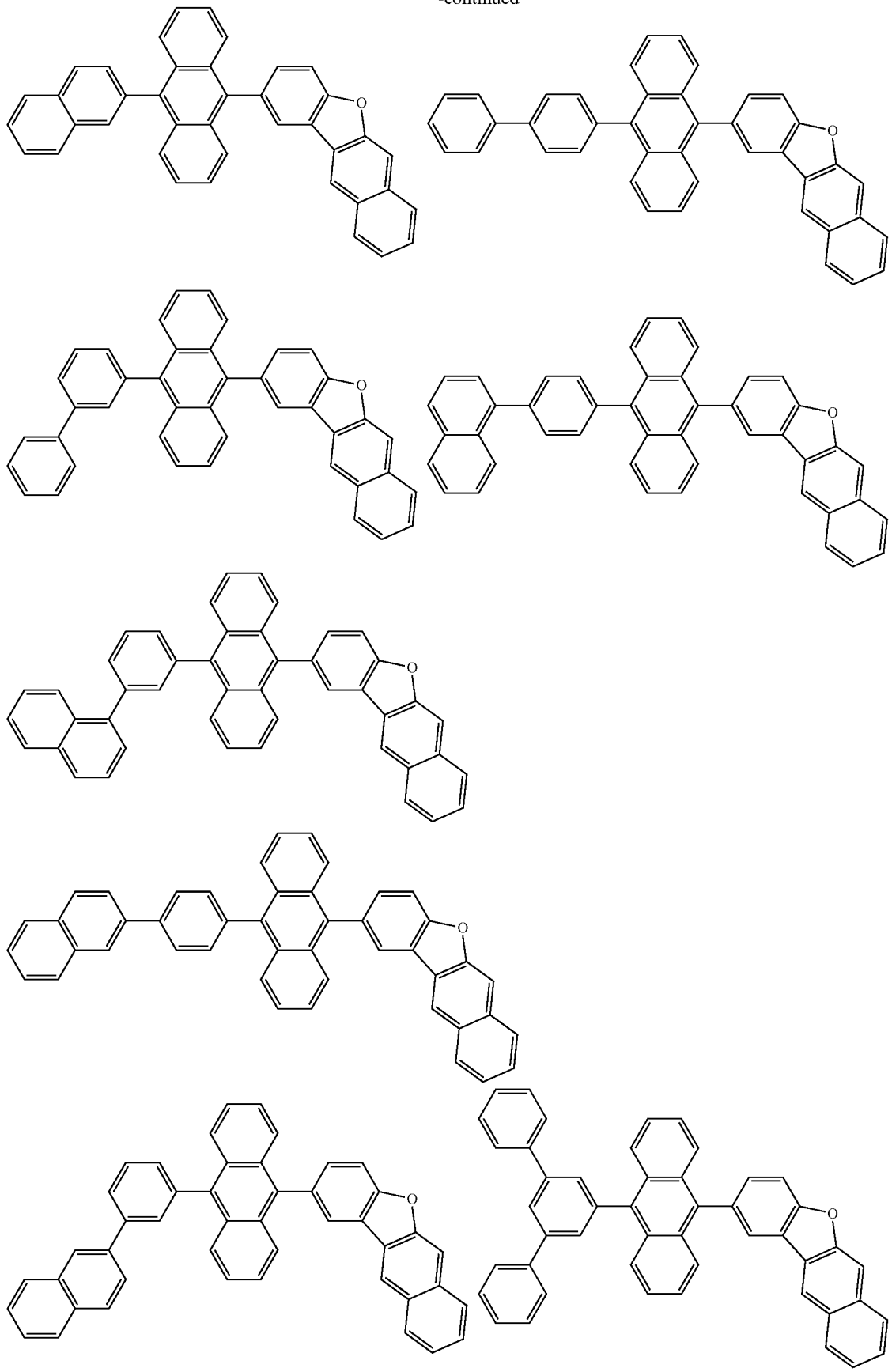

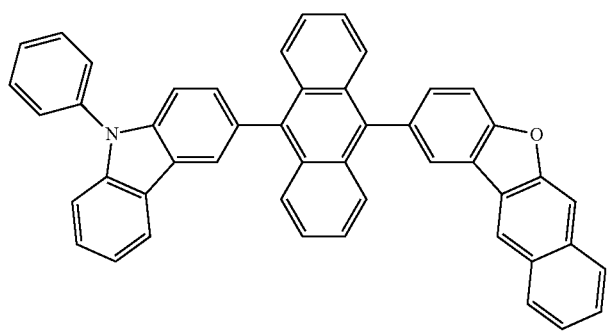
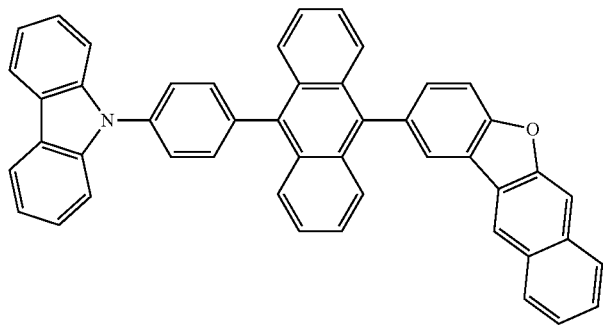
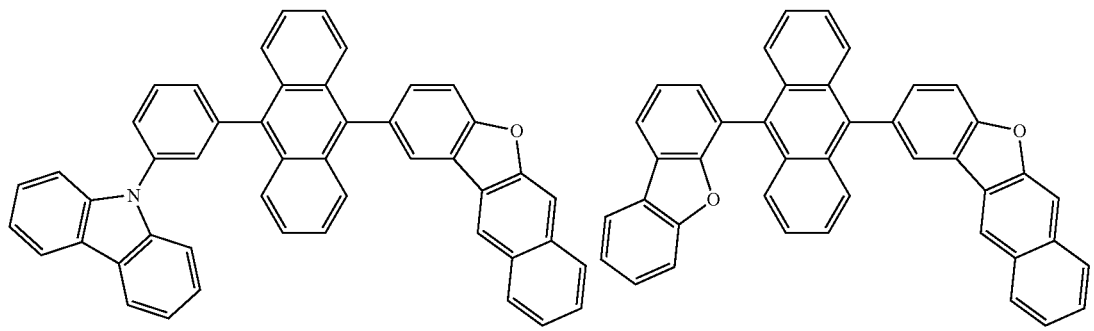
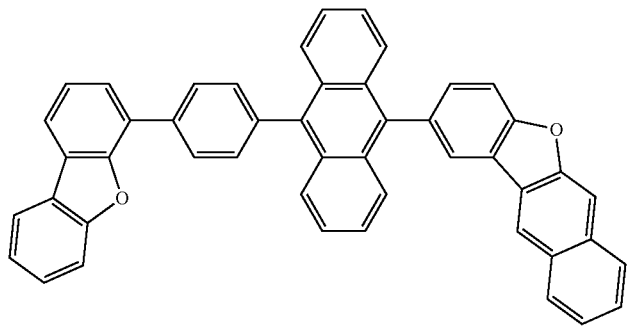
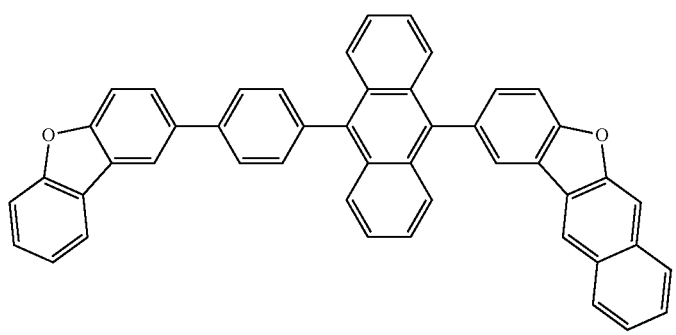

-continued
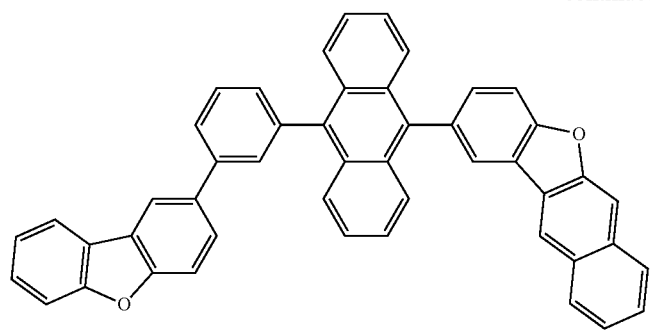
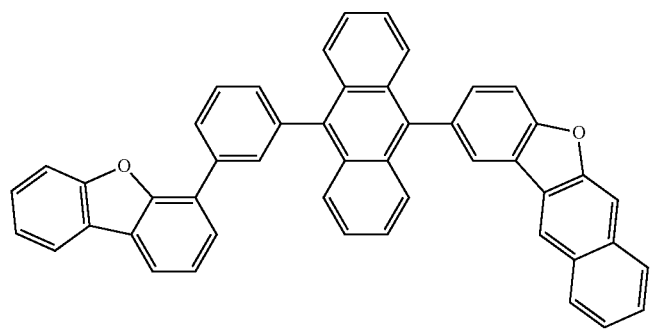
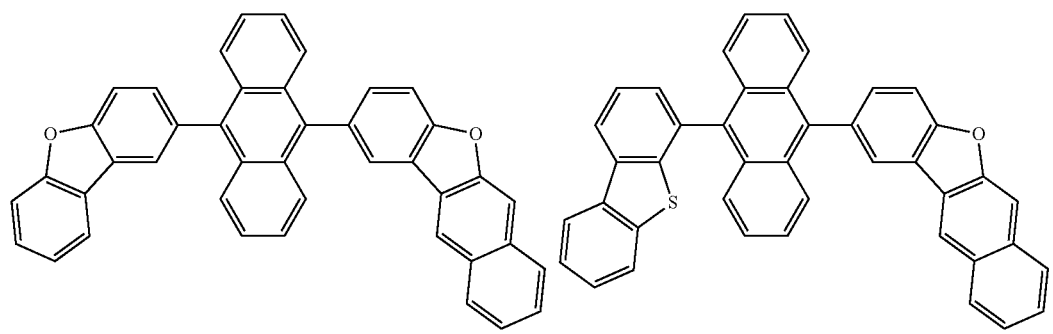
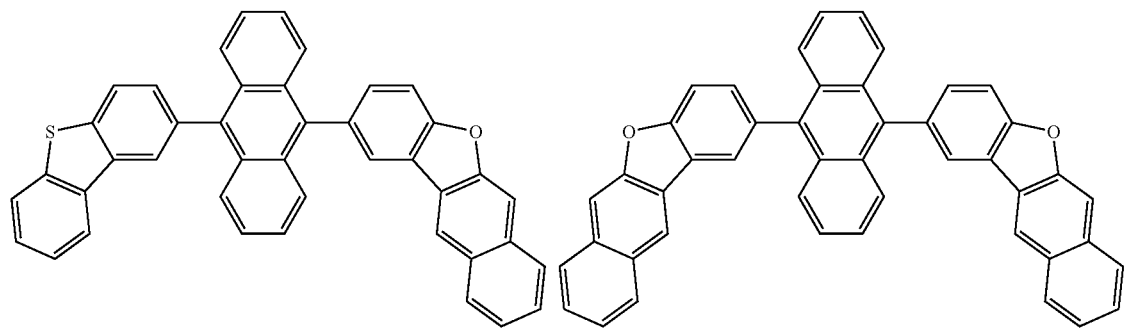
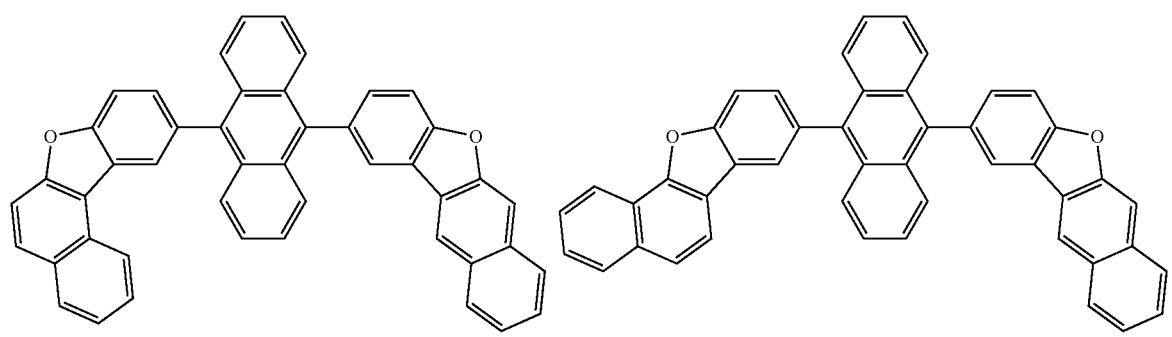

-continued
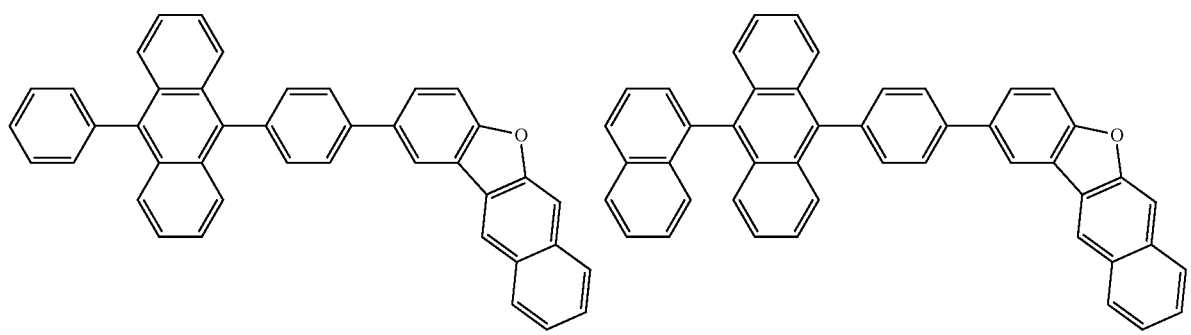
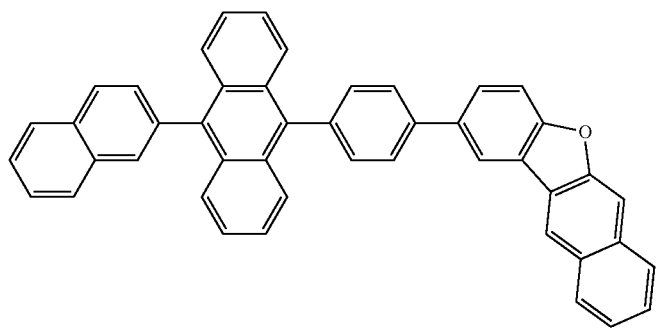
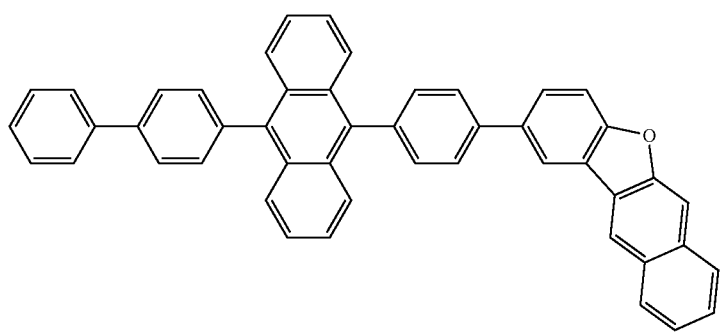
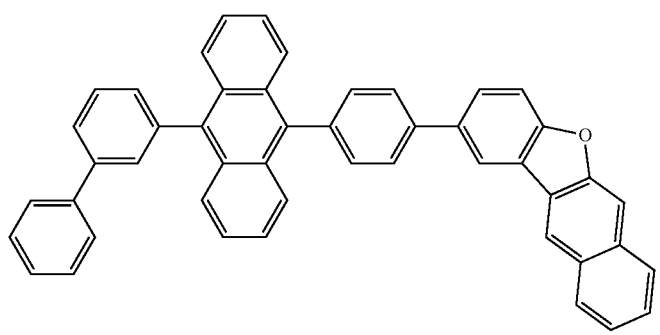
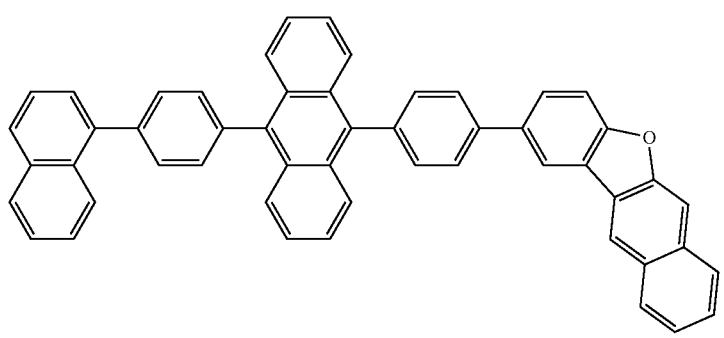

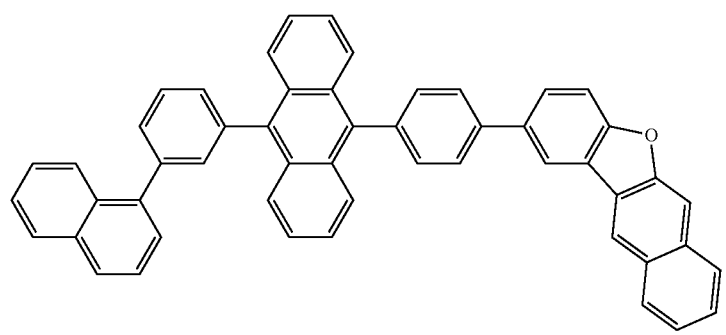
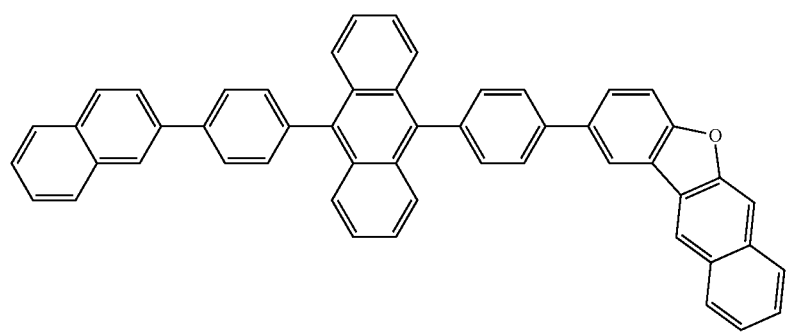
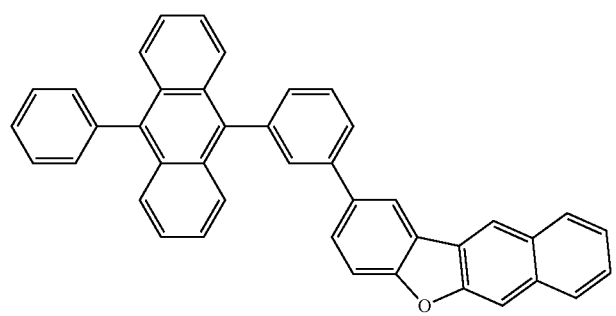
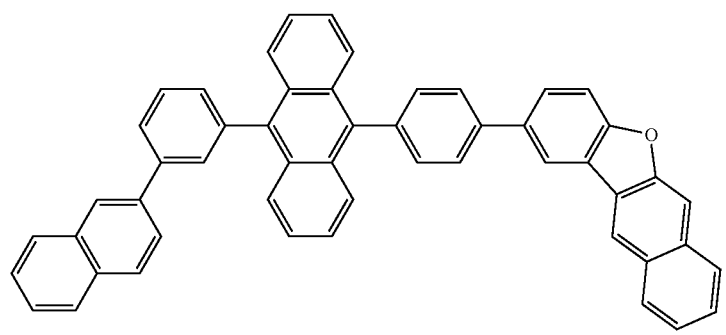
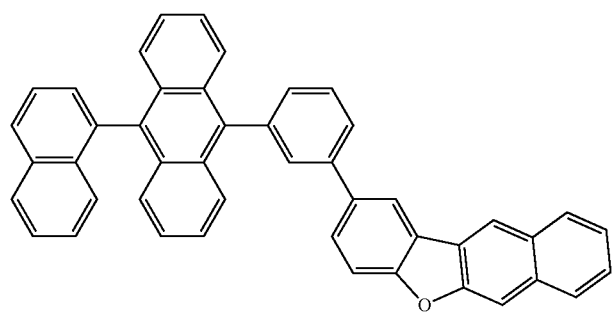

-continued
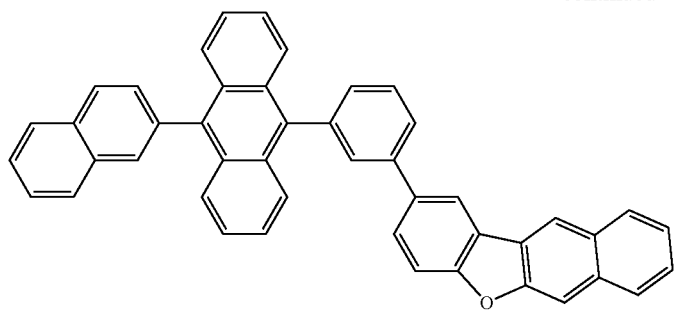 [SMILES: c1cc(-c2ccc3oc4cc5ccccc5cc4c3c2)cc(-c2c3ccccc3c(-c3ccc4ccccc4c3)c3ccccc23)c1]
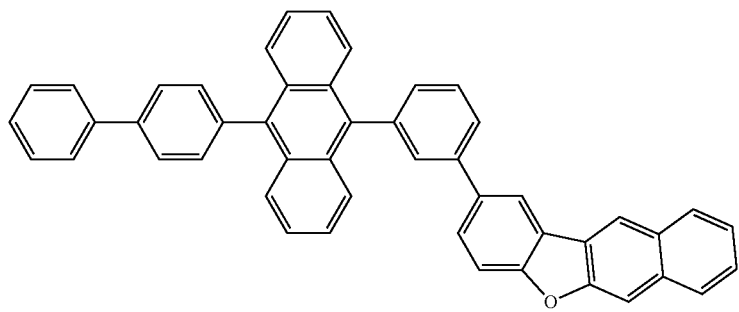
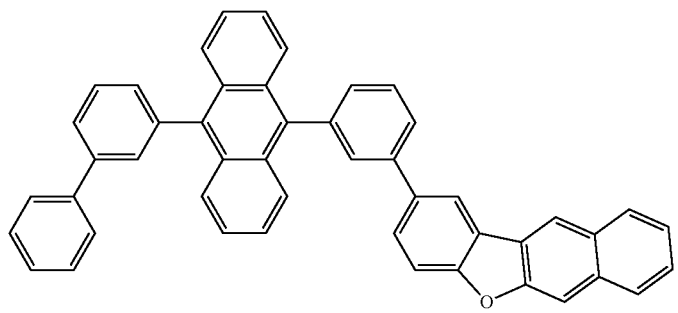
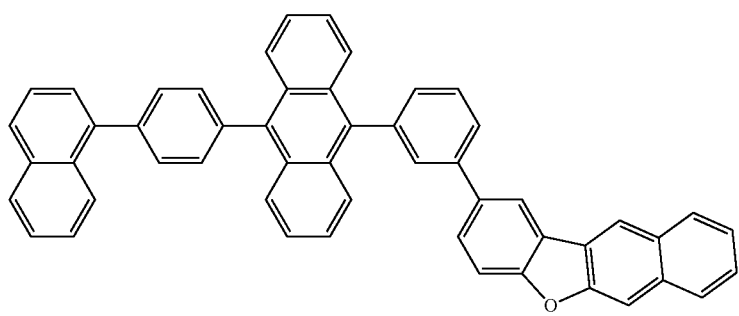
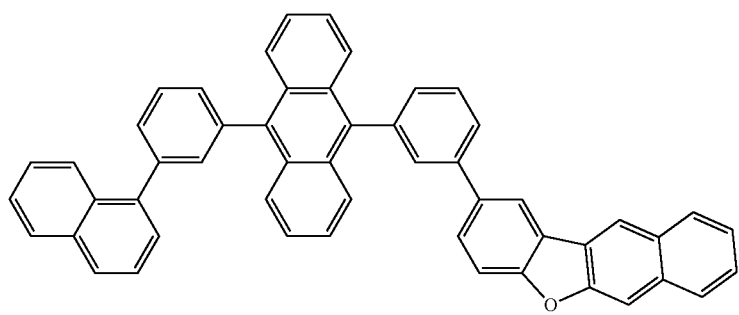

-continued
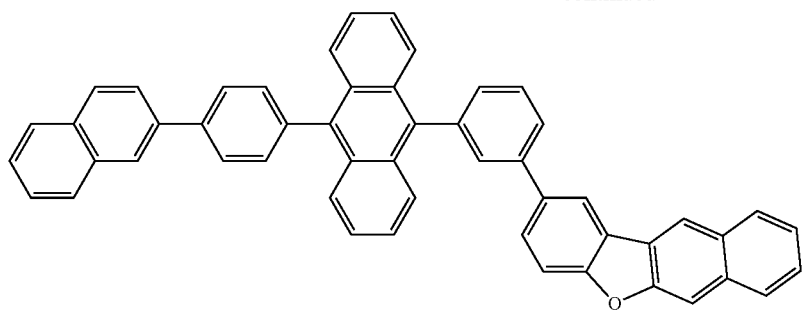
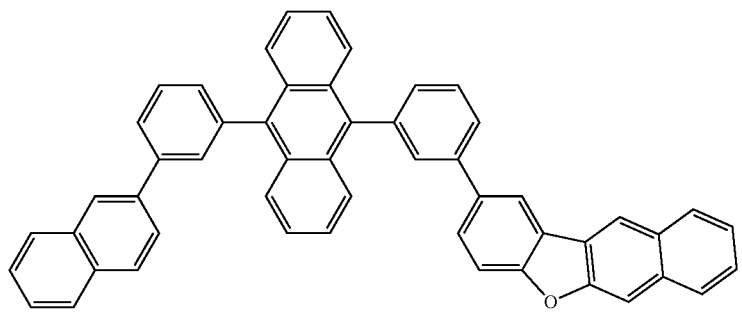
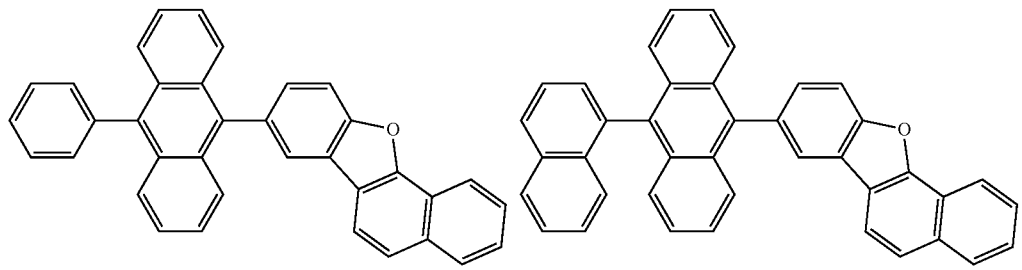
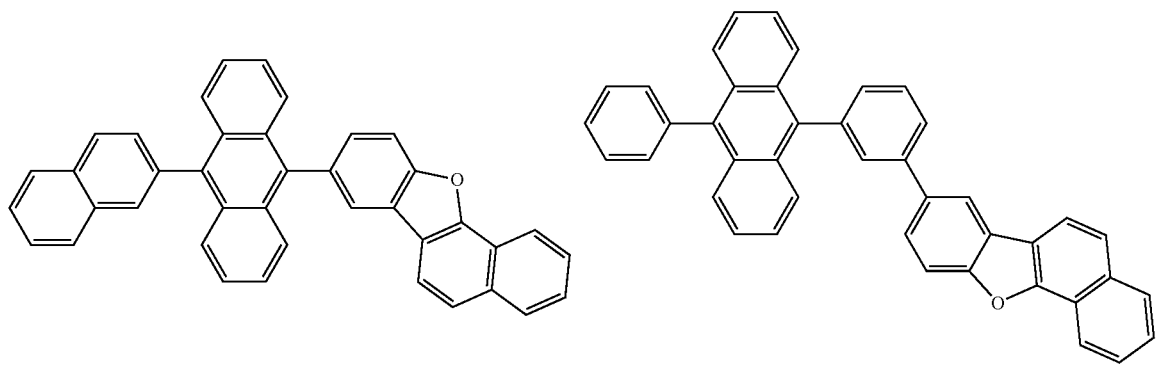
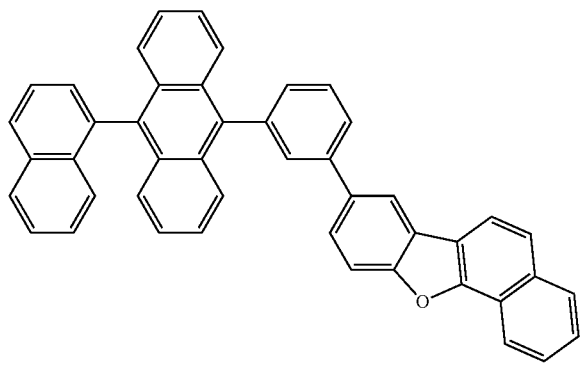

-continued
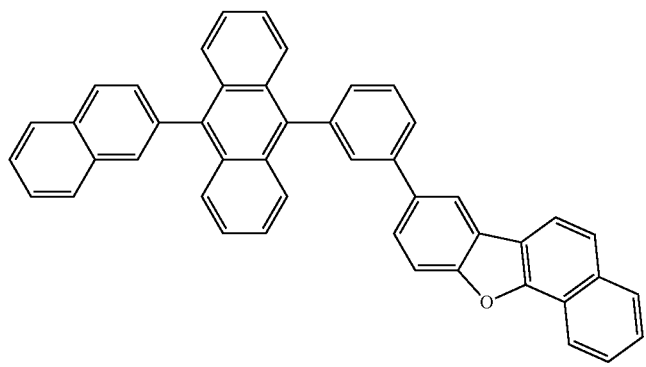
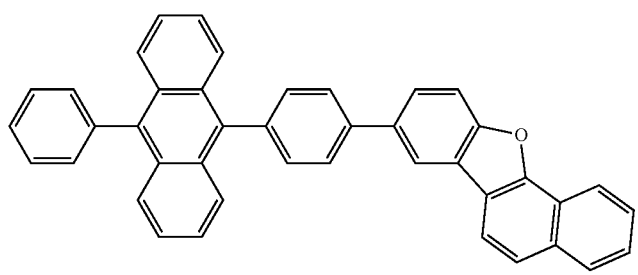
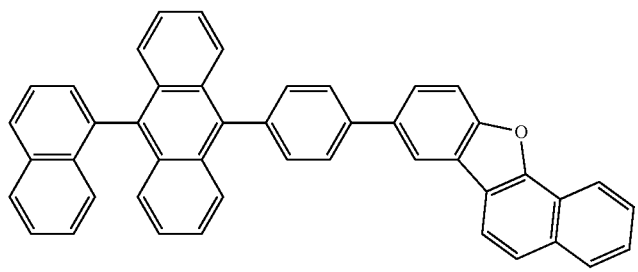
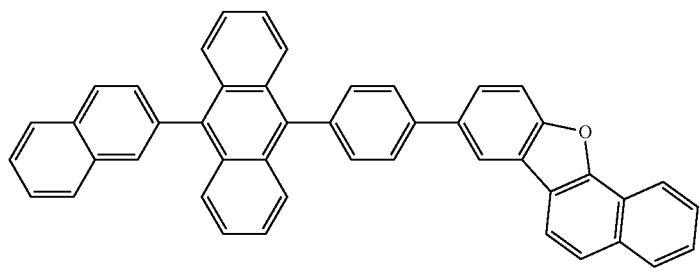
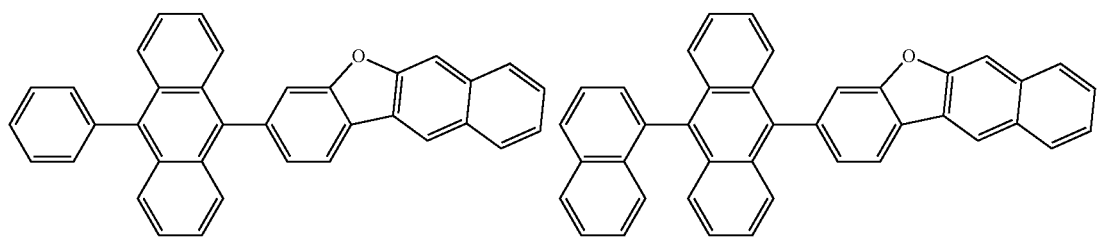

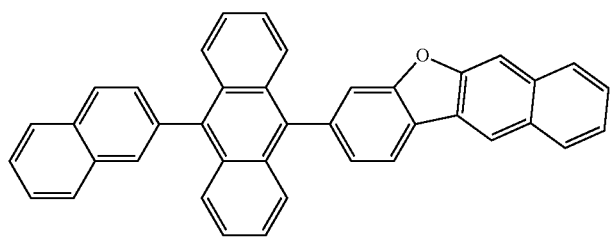
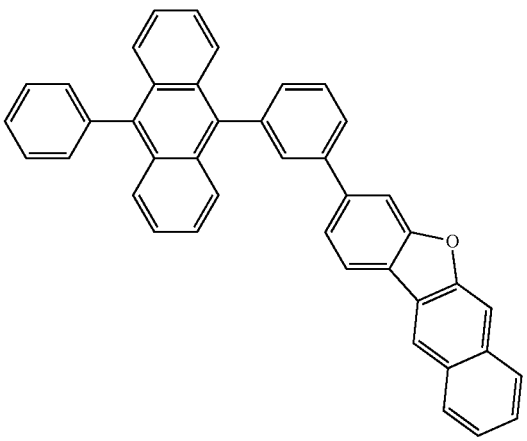
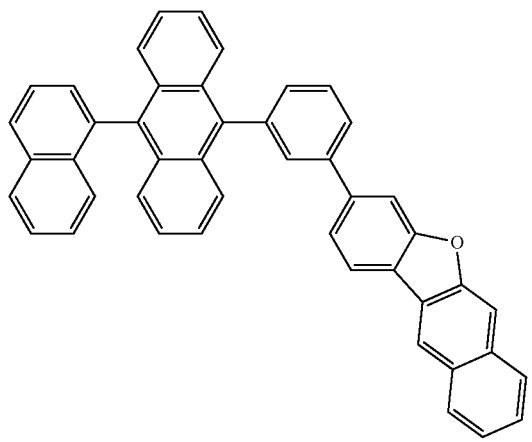
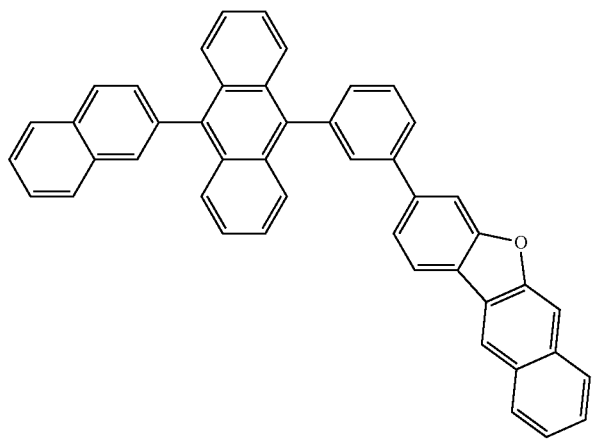
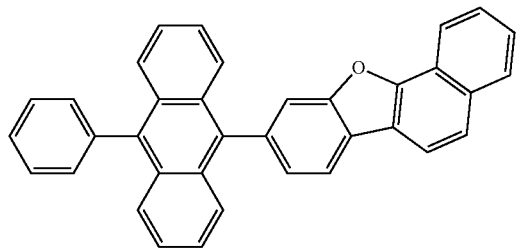
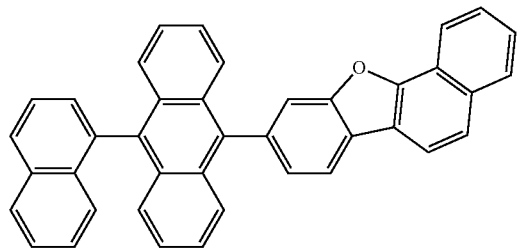
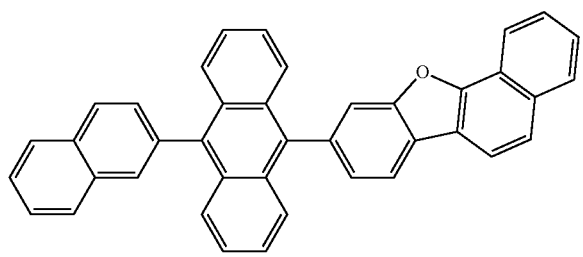

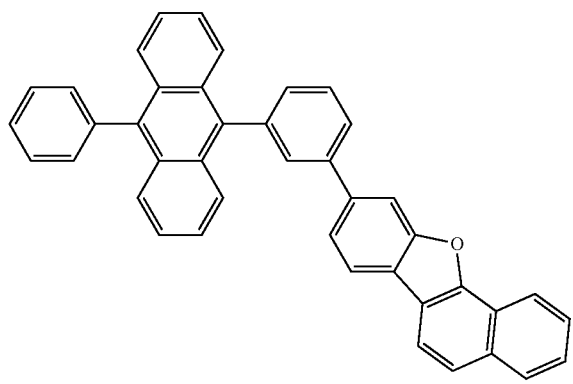
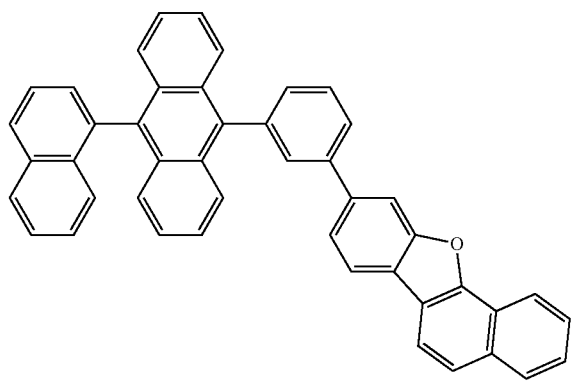
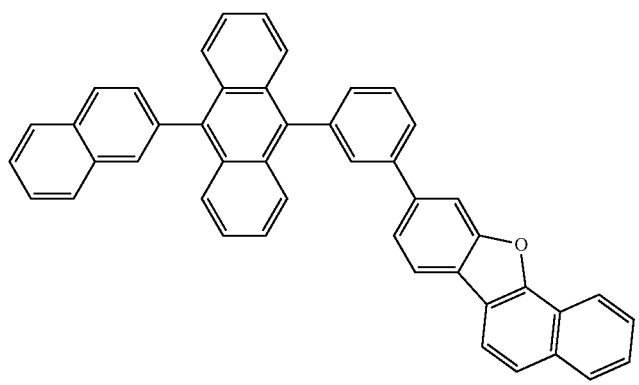
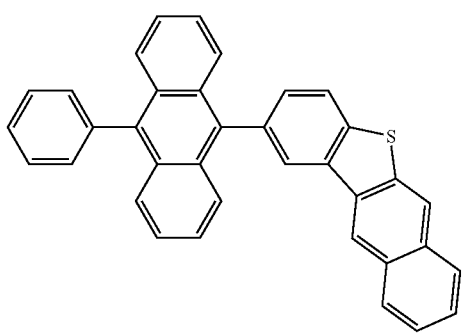
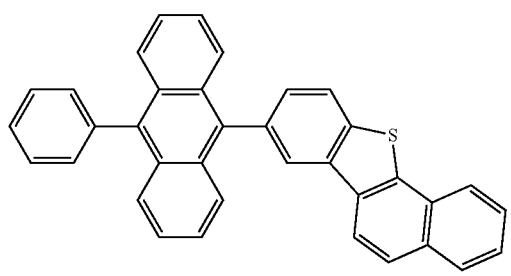
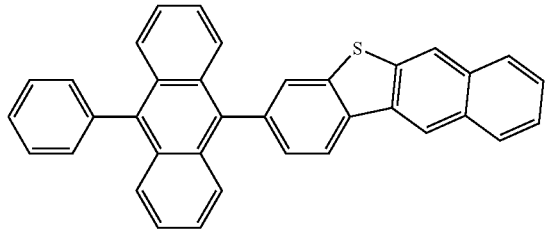
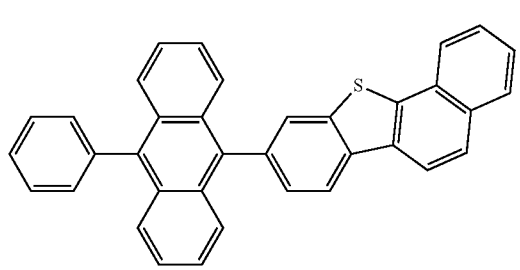
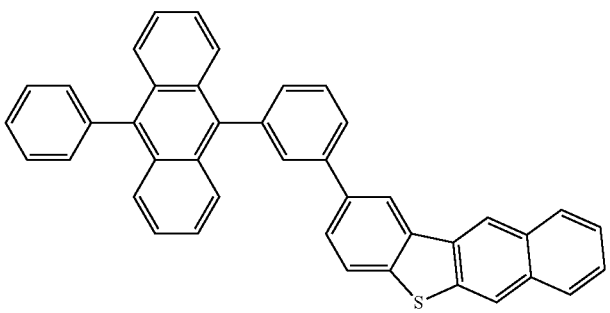
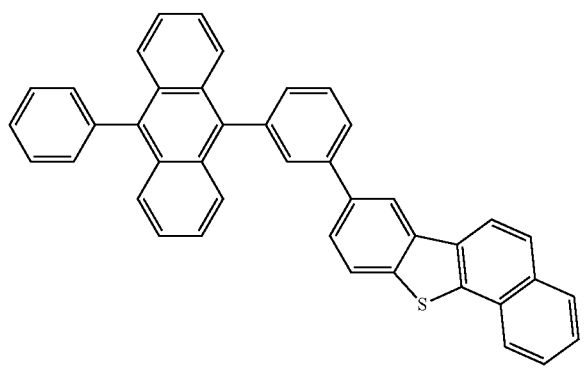

-continued
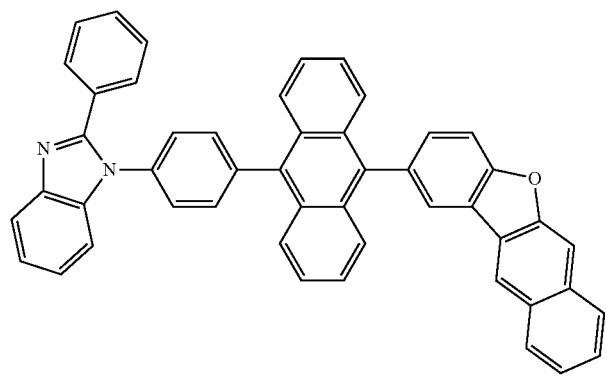
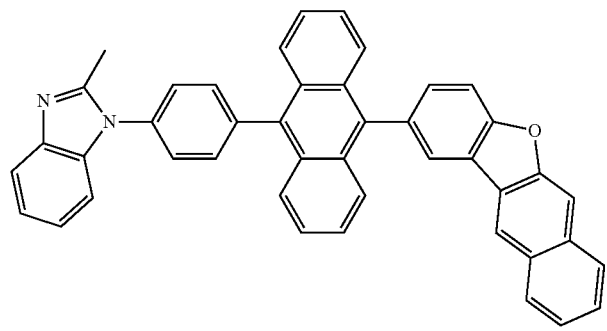
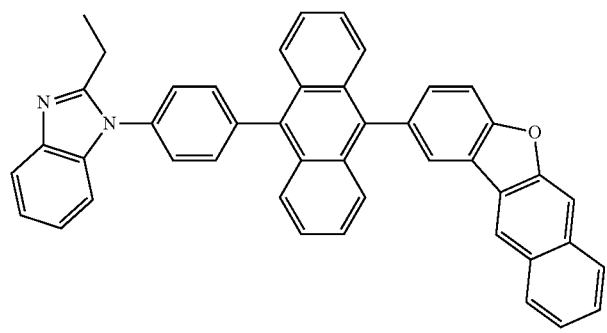
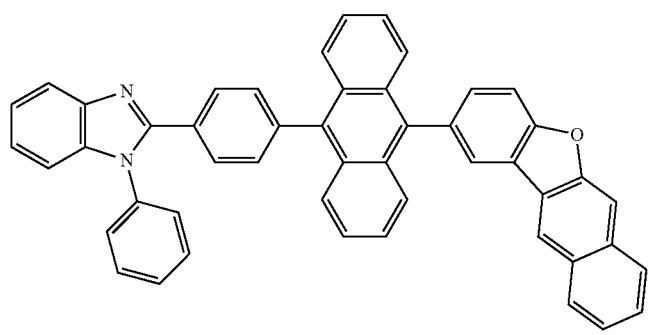
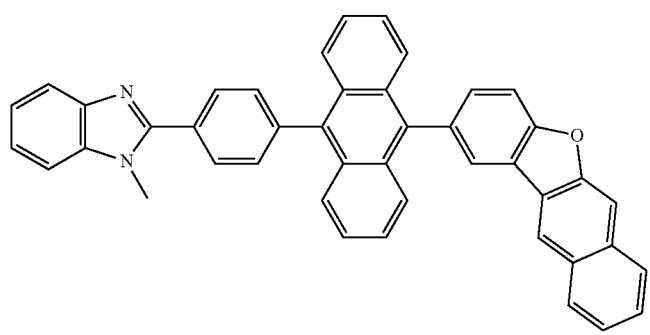

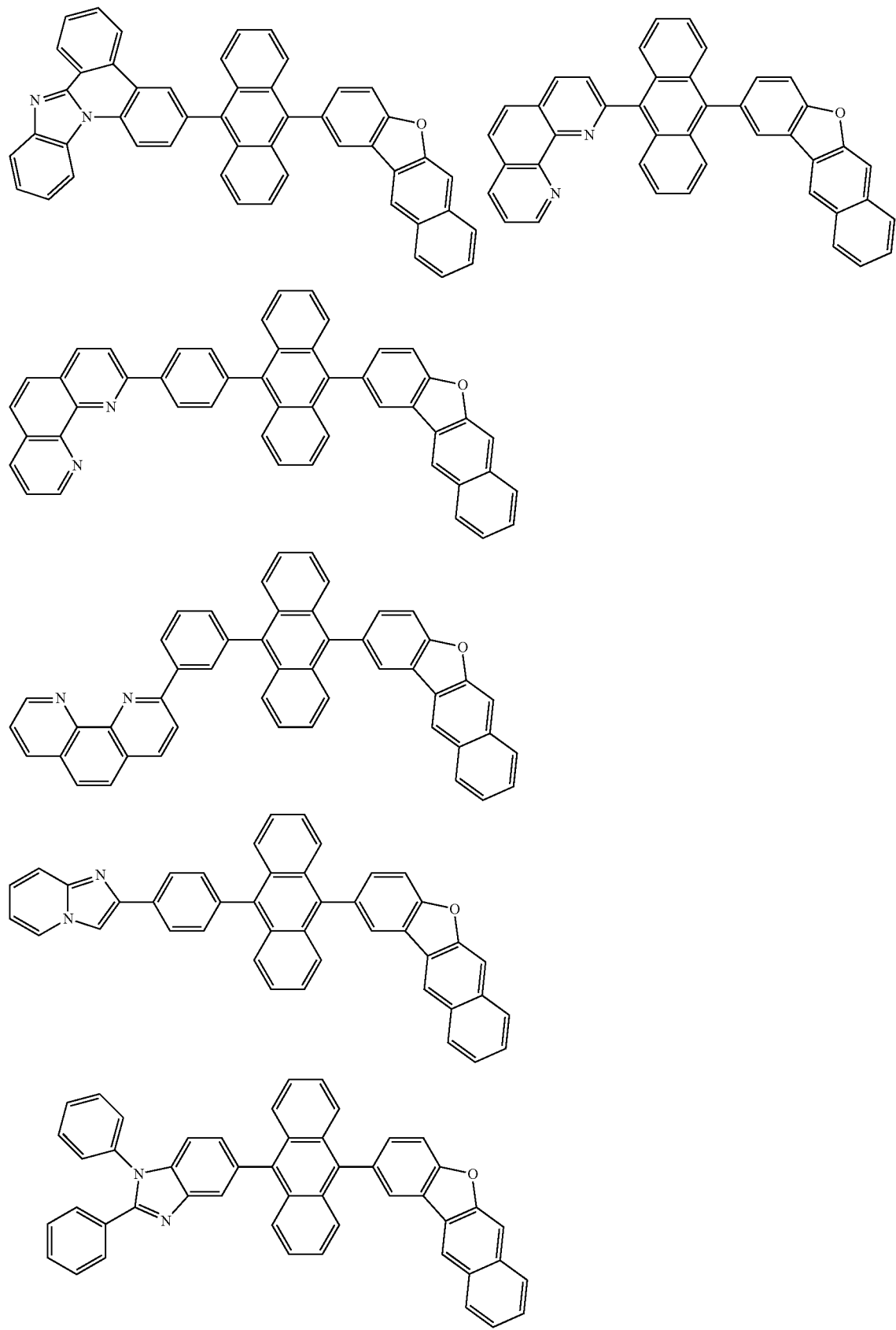

-continued
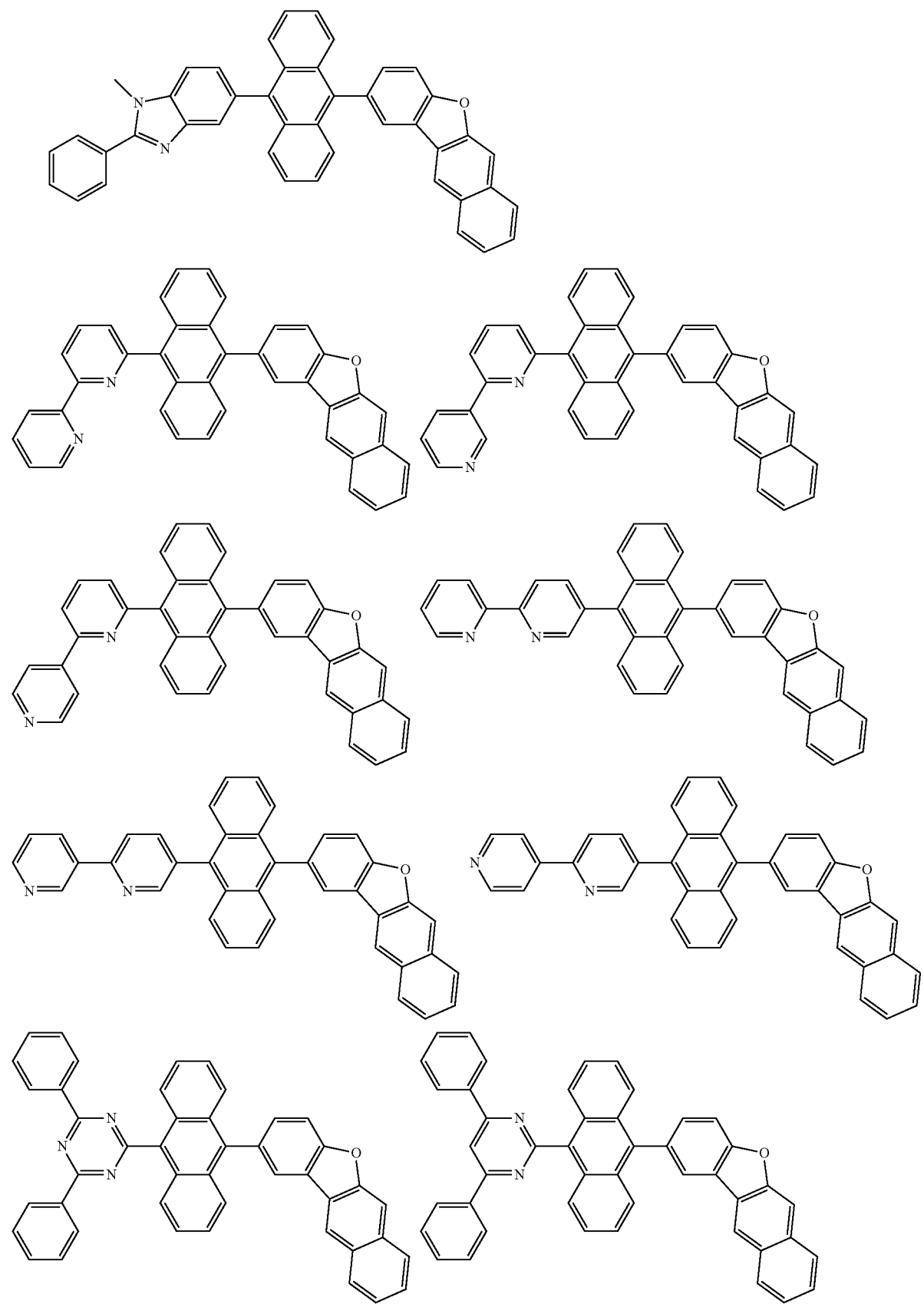

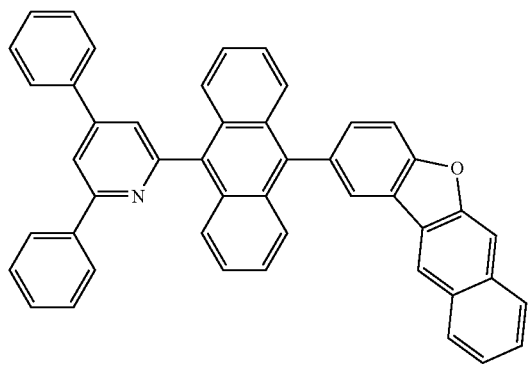
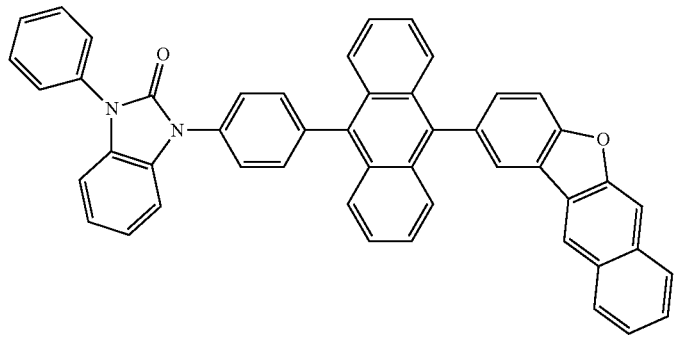
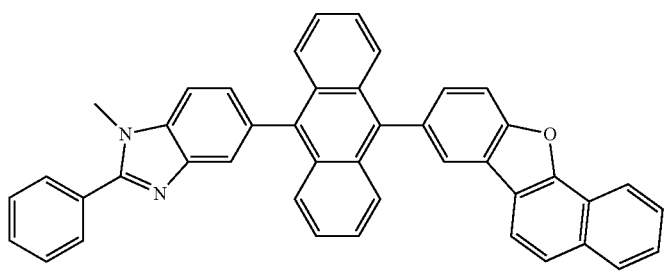
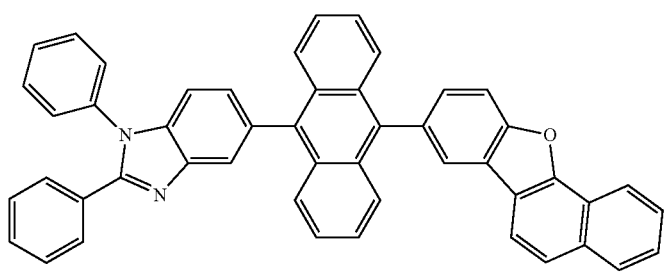
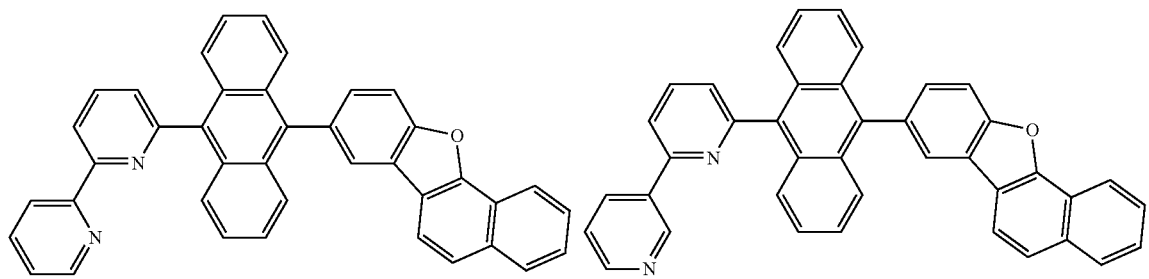

-continued
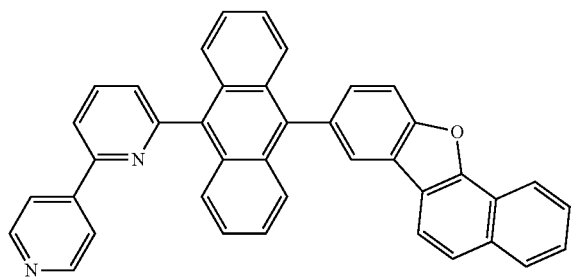
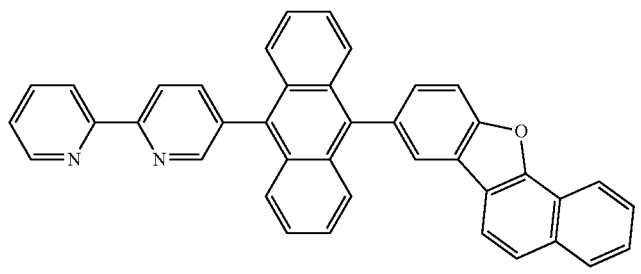
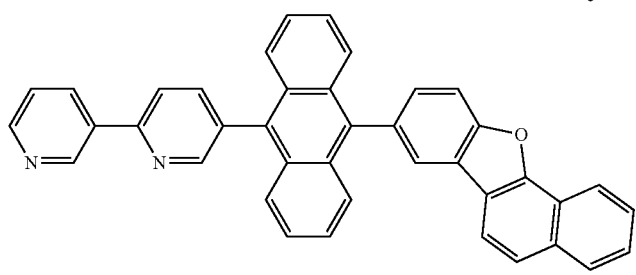
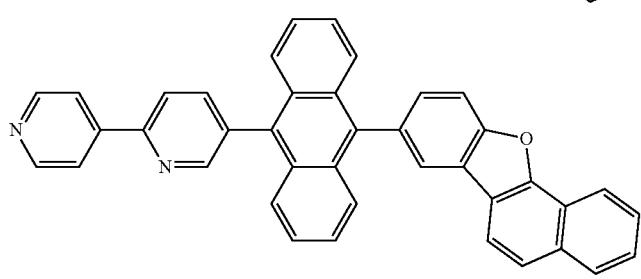
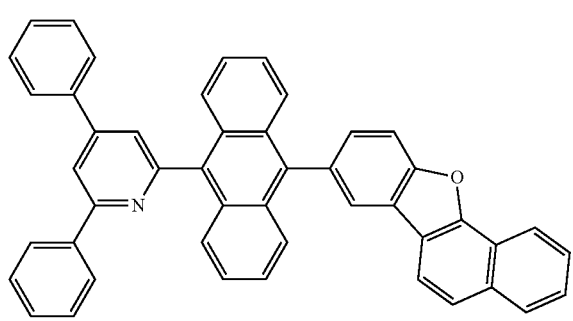
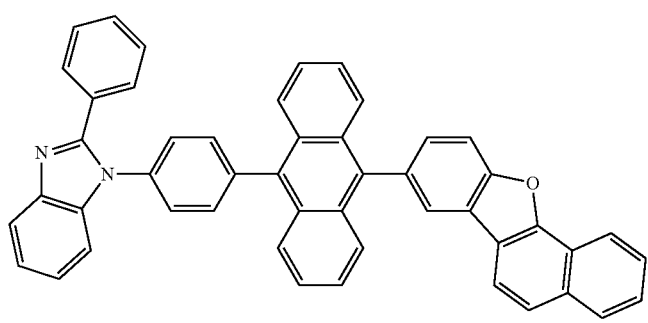

-continued
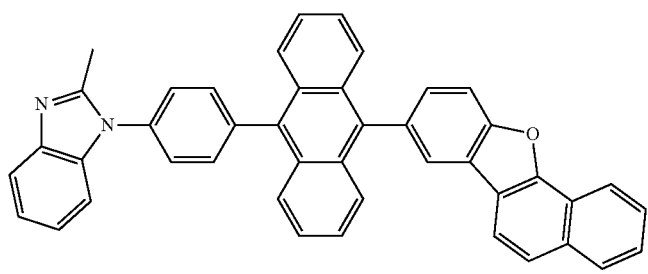
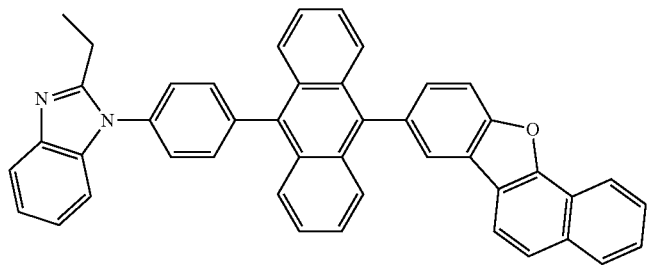
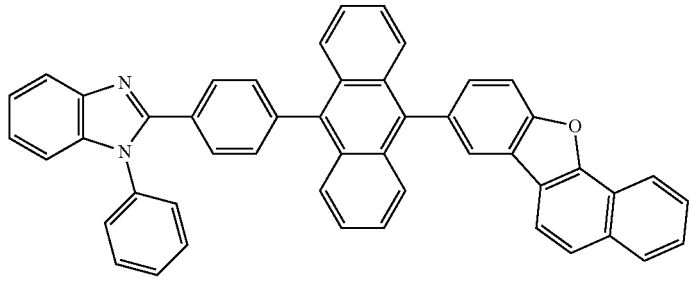
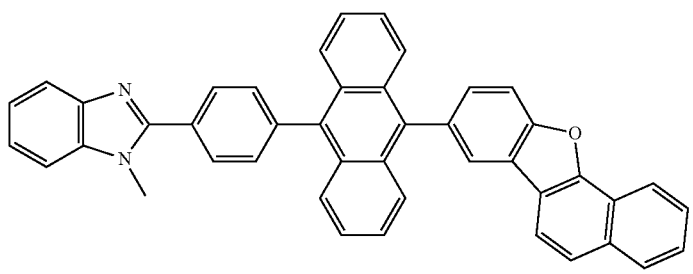
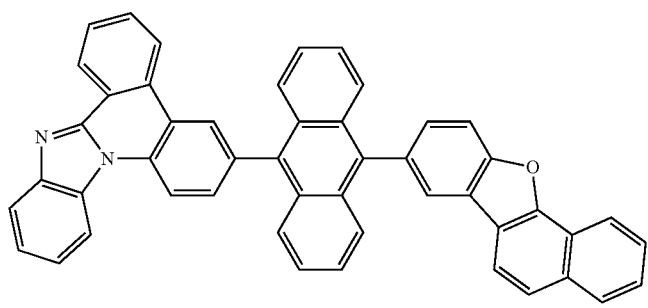
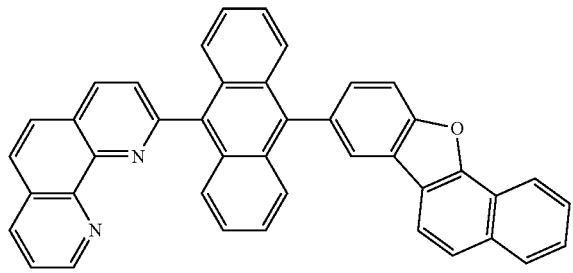

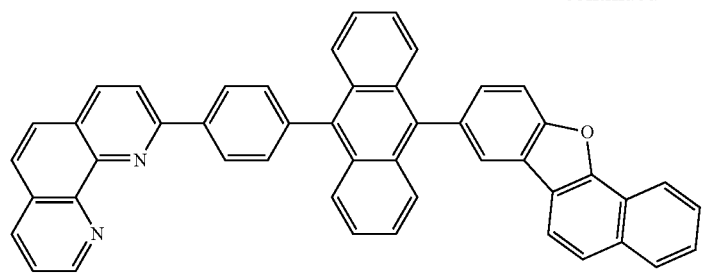
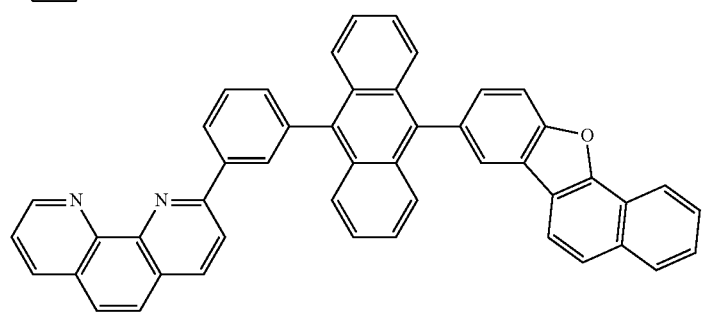
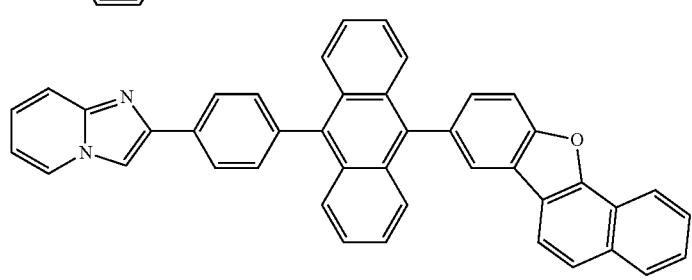
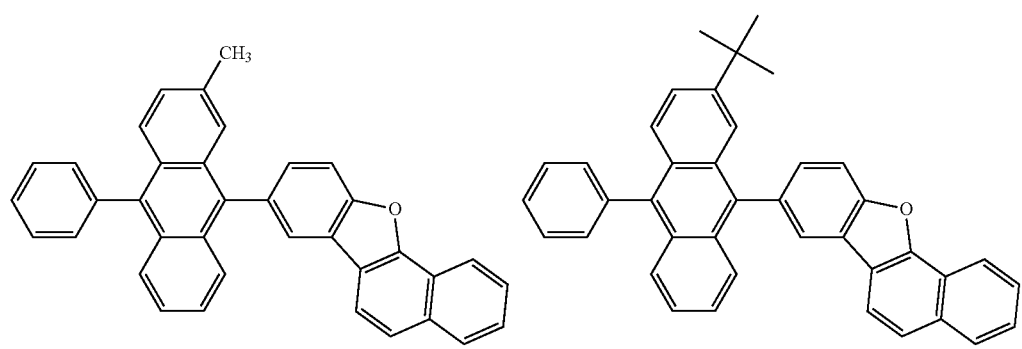
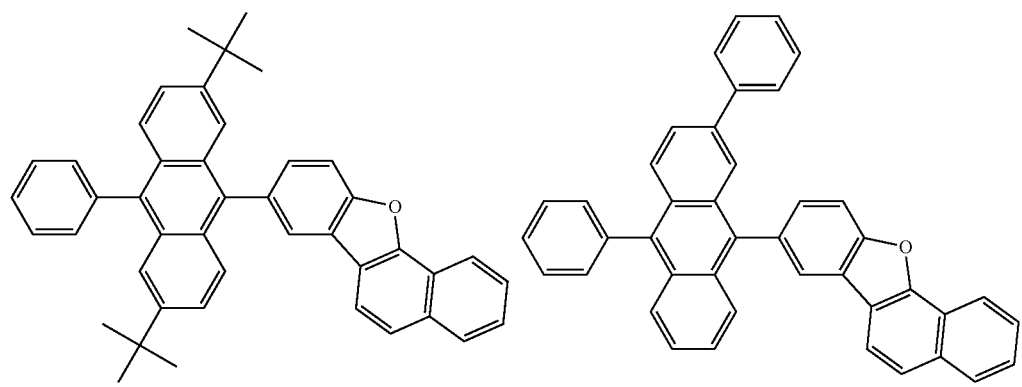

-continued
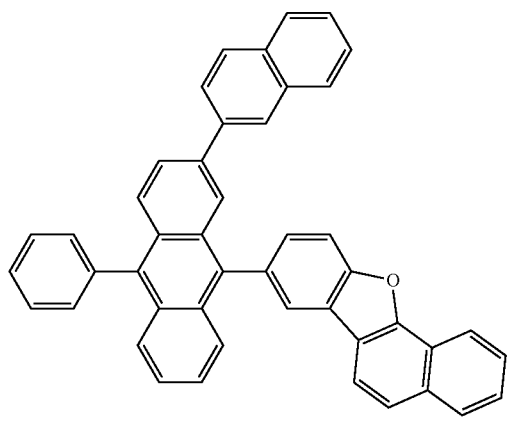
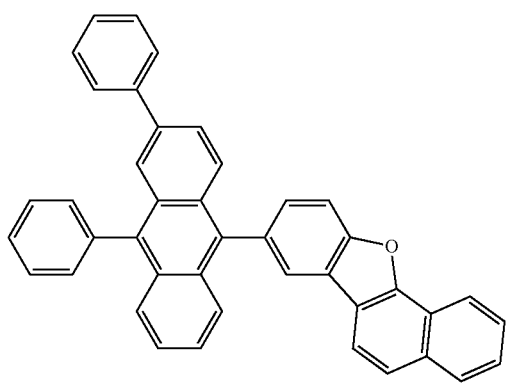
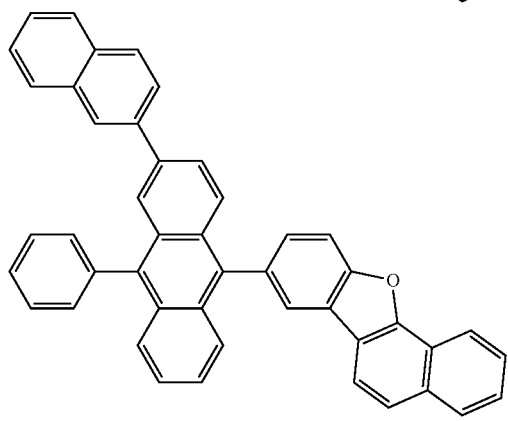
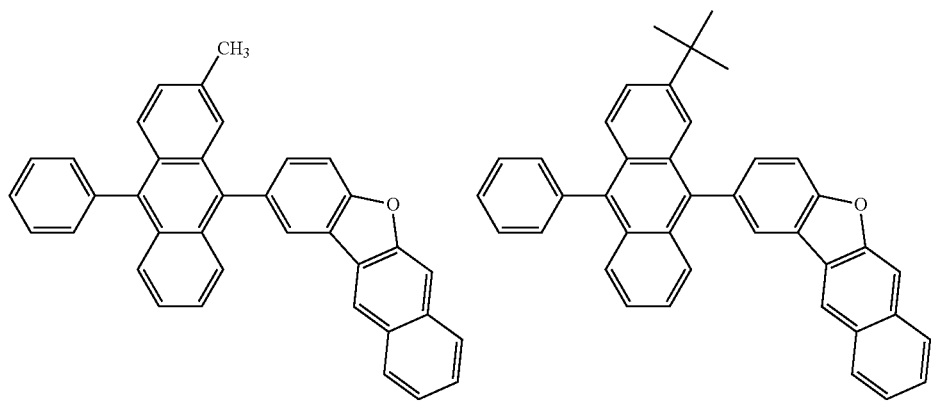
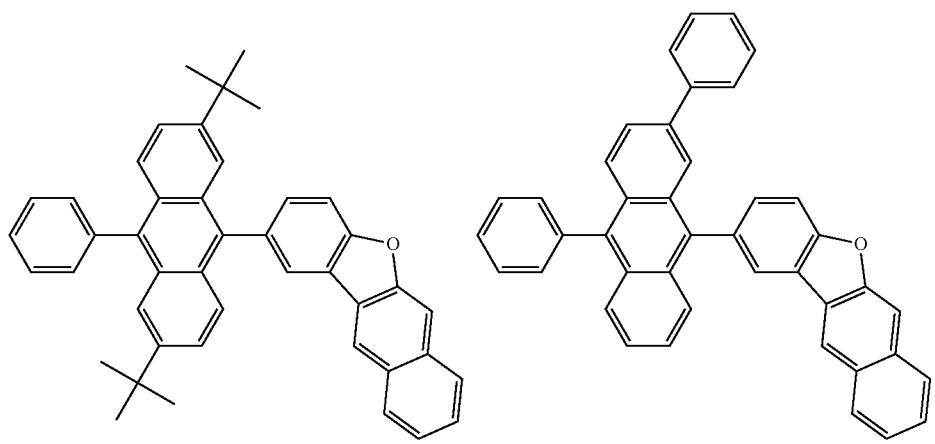

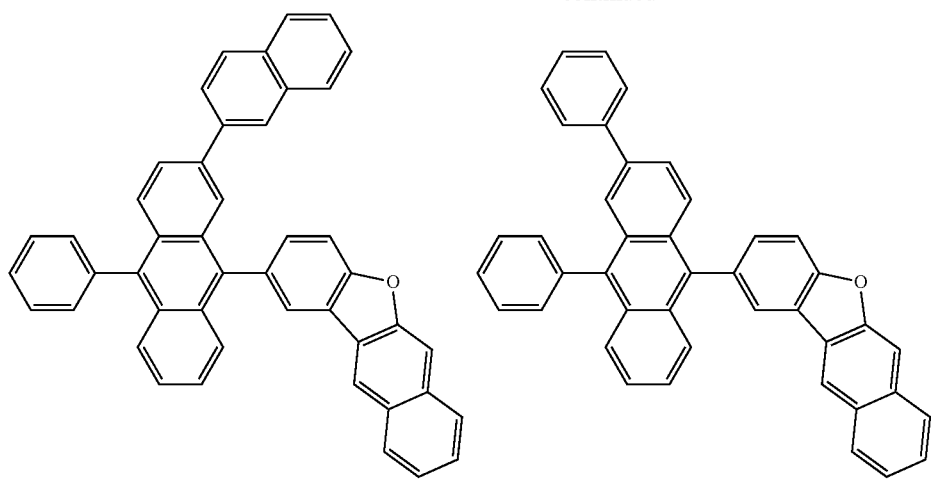
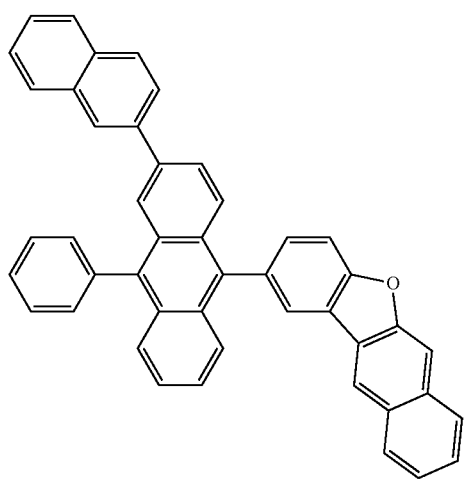
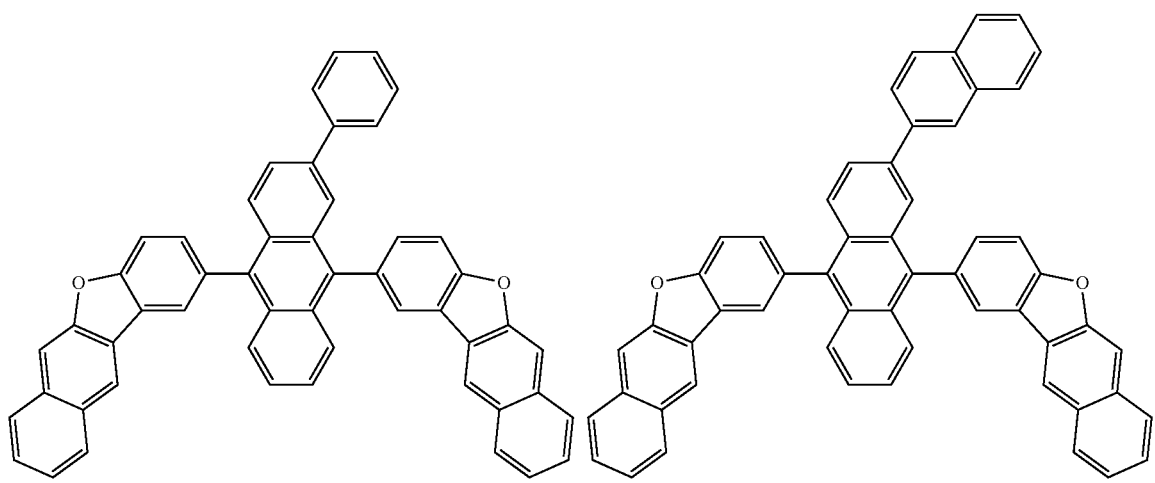

-continued
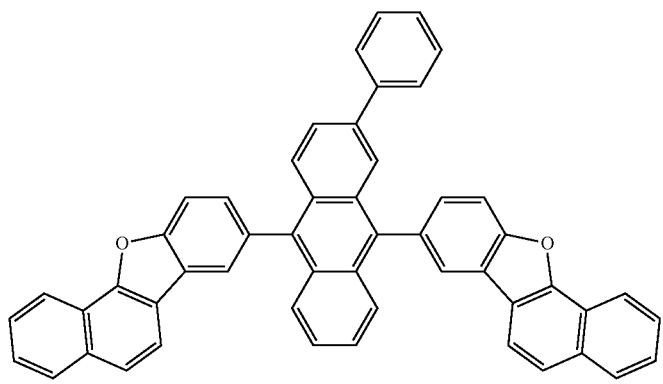
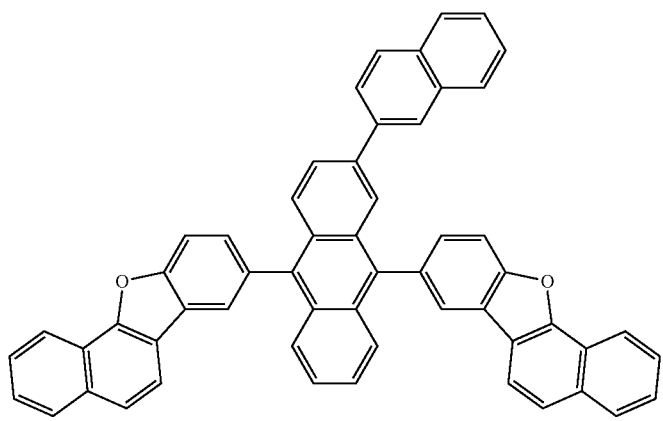
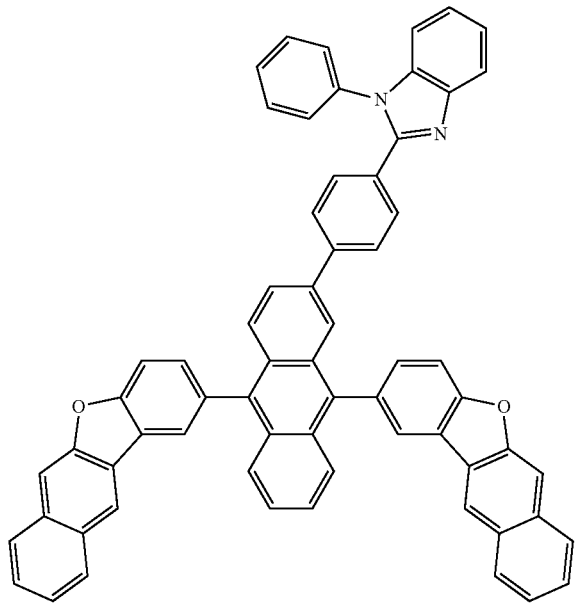

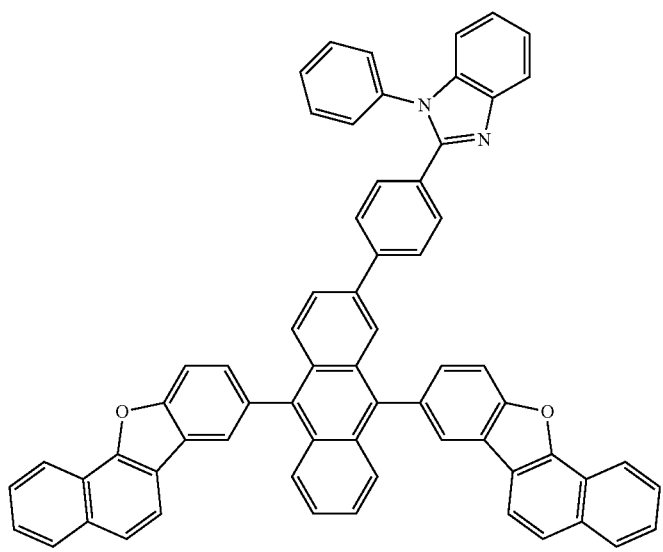
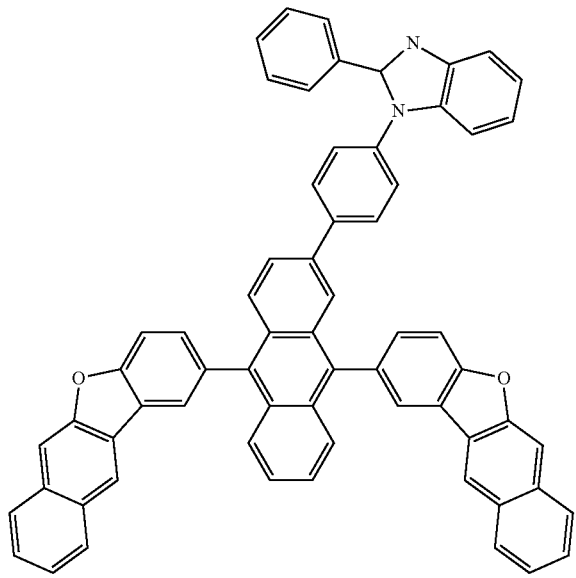
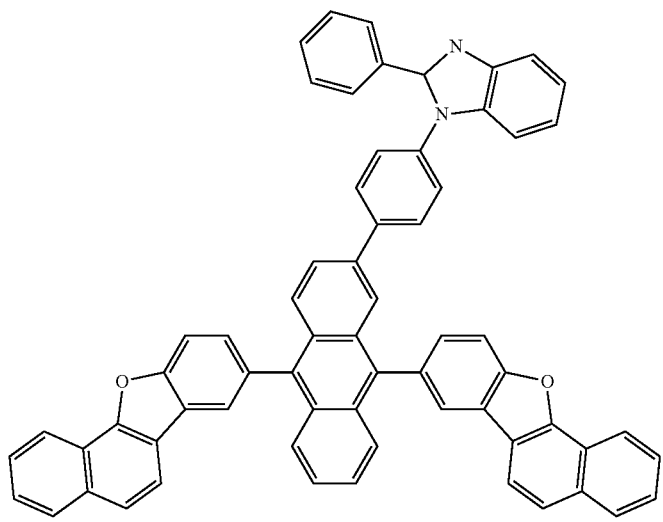

-continued
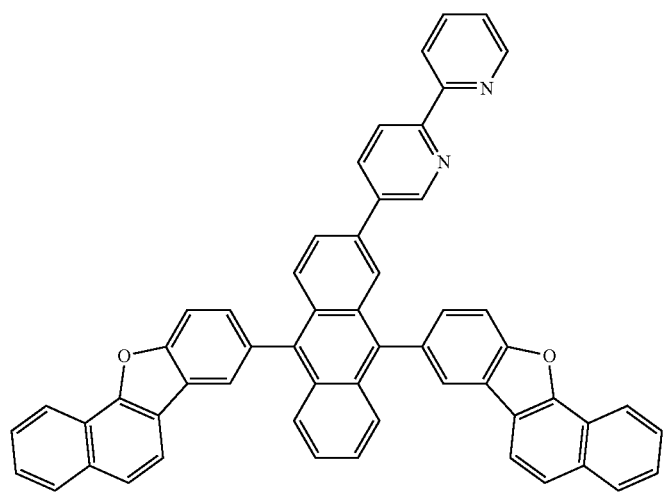
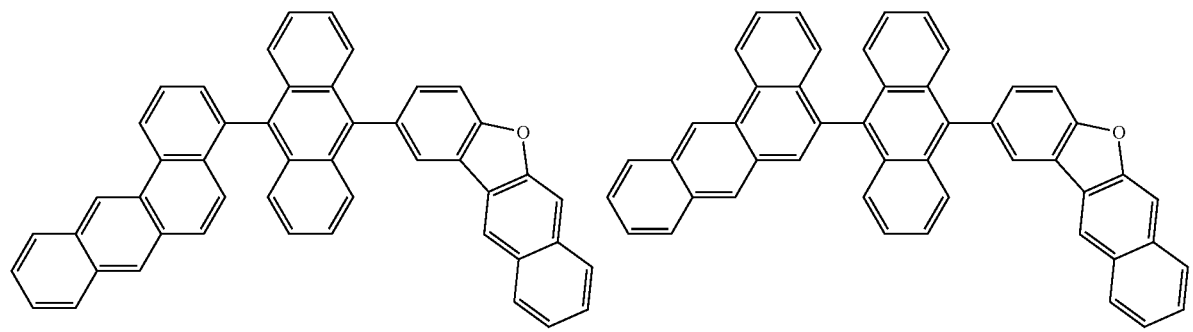
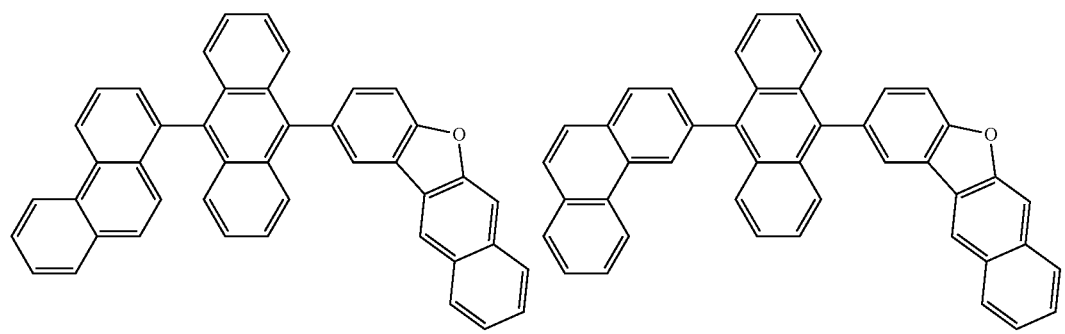
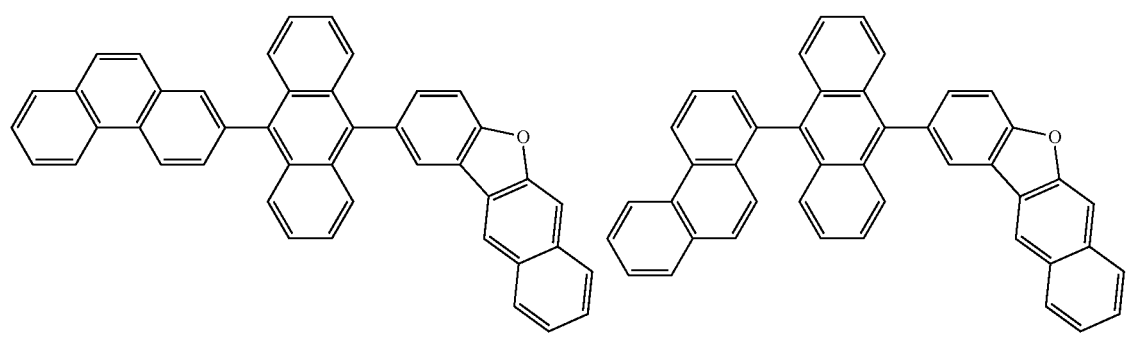

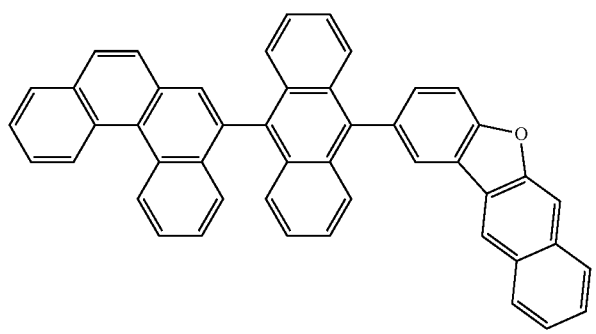
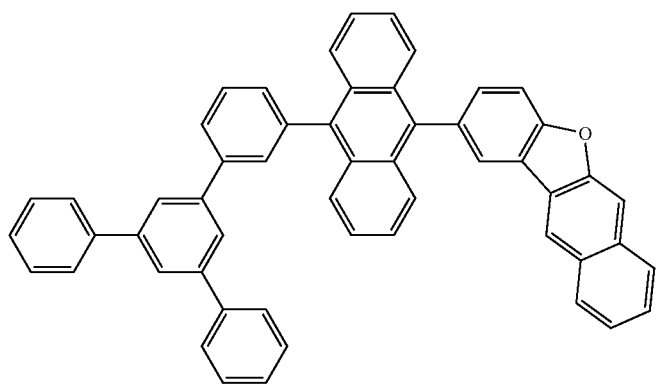
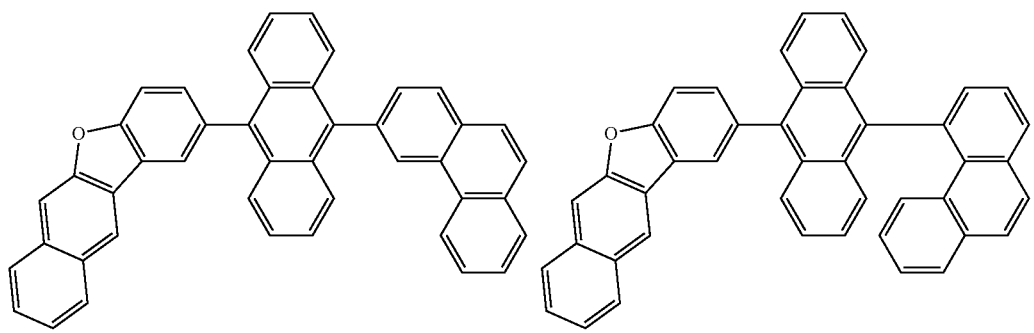
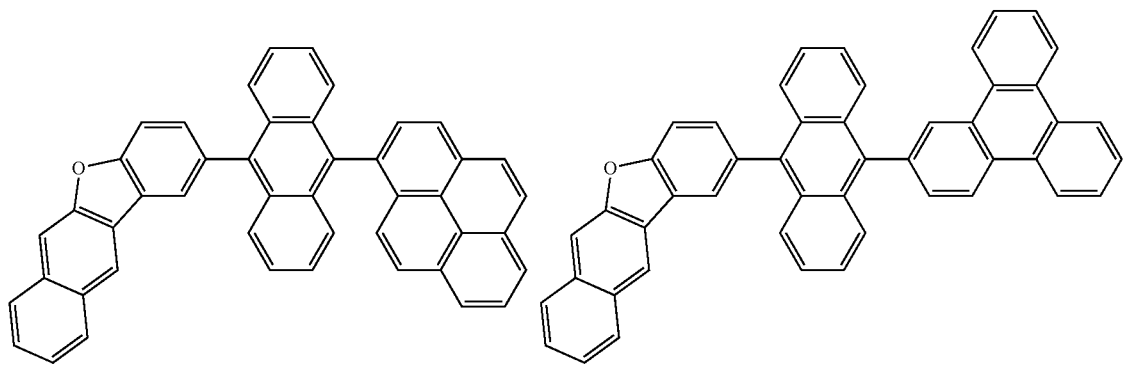

-continued
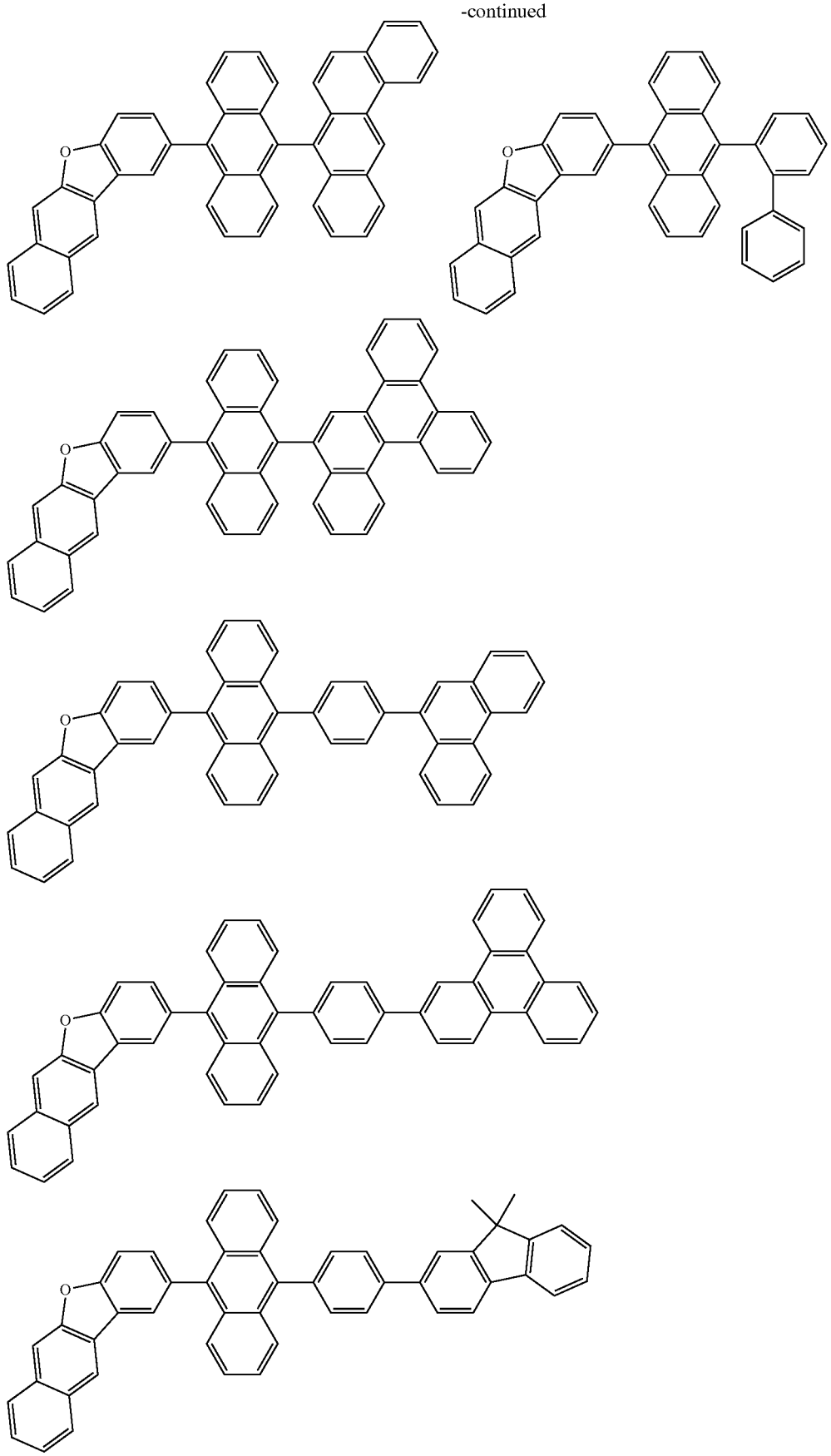

-continued
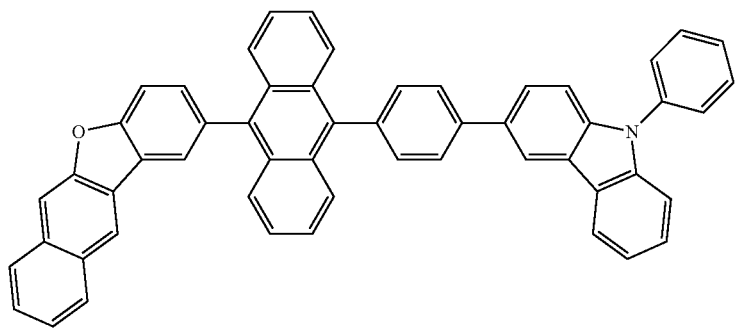
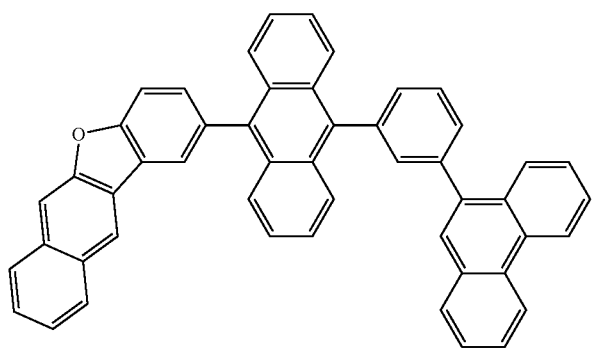
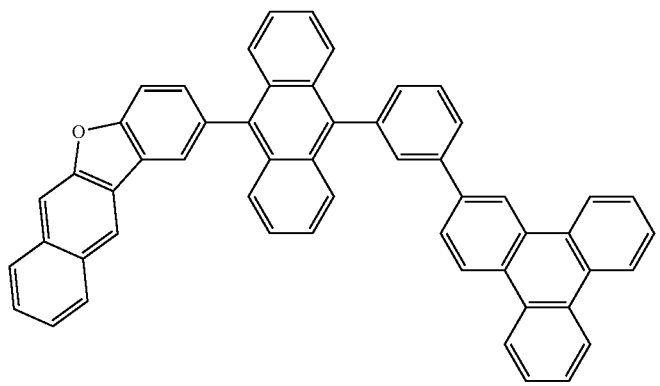
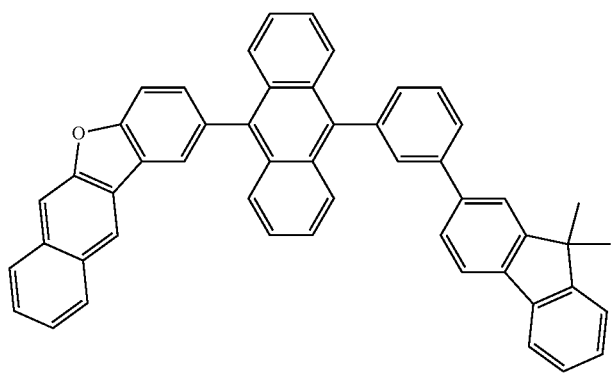

-continued
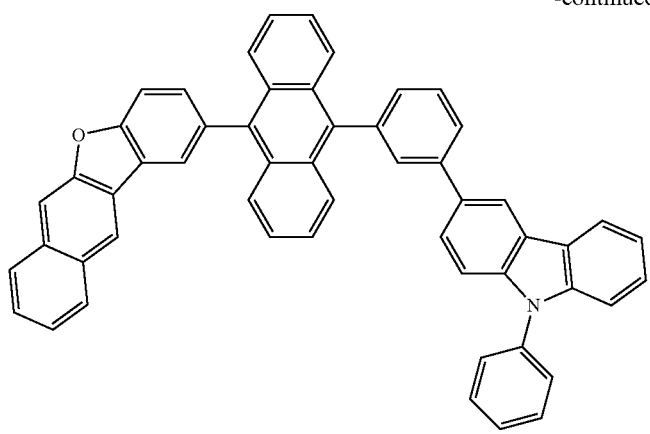

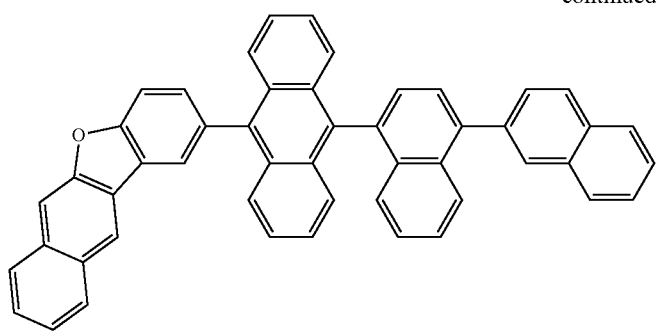
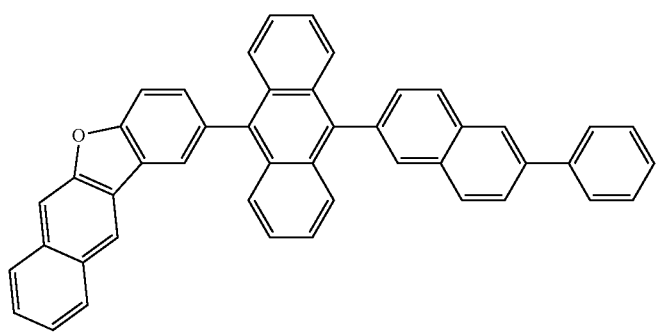
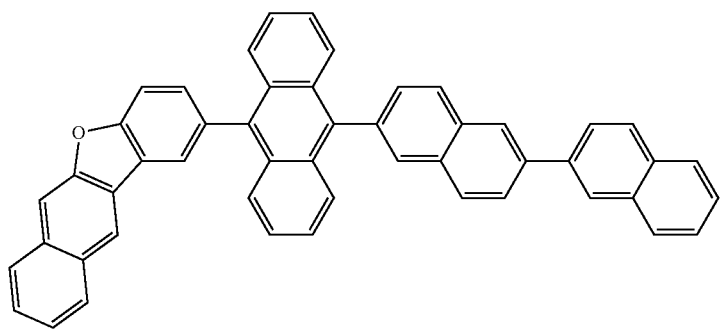
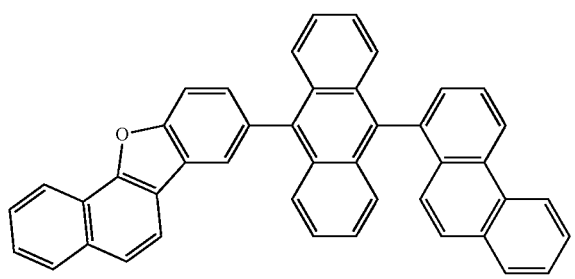
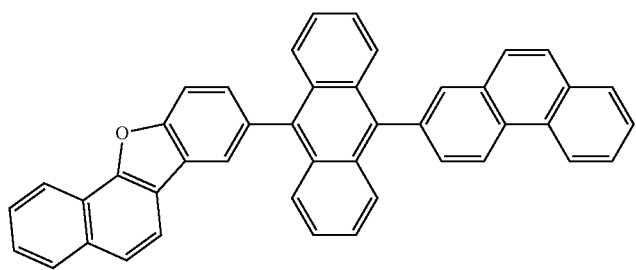

-continued
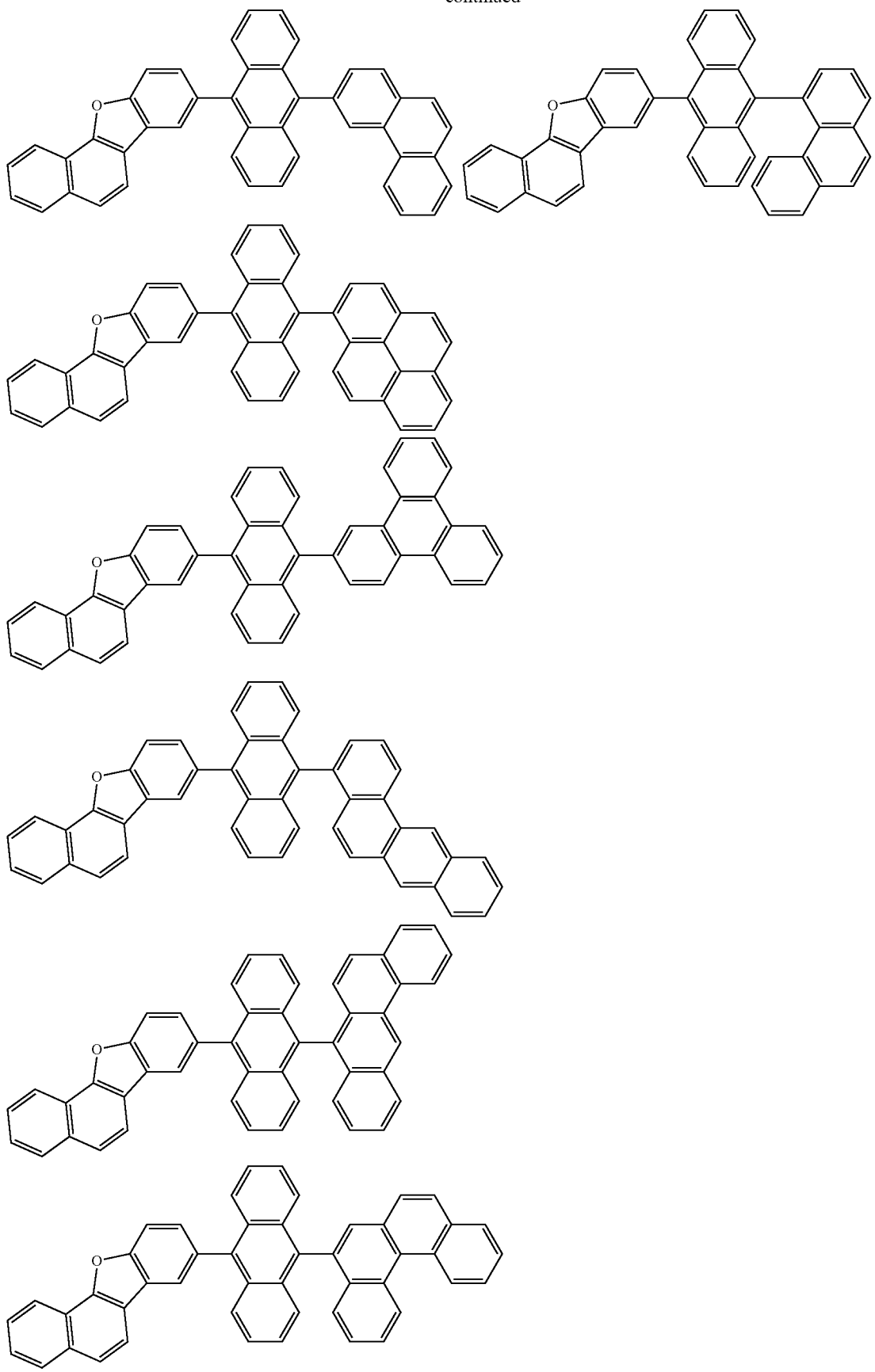

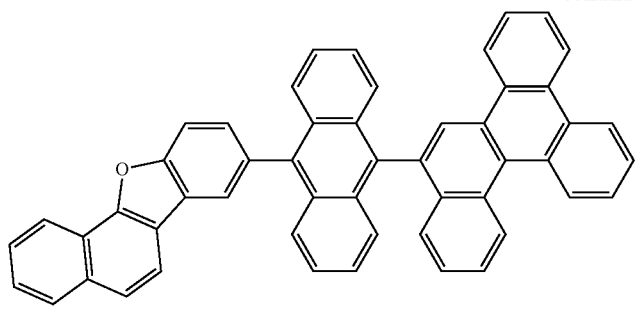
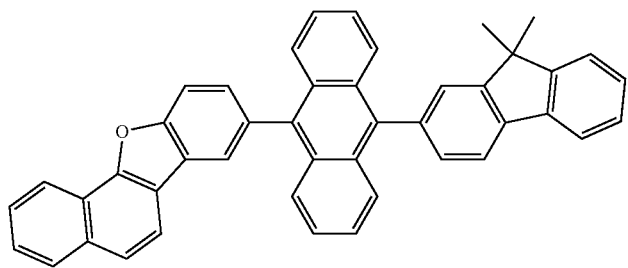
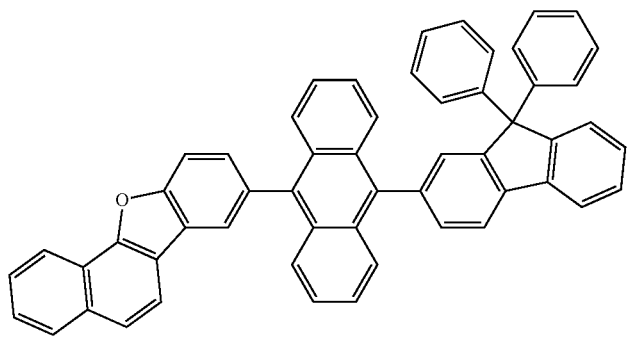 [SMILES: c1ccc(C2(c3ccccc3)c3ccccc3-c3ccc(-c4c5ccccc5c(-c5ccc6oc7c8ccccc8ccc7c6c5)c5ccccc45)cc32)cc1]
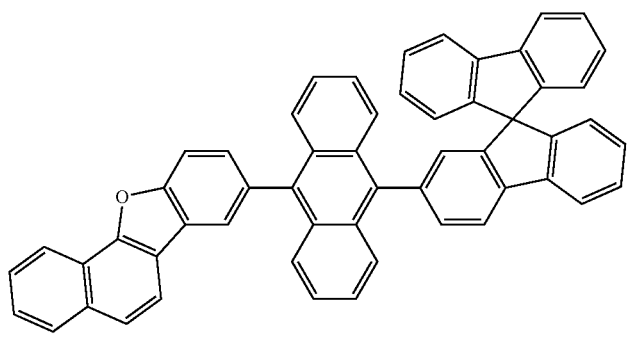
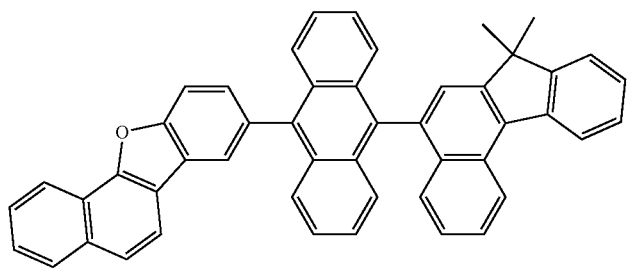

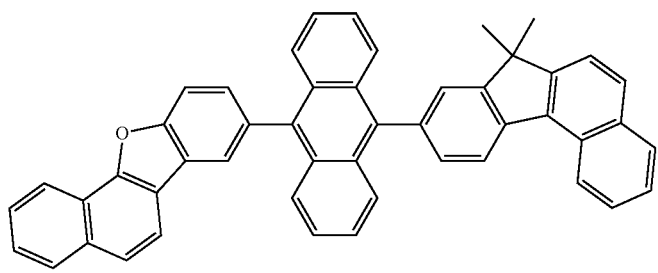
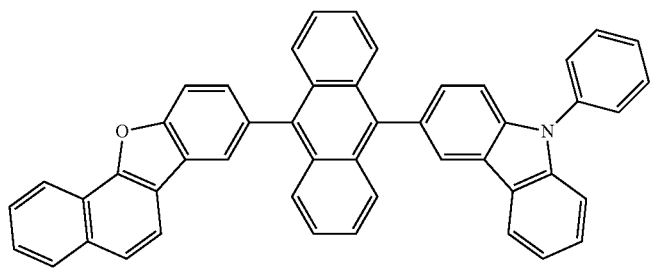
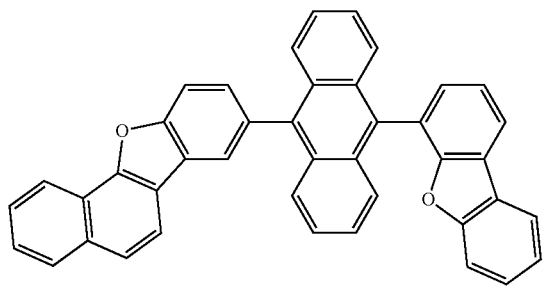
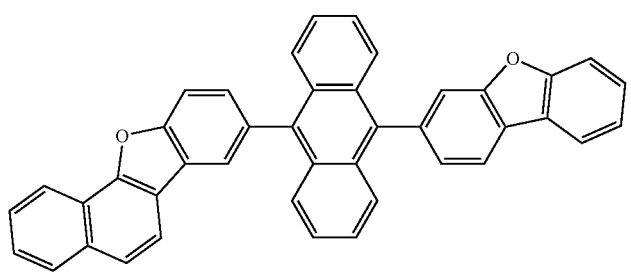
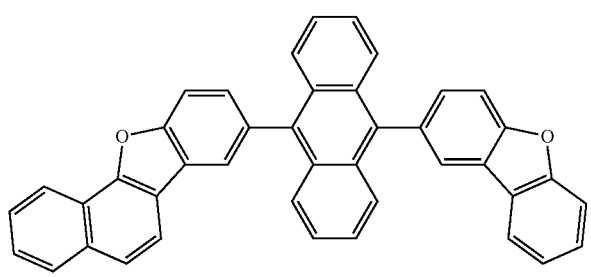
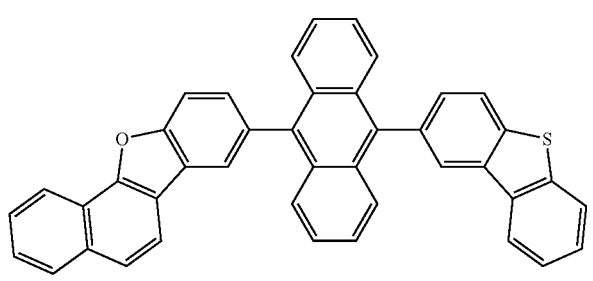

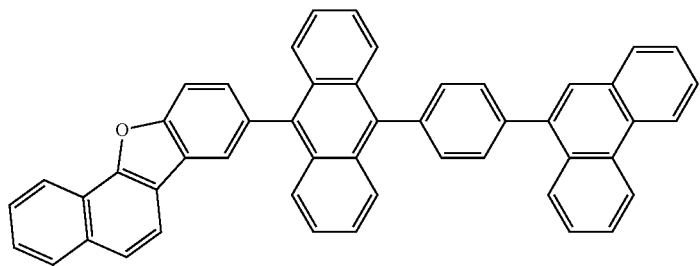
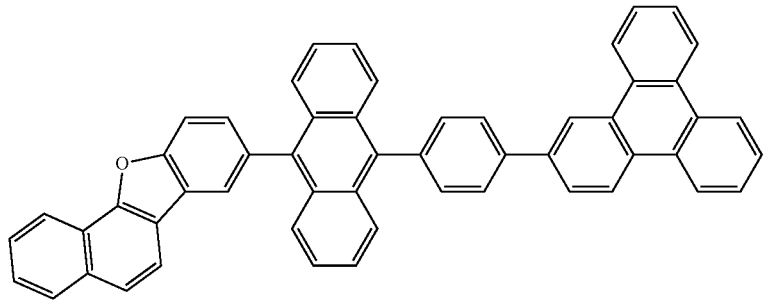
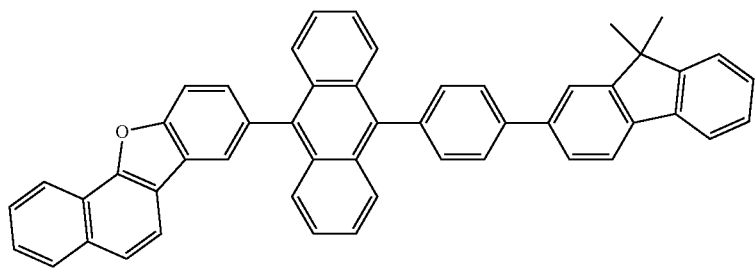
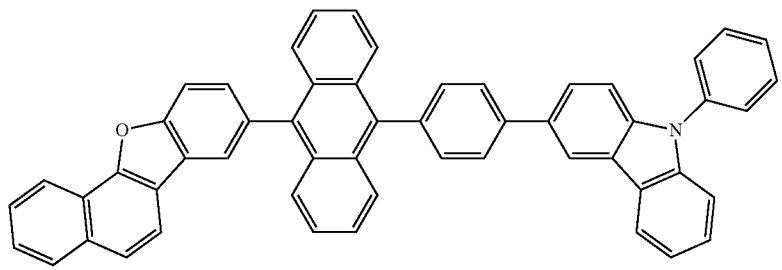
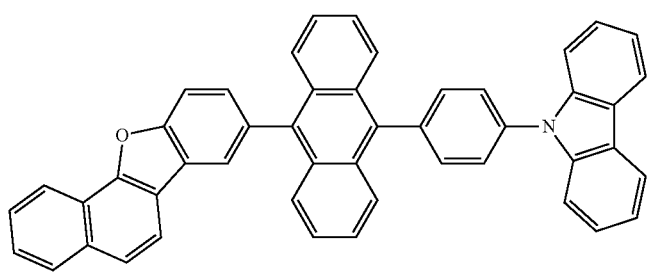
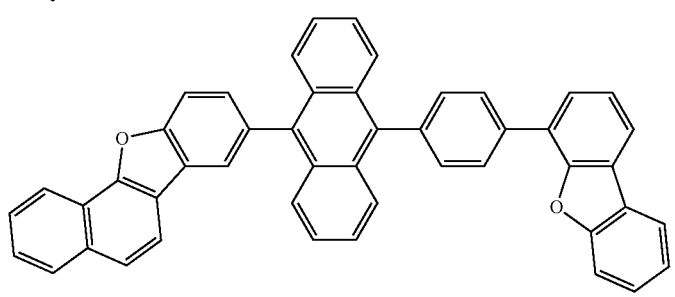

-continued
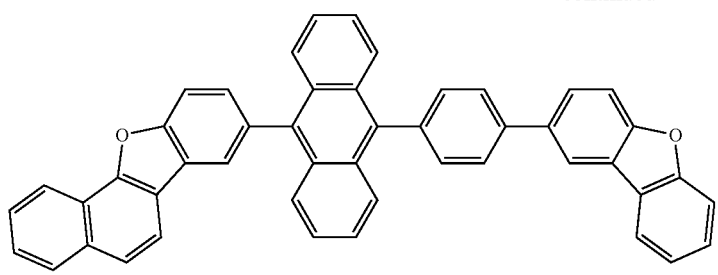
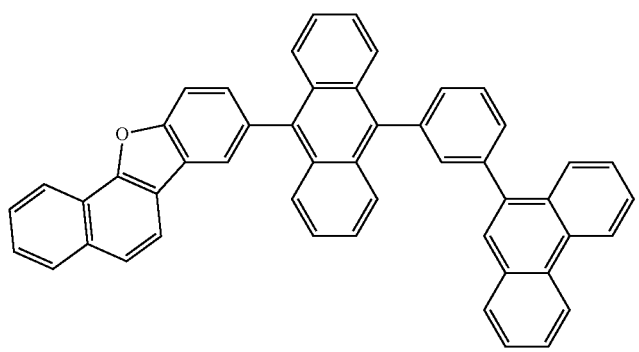
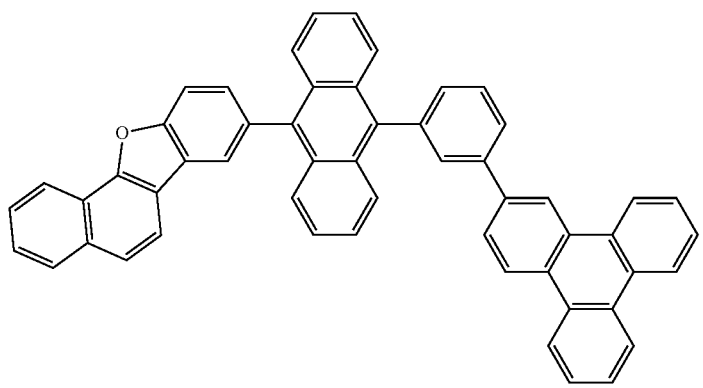
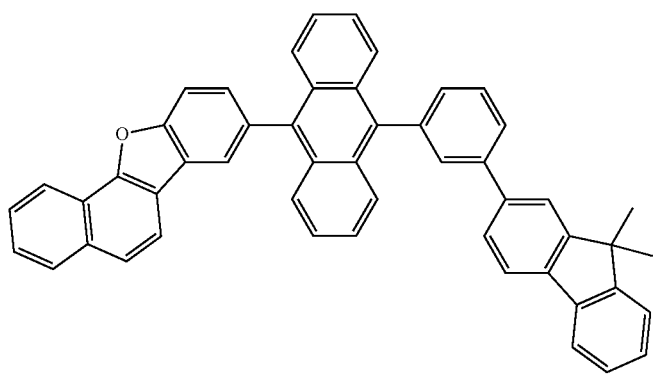

-continued
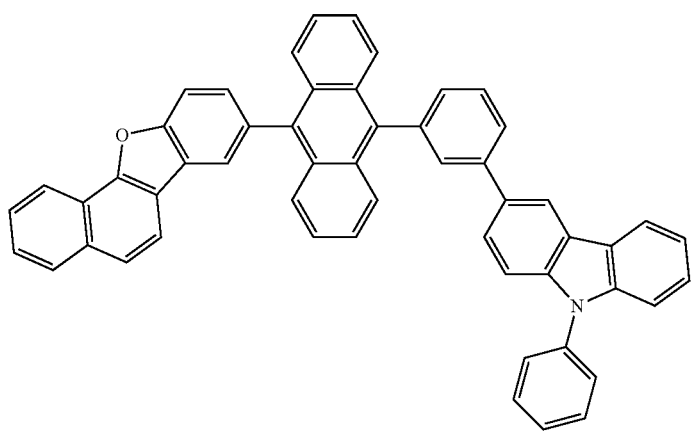
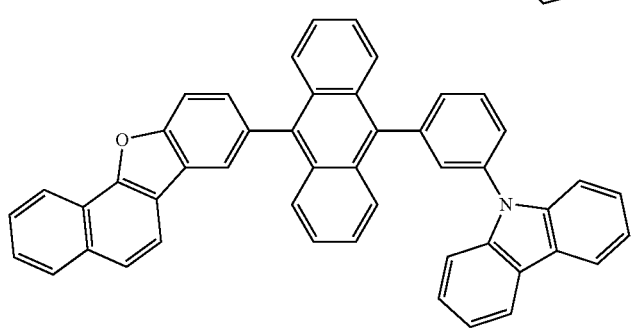
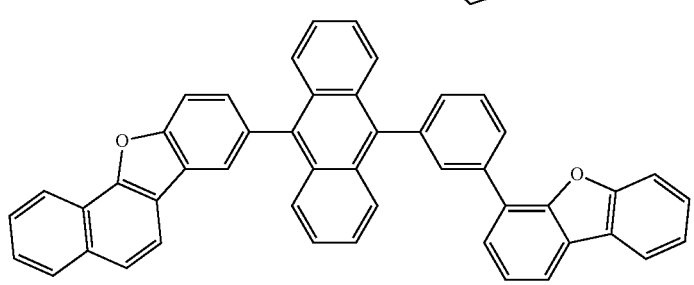
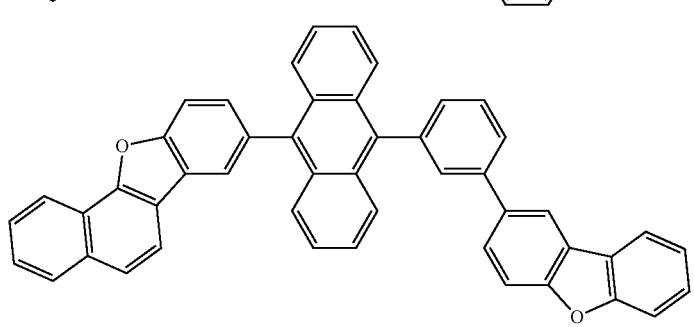
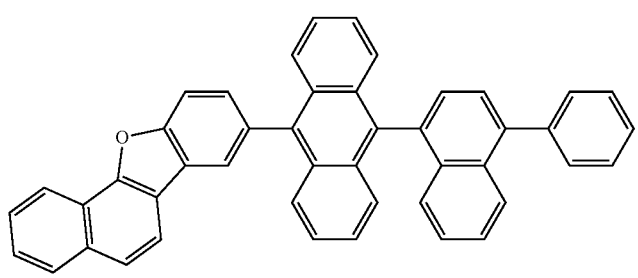

-continued
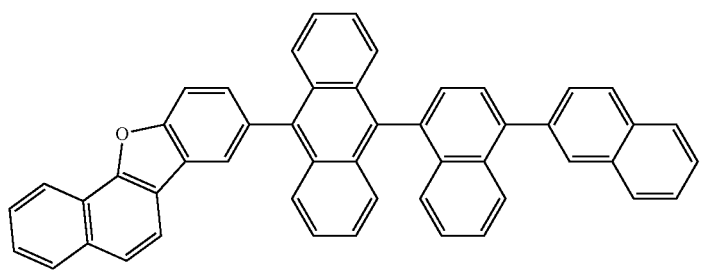
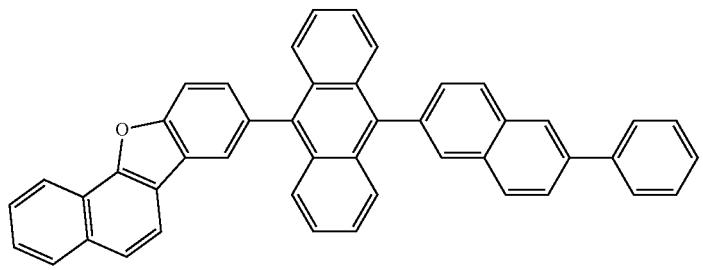
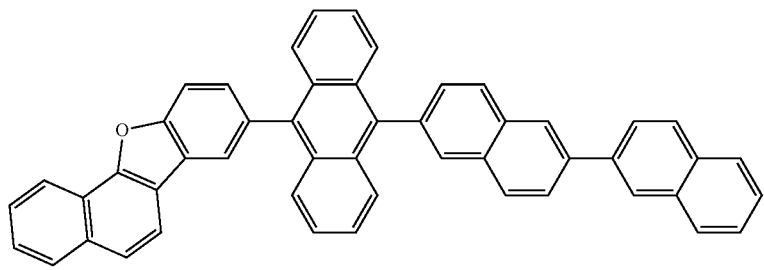
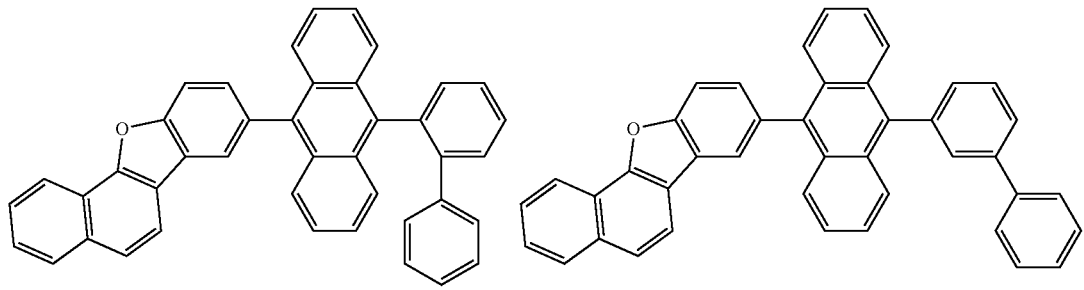
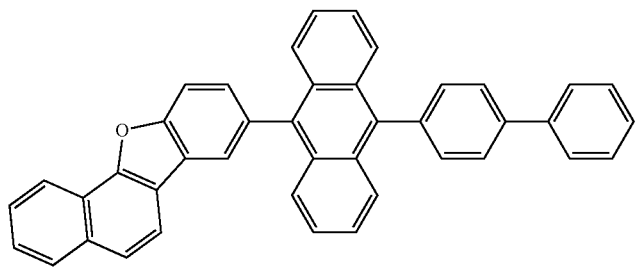
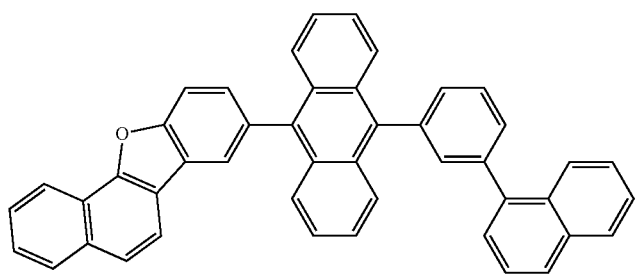

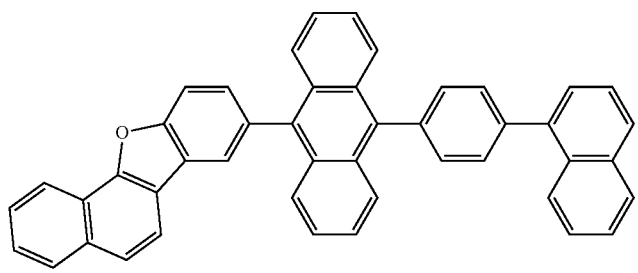
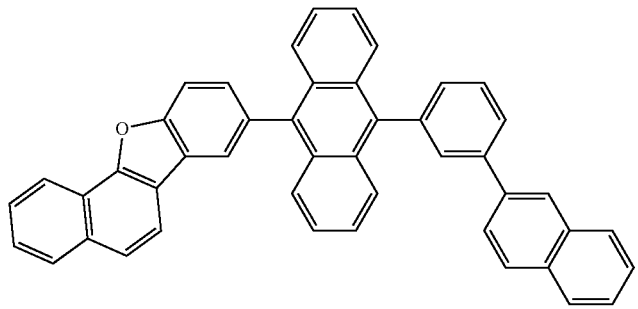
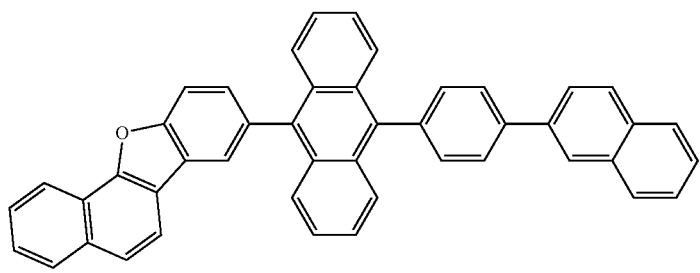
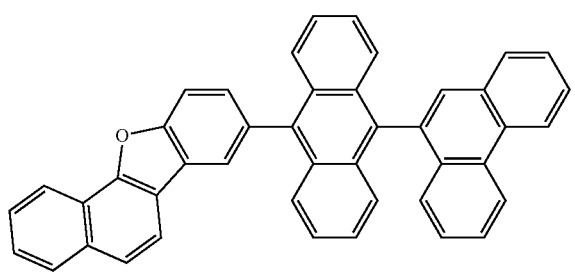
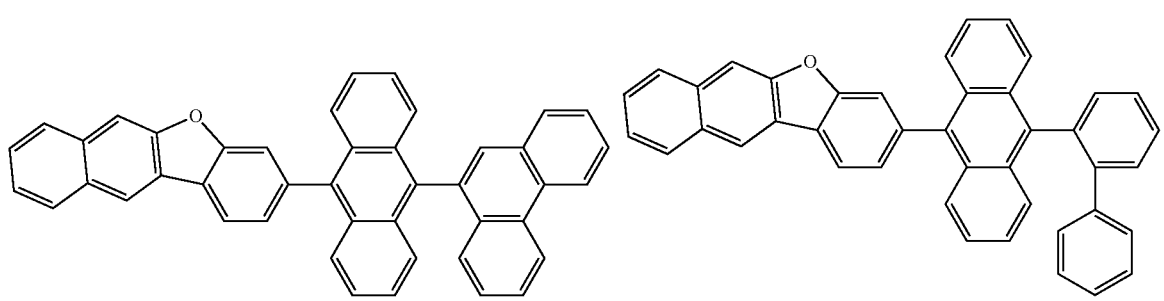
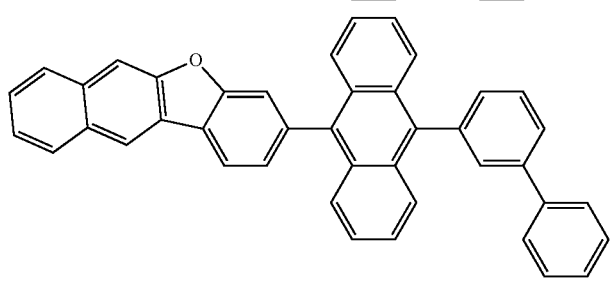

-continued
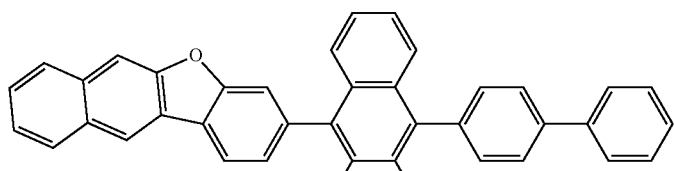
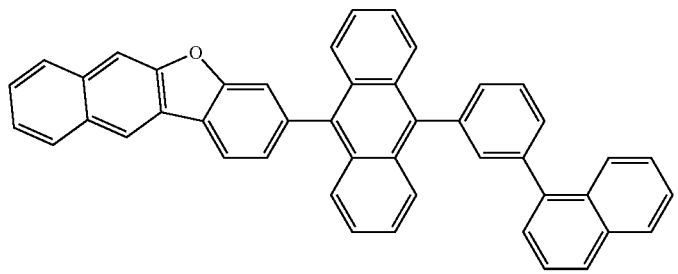
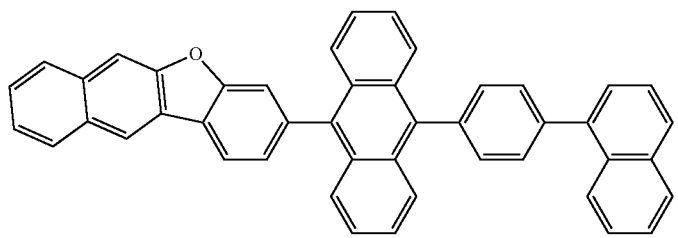
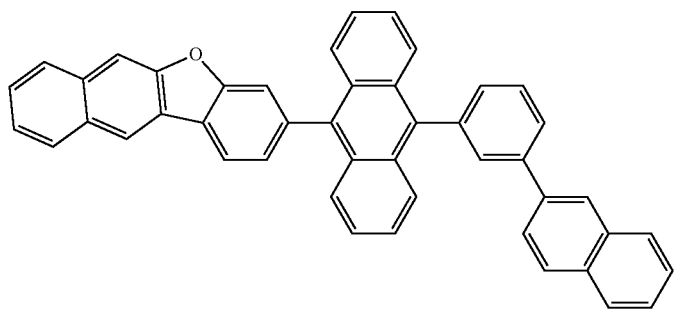
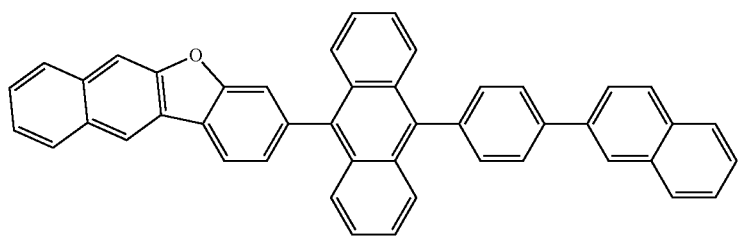
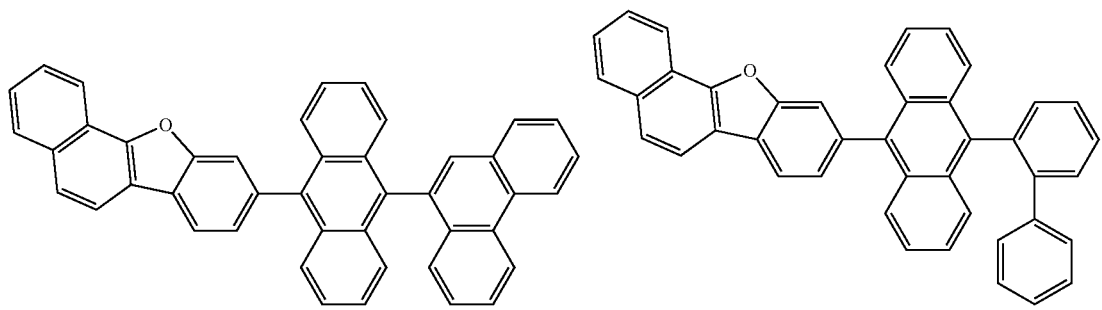

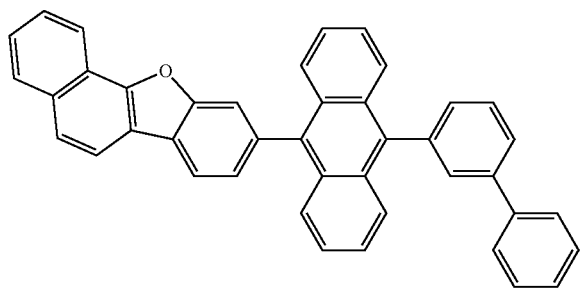
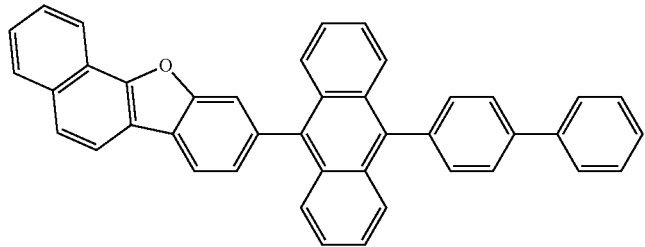
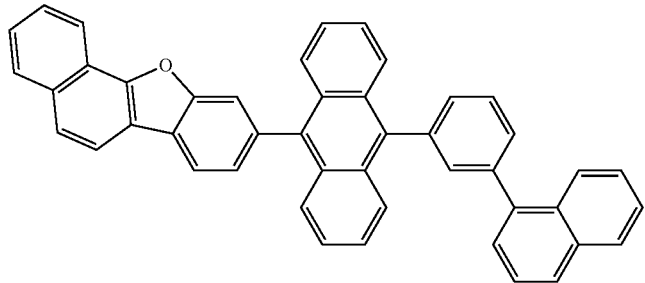
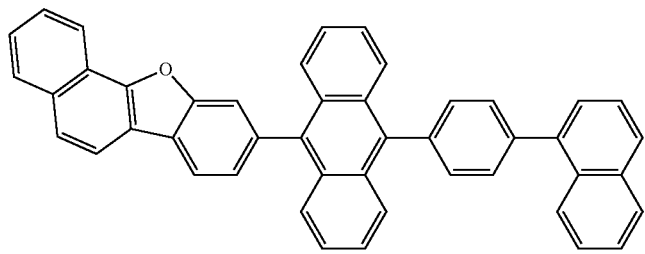
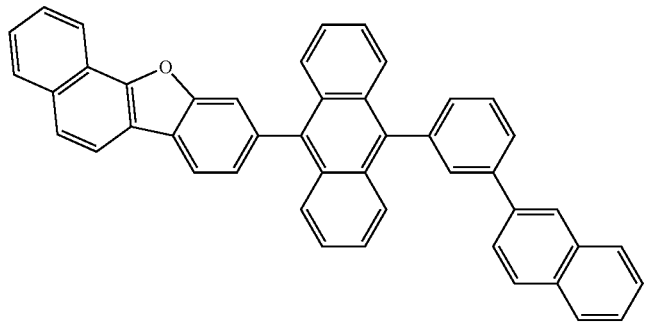
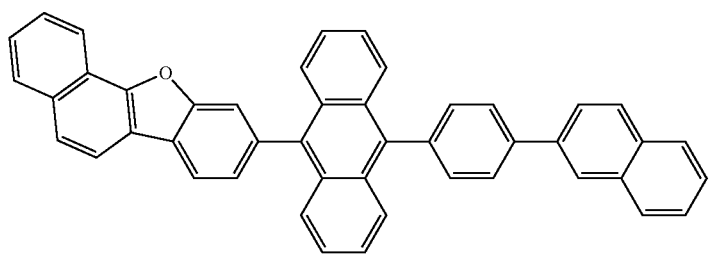

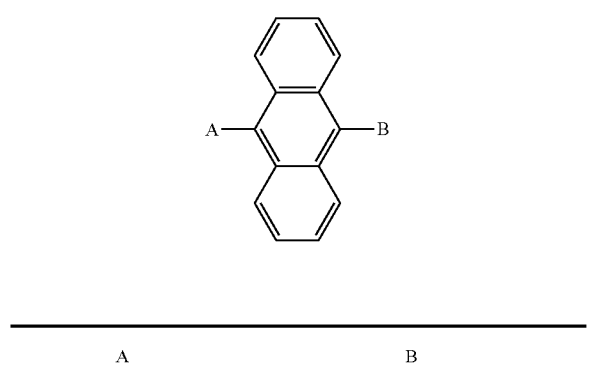
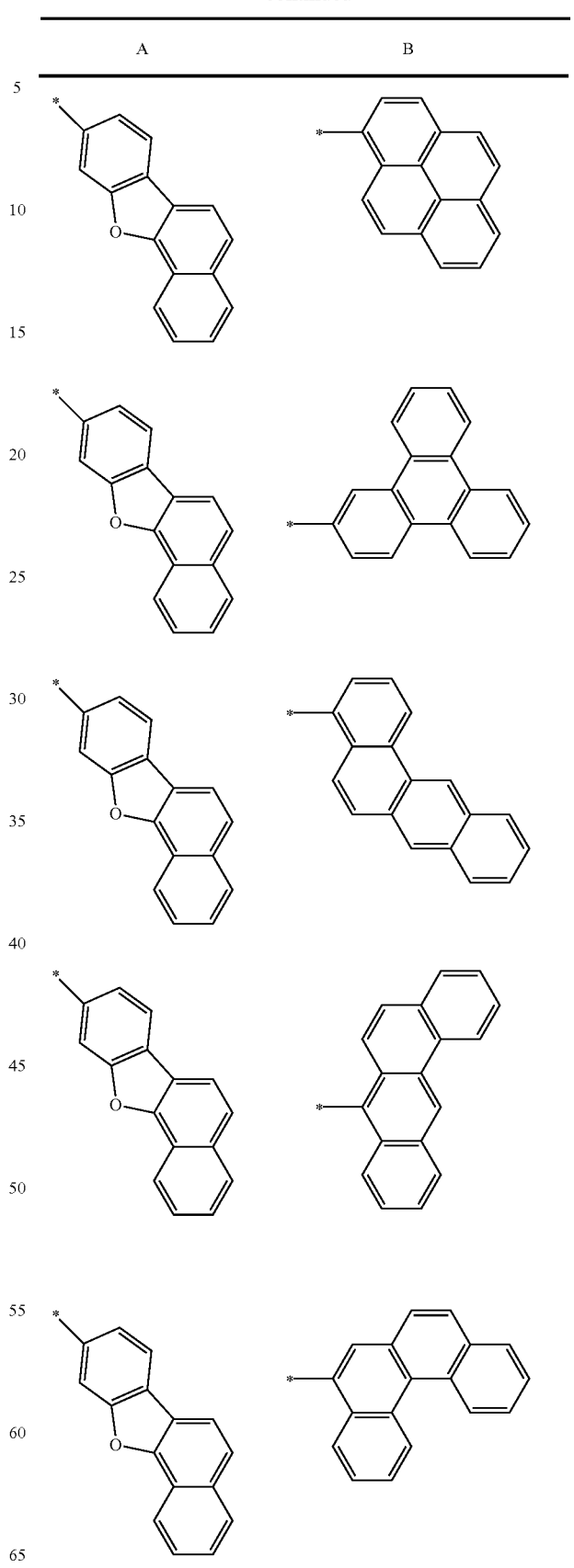

| A | B | A | B |
|---|---|---|---|
| 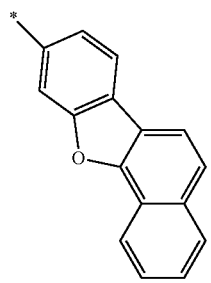 [SMILES: *c1ccc2c(c1)oc1c3ccccc3ccc21] | 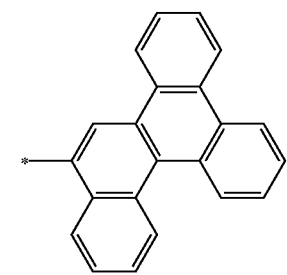 | 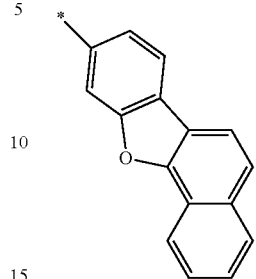 | 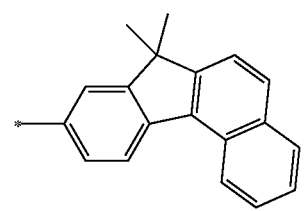 |
| 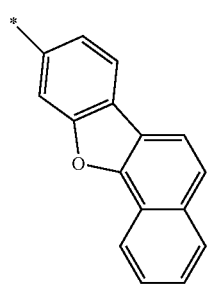 [SMILES: *c1ccc2c(c1)oc1c3ccccc3ccc21] | 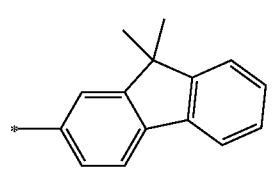 | 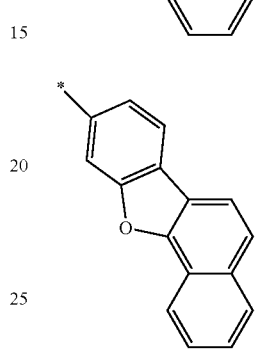 | 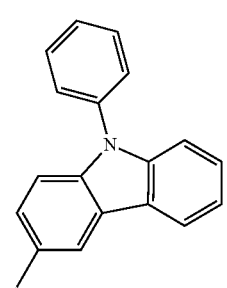 |
| 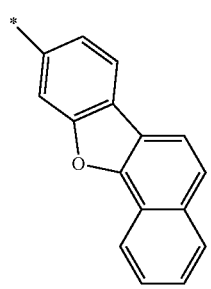 [SMILES: *c1ccc2c(c1)oc1c3ccccc3ccc21] | 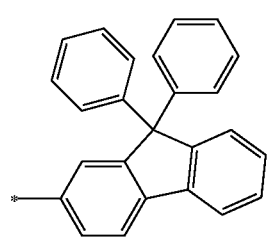 | 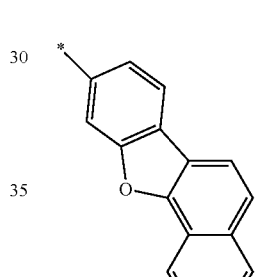 | 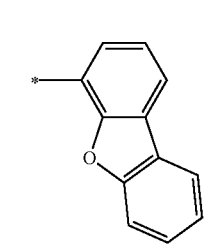 |
| 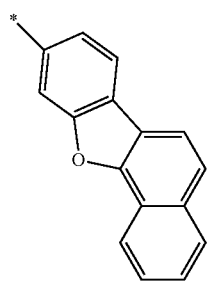 [SMILES: *c1ccc2c(c1)oc1c3ccccc3ccc21] | 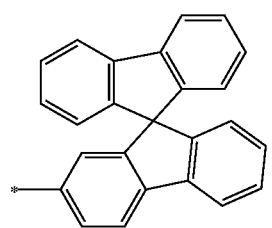 | 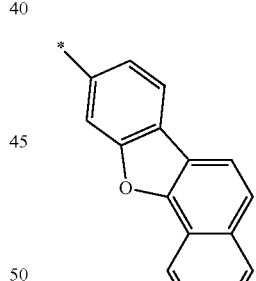 | 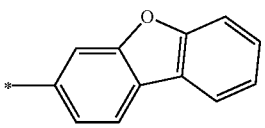 |
| 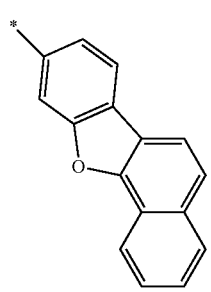 [SMILES: *c1ccc2c(c1)oc1c3ccccc3ccc21] | 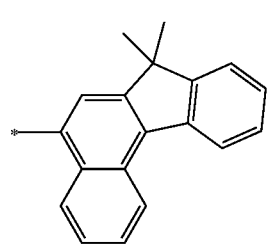 | 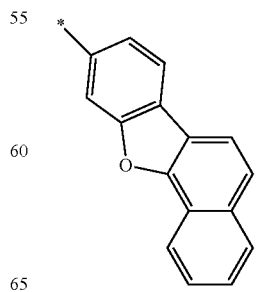 | 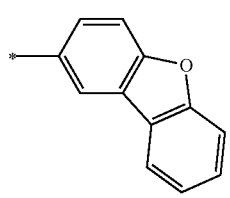 |

| 101 -continued | | 102 -continued | |
|---|---|---|---|
| A | B | A | B |
| 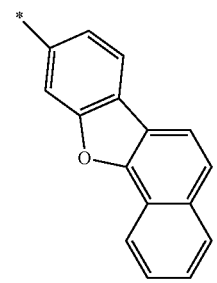 [SMILES: *c1ccc2c(c1)oc1c3ccccc3ccc21] | 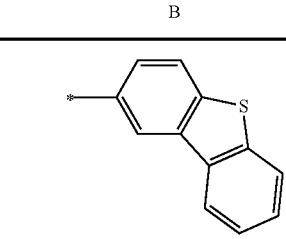 | 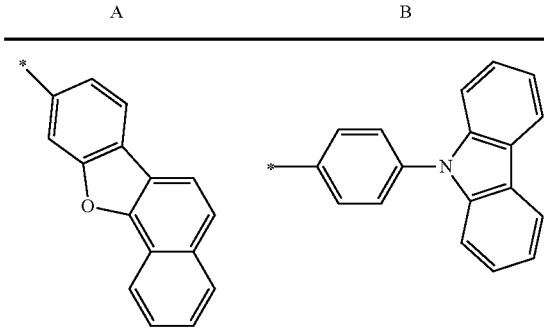 | 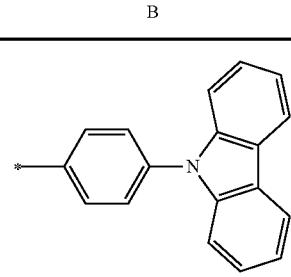 |
| 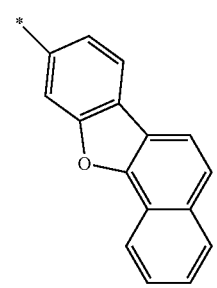 [SMILES: *c1ccc2c(c1)oc1c3ccccc3ccc21] | 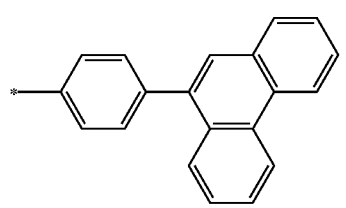 | 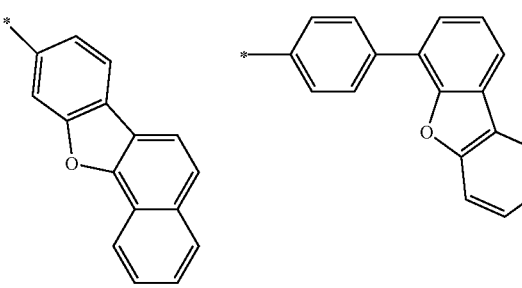 | 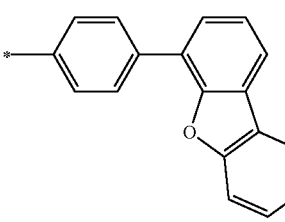 |
| 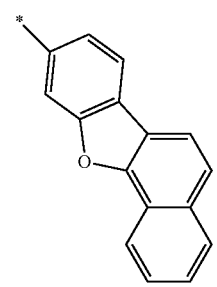 [SMILES: *c1ccc2c(c1)oc1c3ccccc3ccc21] | 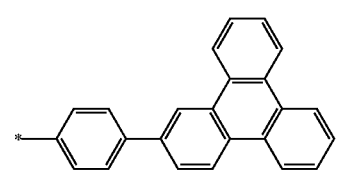 | 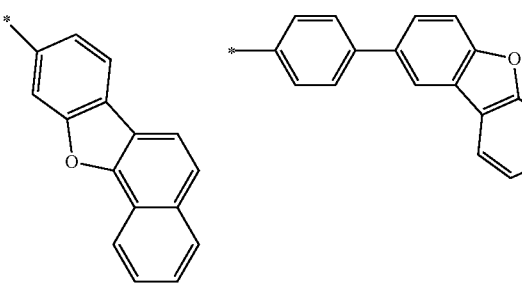 | 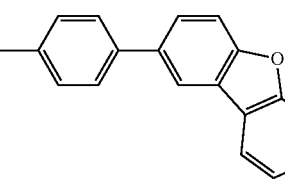 |
| 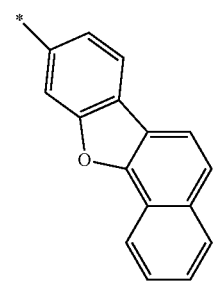 [SMILES: *c1ccc2c(c1)oc1c3ccccc3ccc21] | 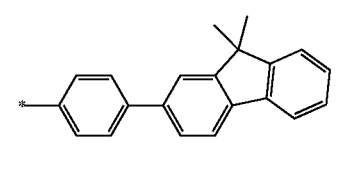 | 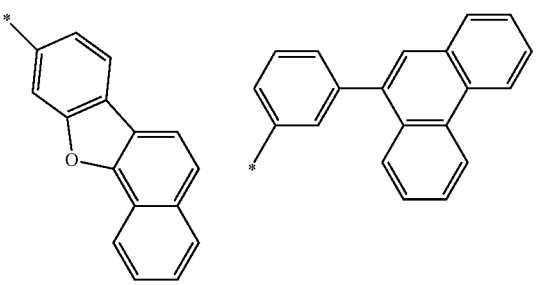 | 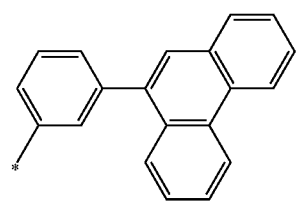 |
| 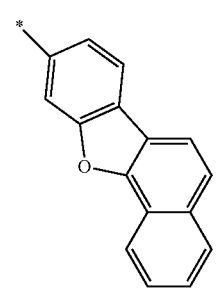 [SMILES: *c1ccc2c(c1)oc1c3ccccc3ccc21] | 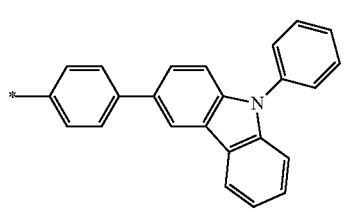 | 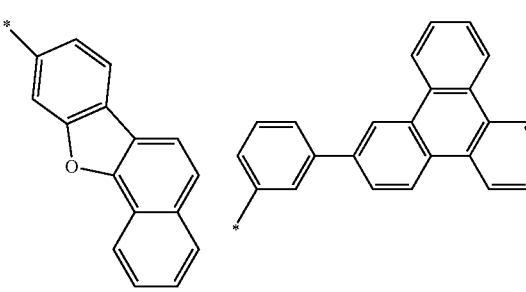 | 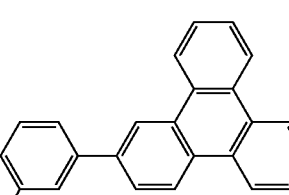 |

103
-continued
| A | B |
|---|---|
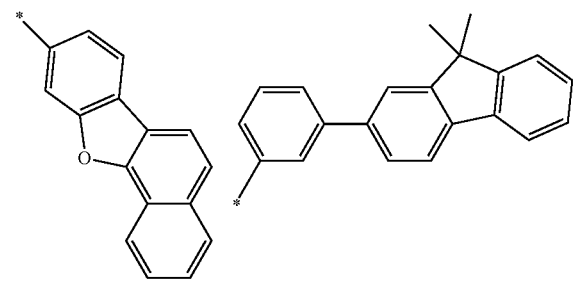
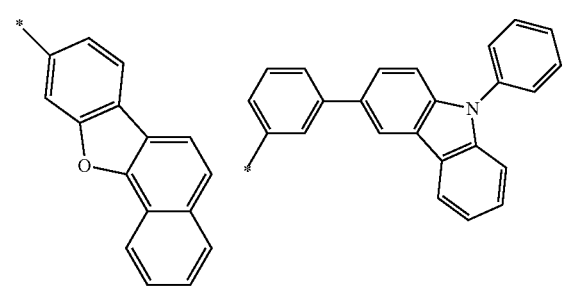
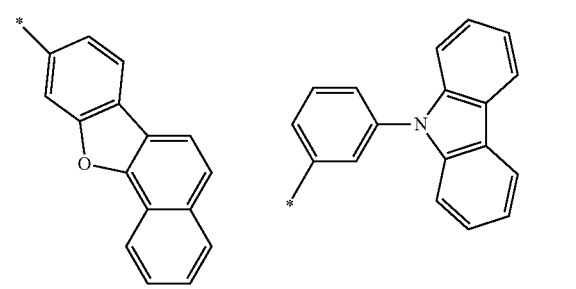
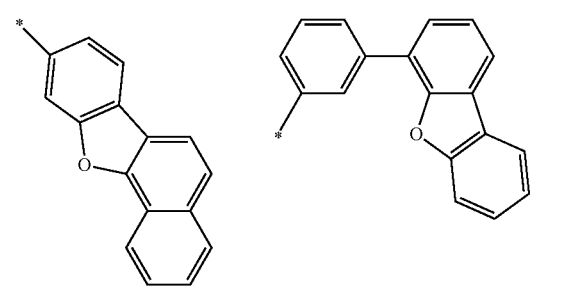
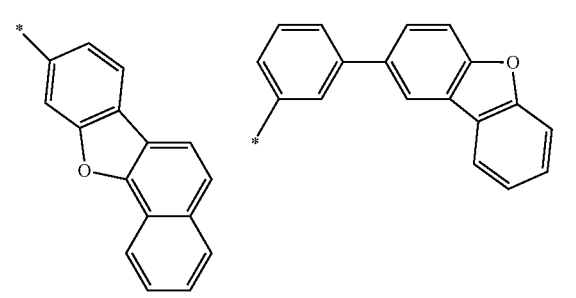
104
-continued
| A | B |
|---|---|
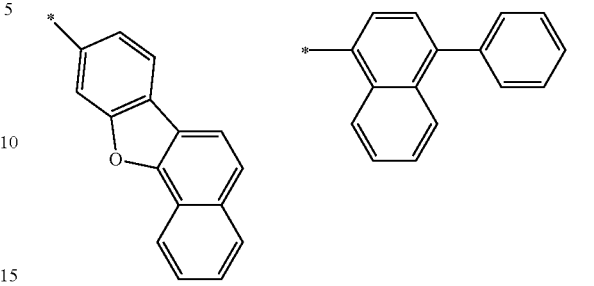
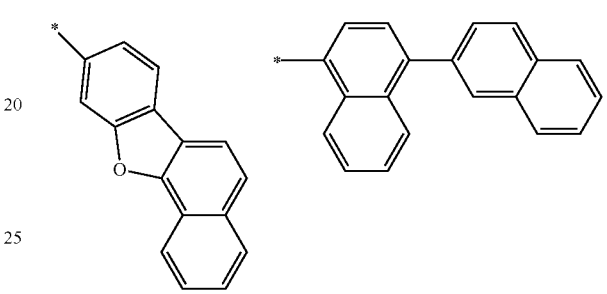
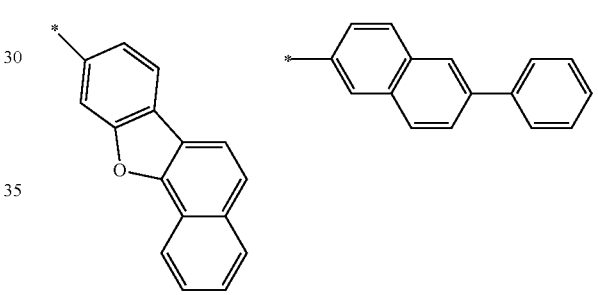
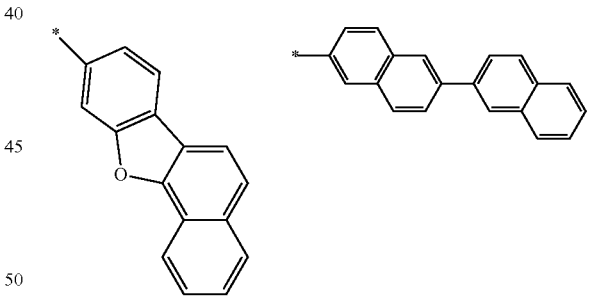
The *s in the table respectively show the bonding position to the anthracene ring.
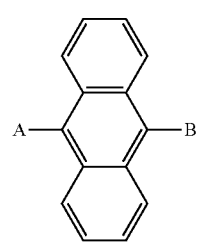

| 105 | | 106 -continued | |
|---|---|---|---|
| A | B | A | B |
| 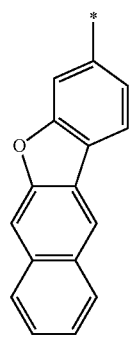 [SMILES: *c1ccc2c(c1)oc1cc3ccccc3cc12] | 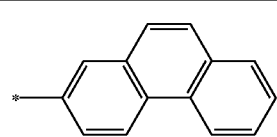 | 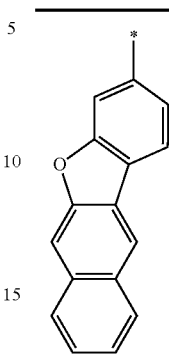 | 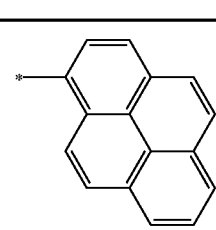 |
| 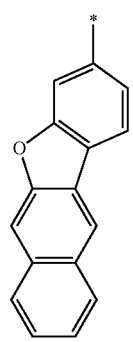 [SMILES: *c1ccc2c(c1)oc1cc3ccccc3cc12] | 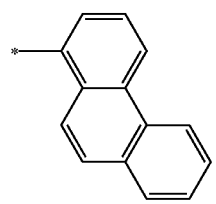 | 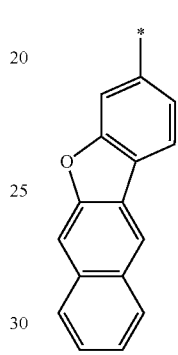 | 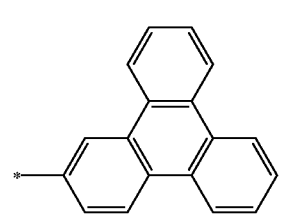 |
| 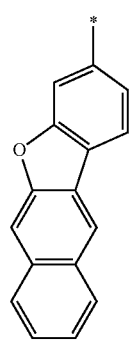 [SMILES: *c1ccc2c(c1)oc1cc3ccccc3cc12] | 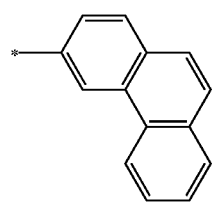 | 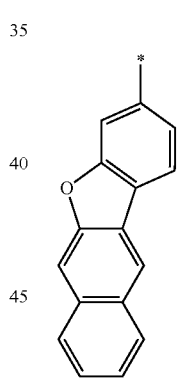 | 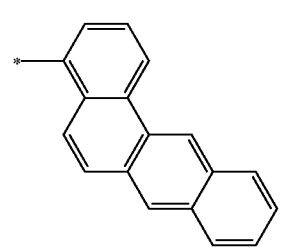 |
| 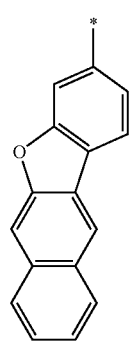 [SMILES: *c1ccc2c(c1)oc1cc3ccccc3cc12] | 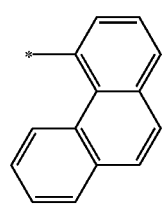 | 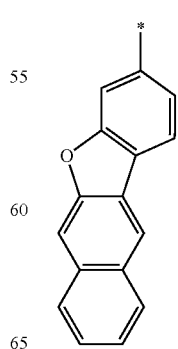 | 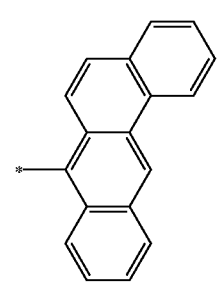 |

| 107 -continued | | 108 -continued | |
|---|---|---|---|
| A | B | A | B |
| 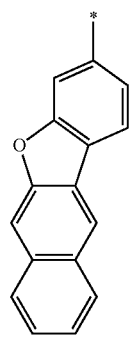 [SMILES: *c1ccc2c(c1)oc1cc3ccccc3cc12] | 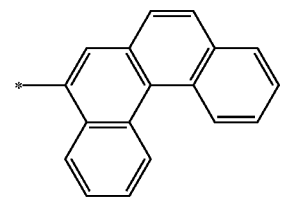 | 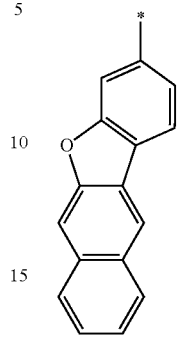 | 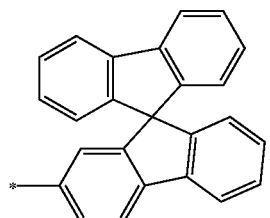 |
| 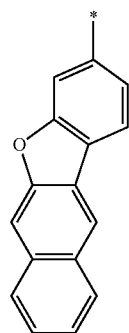 [SMILES: *c1ccc2c(c1)oc1cc3ccccc3cc12] | 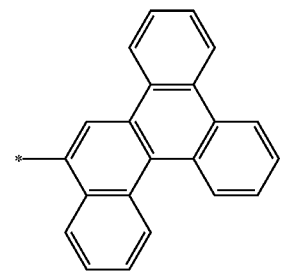 | 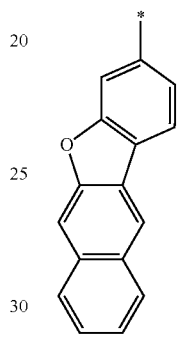 | 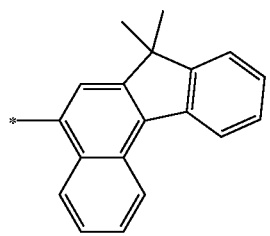 |
| 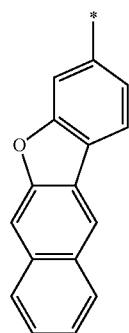 [SMILES: *c1ccc2c(c1)oc1cc3ccccc3cc12] | 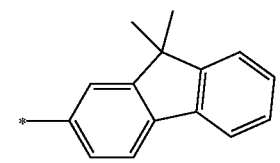 | 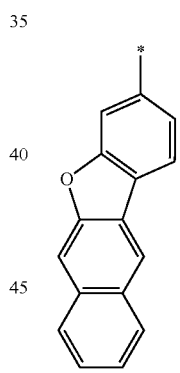 | 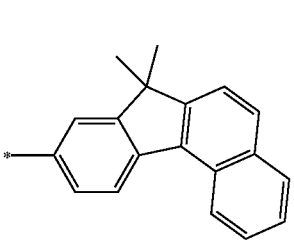 |
| 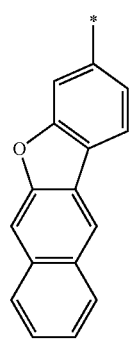 [SMILES: *c1ccc2c(c1)oc1cc3ccccc3cc12] | 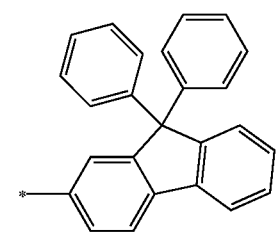 | 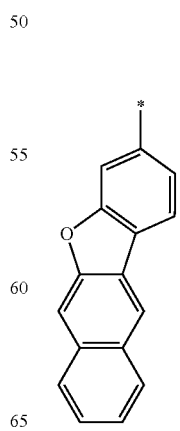 | 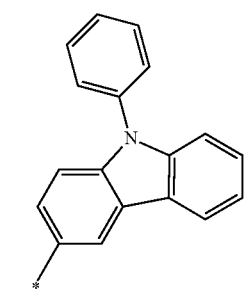 |

| 109 -continued | | | 110 -continued | |
|---|---|---|---|---|
| A | B | | A | B |
| 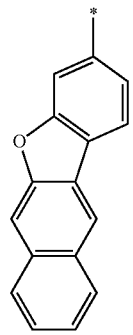 [SMILES: *c1ccc2c(c1)oc1cc3ccccc3cc12] | 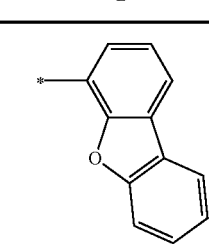 | | 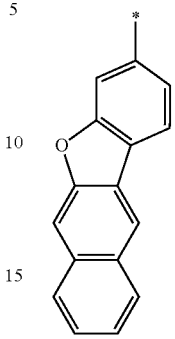 | 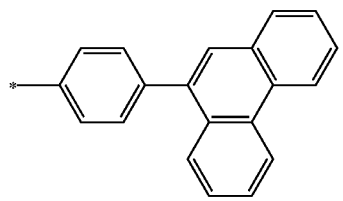 |
| 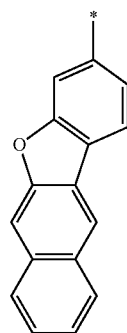 | 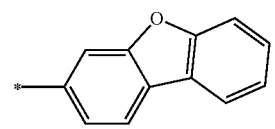 | | 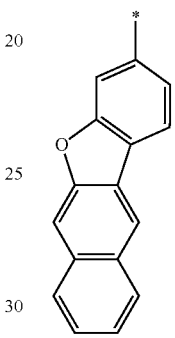 | 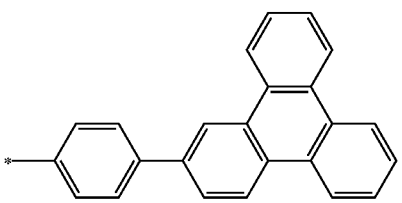 |
| 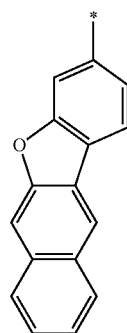 | 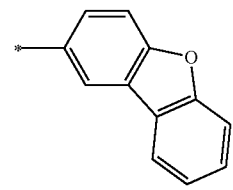 | | 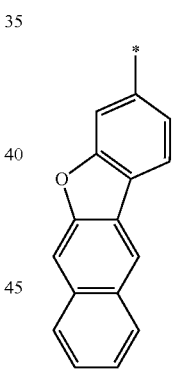 | 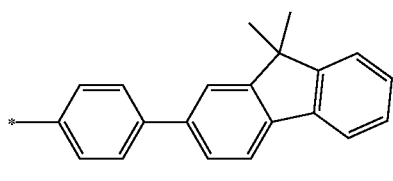 |
| 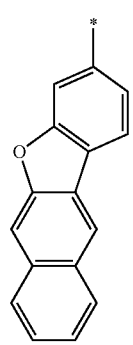 [SMILES: *c1ccc2c(c1)oc1cc3ccccc3cc12] | 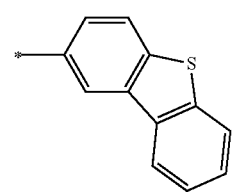 | | 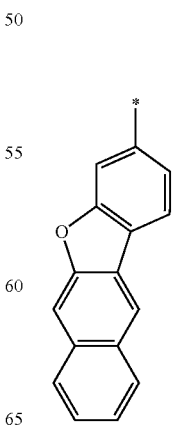 | 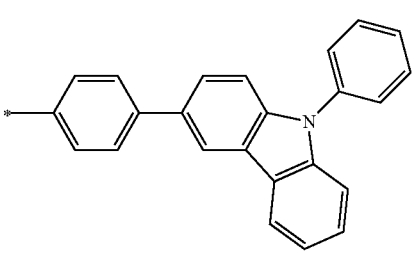 |

111
-continued
| A | B |
|---|---|
| 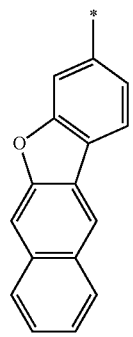 [SMILES: *c1ccc2c(c1)oc1cc3ccccc3cc12] | 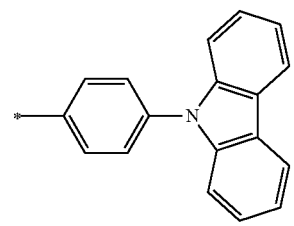 |
| 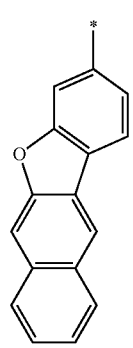 [SMILES: *c1ccc2c(c1)oc1cc3ccccc3cc12] | 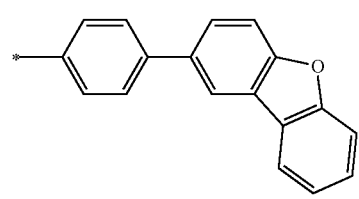 |
|  |  |
| 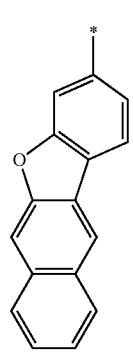 [SMILES: *c1ccc2c(c1)oc1cc3ccccc3cc12] | 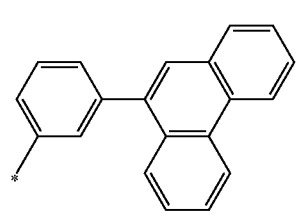 |
112
-continued
| A | B |
|---|---|
| 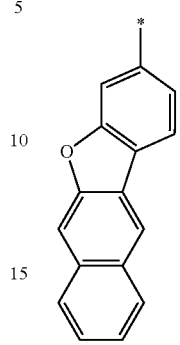 | 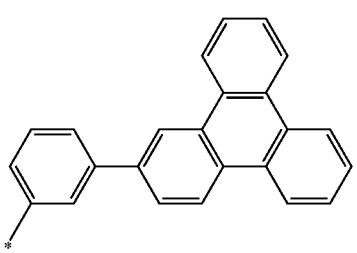 |
| 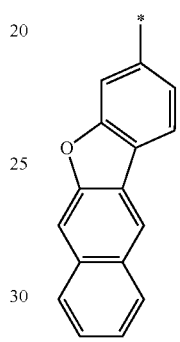 | 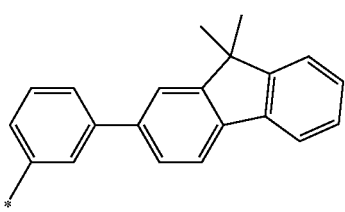 |
| 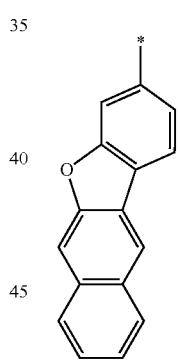 | 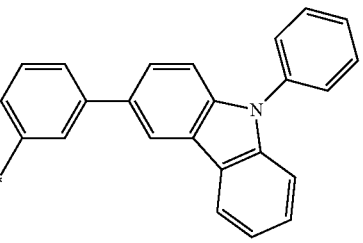 |
| 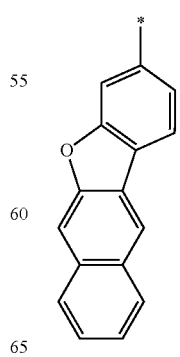 | 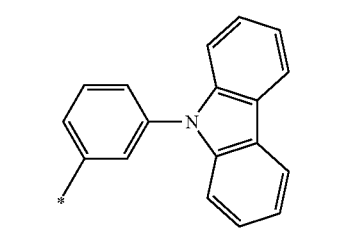 |

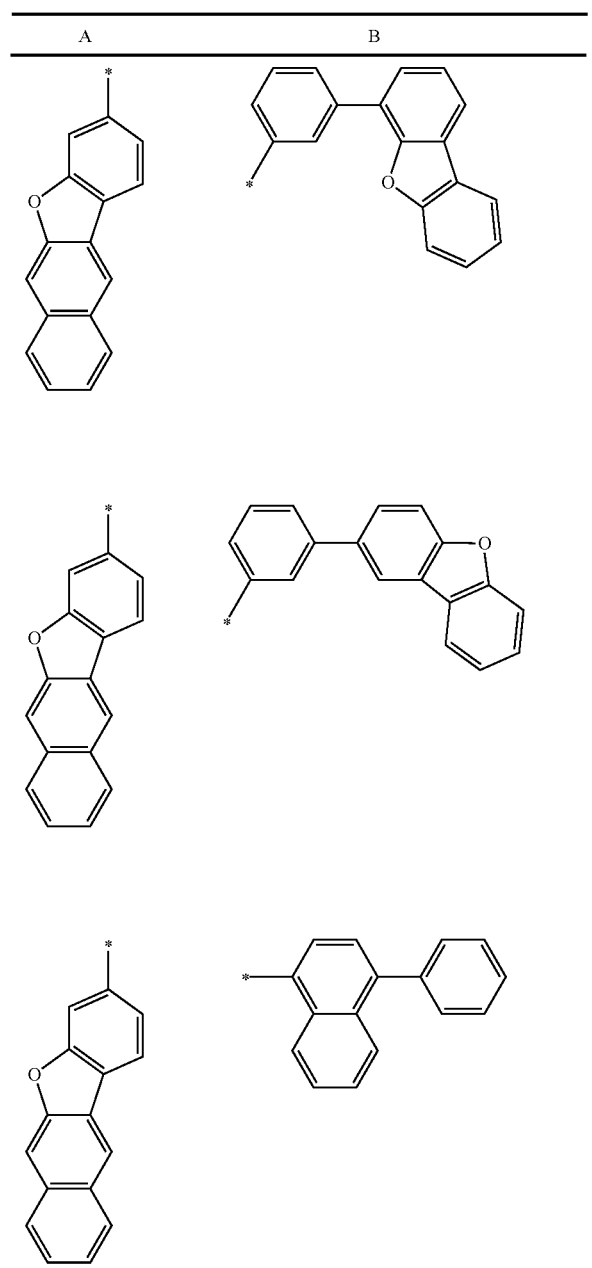
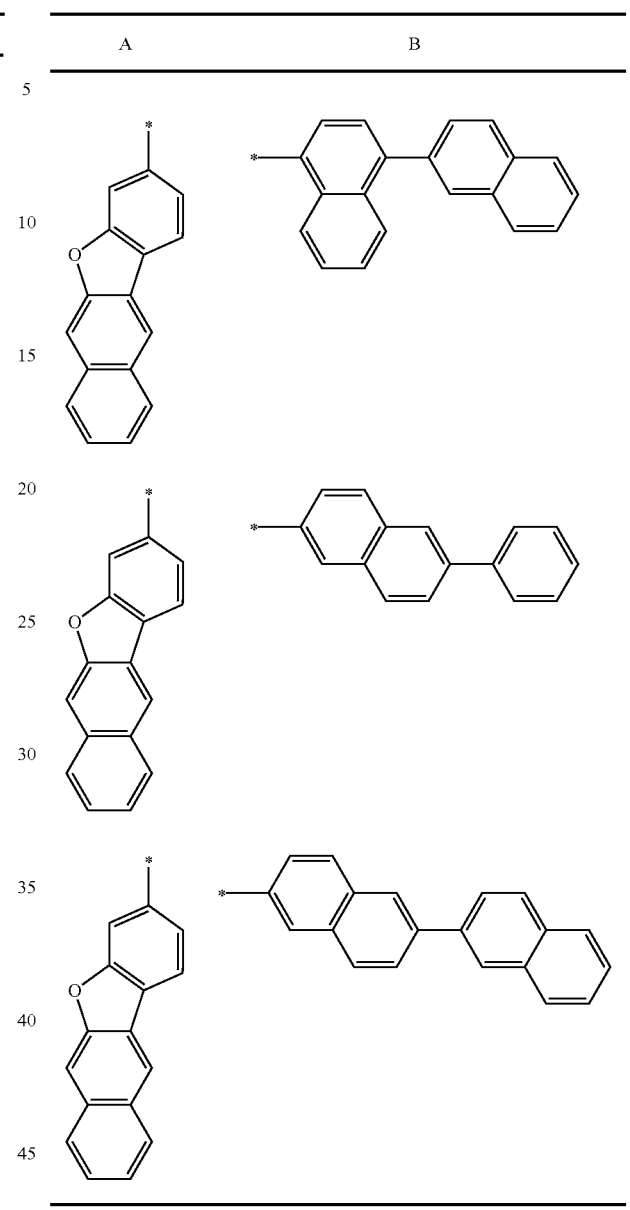
The *s in the table respectively show the bonding position to the anthracene ring.
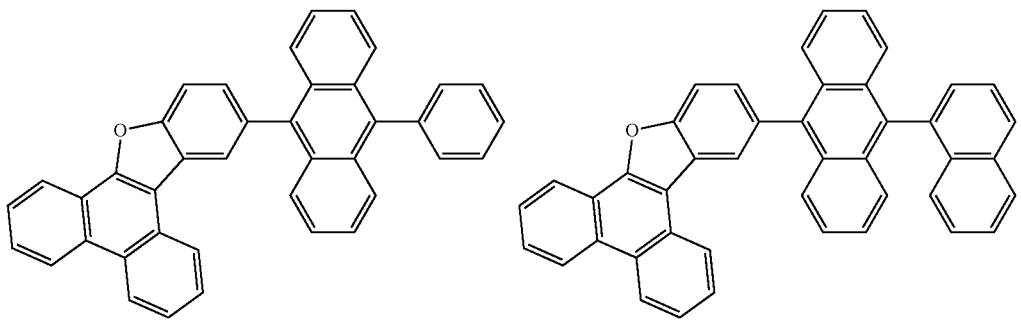

115
116
-continued
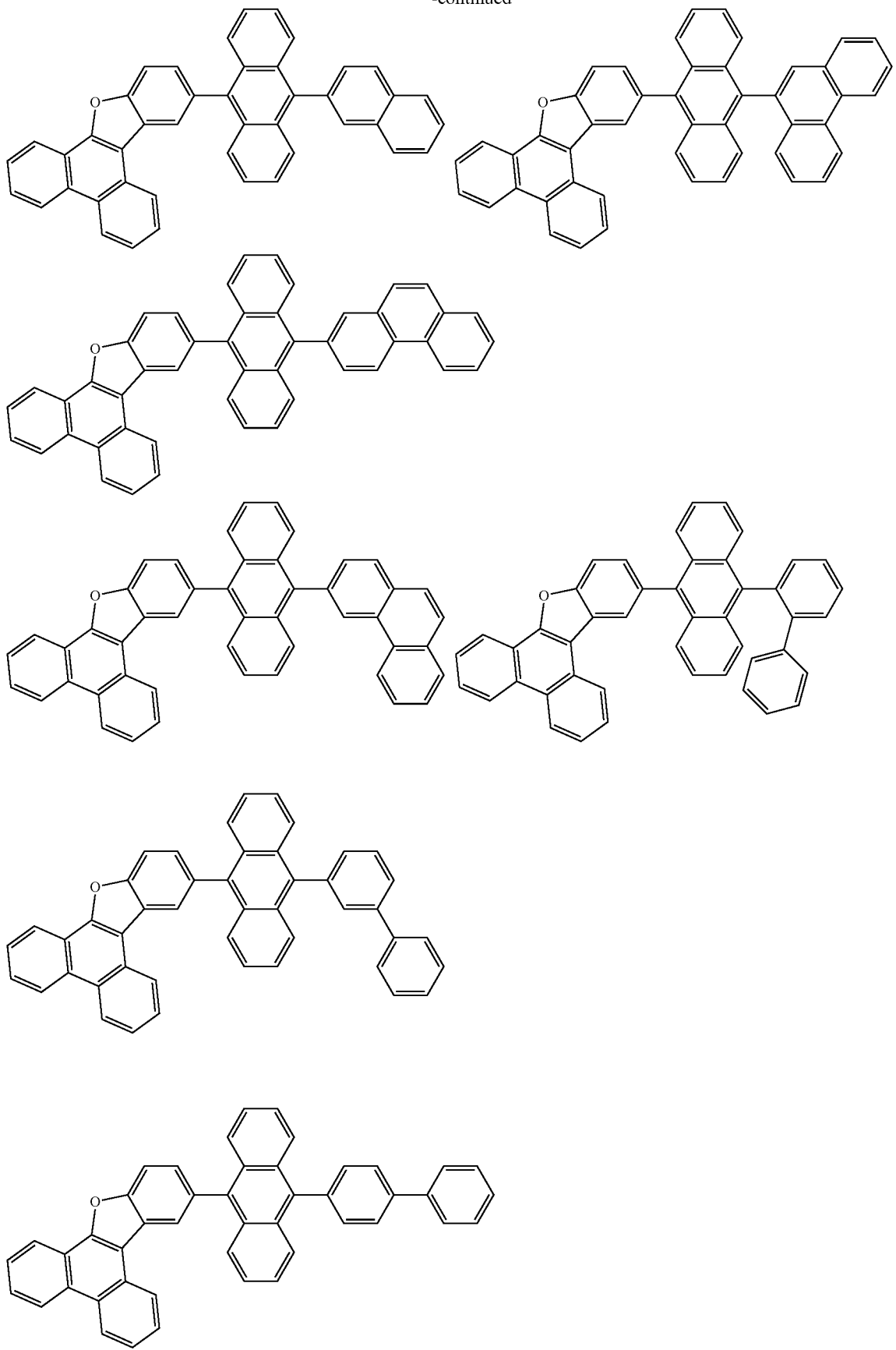

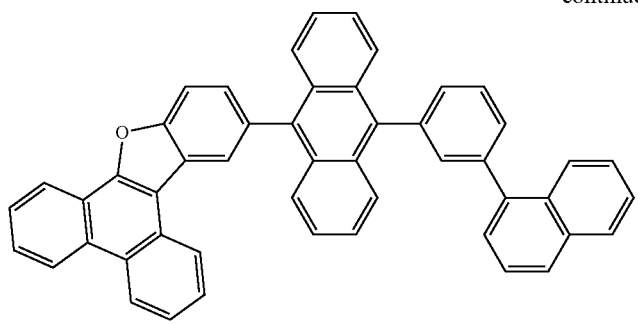
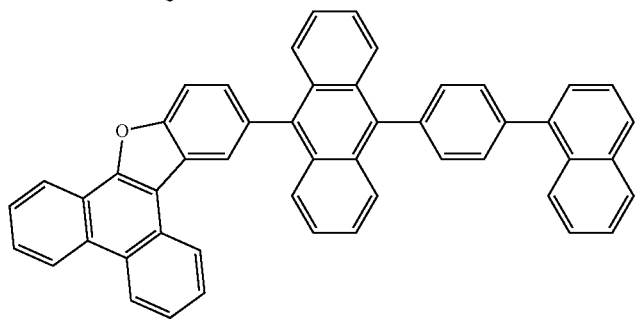
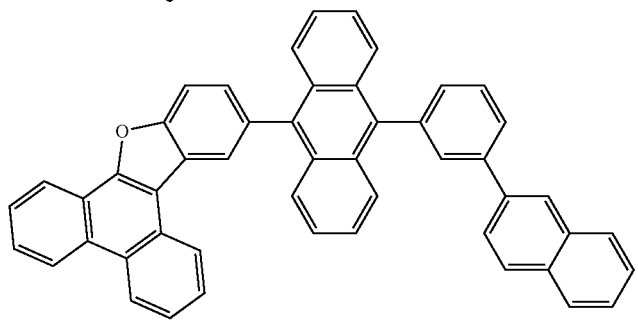
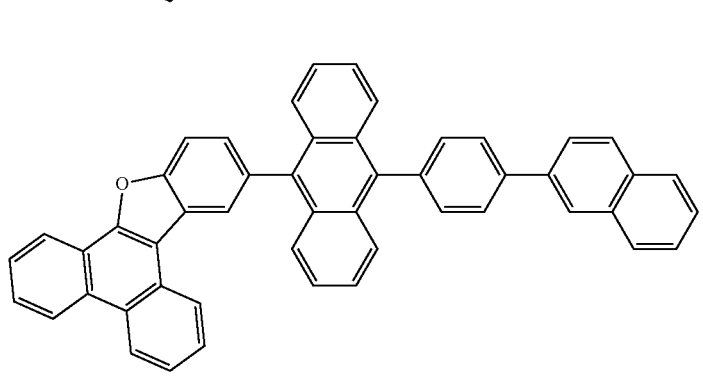
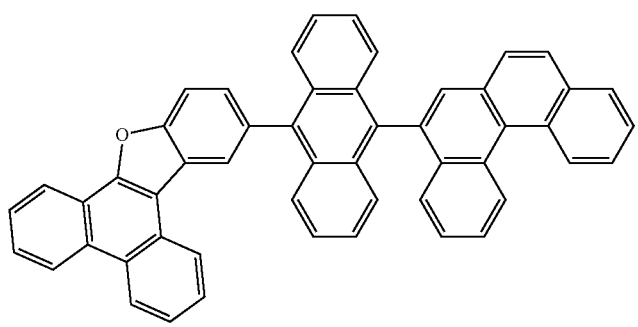

-continued
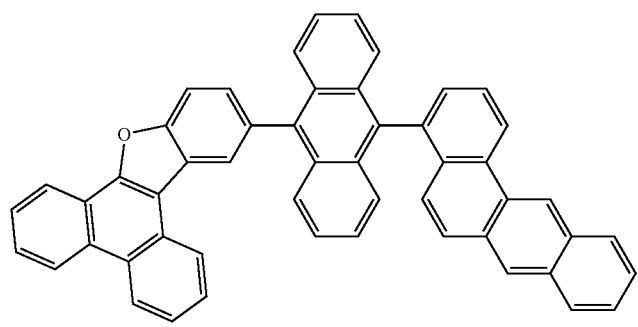
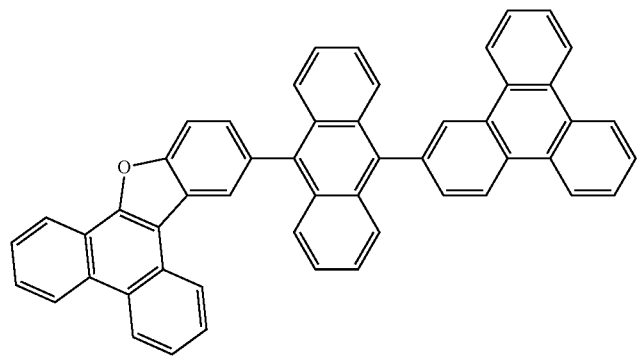
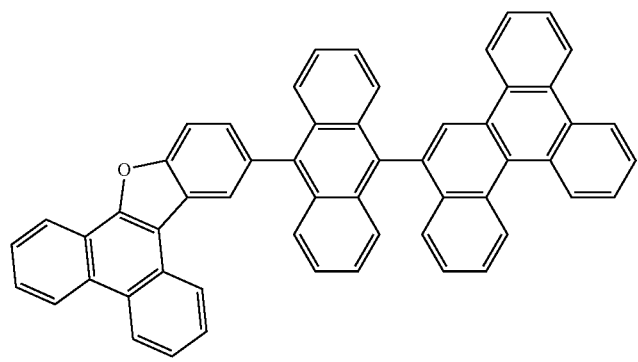
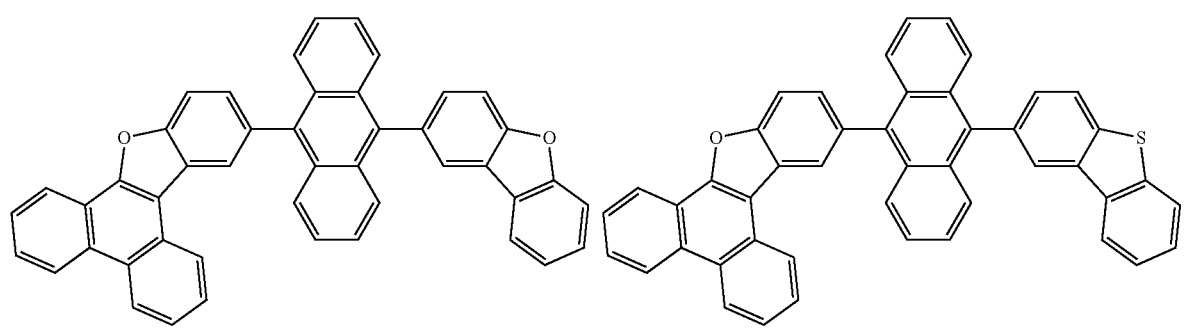
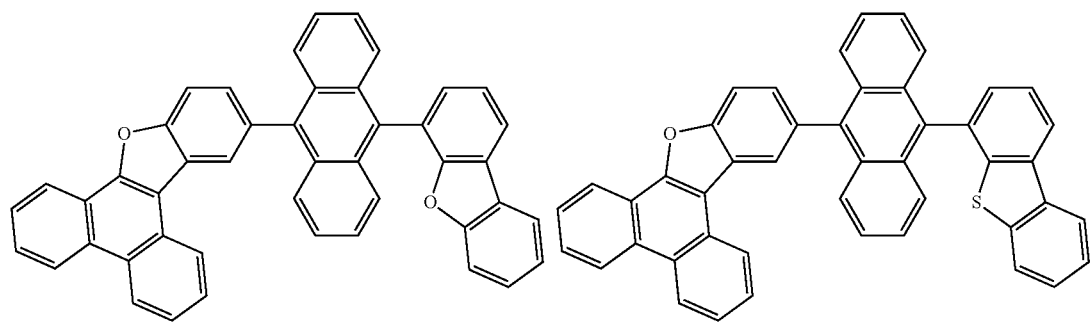

-continued
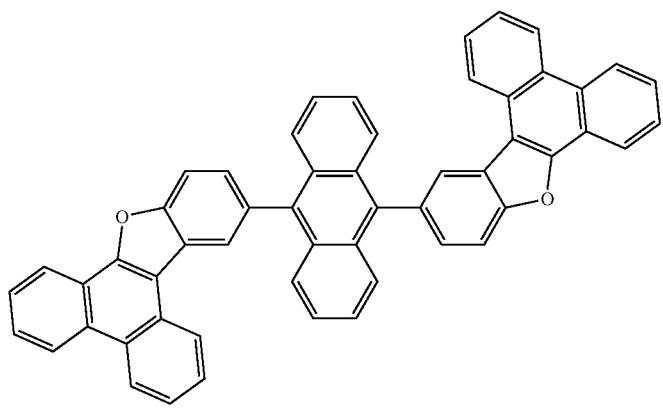
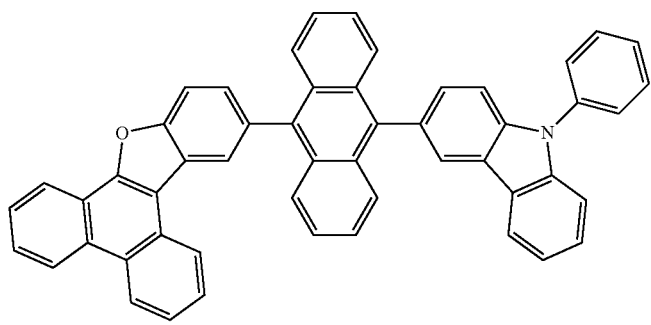
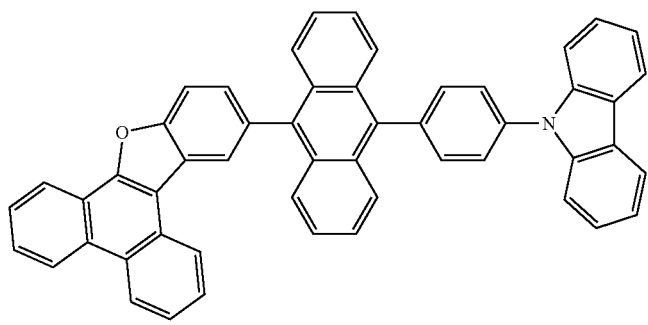
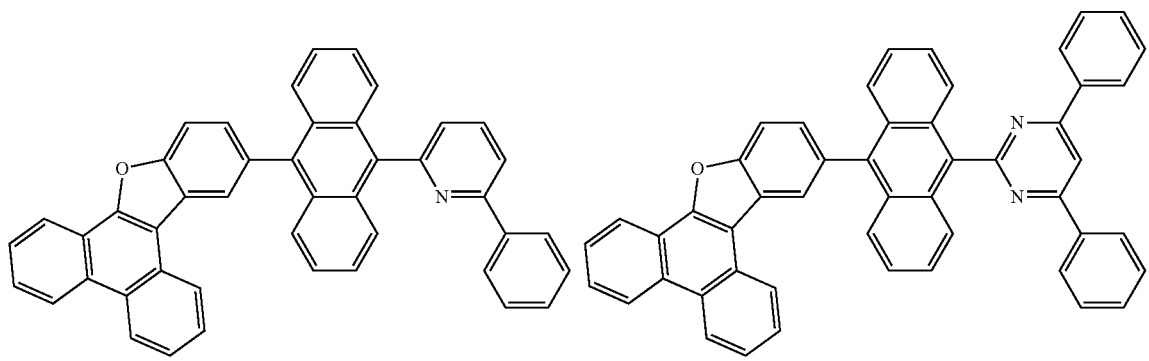

-continued
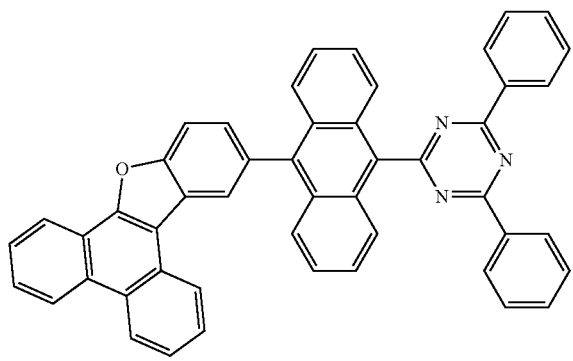
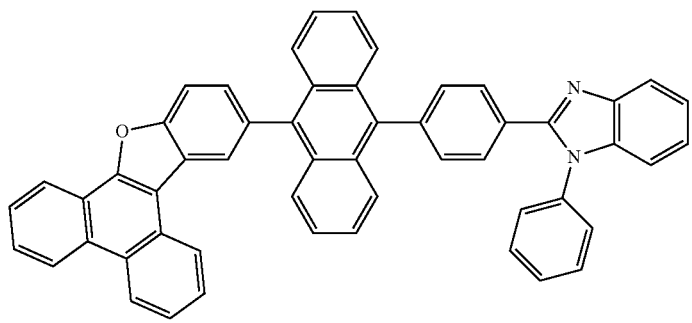
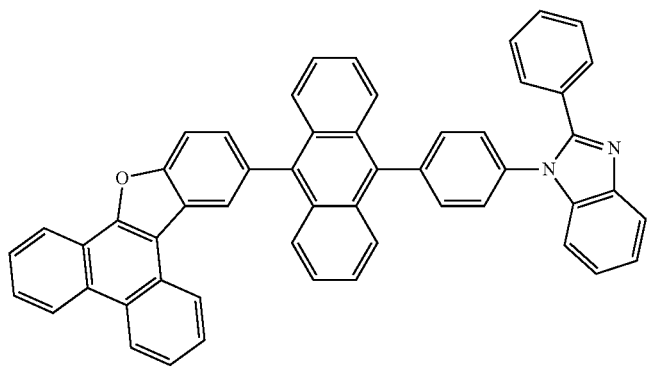
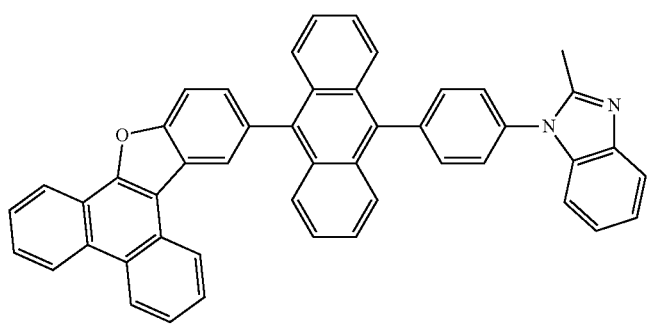
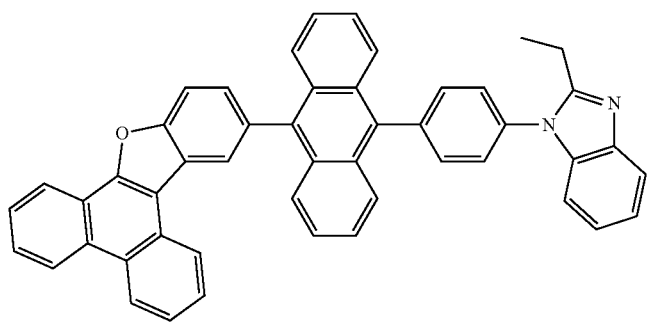

-continued
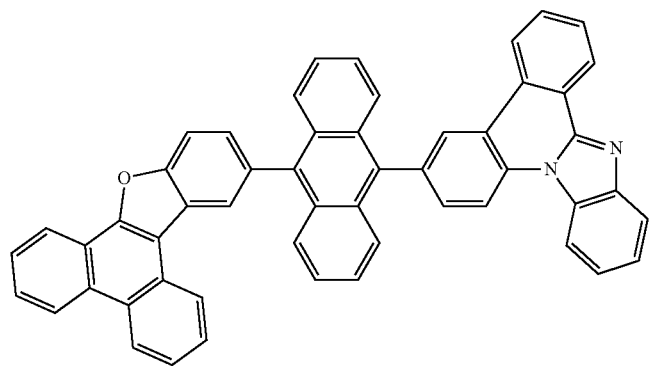
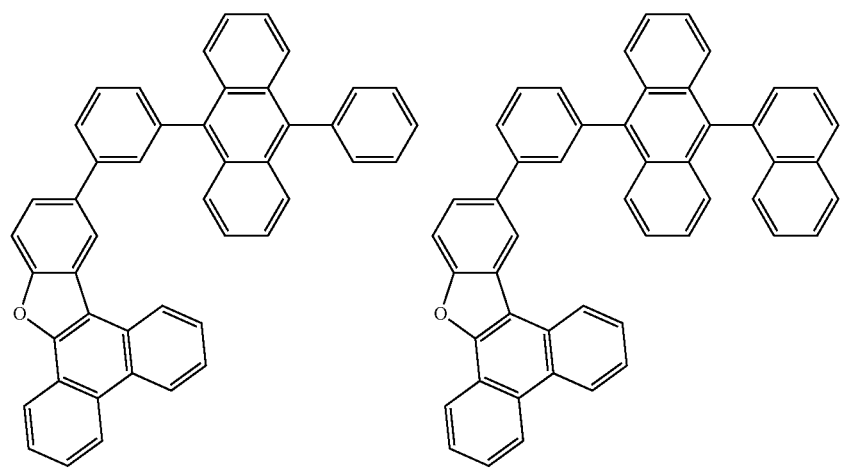
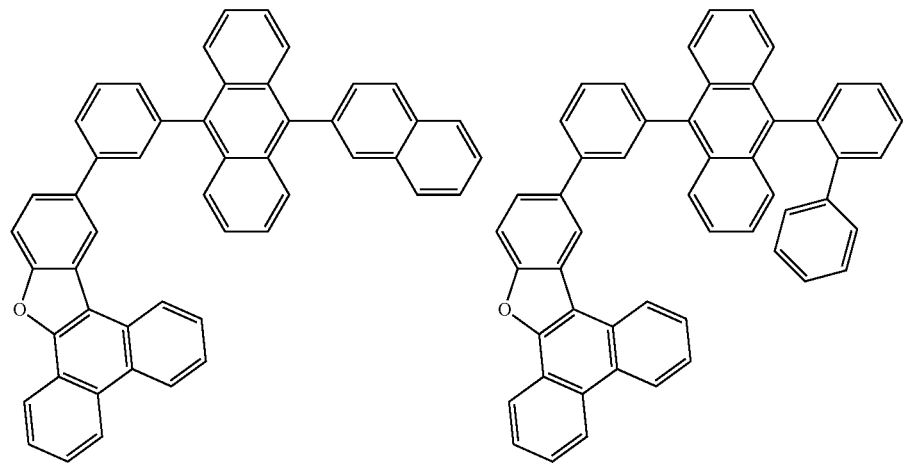

127
128
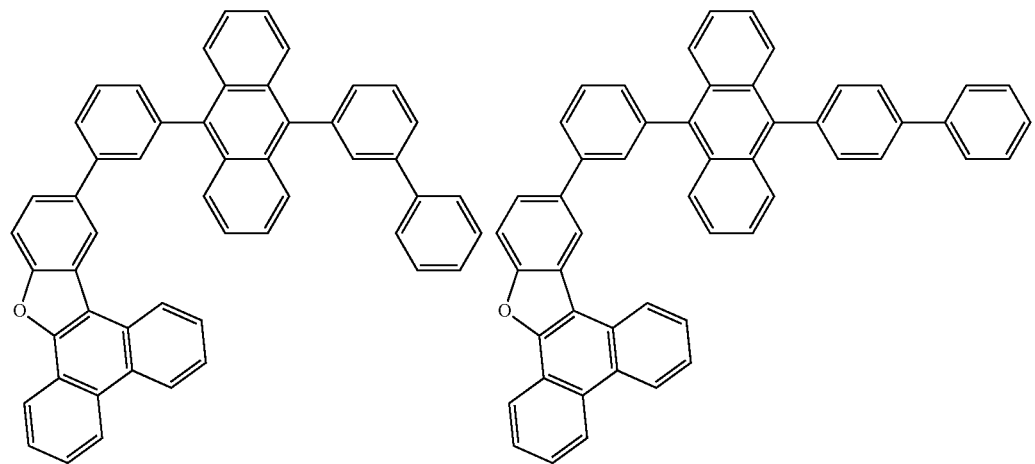
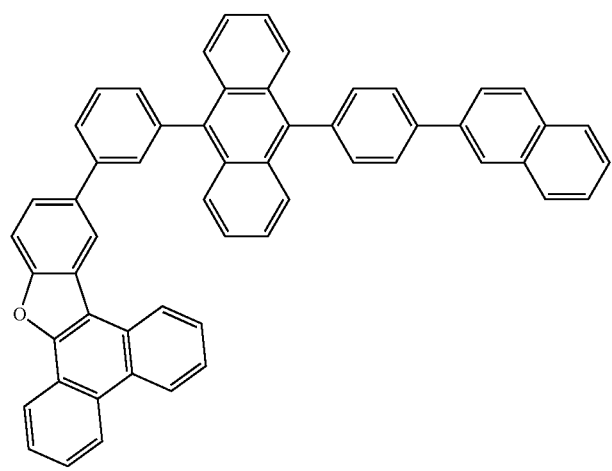
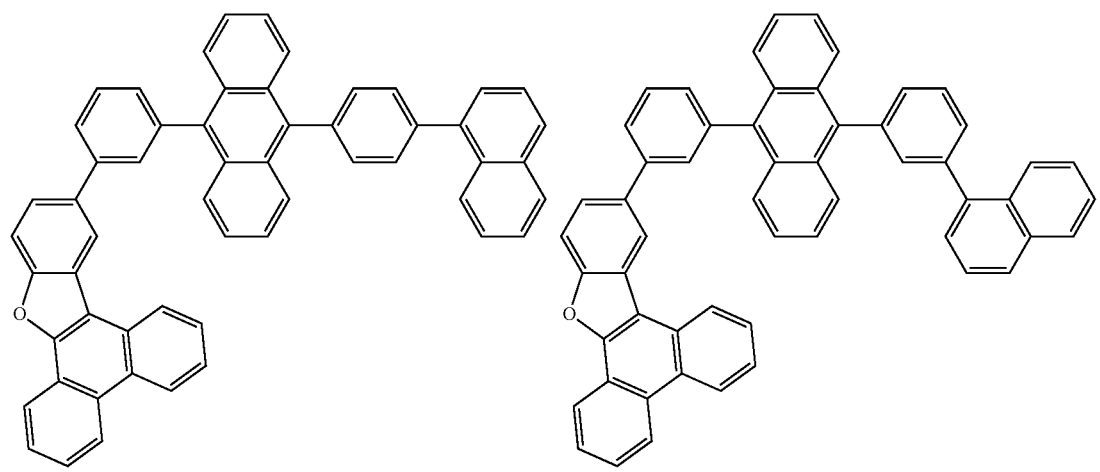

-continued
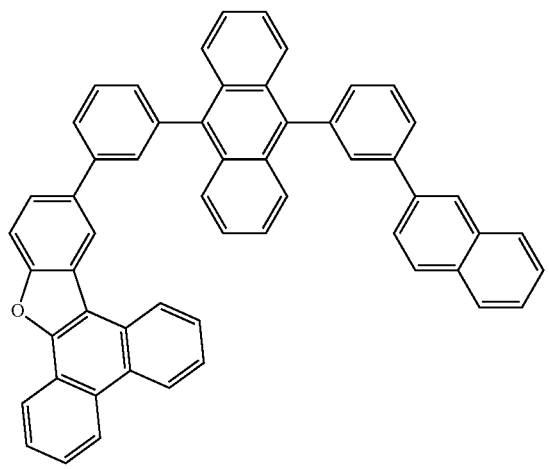
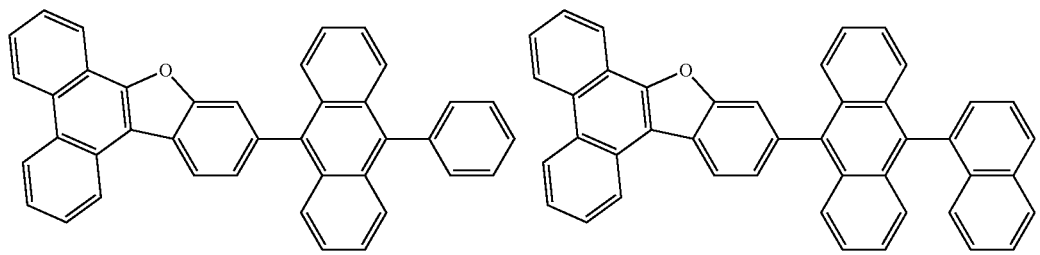
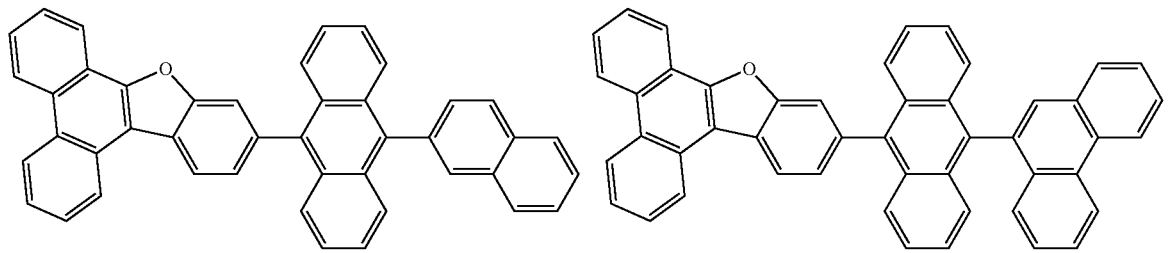
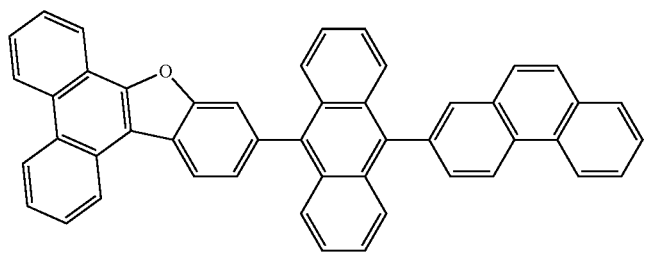
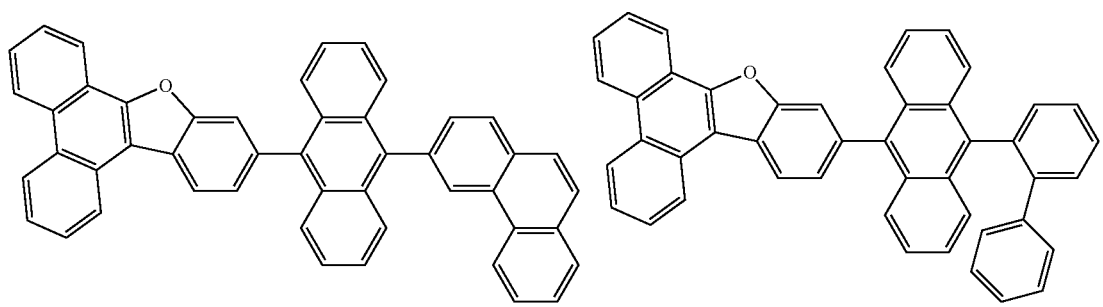

-continued
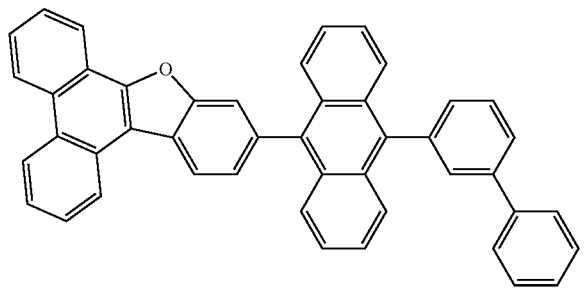
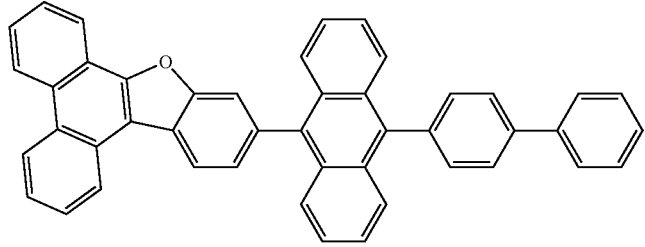
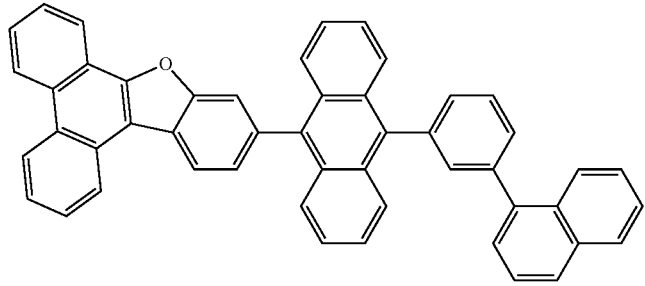
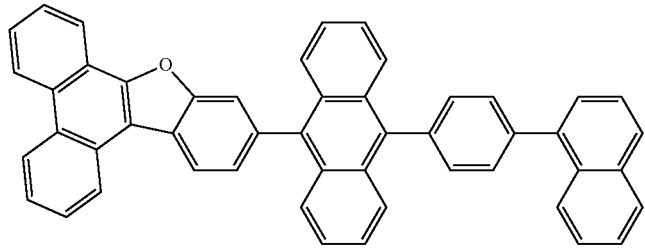
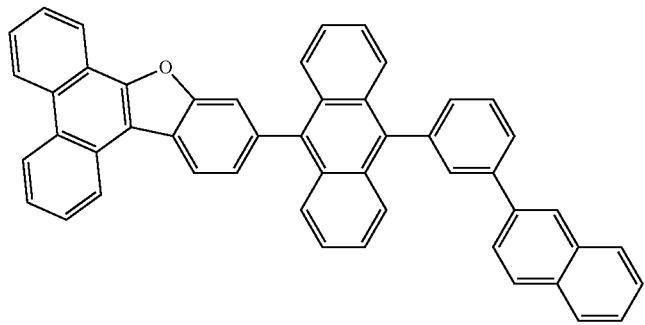
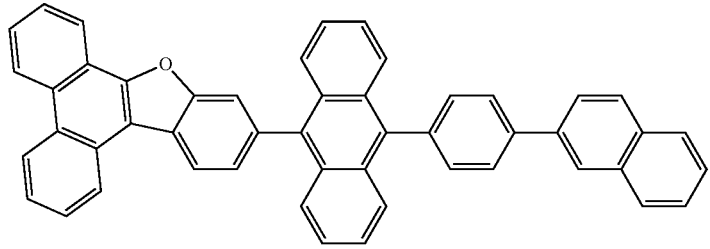

-continued
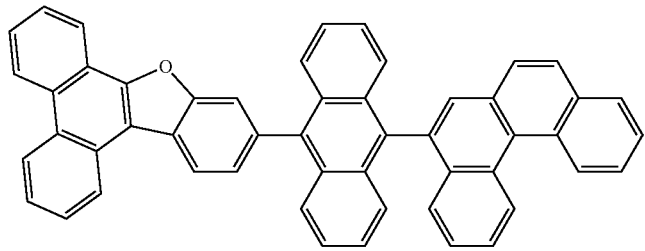
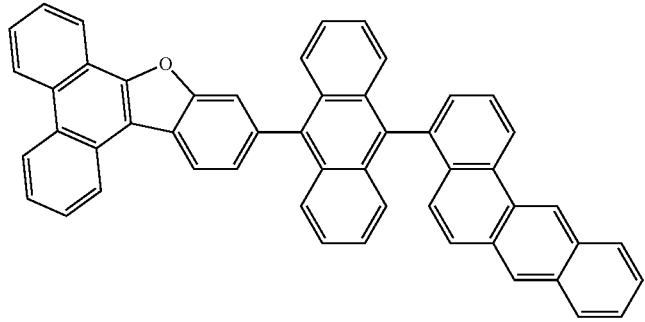
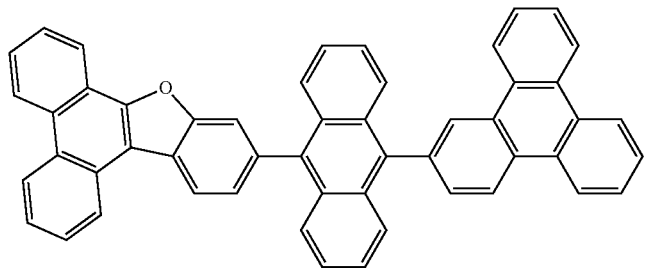
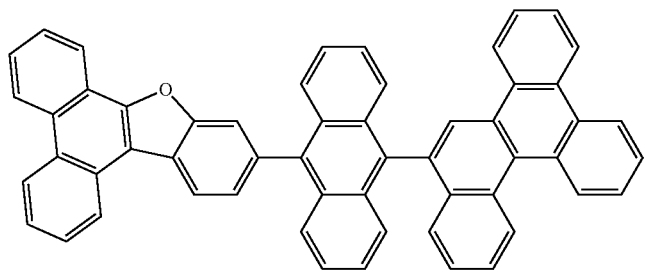
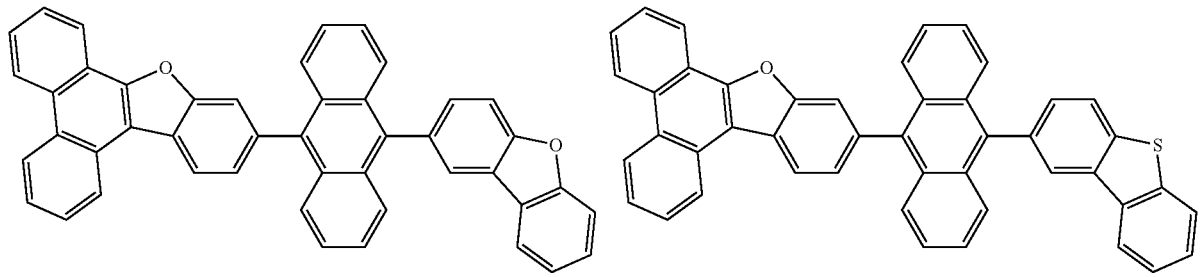
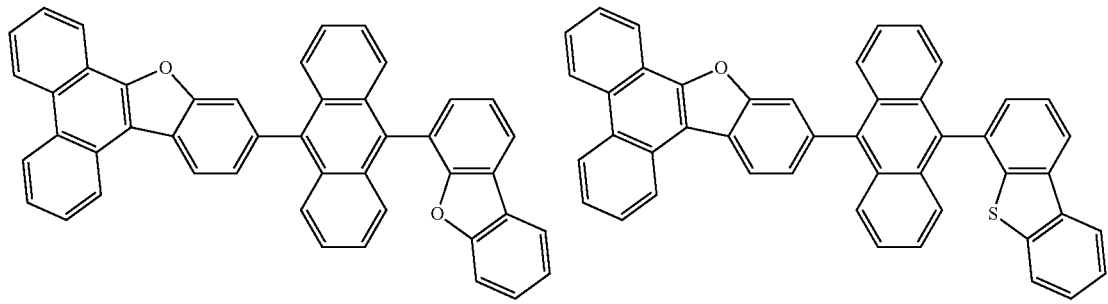

-continued
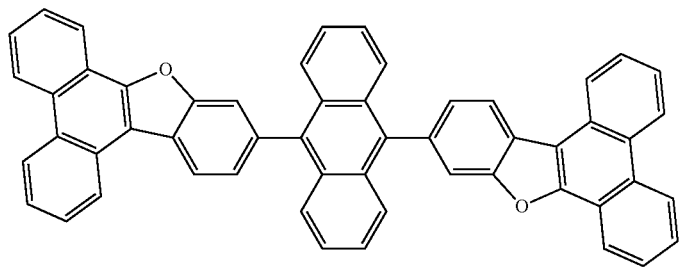
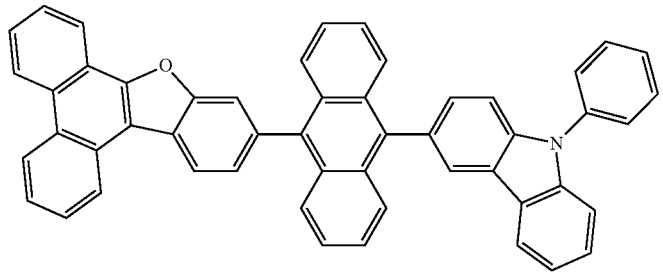
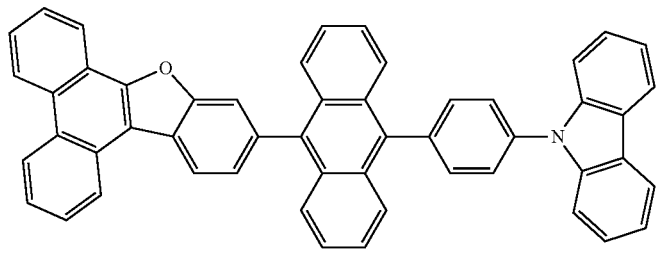
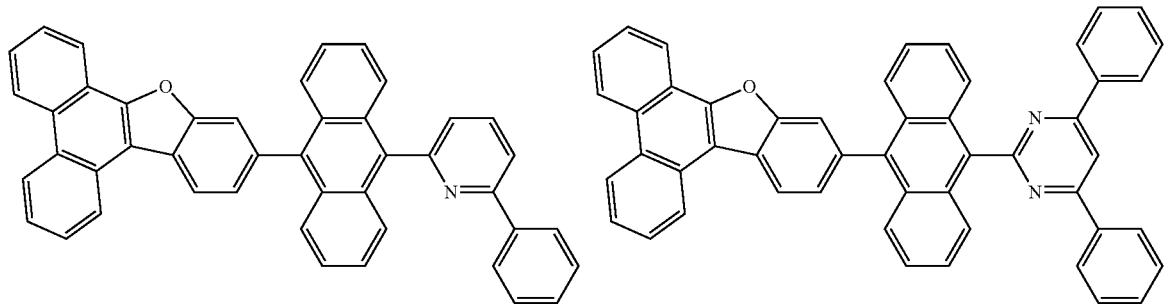
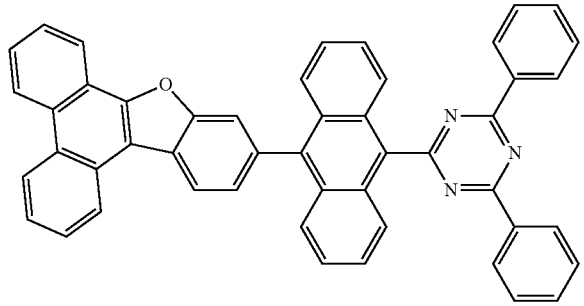
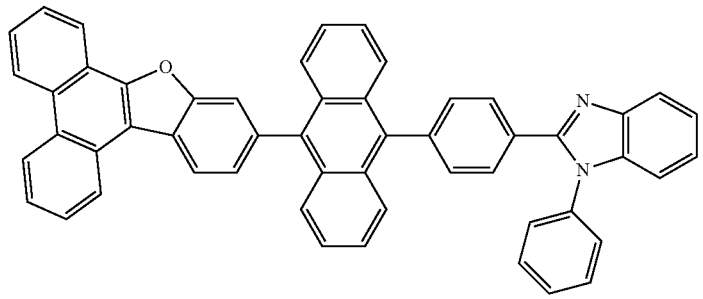

-continued

-continued
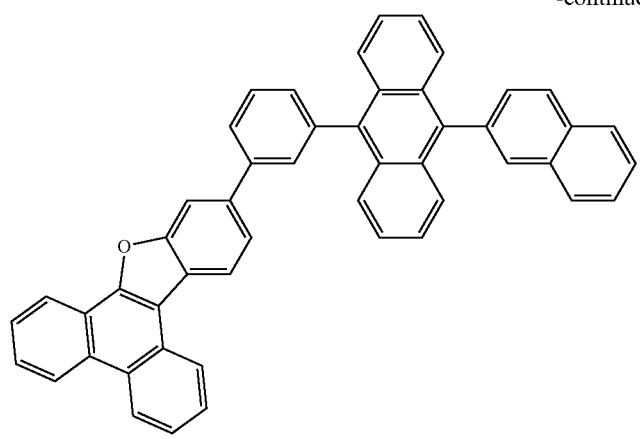
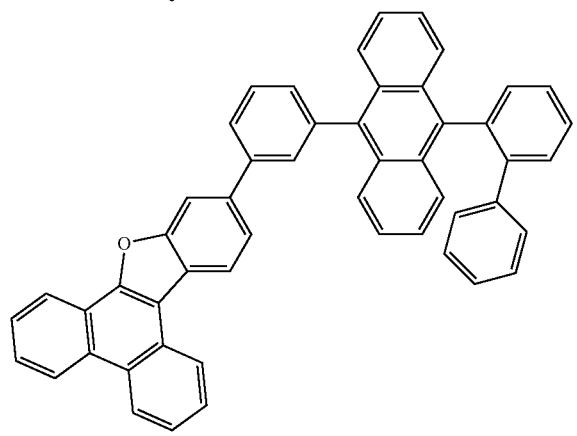
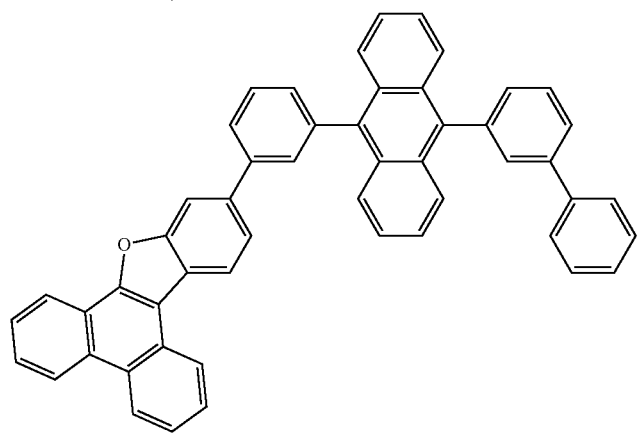
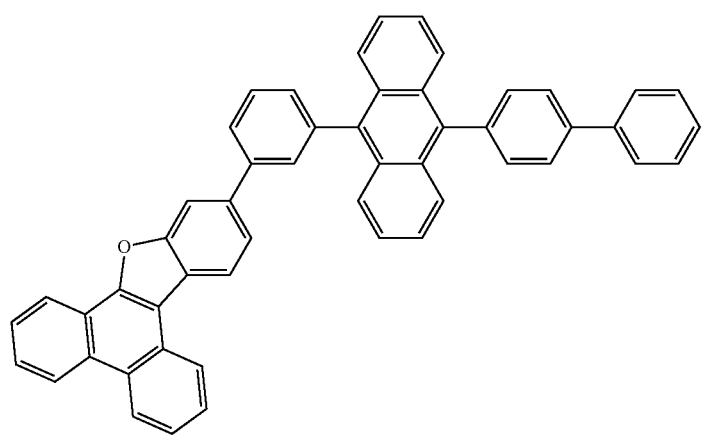

-continued
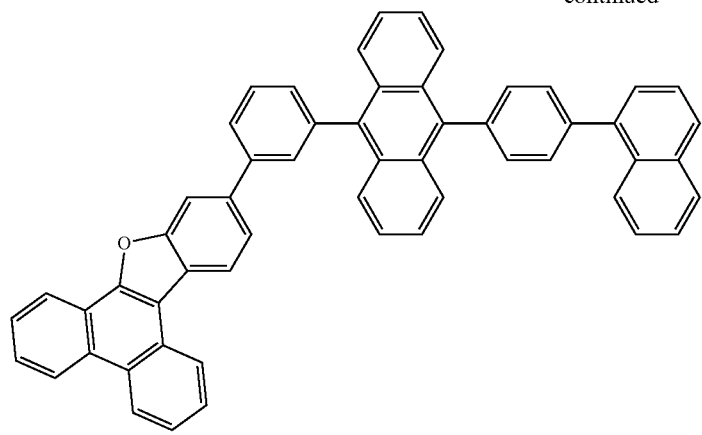
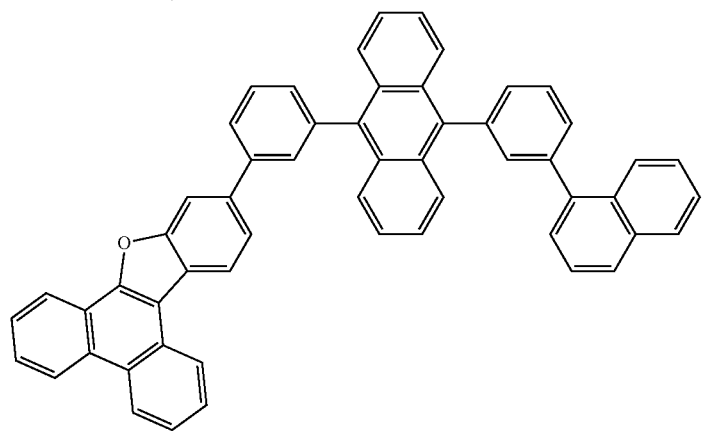
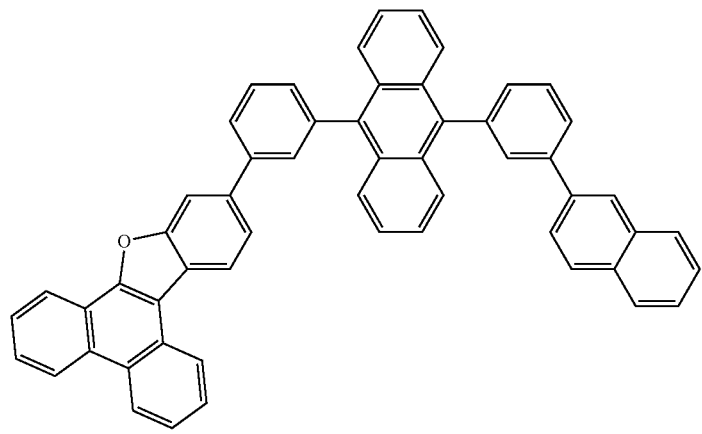
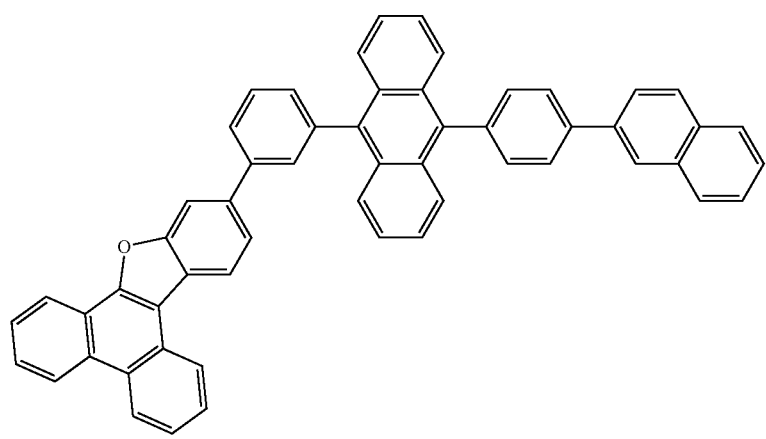 [SMILES: c1cc(-c2ccc3c(c2)oc2c4ccccc4c4ccccc4c32)cc(-c2c3ccccc3c(-c3ccc(-c4ccc5ccccc5c4)cc3)c3ccccc23)c1]

143 144
-continued
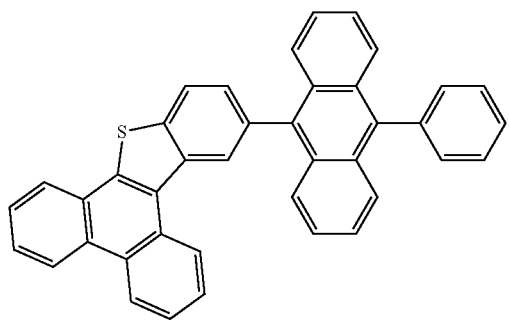
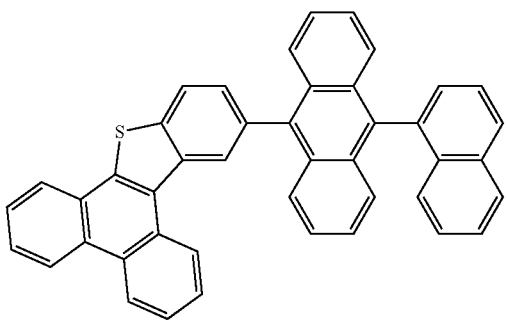
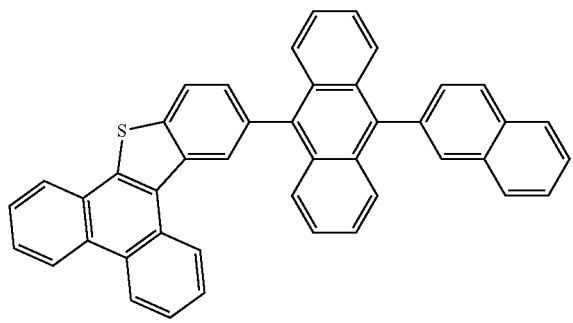
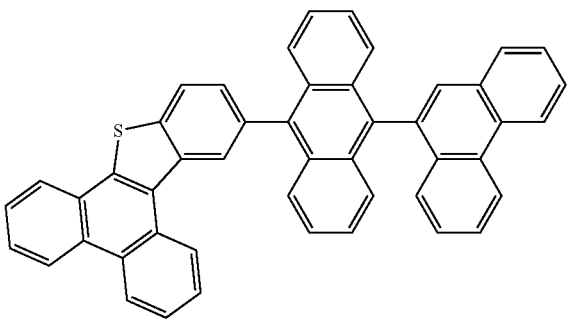
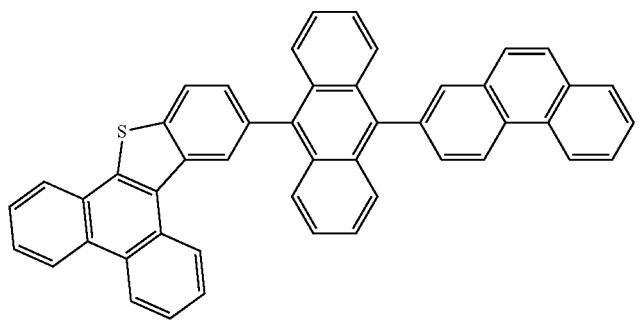
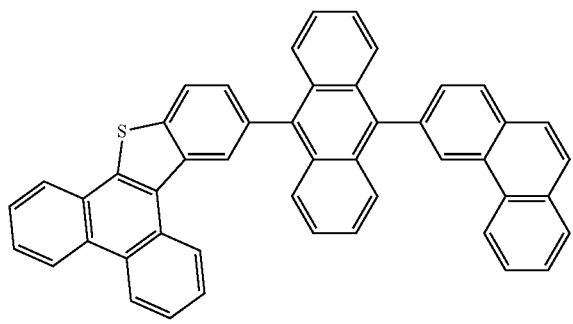
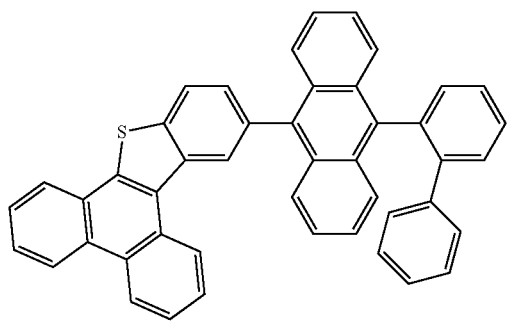
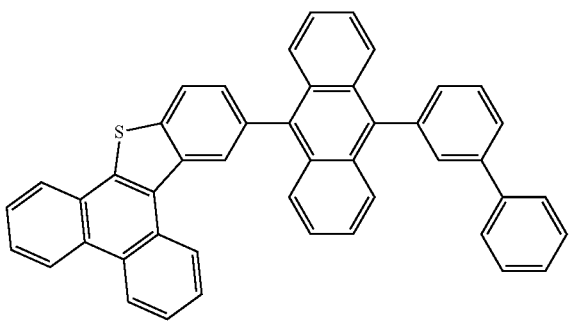

-continued
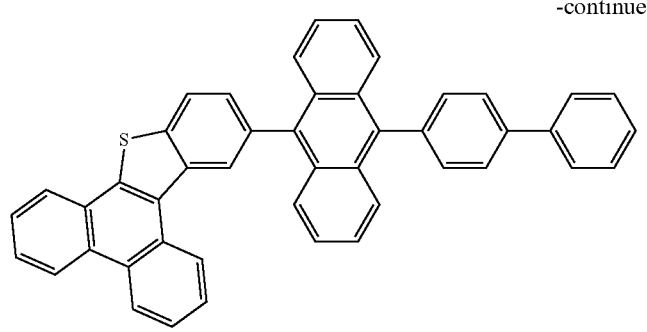
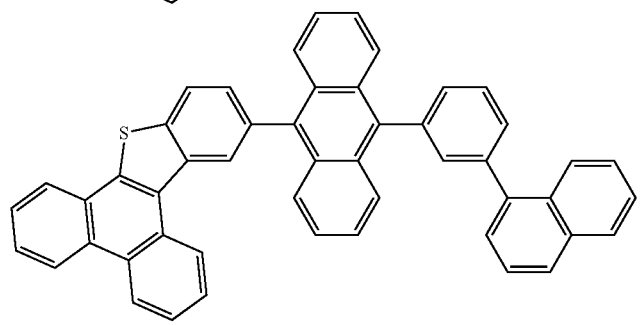
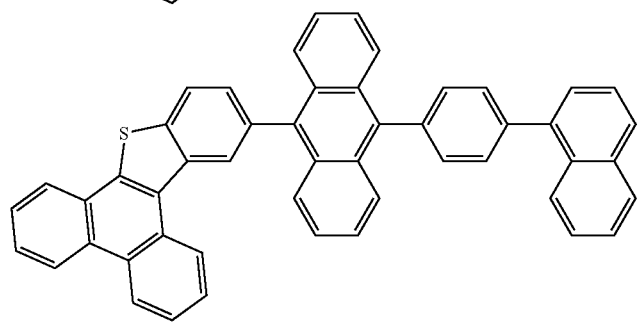
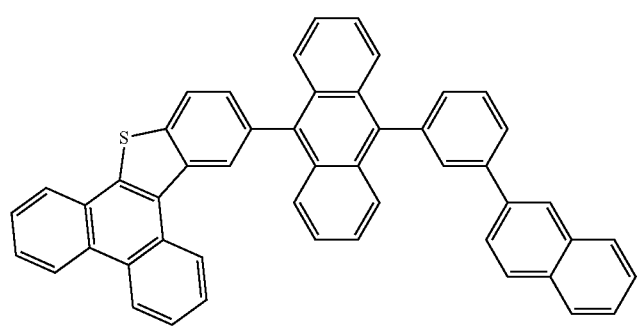
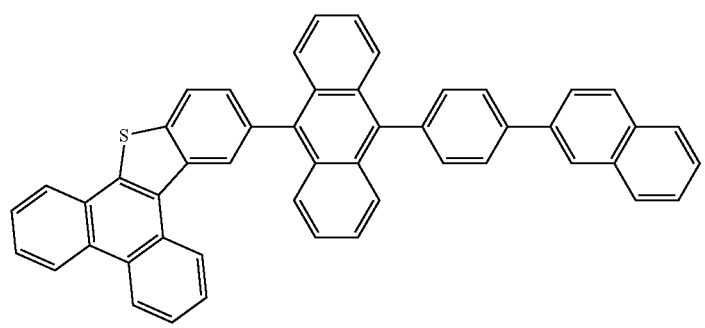

-continued
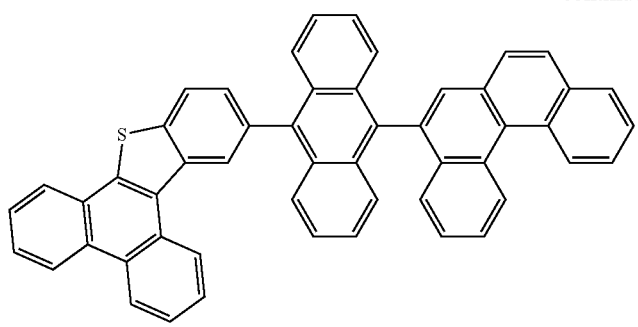
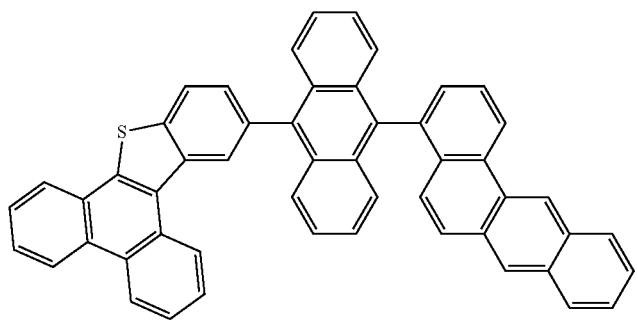
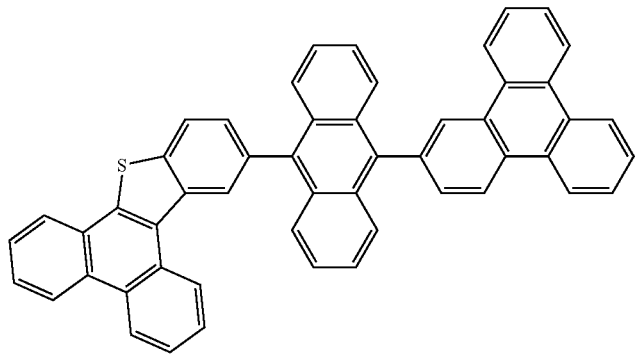
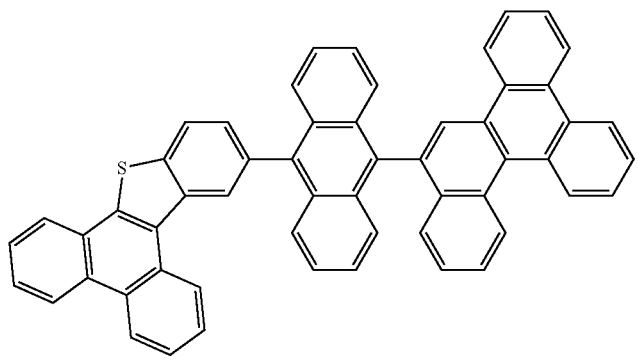
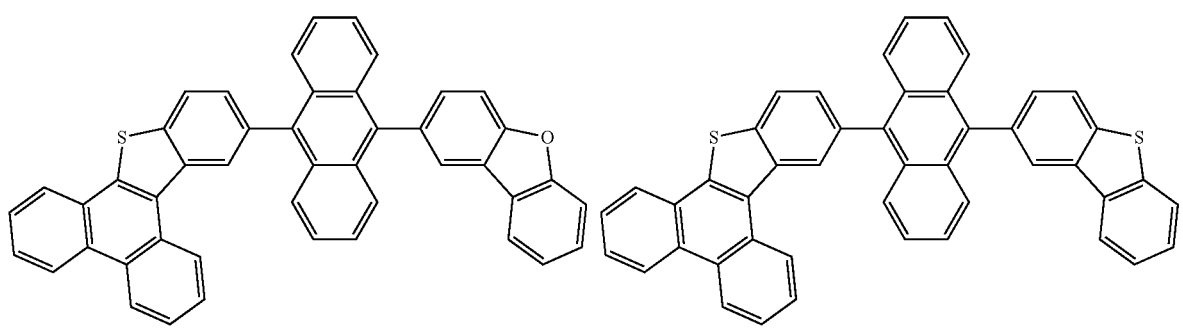

149 150
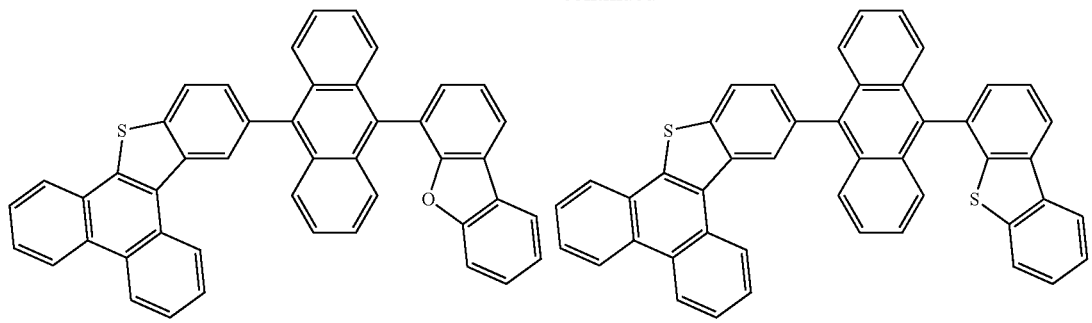
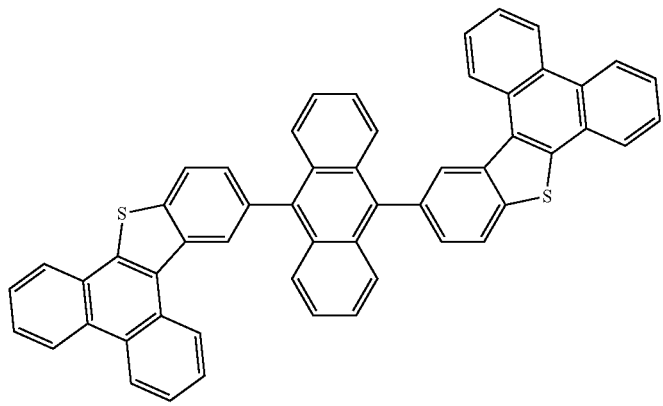
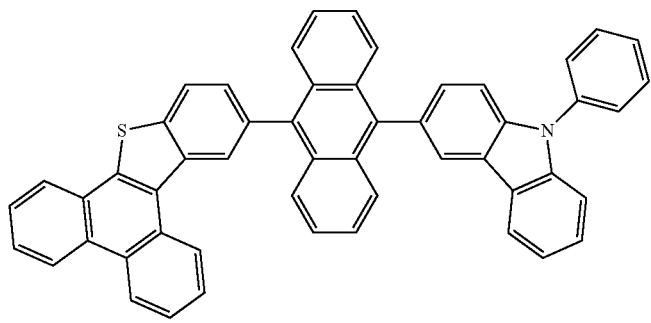
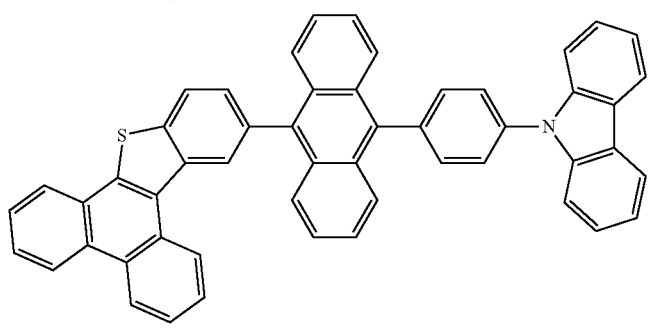 [SMILES: c1ccc2c(-c3ccc4sc5c6ccccc6c6ccccc6c5c4c3)c3ccccc3c(-c3ccc(-n4c5ccccc5c5ccccc54)cc3)c2c1]
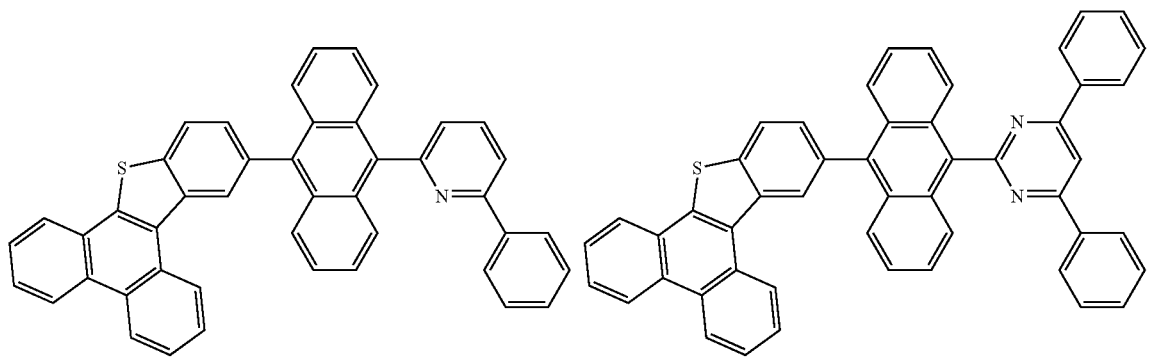

-continued
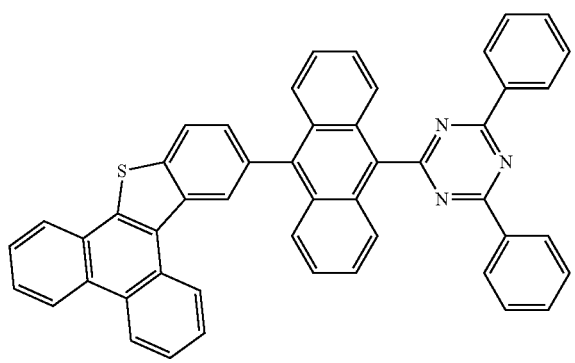
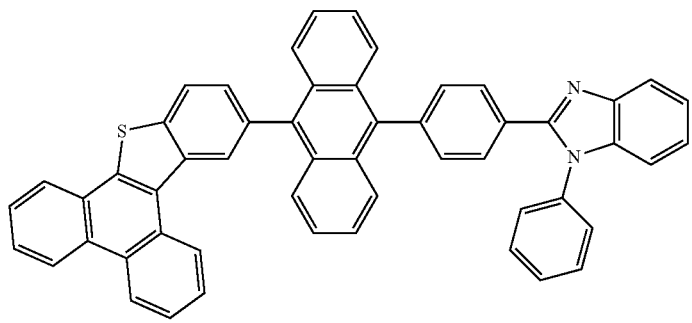
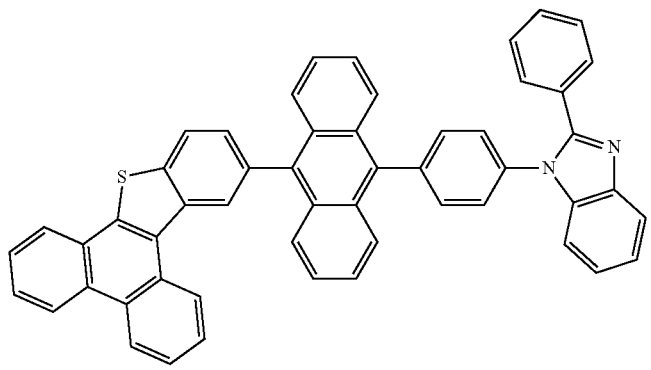
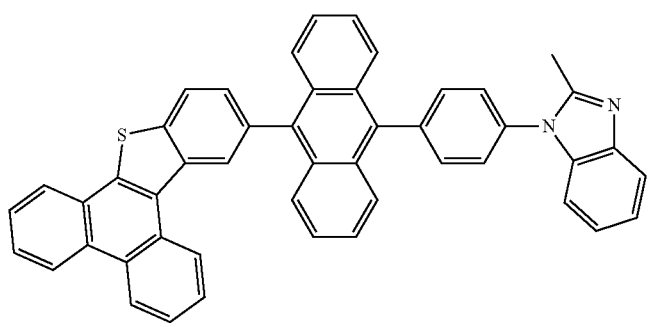
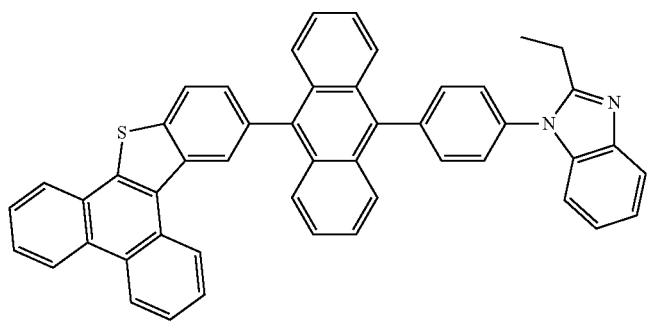

-continued
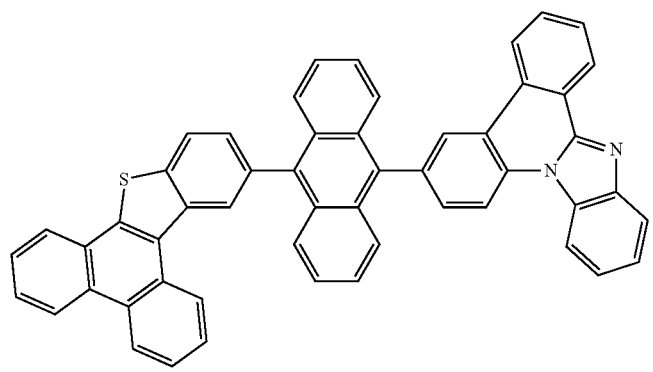
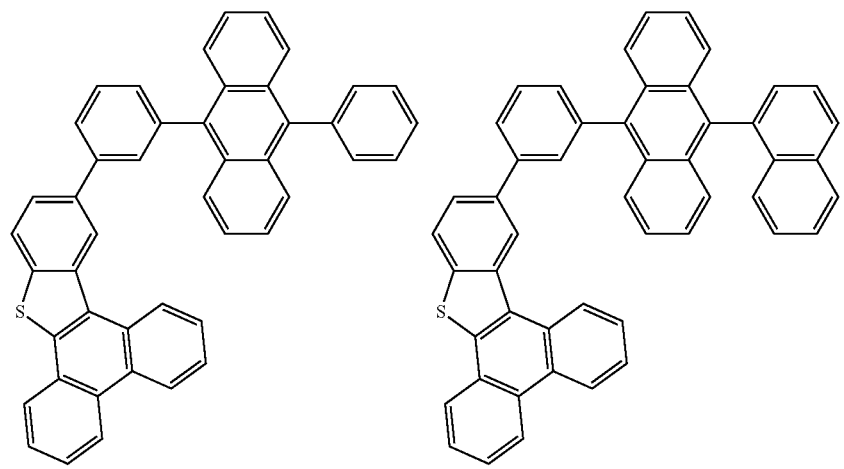
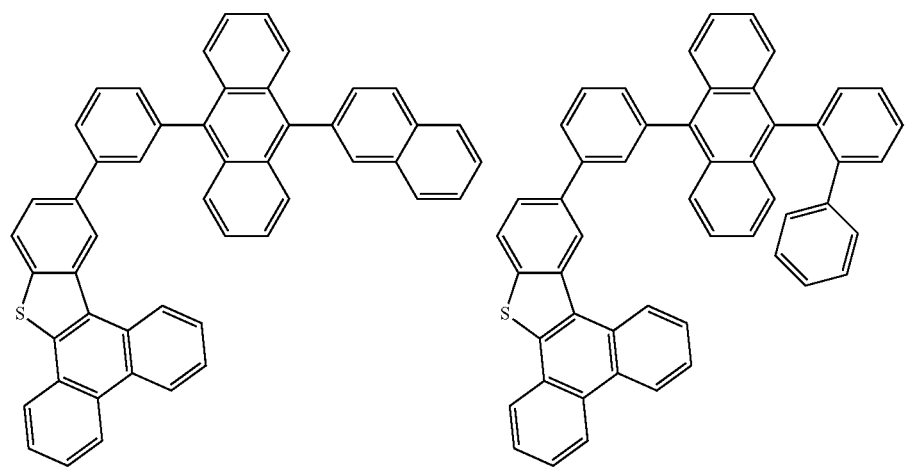

-continued
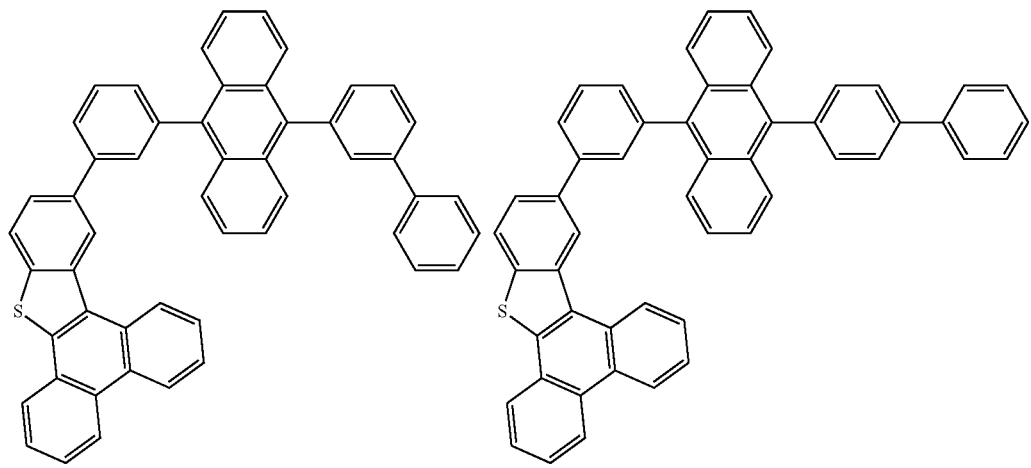
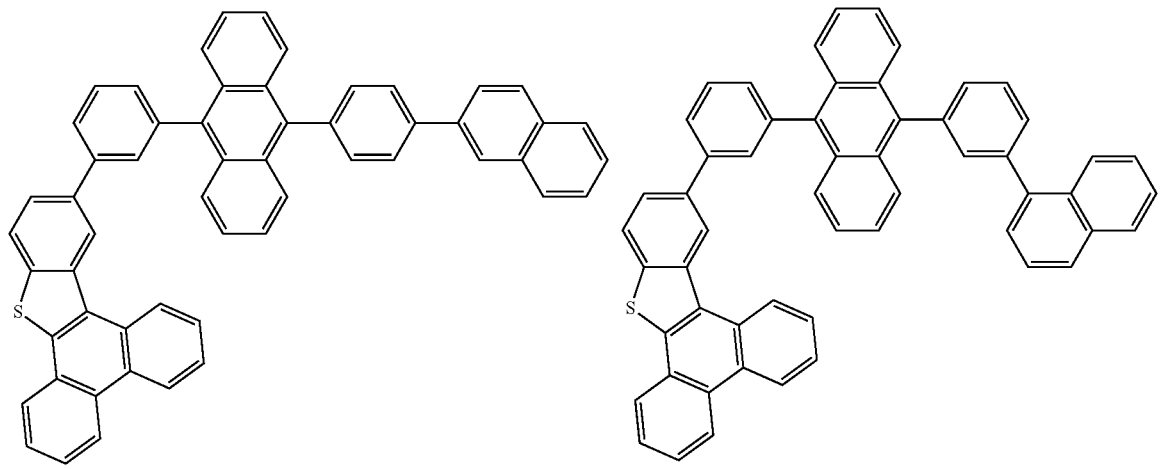
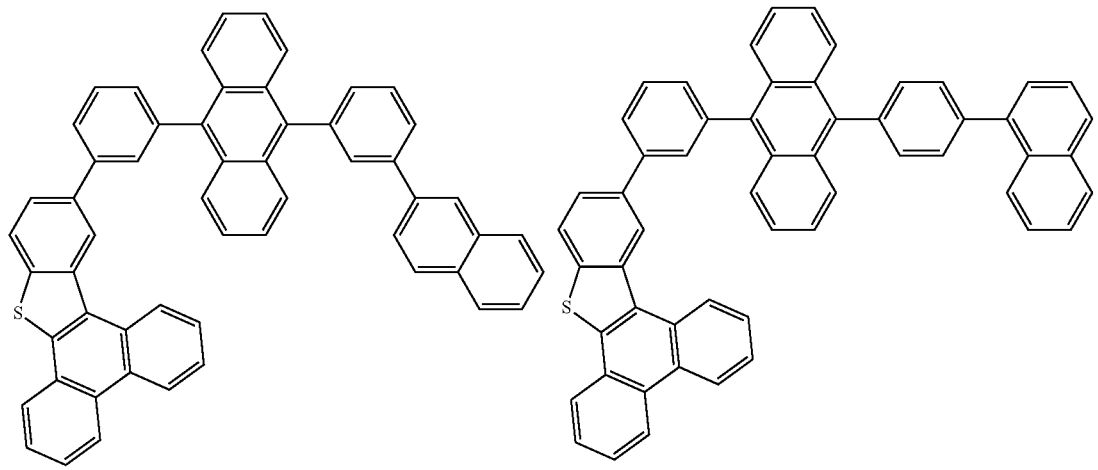
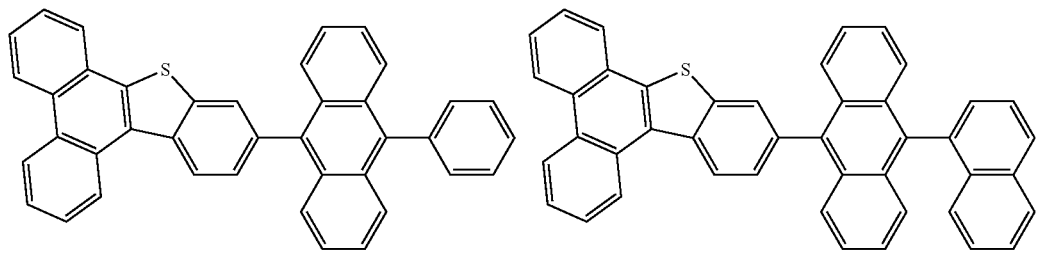

-continued
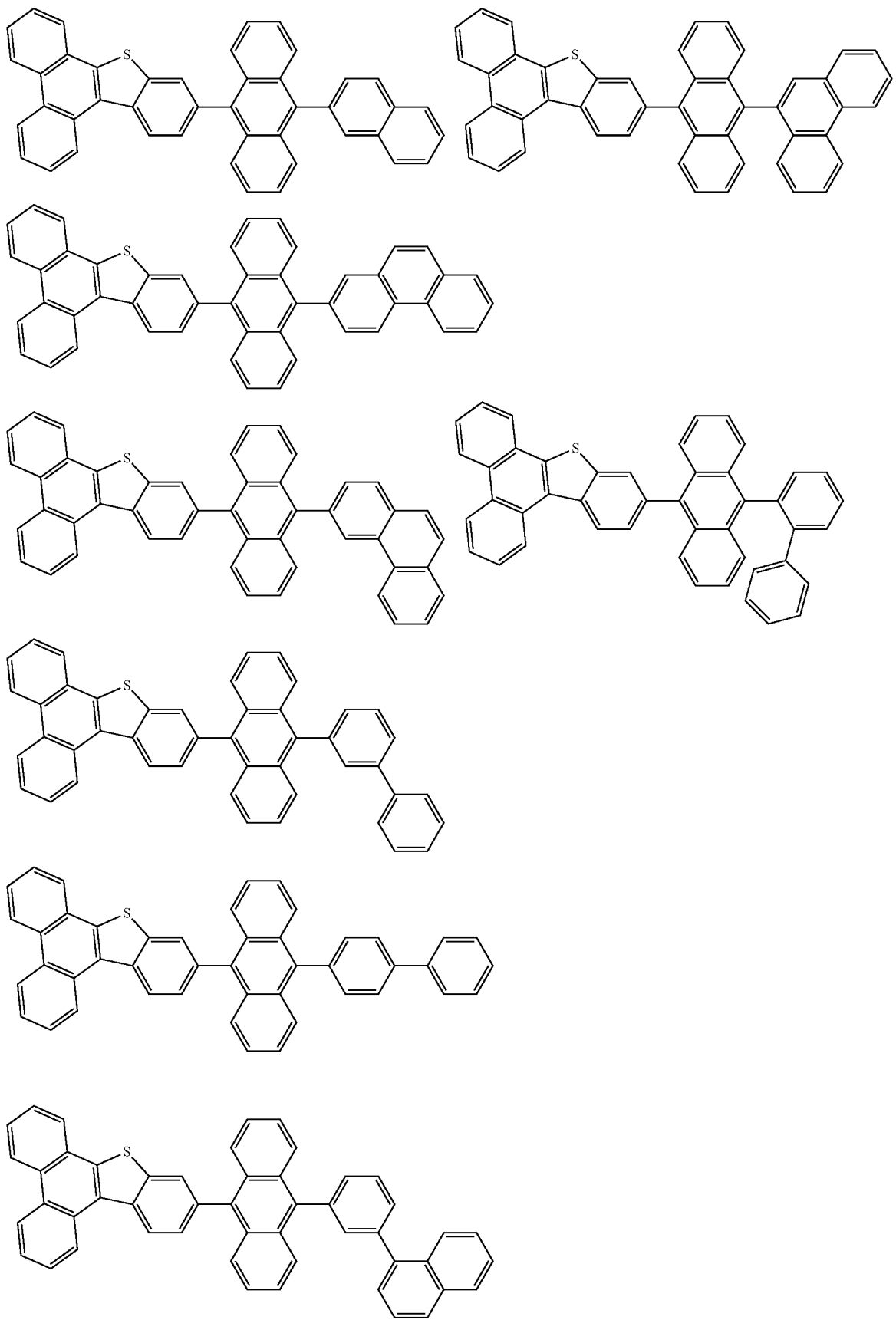

-continued
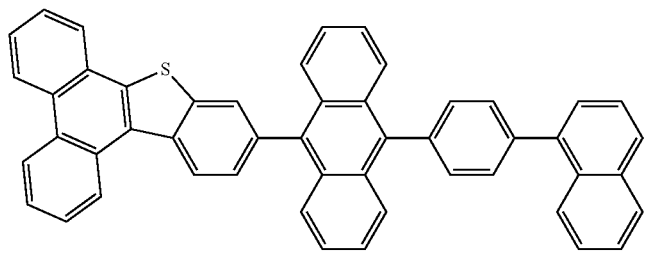
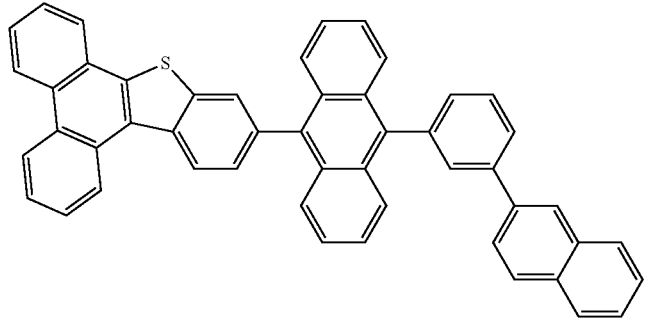
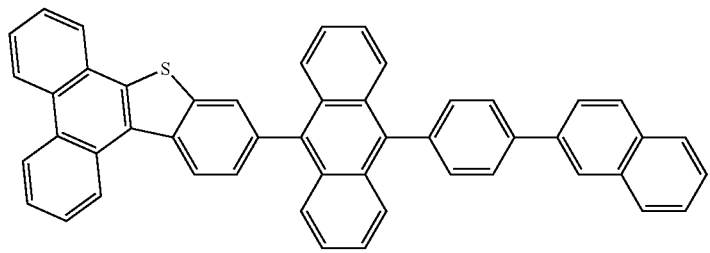
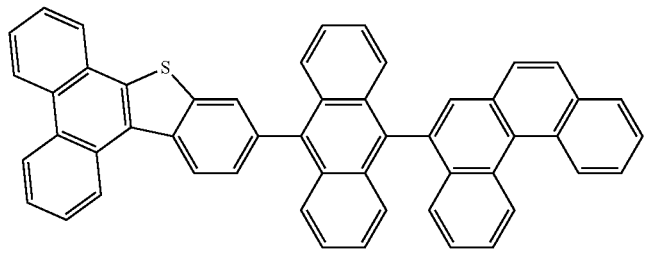
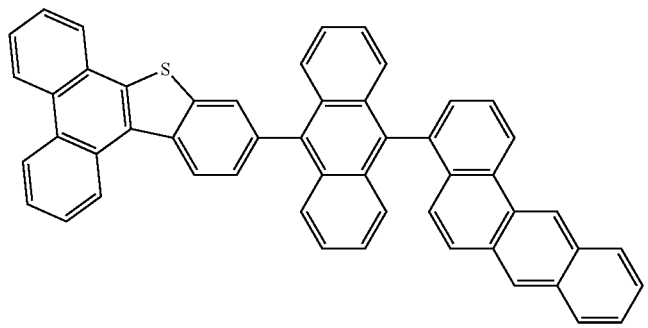
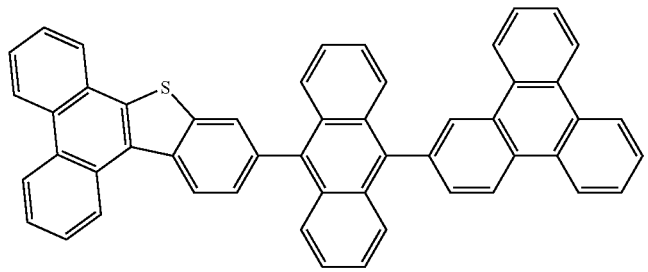

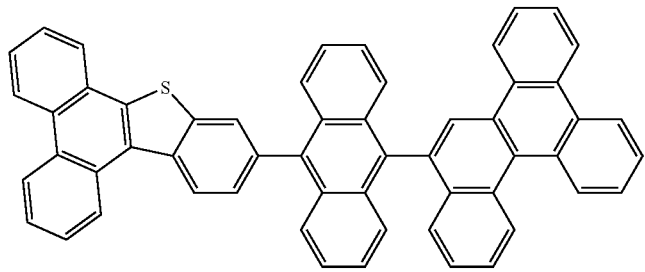
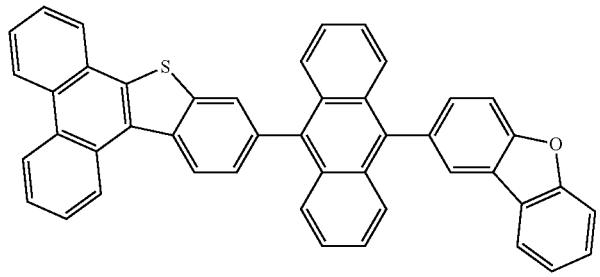
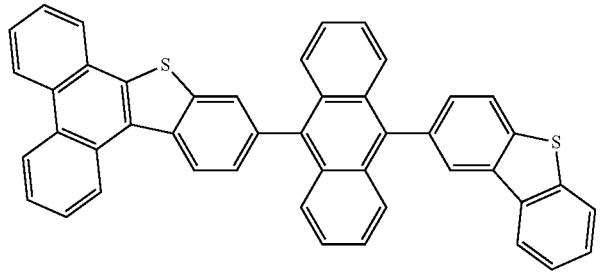
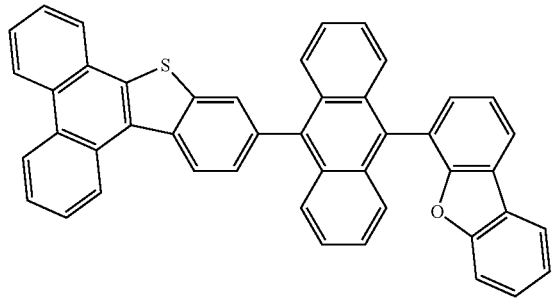
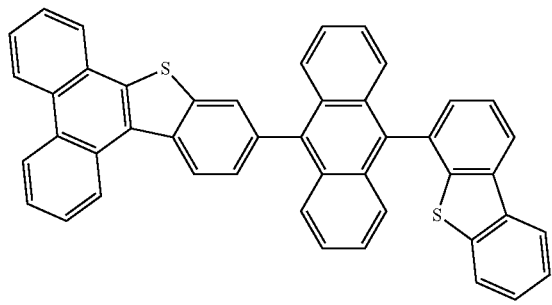
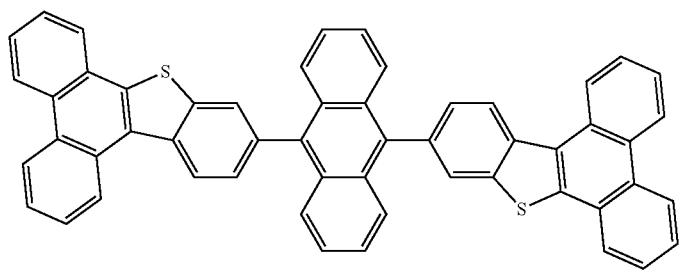

-continued
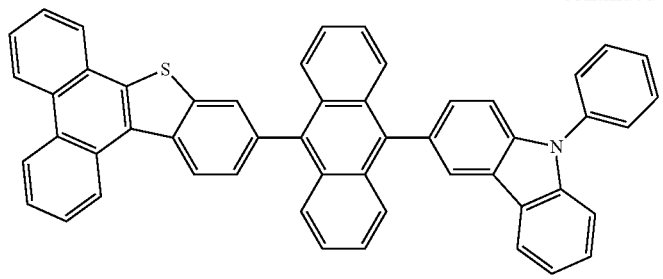
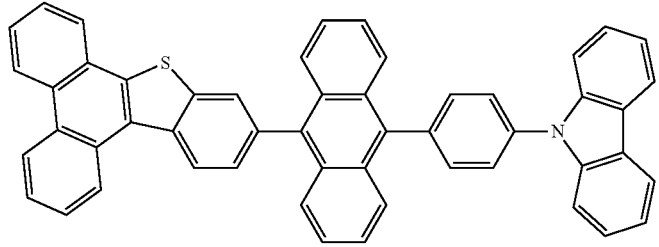
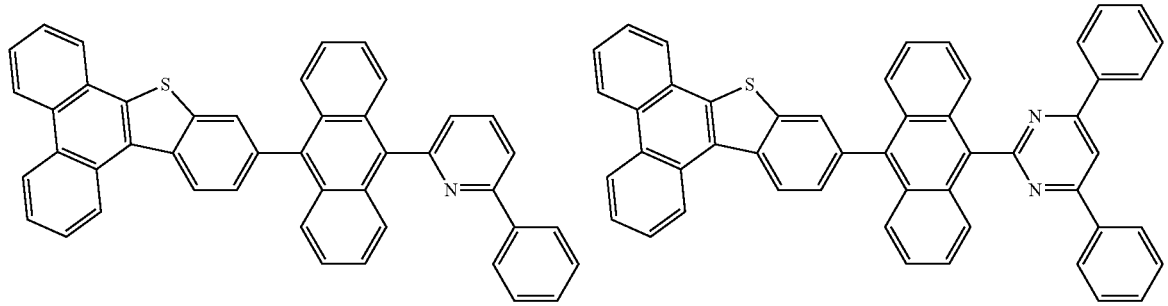
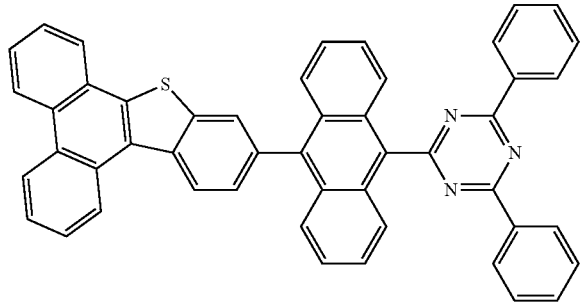
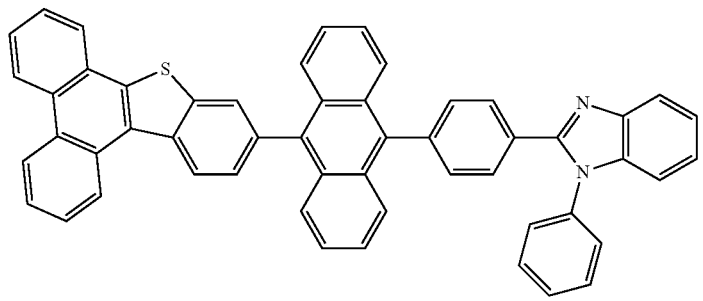
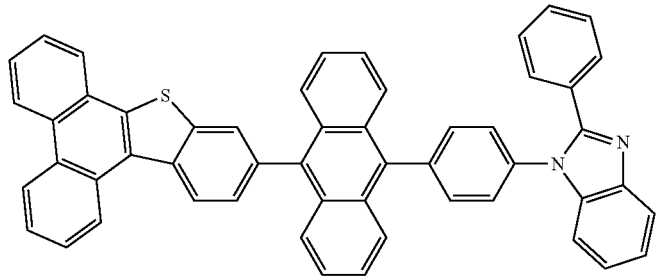

-continued
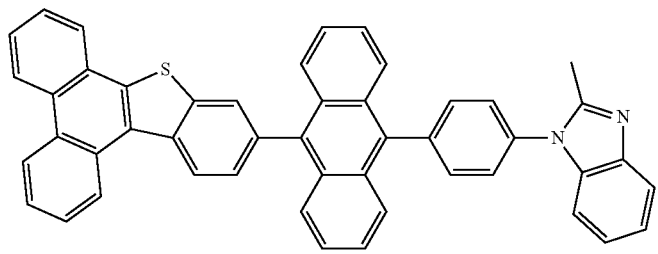
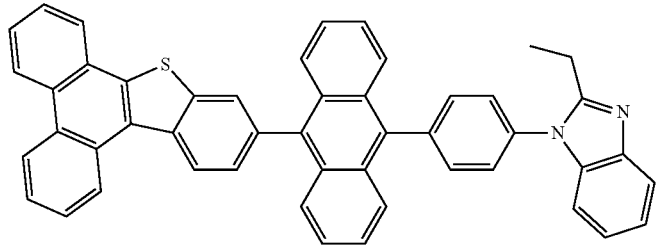
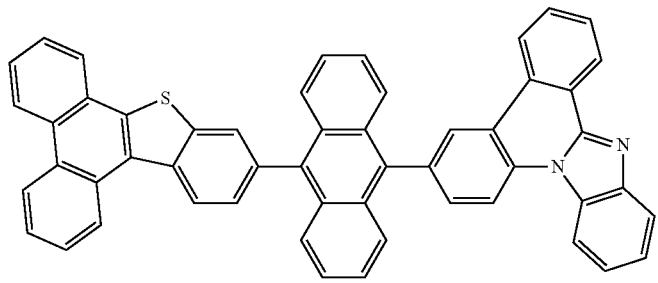
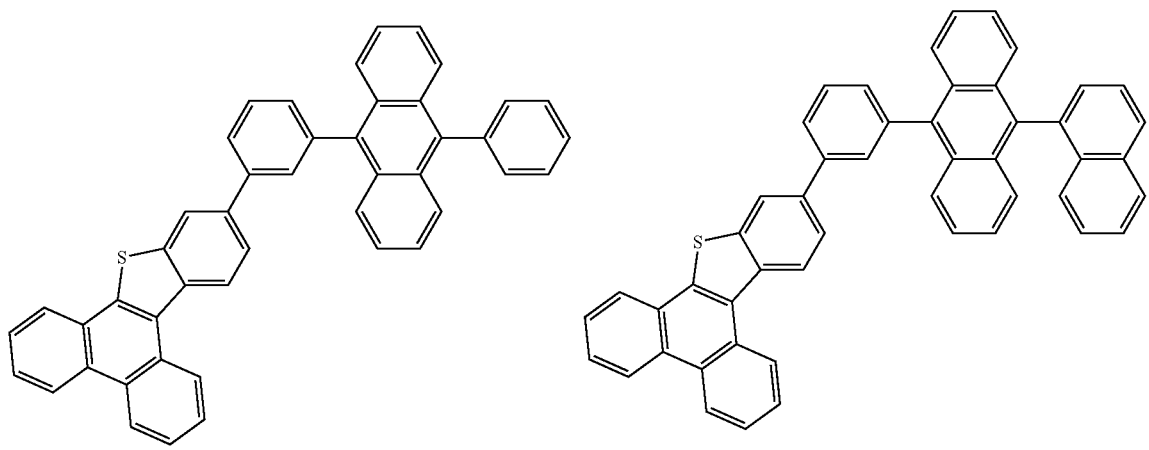
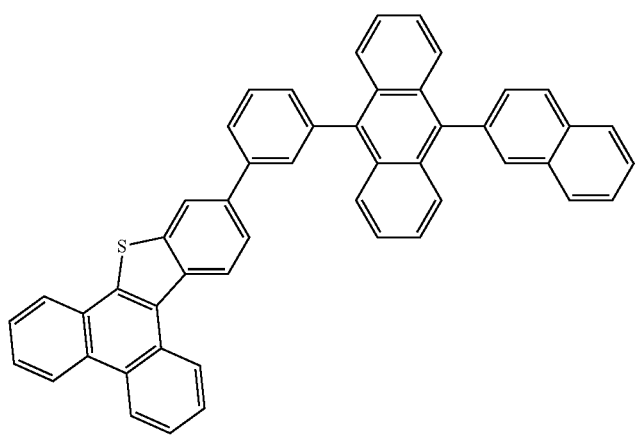

-continued
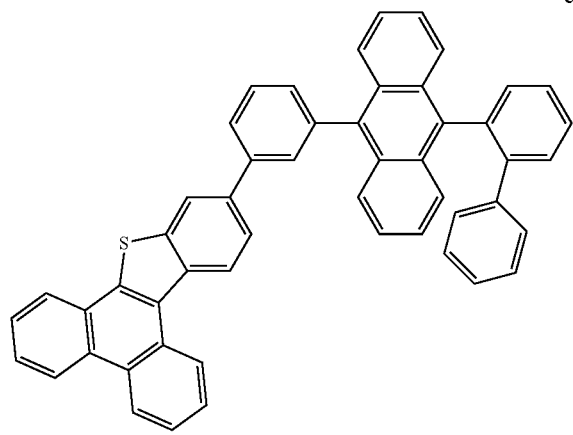
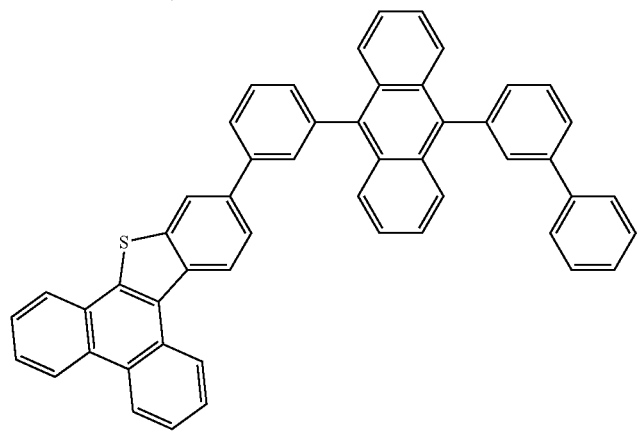
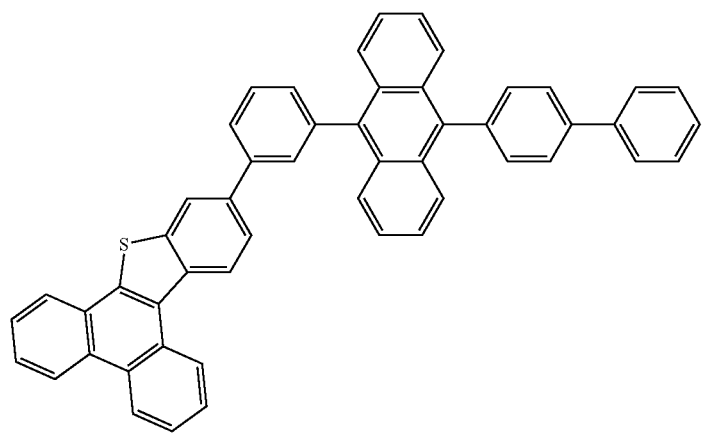
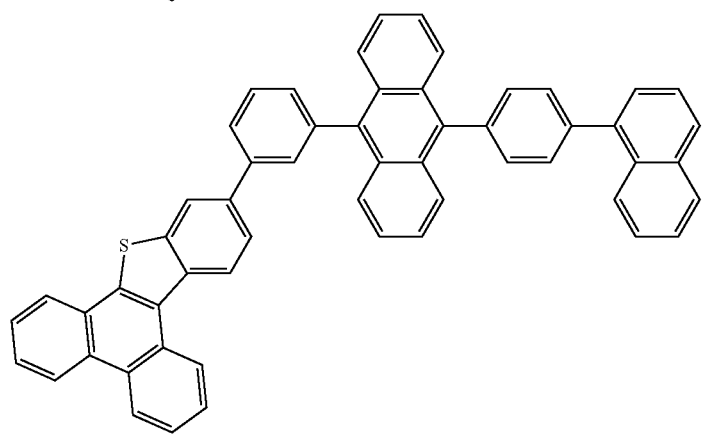

-continued
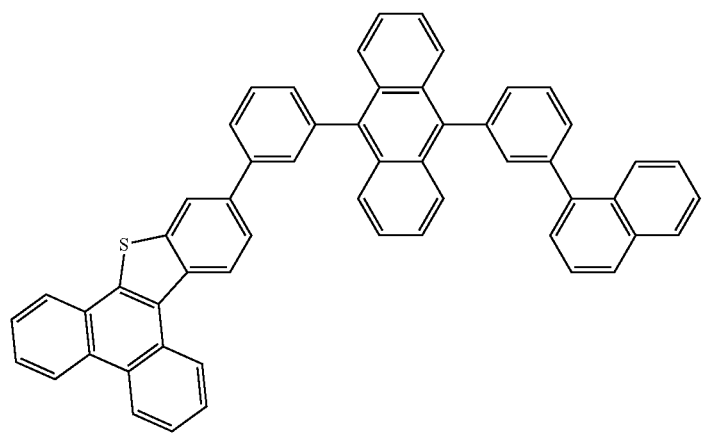
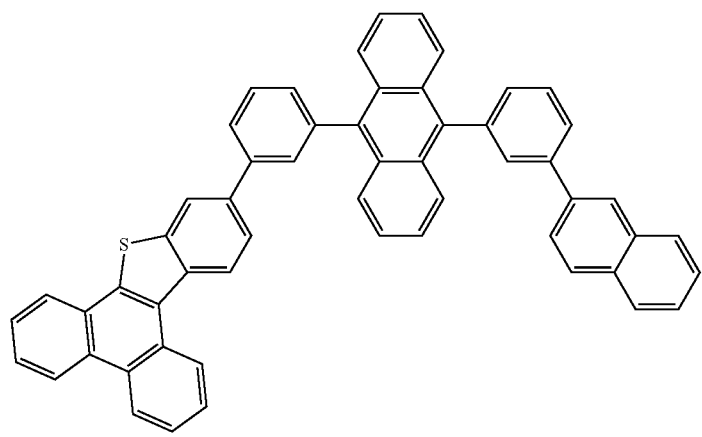
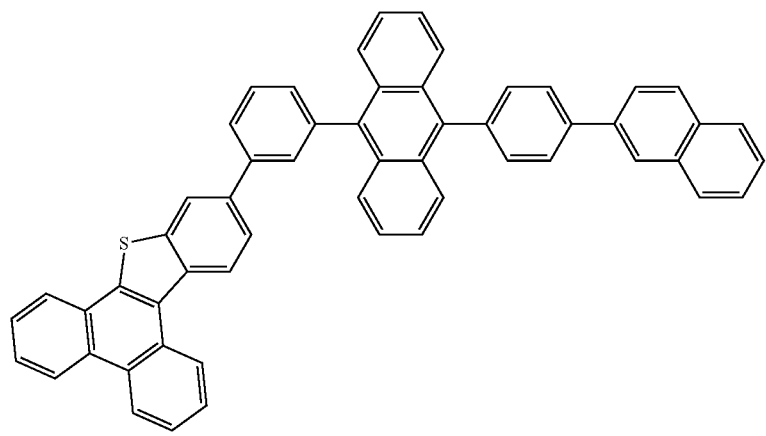
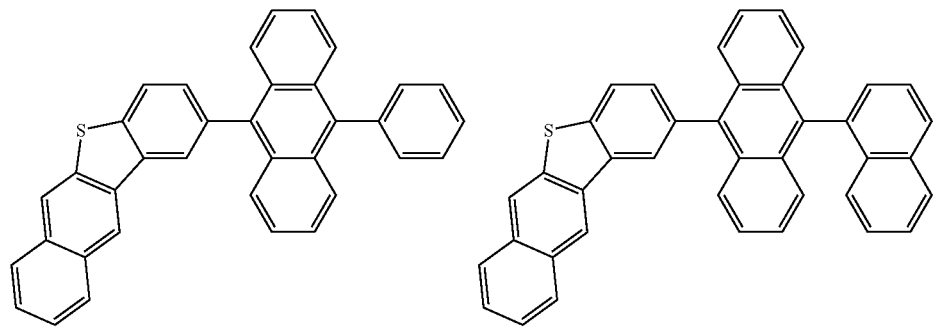

-continued
171
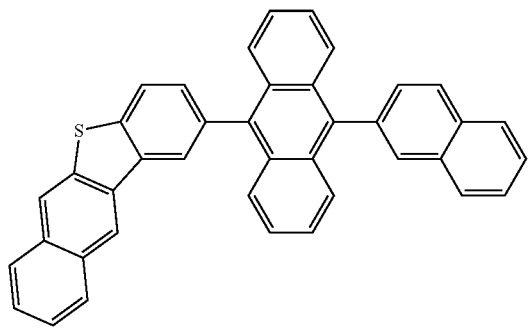
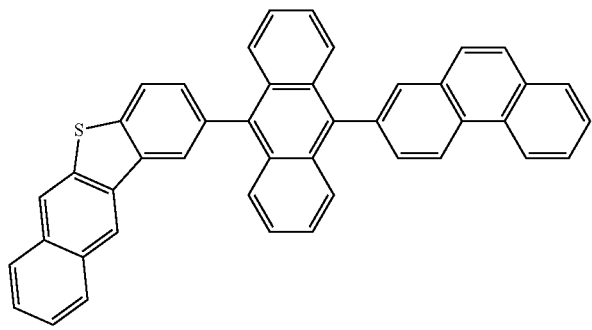
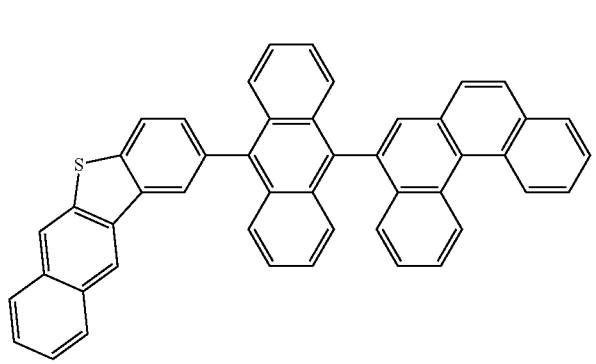
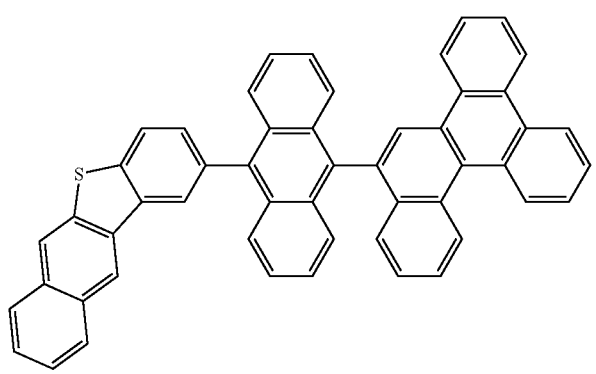
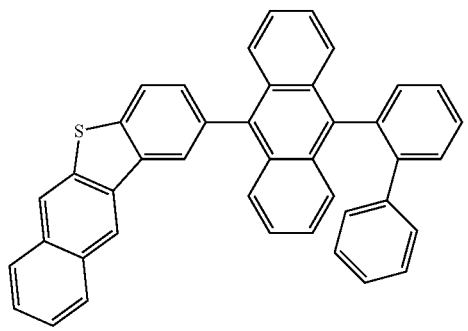
172
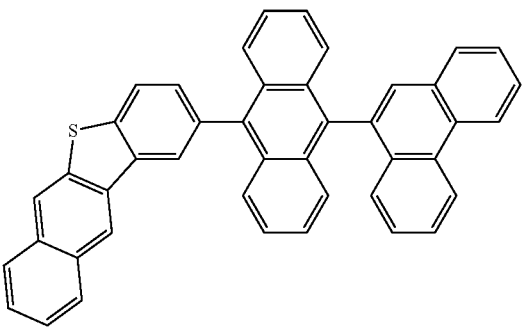
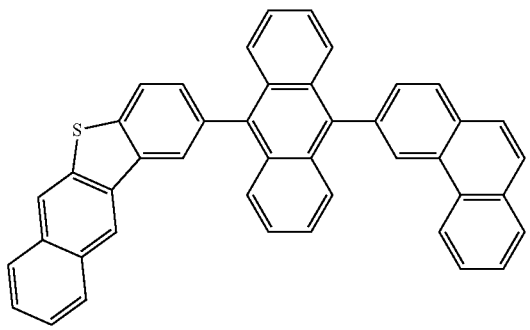
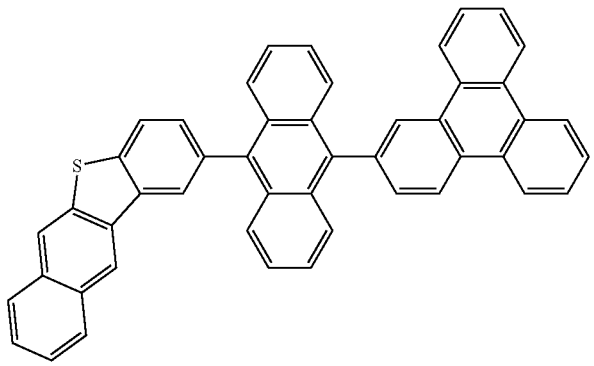
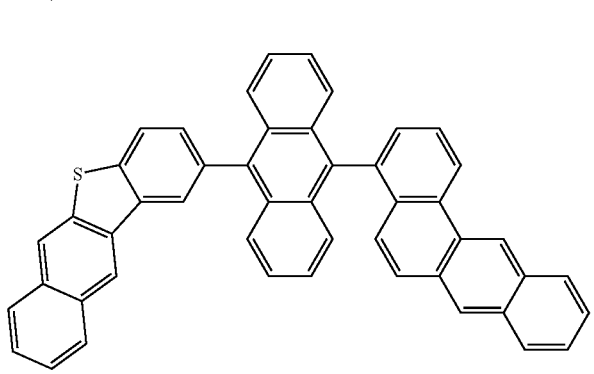
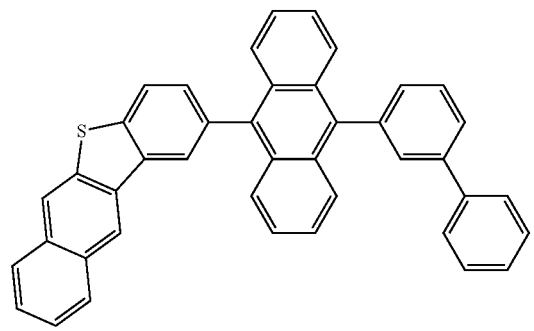

-continued
| 173 | 174 |
|---|---|
| 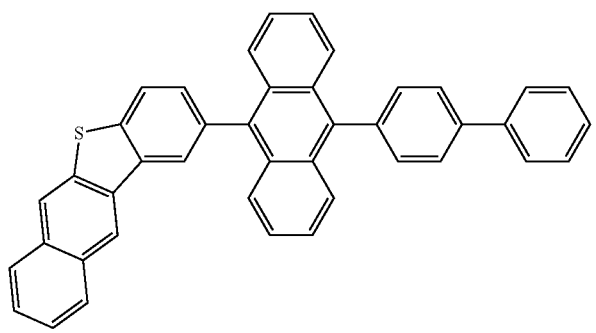 | 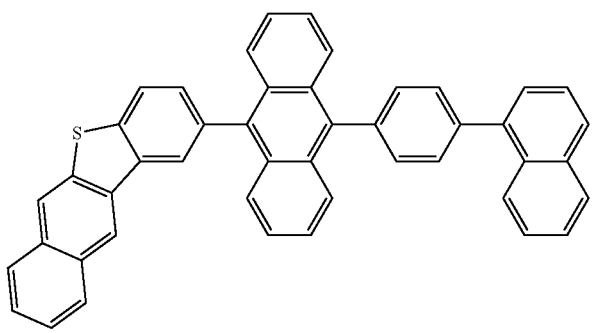 |
| 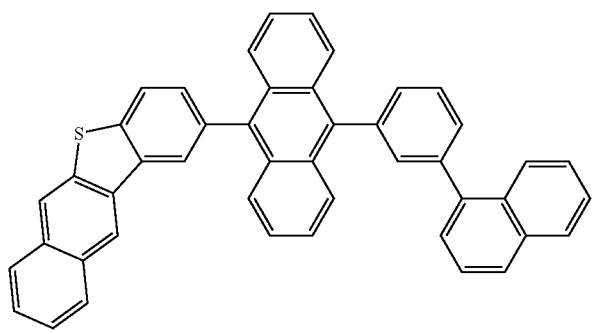 | 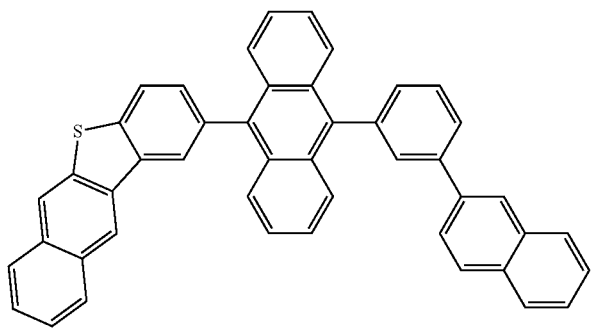 |
| 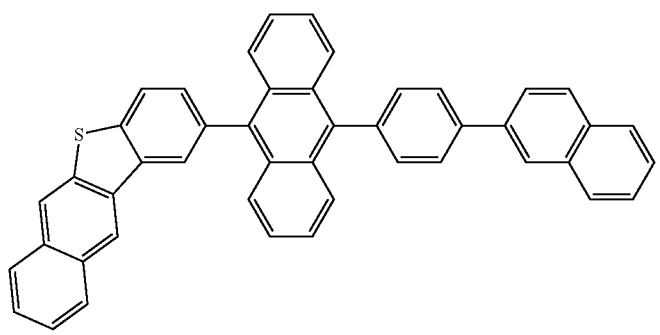 | |
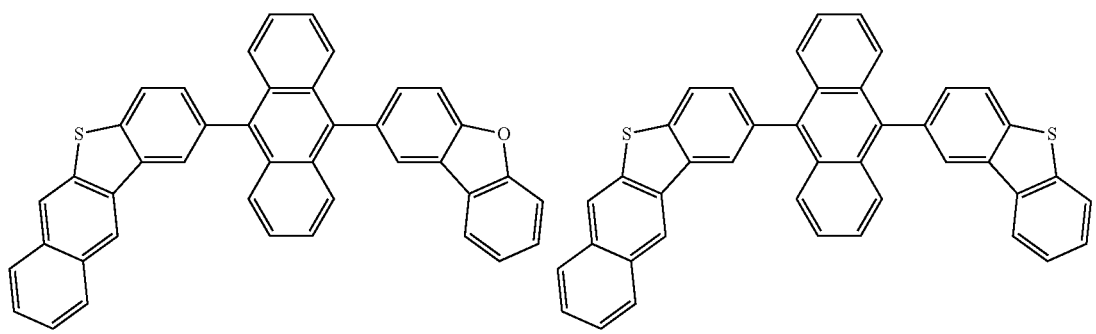
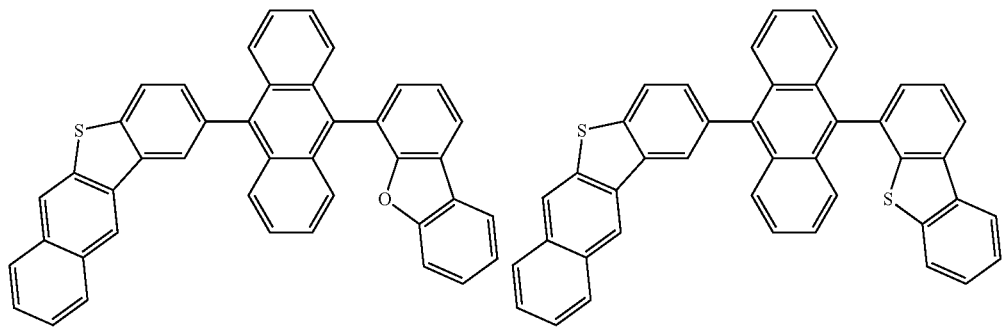

-continued
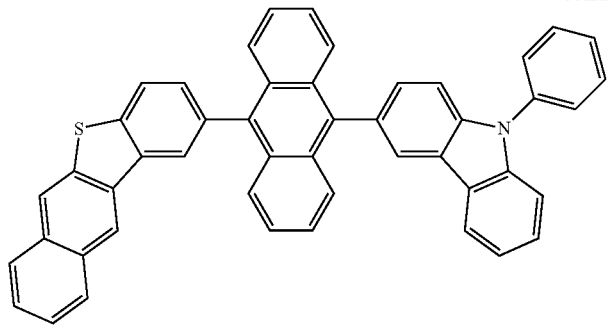

-continued
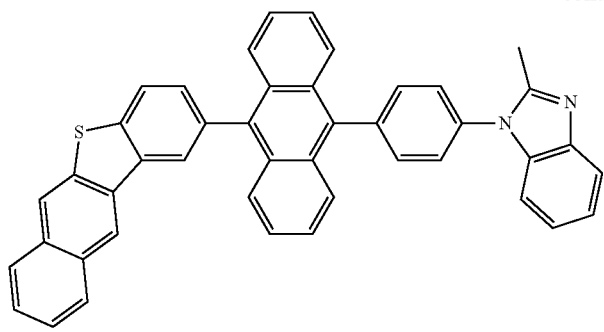
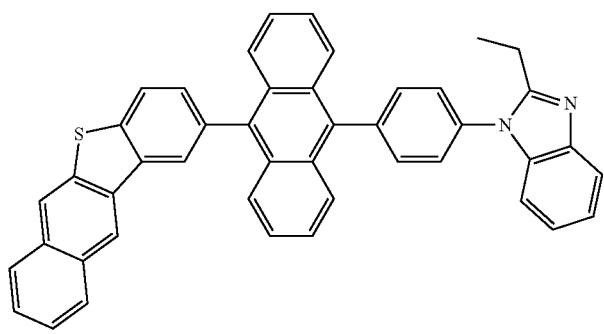
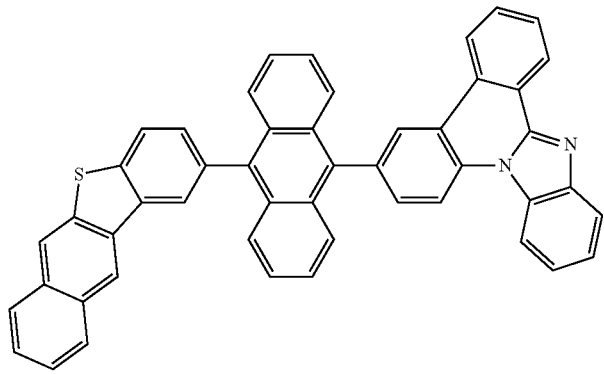 [SMILES: c1ccc2cc3c(cc2c1)sc1ccc(-c2c4ccccc4c(-c4ccc5c(c4)c4ccccc4c4nc6ccccc6n54)c4ccccc24)cc13]
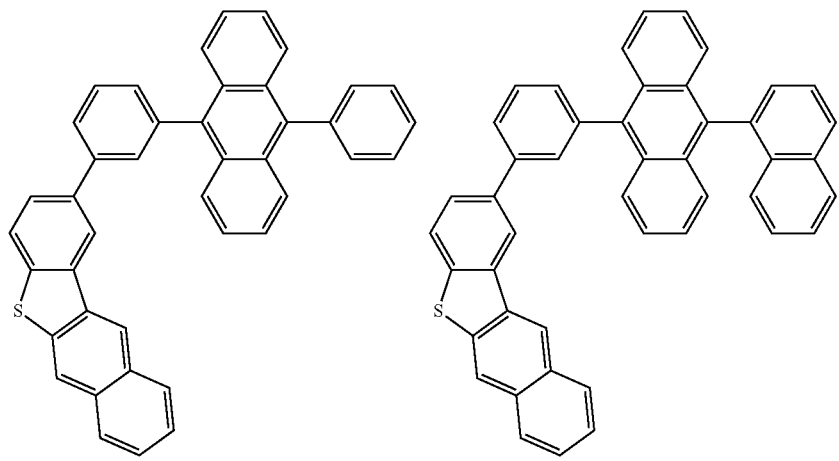

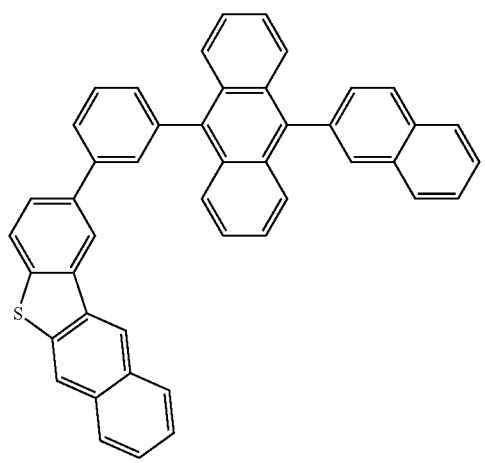
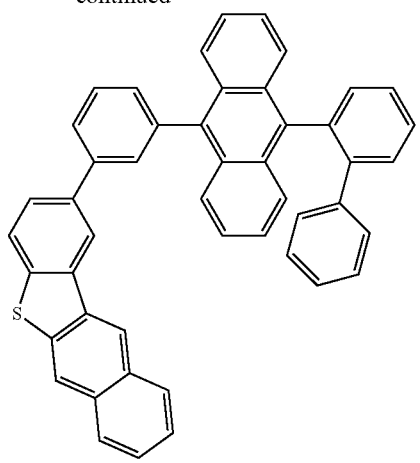
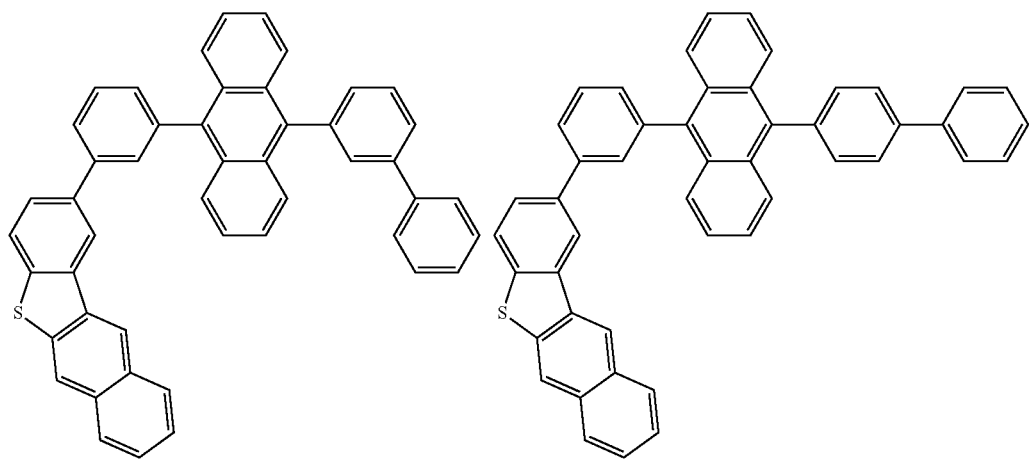
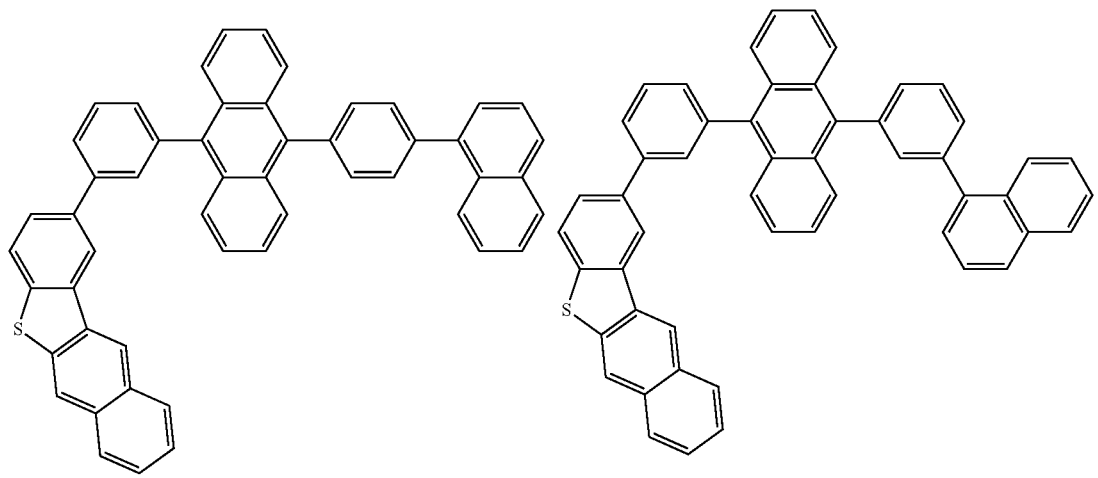

-continued
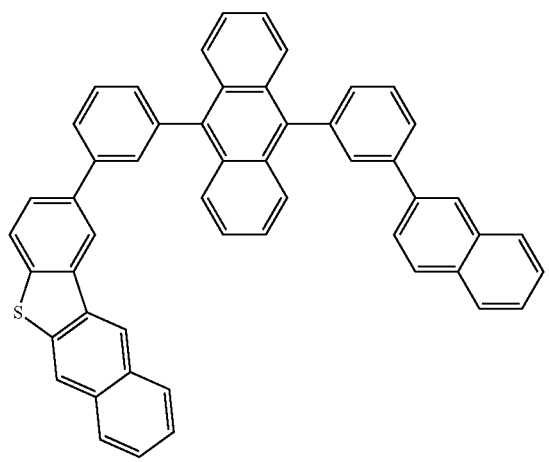
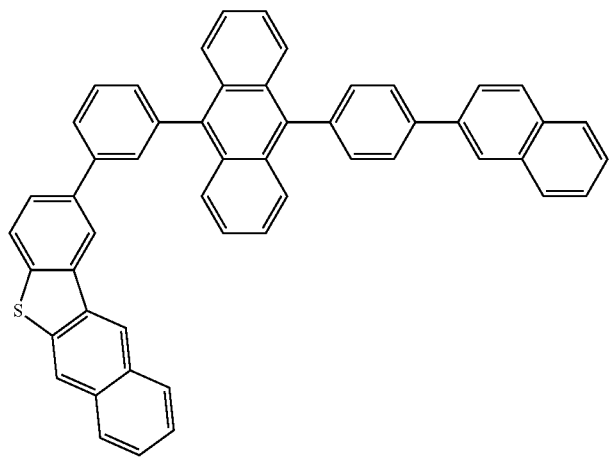
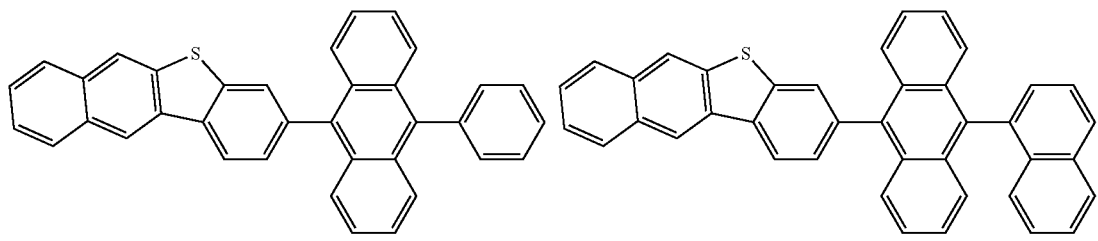
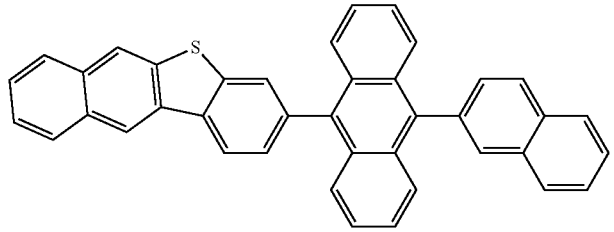
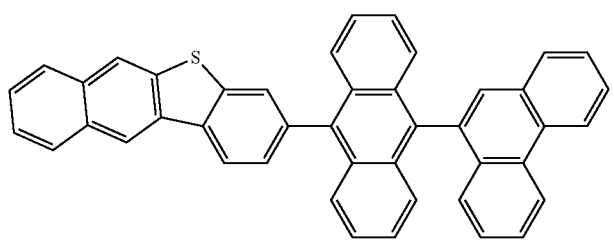

-continued
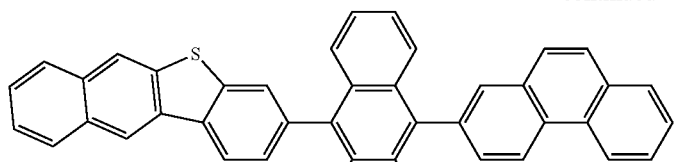
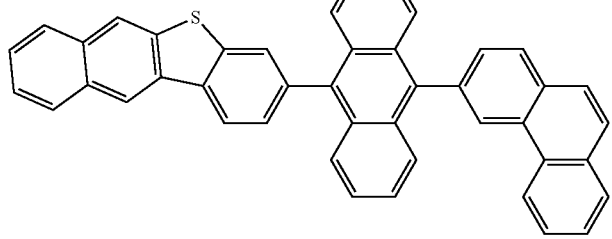
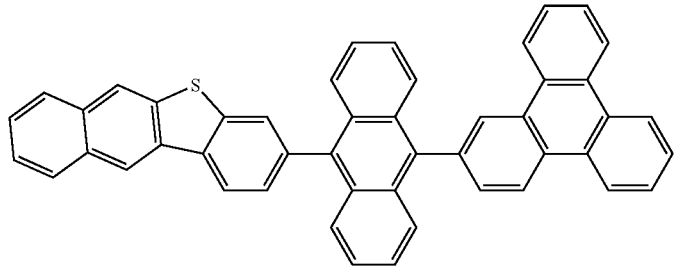
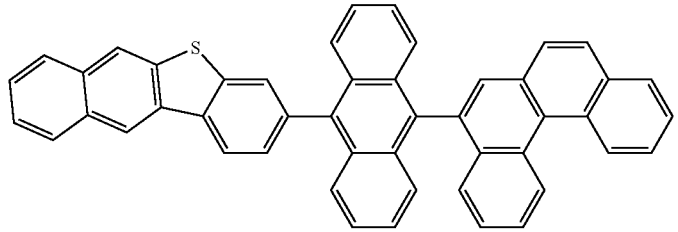
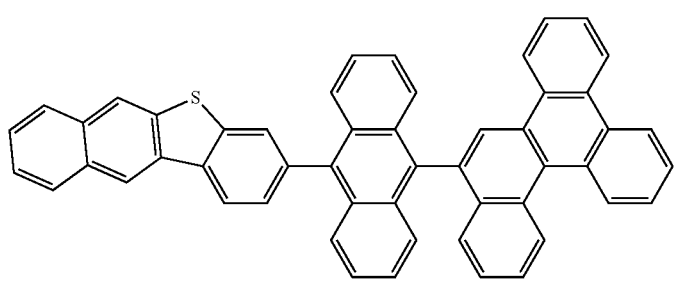
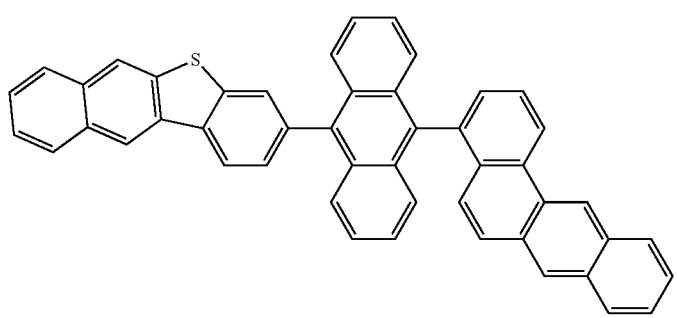

-continued
185
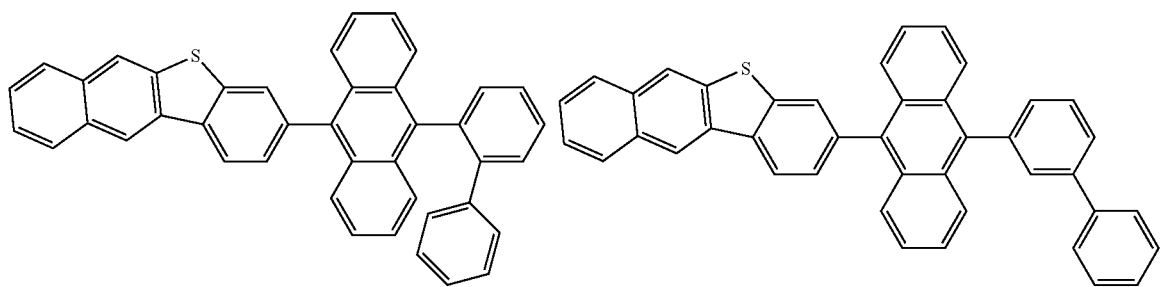
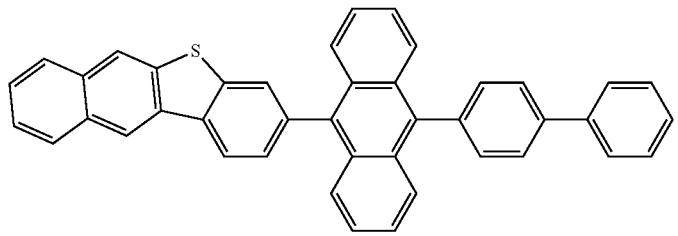
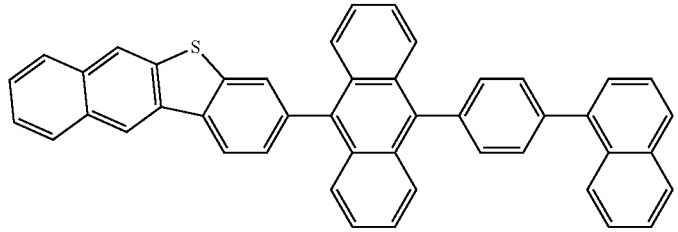
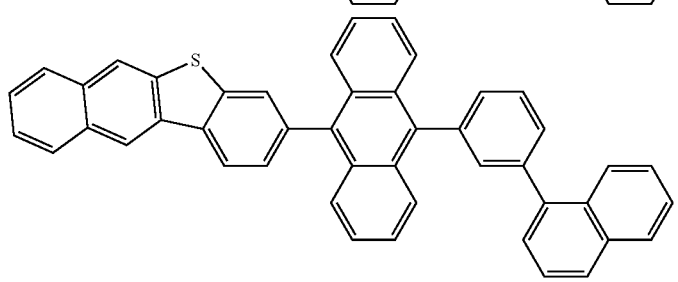
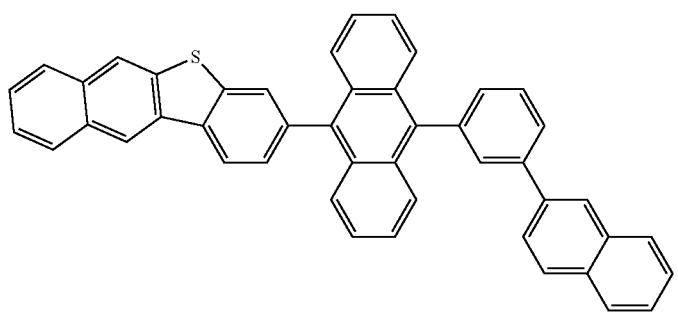
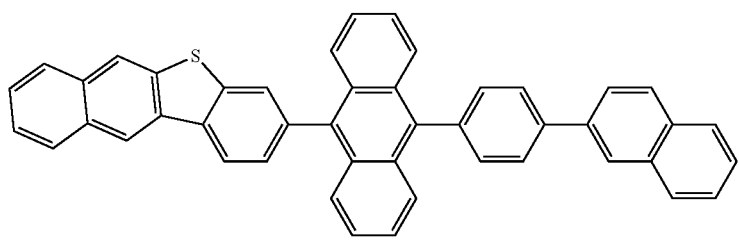
186

-continued
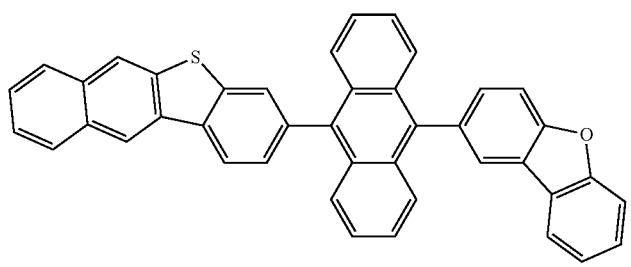
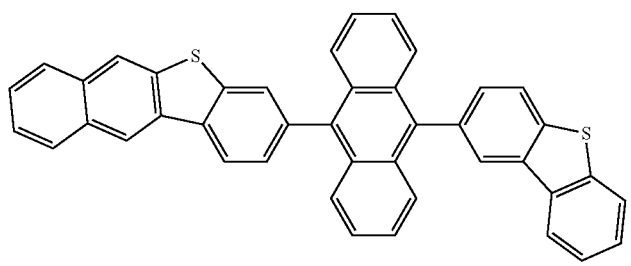
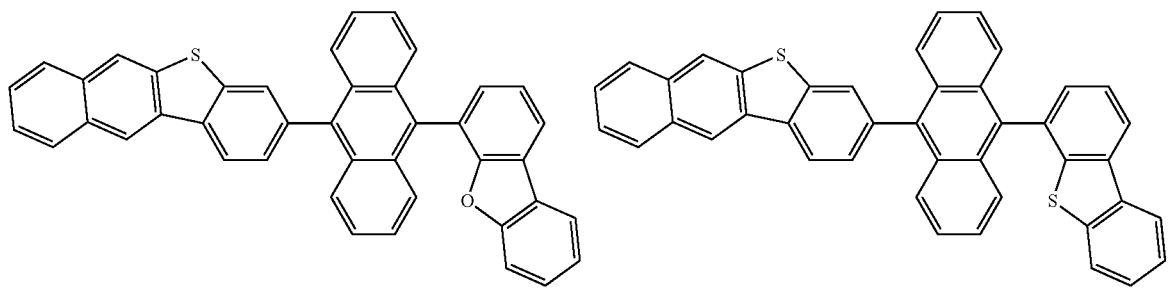
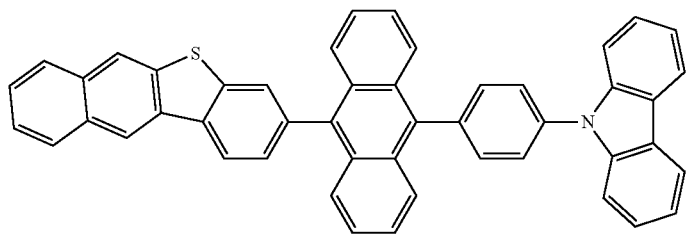
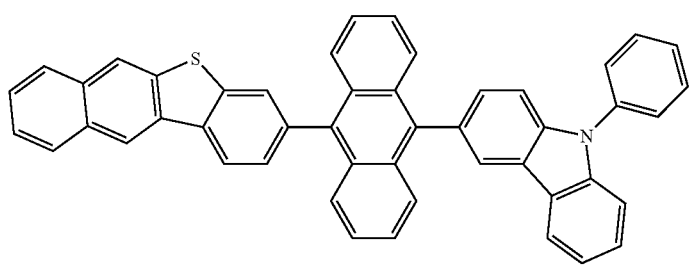
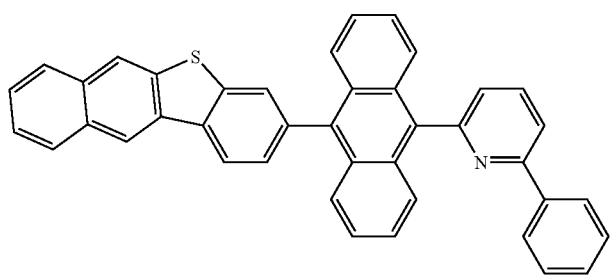

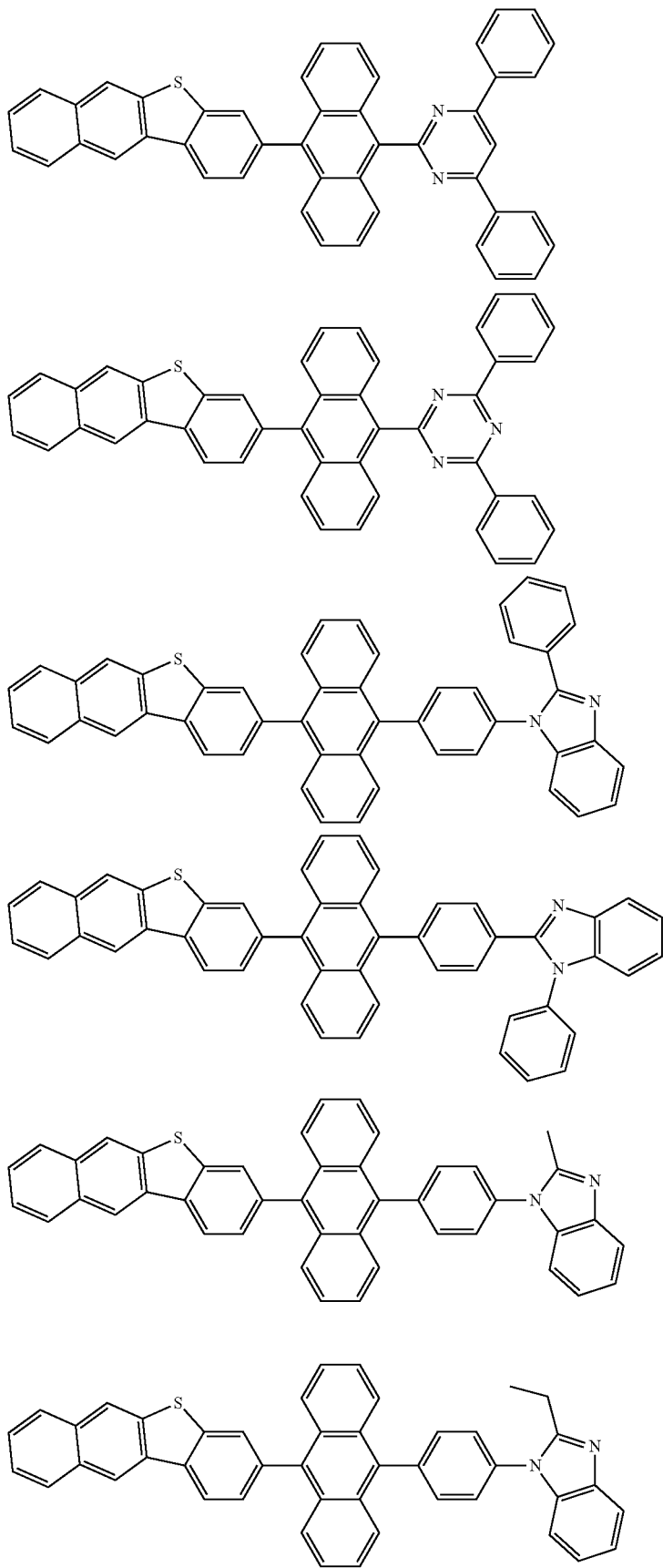

-continued
191
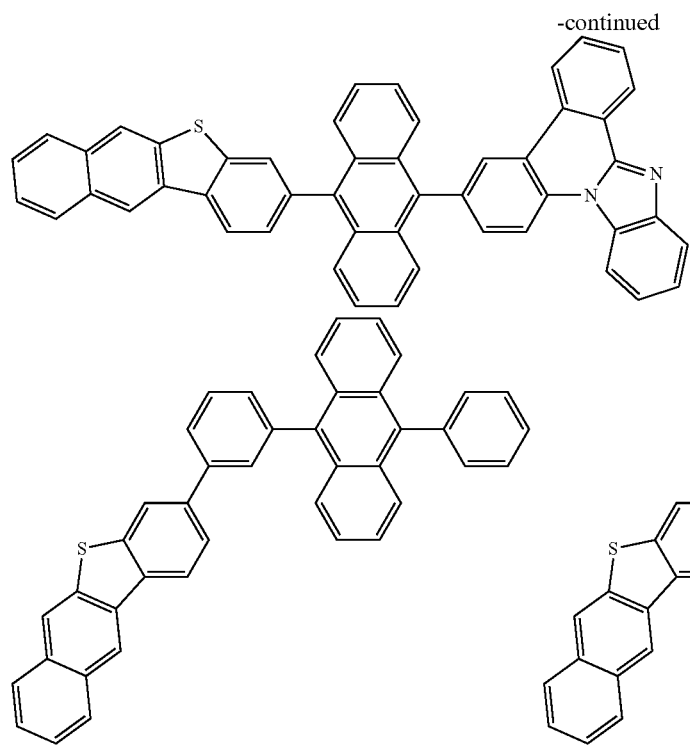
192
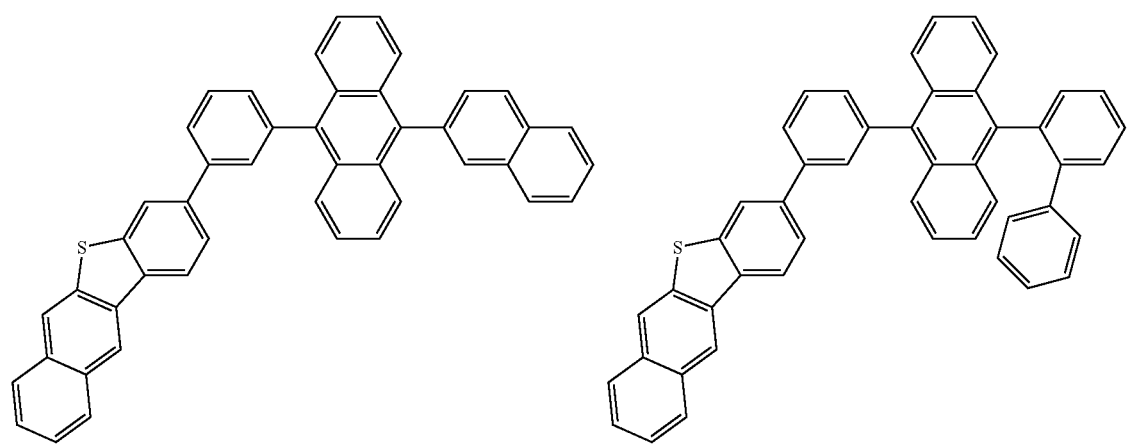
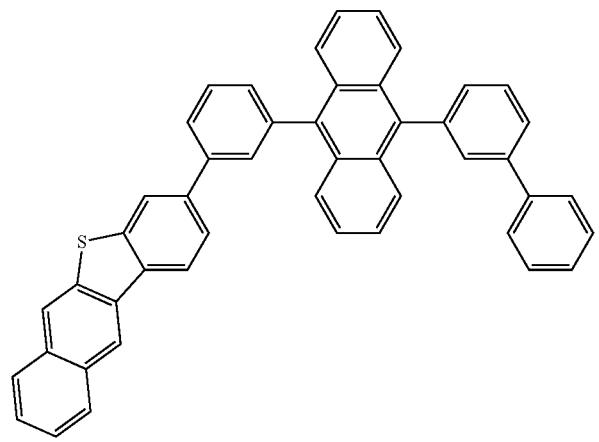

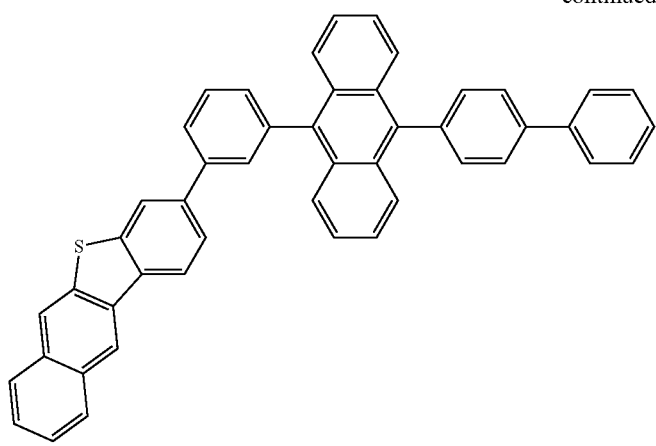
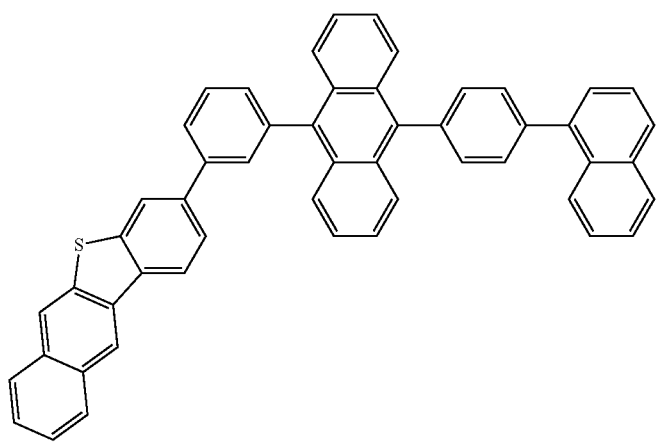
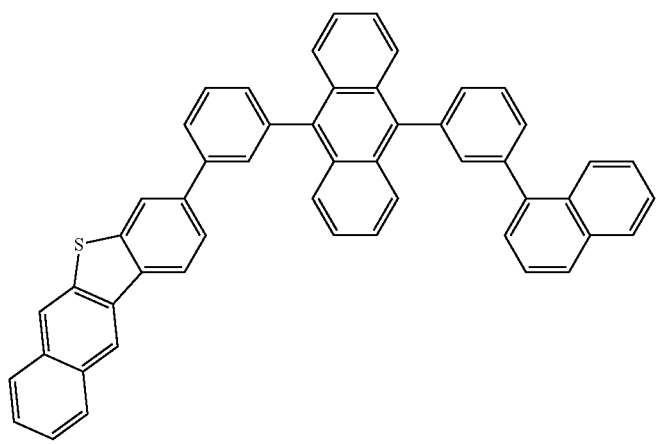

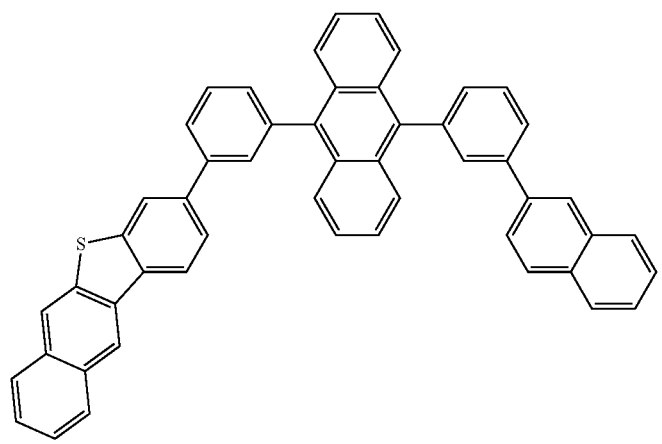
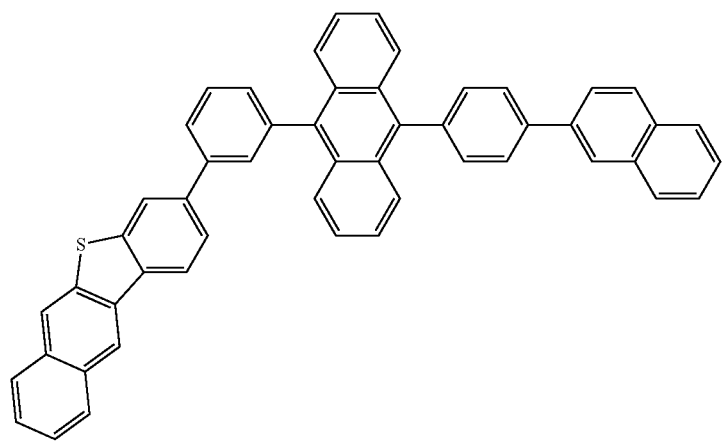
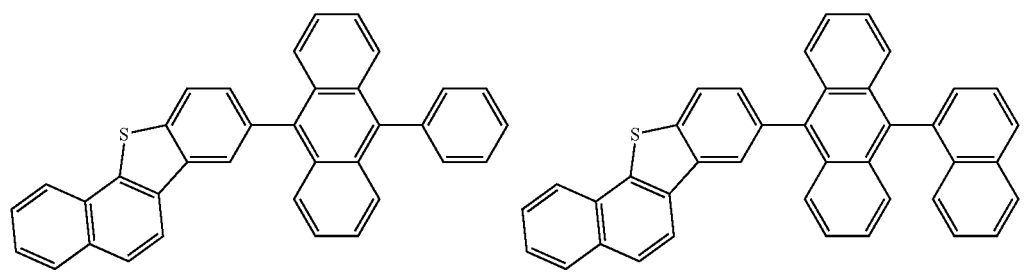
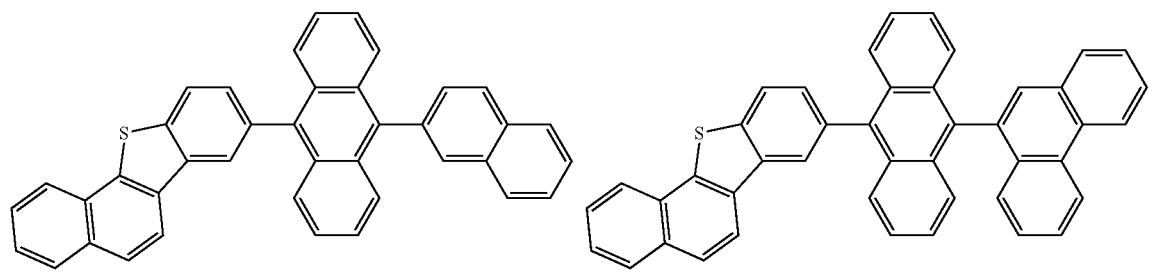
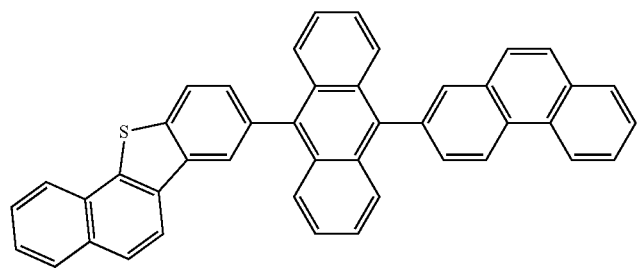

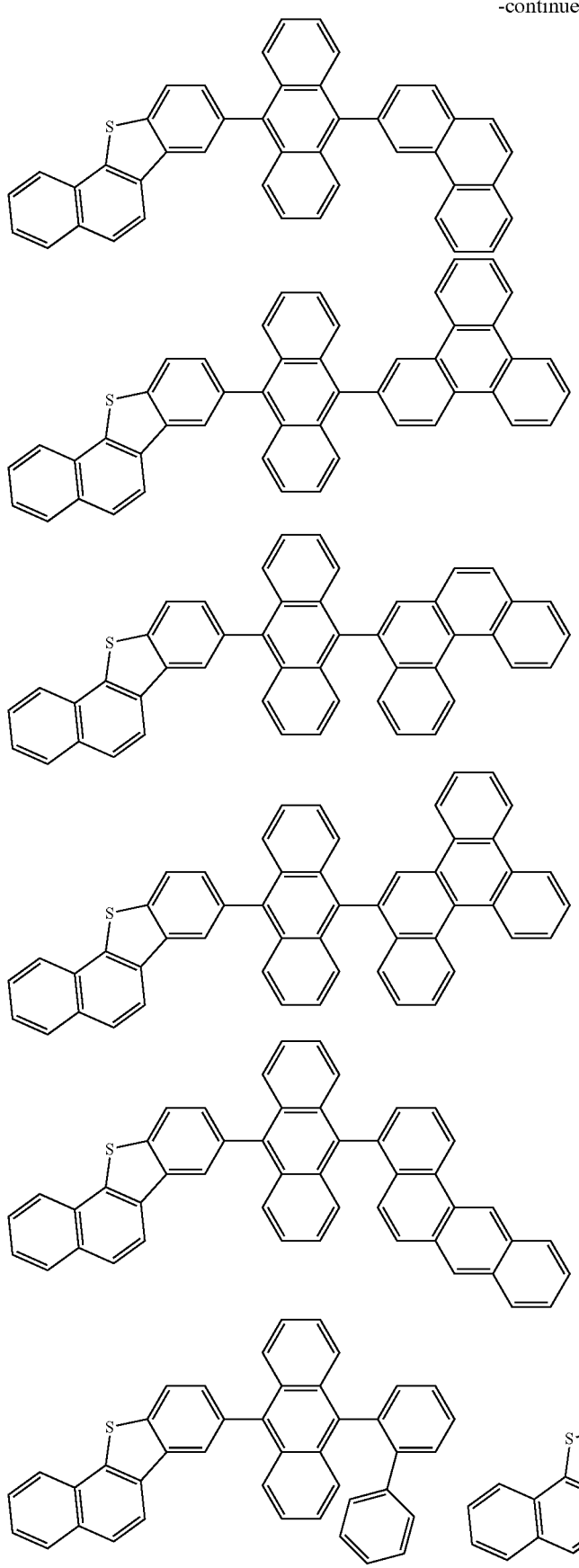

-continued
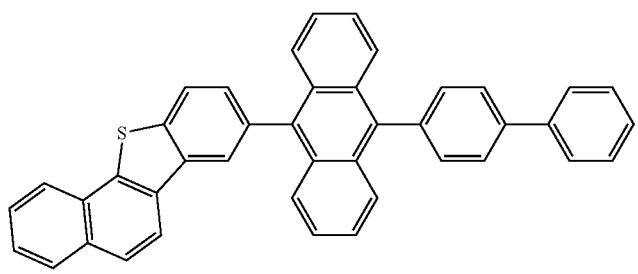
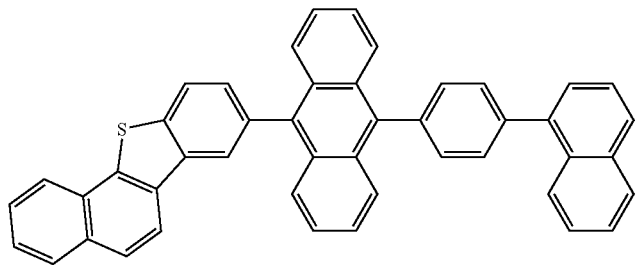
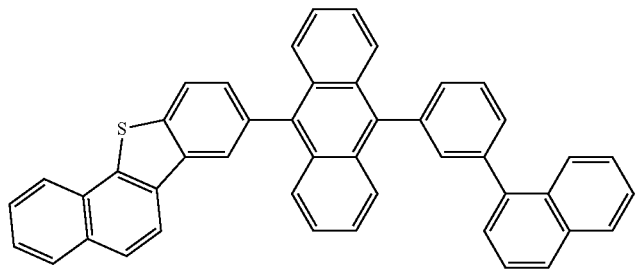
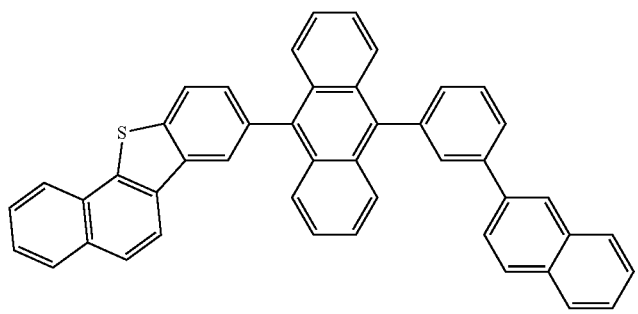
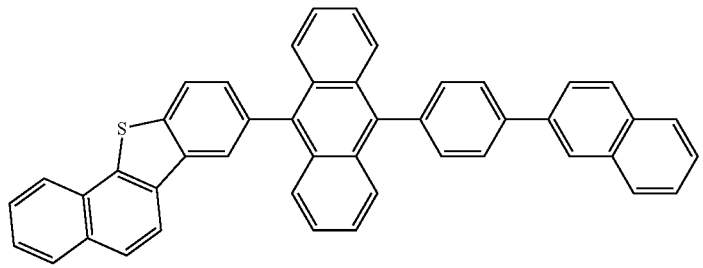
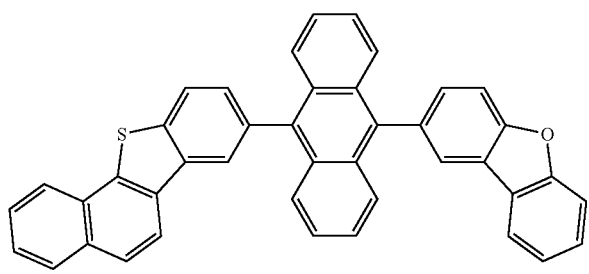

201 202
-continued
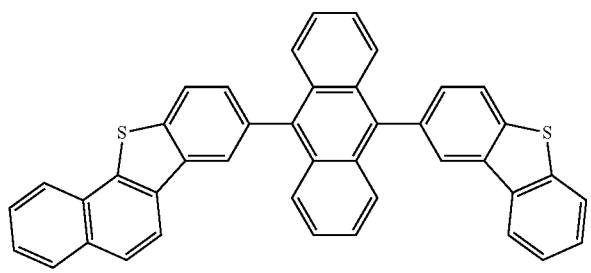
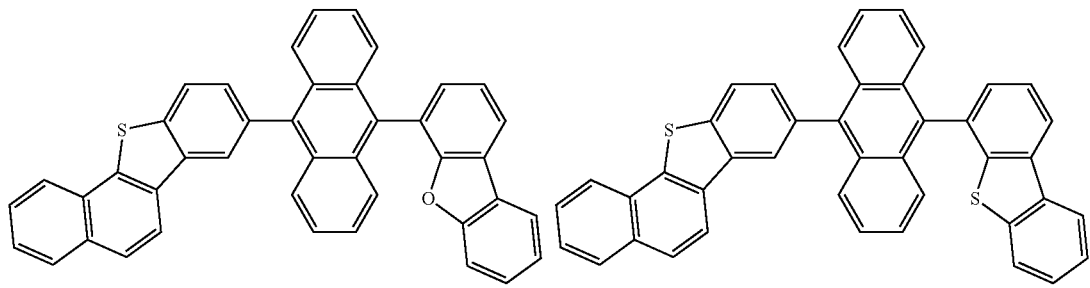
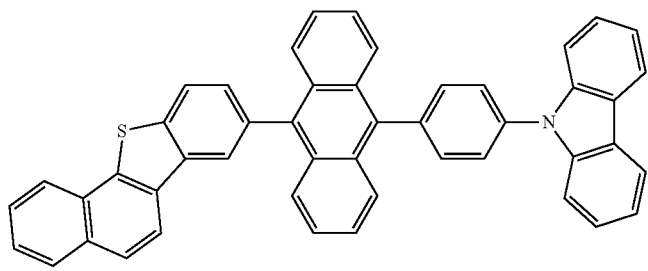
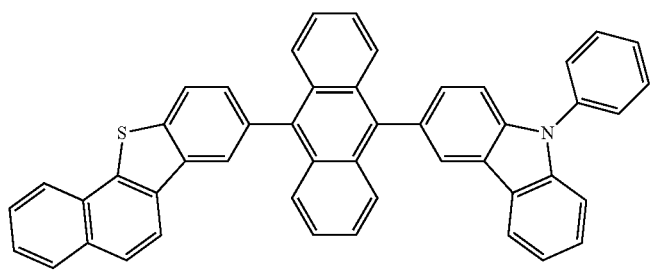
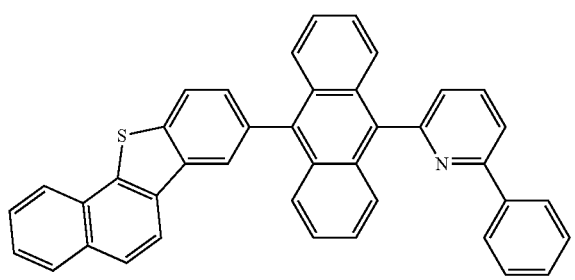
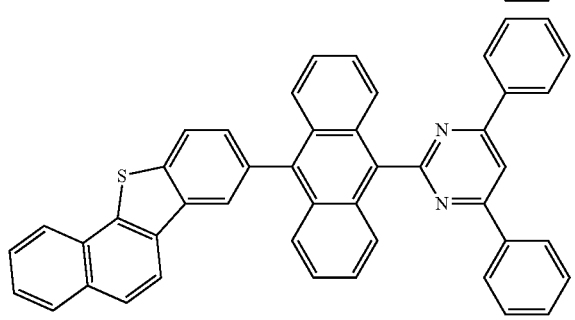

-continued
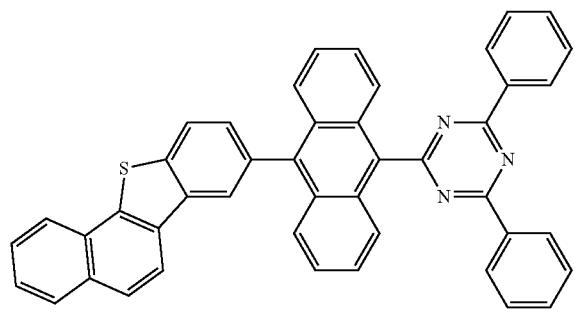
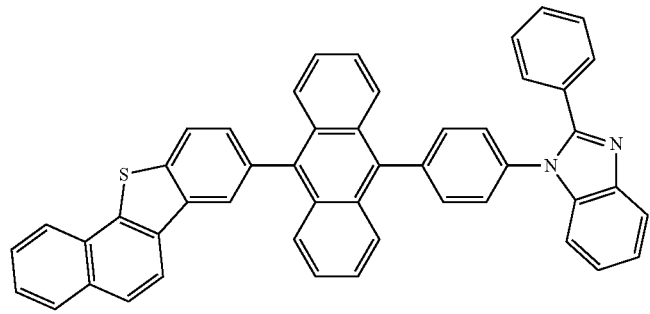
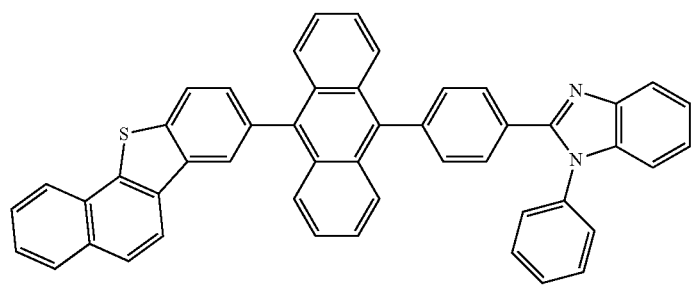
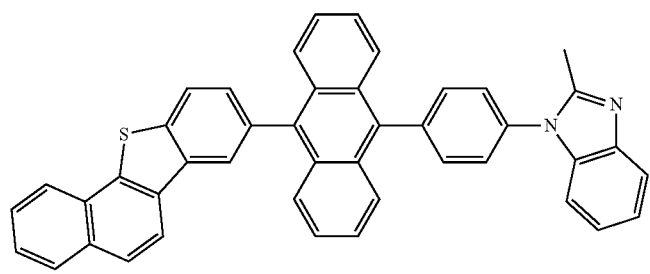
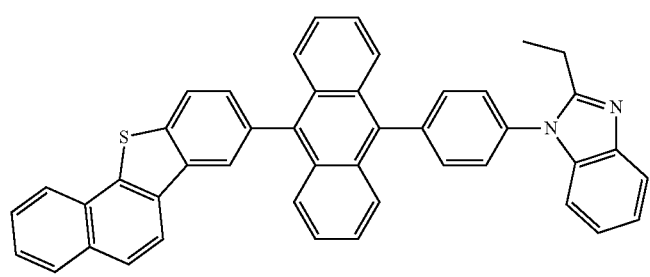

-continued
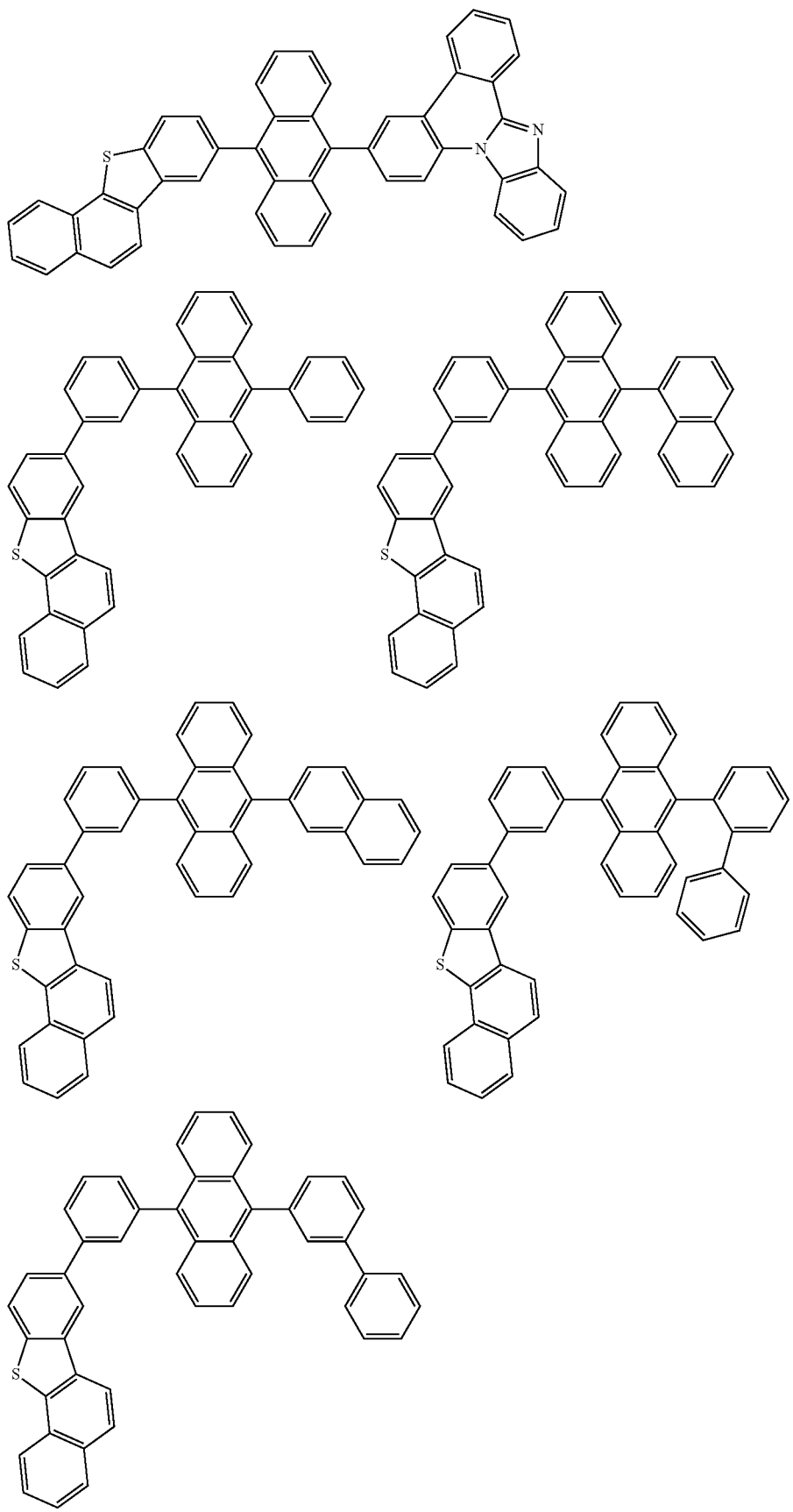

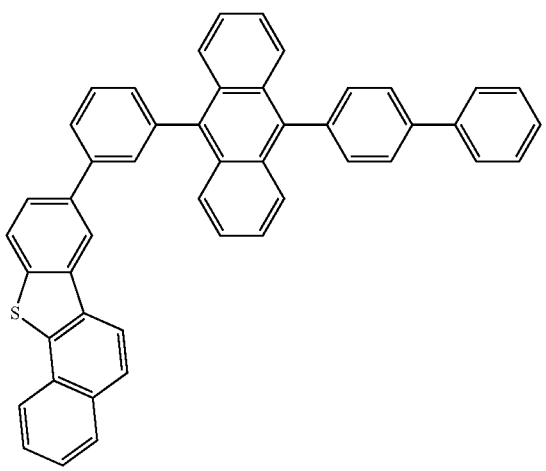
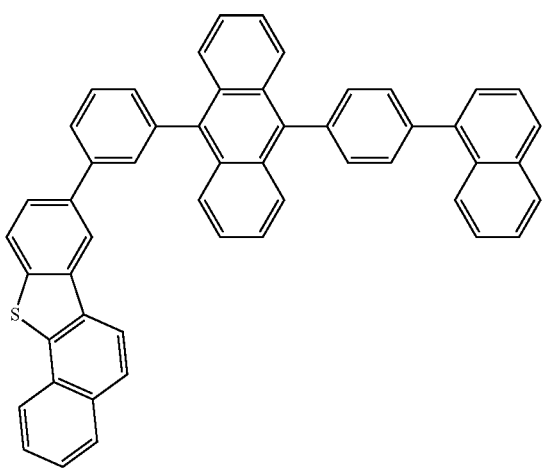
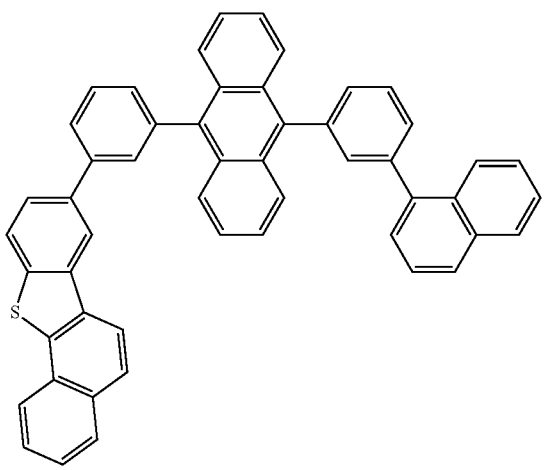

-continued
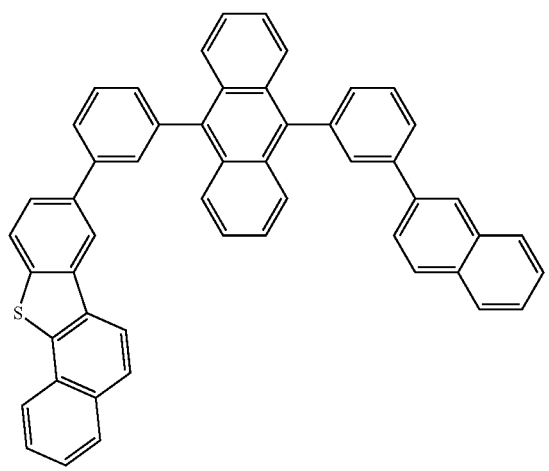
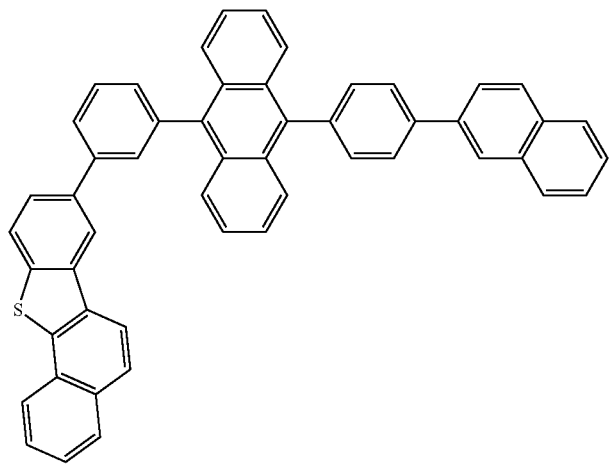
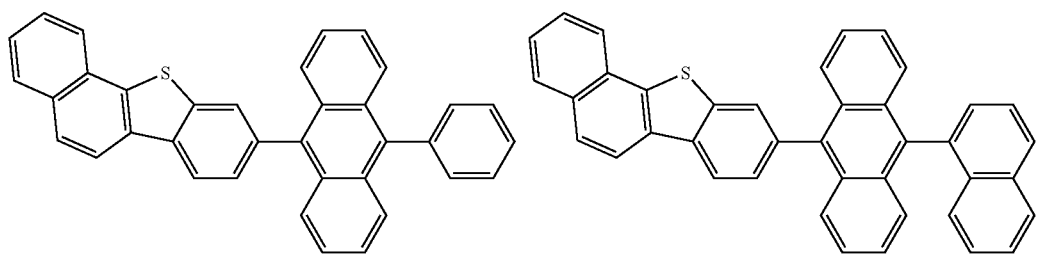
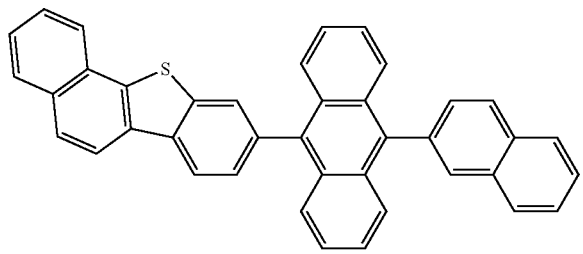
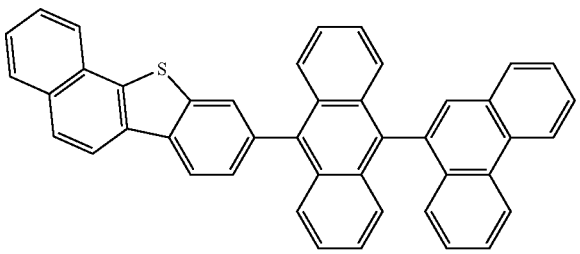
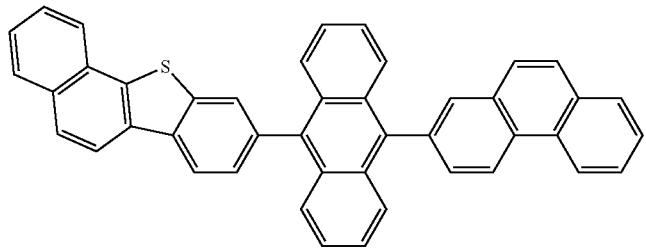

-continued
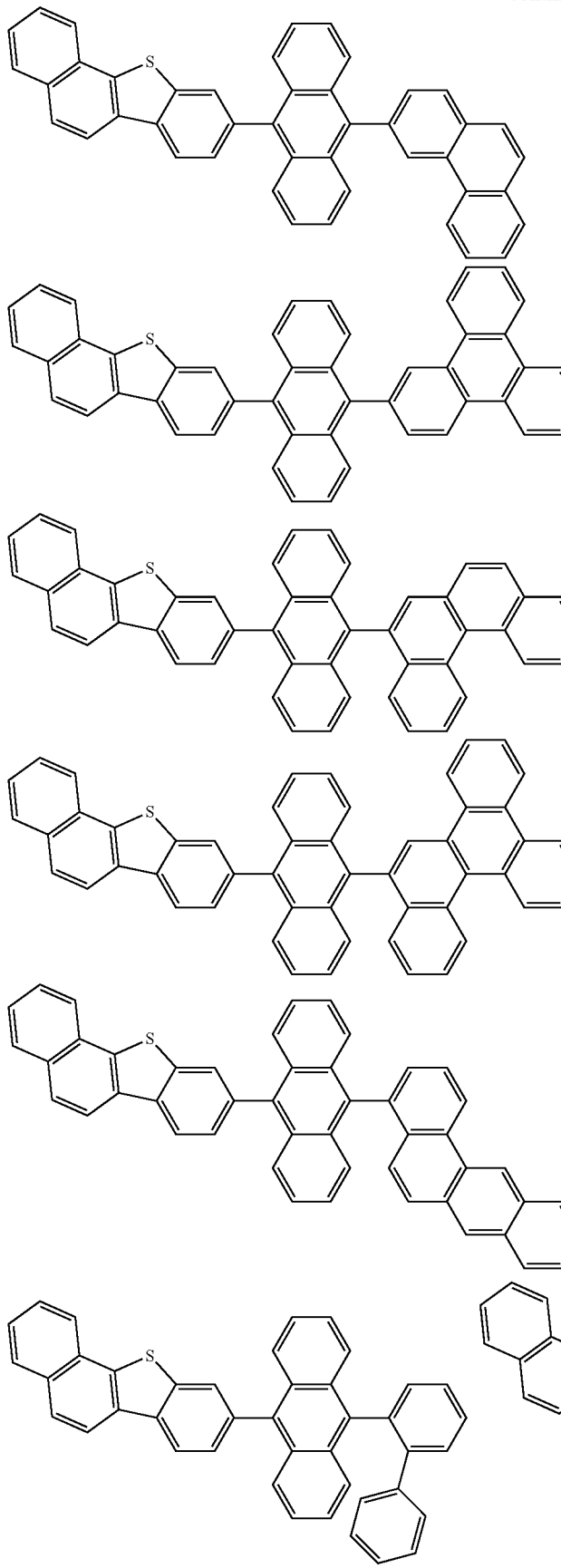

-continued
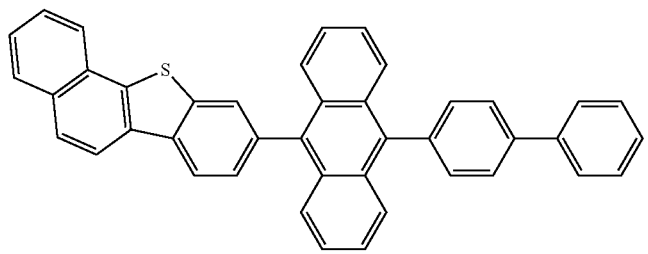
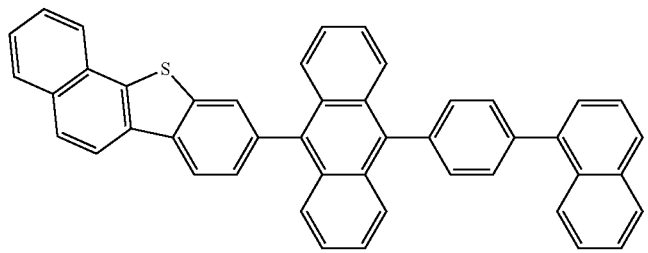
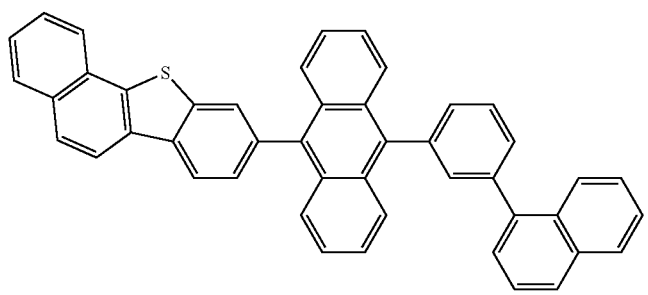
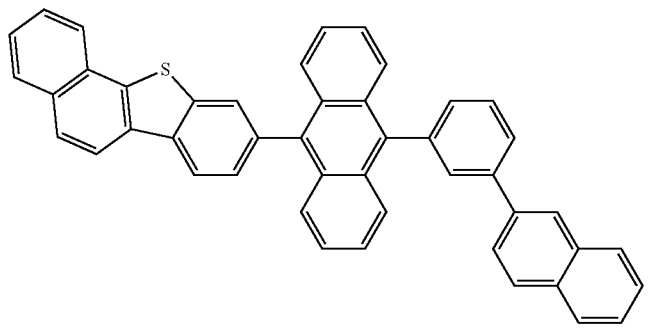
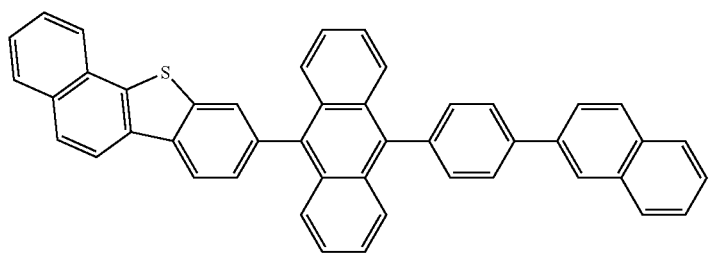
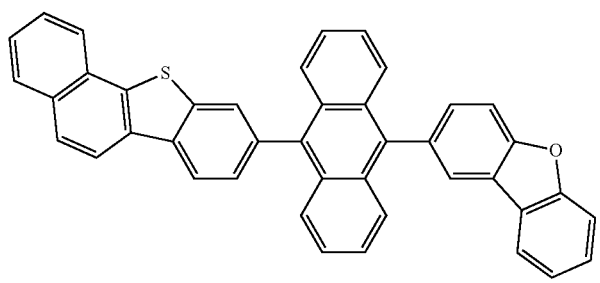

-continued
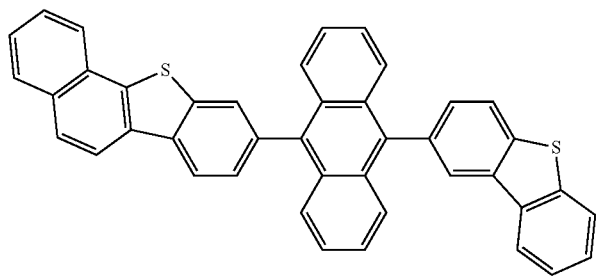
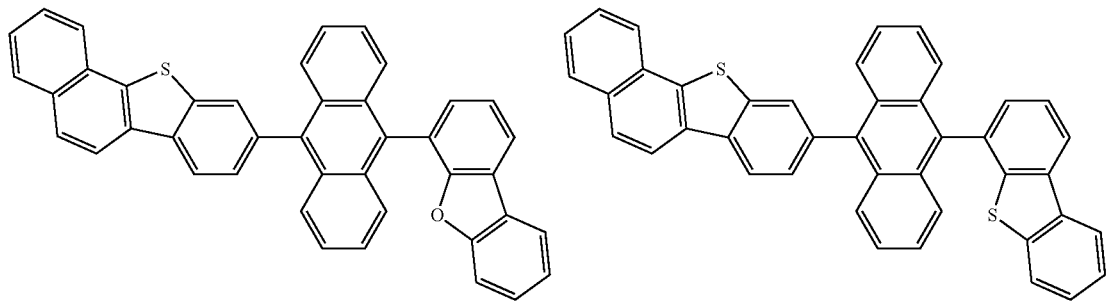
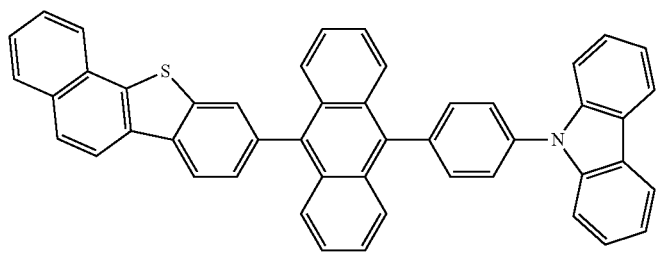
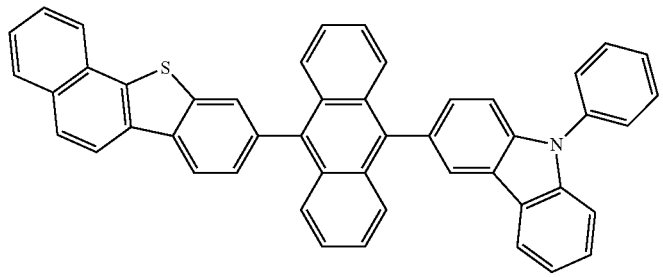
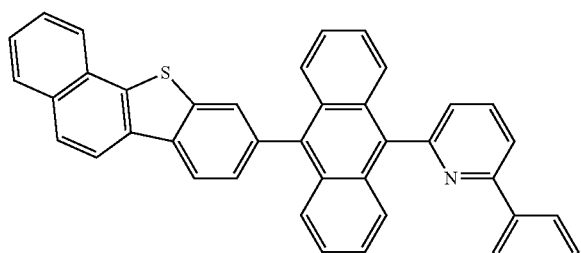
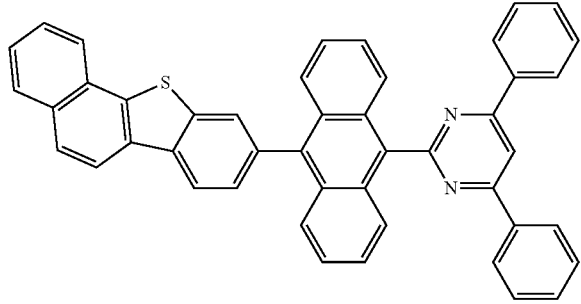

-continued
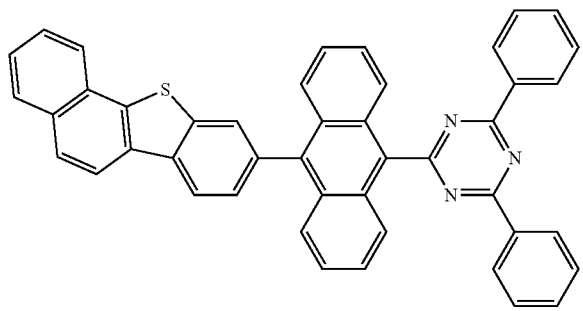
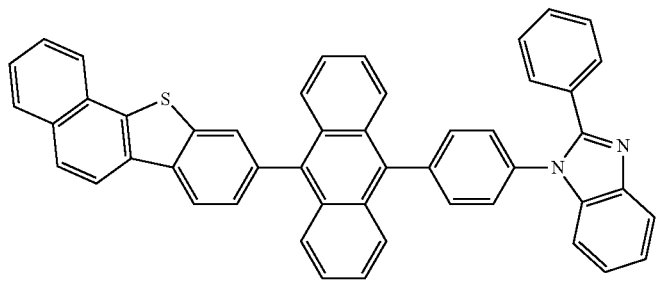
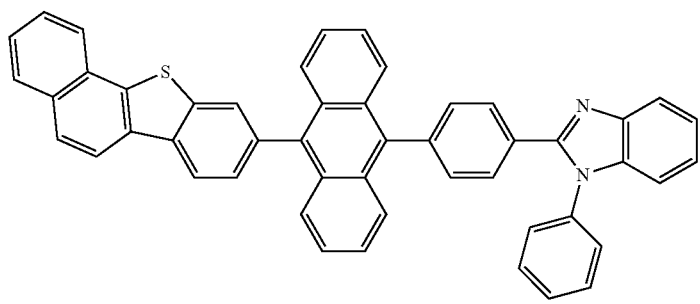
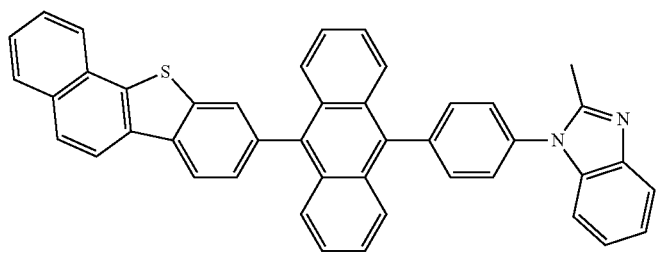
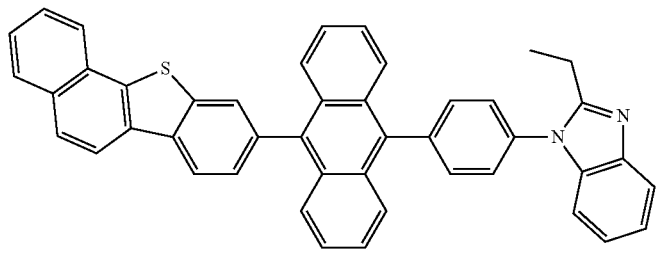
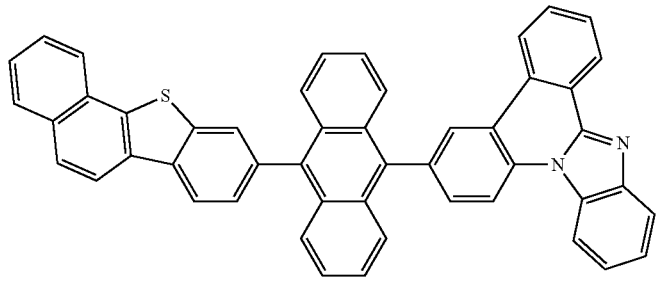

219 220
-continued
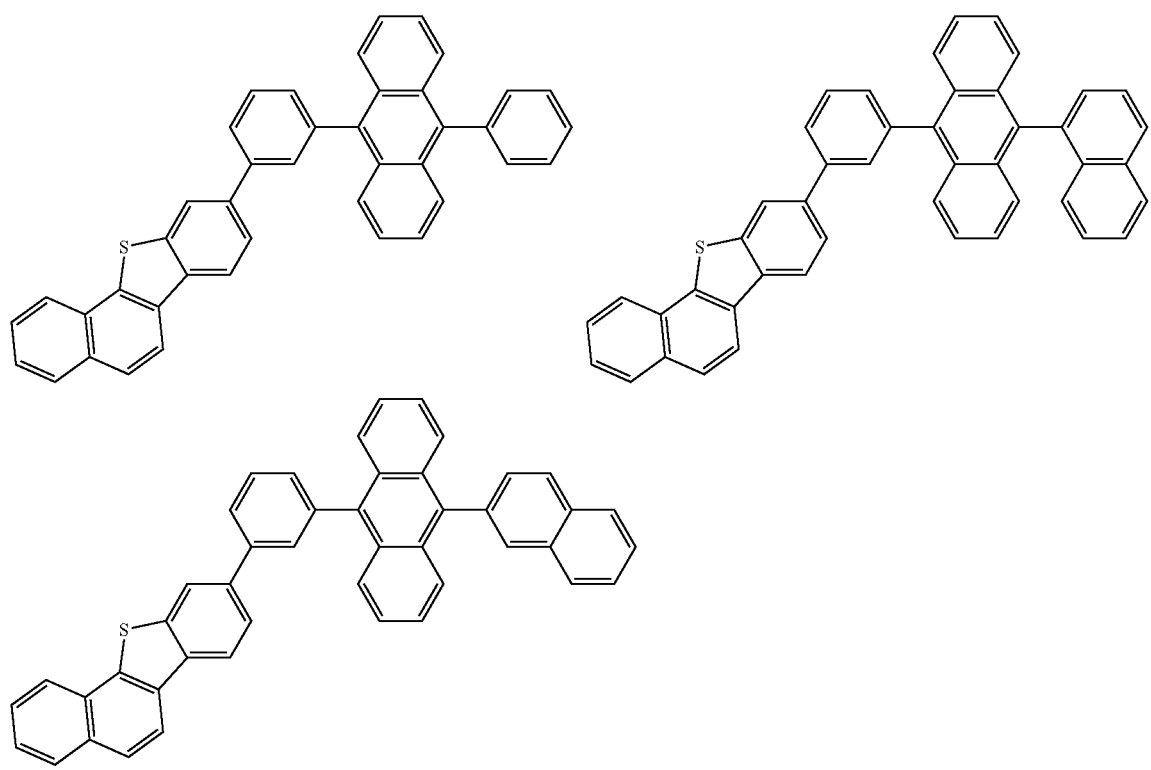
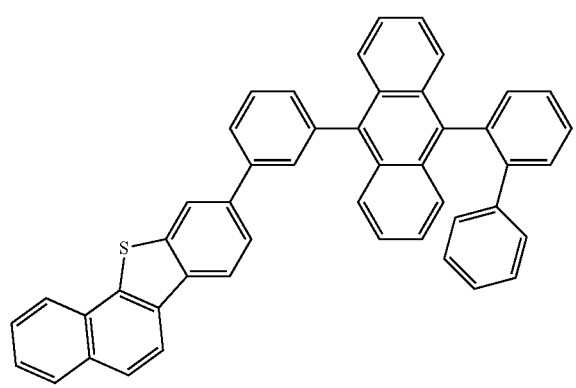
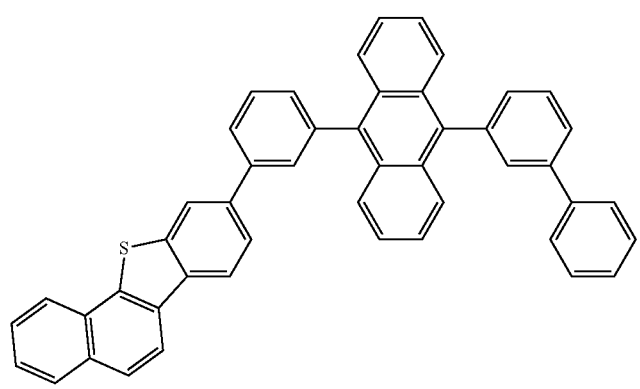

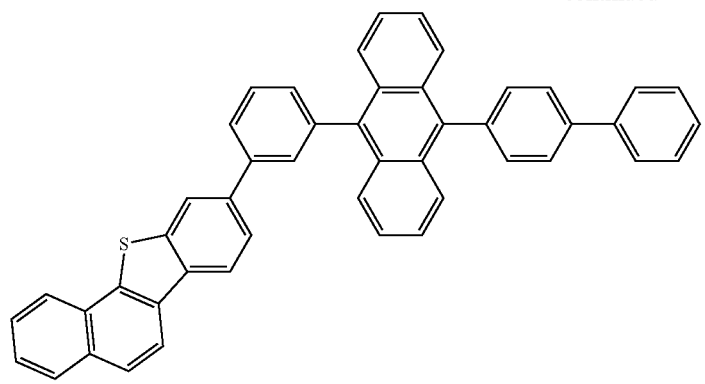
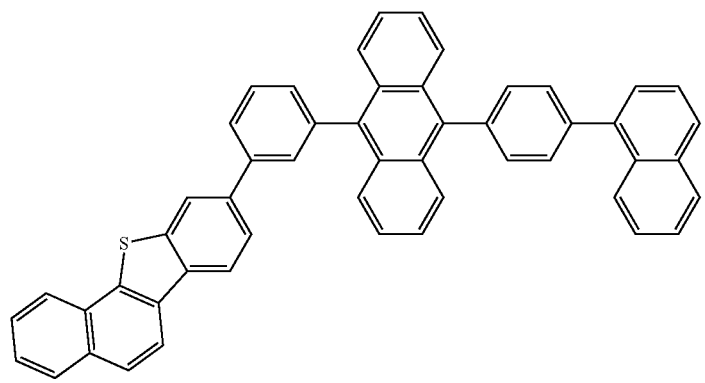
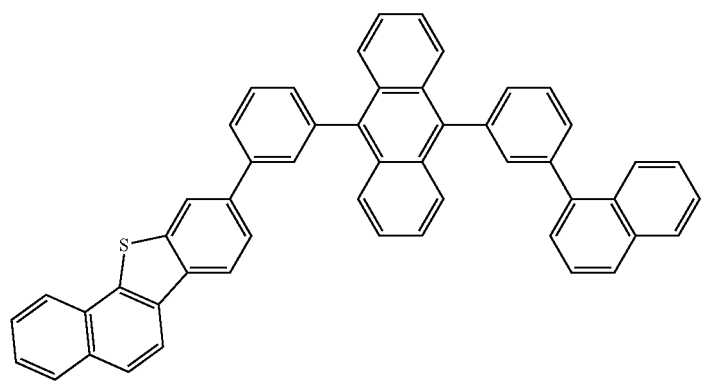
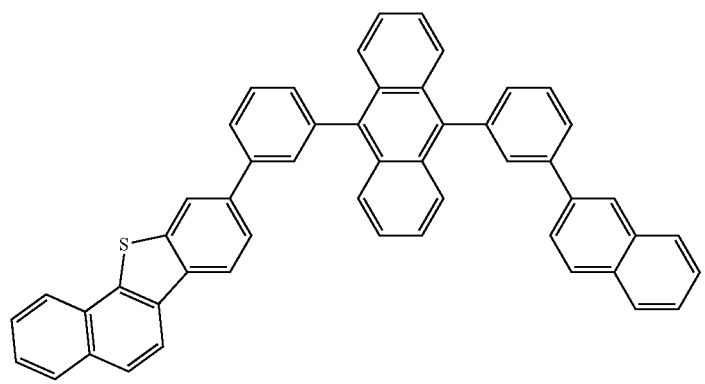

-continued

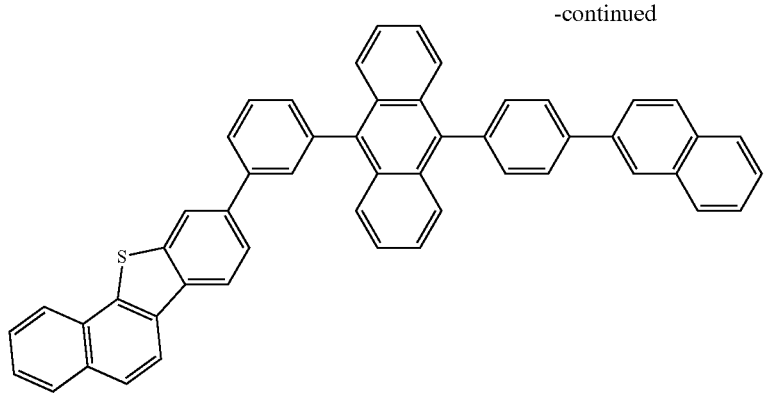

The anthracene derivative mentioned above can be used as the material for an organic EL device or an emitting material for an organic EL device.

The organic electroluminescence (EL) device according to one aspect of the invention includes one or more organic thin film layers including an emitting layer between a cathode and an anode, and at least one layer of the organic thin film layers include the anthracene derivative as a single component or a mixture component.

In the above-mentioned organic EL device, the emitting layer preferably comprise the anthracene derivative mentioned above. It is preferred that the anthracene derivative be a host material of the emitting layer.

As the organic EL device including a plurality of organic thin film layers, one having a configuration in which layers are stacked as follows can be given: (anode/hole-injecting layer/emitting layer/cathode), (anode/emitting layer/electron-injecting layer/cathode), (anode/hole-injecting layer/emitting layer/electron-injecting layer/cathode), (anode/hole-injecting layer/hole-transporting layer/emitting layer/electron-injecting layer/cathode), etc.

In the above-mentioned organic EL device, the anthracene derivative can be used in any of the above-mentioned organic layers. It is preferred that the anthracene derivative be contained in an emission zone. It is particularly preferred that the anthracene derivative be contained in the emitting layer. The content is normally 30 to 100 mol %.

In the organic EL device, by providing a plurality of the above-mentioned organic thin film layers, it is possible to prevent lowering in luminance or life caused by quenching. If necessary, an emitting material, a doping material, a hole-injecting material or an electron-injecting material can be used in combination. Further, by the use of a doping material, the luminance or the luminous efficiency may be improved. The hole-injecting layer, the emitting layer and the electron-injecting layer may respectively be formed into a stacked layer structure composed of two or more layers. In such a layer configuration, in the case of the hole-injecting layer, a layer to which holes are injected from the electrode is referred to as the hole-injecting layer, and a layer for receiving holes from the hole-injecting layer and transporting the holes to the emitting layer is referred to as the hole-transporting layer. Similarly, in the case of the electron-injecting layer, a layer to which electrons are injected from the electrode is referred to as the electron-injecting layer, and a layer for receiving electrons from the electron-injecting layer and transporting the electrons to the emitting layer is referred to as the electron-transporting layer. Each of these layers is selected according to factors such as the energy level of the materials, heat resistance, adhesiveness to the organic layer or the metal electrode.

As the material that can be used together with the above-mentioned anthracene derivative, for example, a fused polycyclic aromatic compound such as naphthalene, phenanthrene, rubrene, anthracene, tetracene, pyrene, perylene, chrysene, decacyclene, coronene, tetraphenyl cyclopentadiene, pentaphenylcyclopentadiene, fluorene, spirofluorene, or the like and a derivative thereof; organic metal complex such as tris(8-quinolinolate)aluminum; a triarylamine derivative; a styrylamine derivative; a stilbene derivative; a cumarine derivative; a pyrane derivative; an oxazone derivative; an benzothiozole derivative; a benzoxazole derivative; a benzimidazole derivative; a pyrazine derivative; a cinnamic acid ester derivative; a diketo-pyrrolo-pyrrole derivative; an acrylidone derivative; a quinacridone derivative or the like can be given. The materials are not limited to those mentioned above.

In the above-mentioned organic EL device, if desired, in addition to the above-mentioned emitting materials, an emitting dopant (phosphorescent dopant and/or fluorescent dopant) may be contained in the emitting layer. An emitting layer that comprises these dopants may be stacked on the emitting layer that comprises the above-mentioned compounds.

A fluorescent dopant is a compound that can emit light from a singlet exciton. A fluorescent dopant is preferably a compound selected from an amine-based compound, an aromatic compound, a chelate complex such as tris(8-quinolinolato)aluminum complex, a coumarin derivative, a tetraphenylbutadiene derivative, a bistyrylarylene derivative and an oxadiazole derivative according to the required emission color. A styrylamine compound, a styryldiamine compound, an arylamine compound and an aryldiamine compound are more preferable, with a fused polycyclic amine derivative being further preferable. These fluorescent dopants may be used singly or in combination of two or more.

As the fused polycyclic amine derivative, those represented by the following formula (20) are preferable.

(20)

In the formula (20), Y is a substituted or unsubstituted fused aromatic hydrocarbon group including 10 to 50 ring carbon atoms.

$Ar_{101}$ and $Ar_{102}$ are independently a substituted or unsubstituted aryl group including 6 to 50 ring carbon atoms or a substituted or unsubstituted heterocyclic ring group including 5 to 50 ring atoms.

Specific examples of Y include the above-mentioned fused aryl group. Y is preferably a substituted or unsubstituted anthryl group, a substituted or unsubstituted pyrenyl group or a substituted or unsubstituted chrysenyl group.

n is an integer of 1 to 4. It is preferred that n be an integer of 1 to 2.

The above-mentioned formula (20) is preferably one represented by the following formulas (21) to (24).

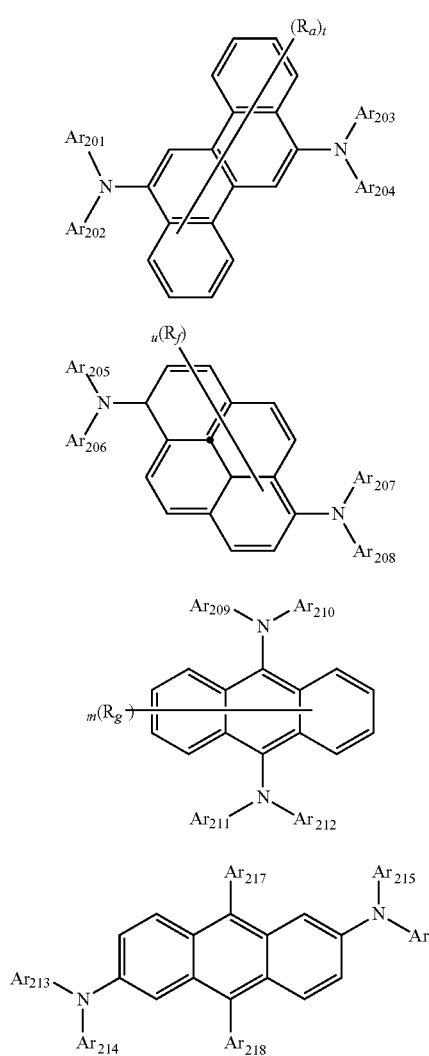

In the formulas (21) to (24), $R_e$, $R_f$ and $R_g$ are independently a substituted or unsubstituted alkyl group including 1 to 20 carbon atoms, a substituted or unsubstituted alkenyl group including 2 to 50 carbon atoms, a substituted or unsubstituted alkynyl group including 2 to 50 carbon atoms, a substituted or unsubstituted aralykyl group including 1 to 20 carbon atoms, a substituted or unsubstituted cycloalkyl group including 3 to 20 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 50 ring carbon atoms, a substituted or unsubstituted silyl group, a substituted or unsubstituted alkyl germanium group including 1 to 50 carbon atoms or a substituted or unsubstituted aryl germanium group including 6 to 50 ring carbon atoms. $R_e$, $R_f$ and $R_g$ may independently be bonded to any of the bonding positions of the benzene rings that constitutes the fused polycyclic skeleton.

As preferable examples of $R_e$, $R_f$ and $R_g$, a substituted or unsubstituted aryl group including 6 to 50 ring carbon atoms can be given. More preferably, $R_e$, $R_f$ and $R_g$ are a substituted or unsubstituted phenyl group, a substituted or unsubstituted naphthyl group, or the like.

t is an integer of 0 to 10. u is an integer of 0 to 8. m is an integer of 0 to 10.

$Ar_{201}$ to $Ar_{218}$ are independently an aryl group including 6 to 50 ring carbon atoms or a substituted or unsubstituted heterocyclic group including 5 to 50 ring atoms.

Preferred examples of $Ar_{201}$ to $Ar_{218}$ include a substituted or unsubstituted phenyl group, a substituted or unsubstituted dibenzofuranyl group or the like. As preferable examples of the substituent of $Ar_{201}$ to $Ar_{218}$, an alkyl group, a cyano group and a substituted or unsubstituted silyl group can be given.

In the formulas (21) to (24), as examples of the alkyl group, the alkoxy group, the aryl group, the aryloxy group and the heterocyclic group, those exemplified above can be given.

As the alkenyl group including 2 to 50 (preferably 2 to 30, more preferably 2 to 20, and particularly preferably 2 to 10) carbon atoms, a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, a 3-phenyl-1-butenyl group or the like can be given. Preferred are a styryl group, a 2,2-diphenylvinyl group, a 1,2-diphenylvinyl group or the like.

As the alkynyl group including 2 to 50 (preferably 2 to 30, more preferably 2 to 20, particularly preferably 2 to 10) carbon atoms, a propargyl group, a 3-pentynyl group or the like can be given.

As the alkyl germanium group, a methylhydrogermyl group, a trimethylgermyl group, a triethylgermyl group, a tripropylgermyl group, a dimethyl-t-butylgermyl group or the like can be given.

As the aryl germanium group, a phenyldihydrogermyl group, a diphenylhydrogermyl group, a triphenylgermyl group, a tritolylgermyl group, a trinaphthylgermyl group or the like can be given.

As the styrylamine compound and the styryldiamine compound, those represented by the following formulas (17) and (18) are preferable.

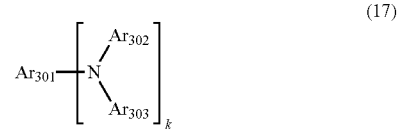

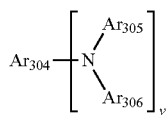

(18)

In the formula (17), $Ar_{301}$ is a k-valent group; a k-valent group corresponding to a phenyl group, a naphthyl group, a biphenyl group, a terphenyl group, a stilbene group, a styrylaryl group and a distyrylaryl group. $Ar_{302}$ and $Ar_{303}$ are independently an aryl group including 6 to 20 ring carbon atoms, and $Ar_{301}$, $Ar_{302}$ and $Ar_{303}$ may be substituted.

k is an integer of 1 to 4, with an integer of 1 and 2 being preferable. Any one of $Ar_{301}$ to $Ar_{303}$ is a group including a styryl group. It is further preferred that at least one of $Ar_{302}$ and $Ar_{303}$ be substituted by a styryl group.

As for the aryl group including 6 to 20 ring carbon atoms, the above-mentioned aryl group can be specifically given. Preferable examples include a phenyl group, a naphthyl group, an anthranyl group, a phenanthryl group, a terphenyl group or the like.

In the formula (18), $Ar_{304}$ to $Ar_{306}$ are a v-valent substituted or unsubstituted aryl group including 6 to 40 ring carbon atoms. v is an integer of 1 to 4, with an integer of 1 and 2 being preferable.

Here, as the aryl group including 6 to 40 ring carbon atoms in the formula (18), the above-mentioned aryl group can be specifically given. A naphthyl group, an anthranyl group, a chrysenyl group, a pyrenyl group or an aryl group represented by the formula (20) is preferable.

As preferable substituents that substitute on the aryl group, an alkyl group including 1 to 6 carbon atoms, an alkoxy group including 1 to 6 carbon atoms, an aryl group including 6 to 40 ring carbon atoms, an amino group substituted by an aryl group including 6 to 40 ring carbon atoms, an ester group including an aryl group that includes 5 to 40 ring carbon atoms, an ester group including an alkyl group that includes 1 to 6 carbon atoms, a cyano group, a nitro group, a halogen atom or the like can be given.

As the hole-injecting material, preferable is a compound that has a hole-transporting capability, exhibits hole-injection effects from the anode, exhibits excellent hole-injection effects for the emitting layer or the emitting material, and has excellent thin-film forming capability. Specific examples thereof include a phthalocyanine derivative, a naphthalocyanine derivative, a porphyrin derivative, a benzidine-type triphenylamine, a diamine-type triphenylamine, hexacyanohexaazatriphenylene or the like, a derivative thereof, a polymeric material such as polyvinyl carbazole, polysilane and conductive polymers. The hole-injecting material is, however, not limited thereto.

Among the hole-injecting materials mentioned above that are usable in an organic EL device, a further effective hole-injecting material is a phthalocyanine derivative.

As the phthalocyanine (Pc) derivative, for example, phthalocyanine derivatives and naphthalocyanine derivatives such as H2Pc, CuPc, CoPc, NiPc, ZnPc, PdPc, FePc, MnPc, ClAlPc, ClGaPc, ClInPc, ClSnPc, Cl2SiPc, (HO)AlPc, (HO)GaPc, VOPc, TiOPc, MoOPc, GaPc-O-GaPc can be given, but the phthalocyanine derivatives are not limited thereto.

Further, by adding to the hole-injection material an electron-acceptor material such as a TCNQ derivative, a carrier can be sensitized.

Preferable hole-transporting materials usable in the above-mentioned organic EL device are aromatic tertiary amine derivatives.

As examples of the aromatic tertiary amine derivatives, N,N'-diphenyl-N,N'-dinaphthyl-1,1'-biphenyl-4,4'-diamine, N,N,N',N'-tetrabiphenyl-1,1'-biphenyl-4,4'-diamine or the like or an oligomer or a polymer having these aromatic tertiary amine skeleton can be given, for example, but the aromatic tertiary amine derivatives are not limited thereto.

As the electron-injecting material, preferable is a compound that has an electron-transporting capability, exhibits electron-injection effects from the anode, exhibits excellent electron-injection effects for the emitting layer or the emitting material, and has excellent thin-film forming capability.

In the above-mentioned organic EL device, a further effective electron-injecting material is a metal complex compound and a nitrogen-containing heterocyclic derivative.

As the metal complex compound, 8-hydroxyquinolinato lithium, bis(8-hydroxyquinolinato)zinc, tris(8-hydroxyquinolinato)aluminum, tris(8-hydroxyquinolinato)gallium, bis(10-hydroxybenzo[h]quinolinato)beryllium, bis(10-hydroxy-benzo[h]quinolinato)zinc or the like can be given, for example. The metal complex compound is not limited thereto.

As the nitrogen-containing heterocyclic derivative, oxazole, thiazole, oxadiazole, thiadiazole, triazole, pyridine, pyrimidine, triazine, phenanthroline, benzimidazole, imidazopyridine or the like can be given, for example. Among them, a benzimidazole derivative, a phenanthroline derivative and an imidazopyridine derivative are preferable.

As a preferable mode, a dopant is further contained in these electron-injecting materials, and in order to facilitate receiving of electrons from the cathode, it is more preferred that the vicinity of the cathode interface of the second organic layer be doped with a dopant represented by an alkali metal.

As the dopant, a donar metal, a donar metal compound and a donar metal complex can be given. These reductive dopants can be used singly or in combination of two or more.

In the above-mentioned organic EL device, in the emitting layer, in addition to at least one selected from the anthracene derivatives represented by the formula (1), at least one of an emitting material, a doping material, a hole-injecting material, a hole-transporting material and an electron-injecting material may be contained in the same layer. In addition, in order to improve stability of the obtained organic EL device against temperature, moisture, atmosphere or the like, it is possible to provide a protective layer on the surface, or to protect the entire device by silicone oil, a resin or the like.

As the conductive material used in the anode of the above-mentioned organic EL device, one having a work function larger than 4 eV is suitable, and carbon, aluminum, vanadium, iron, cobalt, nickel, tungsten, silver, gold, platinum, palladium, and an alloy thereof; an oxide metal such as tin oxide and indium oxide used in an ITO substrate or a NESA substrate, and an organic conductive resin such as polythiophene or polypyrrole or the like are used. As the conductive material used in the cathode, one having a work function smaller than 4 eV is suitable, and magnesium, calcium, tin, lead, titanium, yttrium, lithium, ruthenium, manganese, aluminum, lithium fluoride and an alloy thereof are used, but the conductive material is not limited thereto. As the alloy, a magnesium/silver alloy, a magnesium/indium alloy, a lithium/aluminum alloy or the like can be given as representative examples, but the alloy is not limited thereto. The ratio of the alloy is controlled by the temperature of the deposition source, atmosphere, vacuum degree, etc. and an adequate ratio is selected. The cathode and the anode may be formed in a stacked layer structure of two or more layers, if necessary.

In the above-mentioned organic EL device, in order to realize efficient emission, it is desired that at least one surface be fully transparent in an emission wavelength region of the device. Further, it is desired that the substrate be transparent. The transparent electrode is set such that prescribed transparency can be ensured by using the above-mentioned electroconductive material and by a method such as deposition and sputtering. It is desired that the electrode on the emission surface have a light transmittance of 10% or more. Although no specific restrictions are imposed on the substrate, as long as it has a mechanical or thermal strength and has transparency, a glass substrate and a transparent resin film can be mentioned.

For forming each of the layers constituting the above-mentioned organic EL device, any of dry film-forming methods such as vacuum deposition, sputtering, plasma coating, ion plating or the like and wet film-forming methods such as spin coating, dip coating and flow coating can be applied. The film thickness is not particularly restricted, but is required to be set to an appropriate film thickness. If the film thickness is too large, a large voltage is required to be applied in order to obtain a specific optical output, resulting in poor efficiency. If the film thickness is too small, pin holes or the like are generated, and a sufficient luminance may not be obtained even when an electrical field is applied. Normally, the film thickness is suitably 5 nm to 10 μm, further preferably 10 nm to 0.2 μm.

In the case of the wet film-forming method, a thin film is formed by using a solution or dispersion in which materials constituting each layer is dissolved or dispersed in an adequate solvent such as ethanol, chloroform, tetrahydrofuran and dioxane. Any of these solvents may be used.

As the solution suited for the wet film-forming method, an organic EL device material-containing solution that contains, as an organic EL material, the above-mentioned anthracene derivative and a solvent can be used.

In any of the organic thin film layers, in order to improve film-forming properties, to prevent generation of pin holes or for other purposes, an adequate resin or an adequate additive may be used.

The above-mentioned organic EL devices can be used in various electric appliances. For example, it can be used for a planar emitting body such as a flat panel display of a wall-hanging television, a copier, a printer, a backlight of a liquid crystal display, or a light source in instruments or the like, a sign board, a signal light or the like. In addition, the compound of the invention can be used not only in an organic EL device, but also in the fields of an electrophotographic photoreceptor, a photoelectric conversion element, a solar cell and an image sensor.

EXAMPLES

Production Example 1 [Synthesis of Intermediate]

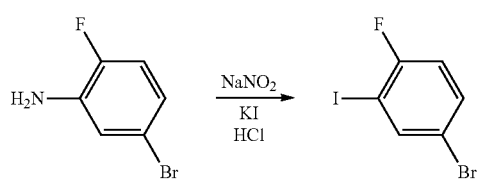

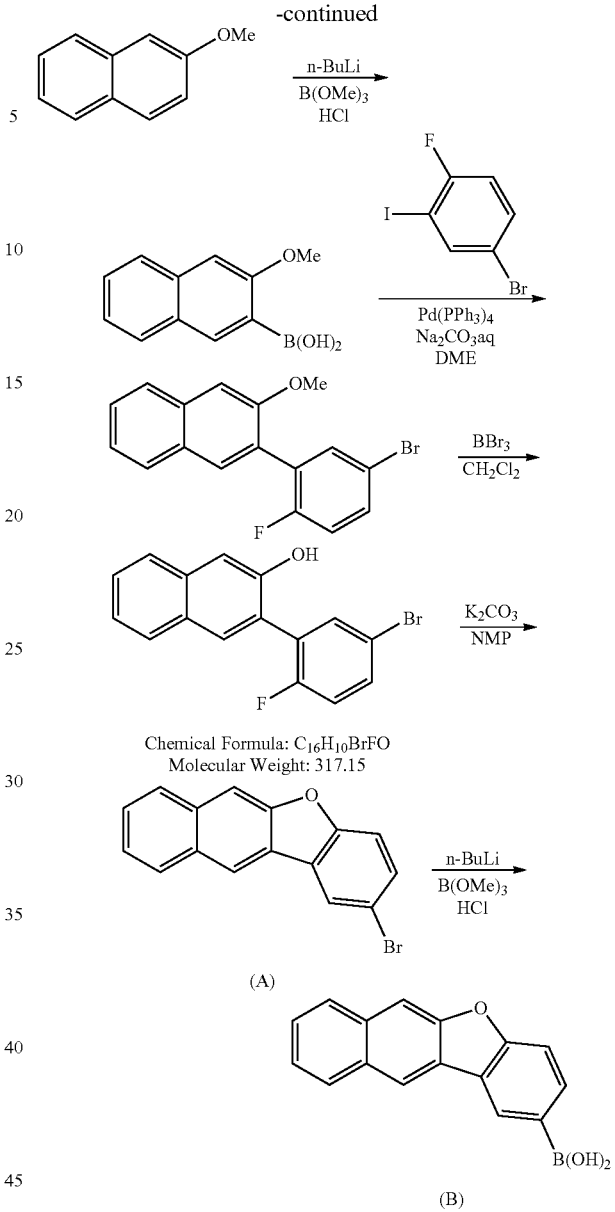

(1) Synthesis of 5-bromo-2-fluoroiodobenzene

In an argon atmosphere, 106 mL of water was added to 10 g of 5-bromo-2-fluoroaniline, and the mixture was stirred, followed by addition of 79.2 mL of concentrated hydrochloric acid. The resulting mixture was cooled in ice, and an aqueous solution of 4.36 g of sodium nitrate was added dropwise. While cooling in ice, the resultant was stirred for 30 minutes, and then an aqueous solution of 87.3 g of potassium iodide was added. After extraction with ethyl acetate, an organic layer was washed with an aqueous solution of a saturated sodium hydrogen carbonate and an aqueous solution of sodium sulfite and dried with magnesium sulfate. Then, the solvent was distilled off under reduced pressure. Residues were purified by silica gel column chromatography, whereby 11.5 g (yield: 73%) of 5-bromo-2-fluoroiodebenzene was obtained.

(2) Synthesis of 3-methoxynaphthalene-2-boronic acid 15.8 g of 2-methoxynaphthalene and 300 mL of tetrahydrofuran (dehydrated) were put in a flask, and cooled to −78° C. Then, 66 mL of n-BuLi (1.60M in hexane) was added, followed by stirring at room temperature for 4 hours. Then, the solution was again cooled to −78° C. 27.3 g of B(OMe)$_3$ was added, followed by stirring at −78° C. for 10 minutes. Then, the resultant was stirred at room temperature for 5 hours.

After completion of the reaction, 1N HCl aq. (200 mL) was added, and the reaction solution was stirred at room temperature for 1 hour. Then, the solution was transferred to a separating funnel, and extracted with ethyl acetate.

This solution was dried with MgSO$_4$, concentrated and washed with hexane, whereby 14.3 g (yield: 71%) of white solids of 3-methoxynaphthalene-2-boronic acid were obtained.

(3) Synthesis of 2-methoxy-3-(2-fluoro-5-bromophenyl)naphthalene

In an argon atmosphere, 14.3 g of 3-methoxynaphthalene-2-boronic acid, 21.3 g of 5-bromo-2-fluoroiodobenzene, 1.64 g of tetrakistriphenylphosphine palladium (0), 220 mL of toluene and 110 mL of a 2M aqueous solution of sodium carbonate were put in a flask, and the mixture was stirred for 8 hours while heating under reflux. After cooling to room temperature, the reaction solution was extracted with toluene. After removing an aqueous layer, an organic layer was washed with saturated saline. After drying the organic layer with magnesium sulfate, the organic layer was concentrated, and the residues were purified by means of silica gel chromatography, whereby 17.6 g (yield: 75%) of 2-methoxy-3-(2-fluoro-5-bromophenyl)naphthalene was obtained.

(4) Synthesis of 2-hydroxy-3-(2-fluoro-5-bromophenyl)naphthalene 15.8 g of 2-methoxy-3-(2-fluoro-5-bromophenyl)naphthalene and 200 mL of dichloromethane (dehydrated) were put in a flask, and the resultant was cooled to 0° C. Then, 18.0 g of BBr$_3$ was added, and stirred at room temperature for 24 hours.

After completion of the reaction, the solution was cooled to −78° C., and deactivated carefully with methanol, and further deactivated with a sufficient amount of water. The solution was transferred to a separating funnel, extracted with dichloromethane, and dried with MgSO$_4$. By passing through a silica gel short column, origin impurities were removed. The solution was concentrated, and the obtained sample was dried in vacuum at 60° C. for 5 hours, whereby 15.1 g of white solids of 2-hydroxy-3-(2-fluoro-5-bromophenyl)naphthalene were obtained.

(5) Synthesis of Intermediate (A)

15.1 g of 2-hydroxy-3-(2-fluoro-5-bromophenyl)naphthalene, 150 mL of N-methyl-2-hydrolidinone (dehydrated) and 13.2 g of K$_2$CO$_3$ were put in a flask. Thereafter, the resultant was stirred at 120° C. for 2 hours.

After completion of the reaction, the solution was cooled to room temperature. Toluene (200 mL) was added, and the solution was transferred to a separating funnel, and washed with water. After drying this solution with MgSO$_4$, purification was conducted by means of a silica gel column chromatography, whereby 12.6 g (yield: 89%) of white solids of intermediate (A) were obtained.

(6) Synthesis of Intermediate (B)

12.6 g of intermediate (A) and 500 mL of tetrahydrofuran (dehydrated) were put in a flask, and the resultant was cooled to −78° C. 28 mL of n-BuLi (1.60M in hexane) was added, and stirring was conducted for 2 hours while elevating the temperature to 0° C. Then, the solution was again cooled to −78° C., and 11.6 g of B(OMe)$_3$ was added. After stirring at 10 minutes at −78° C., stirring was further conducted for 5 hours while gradually elevating the temperature to room temperature.

After completion of the reaction, 1N HCl aq. (100 mL) was added, and the reaction solution was stirred at room temperature for 1 hour. Then, the solution was transferred to a separating funnel, and extracted with ethyl acetate.

This solution was dried with MgSO$_4$, concentrated and washed with hexane, whereby 7.2 g (yield: 65%) of white solids of intermediate (B) were obtained.

(7) Synthesis of Intermediates (C) and (D)

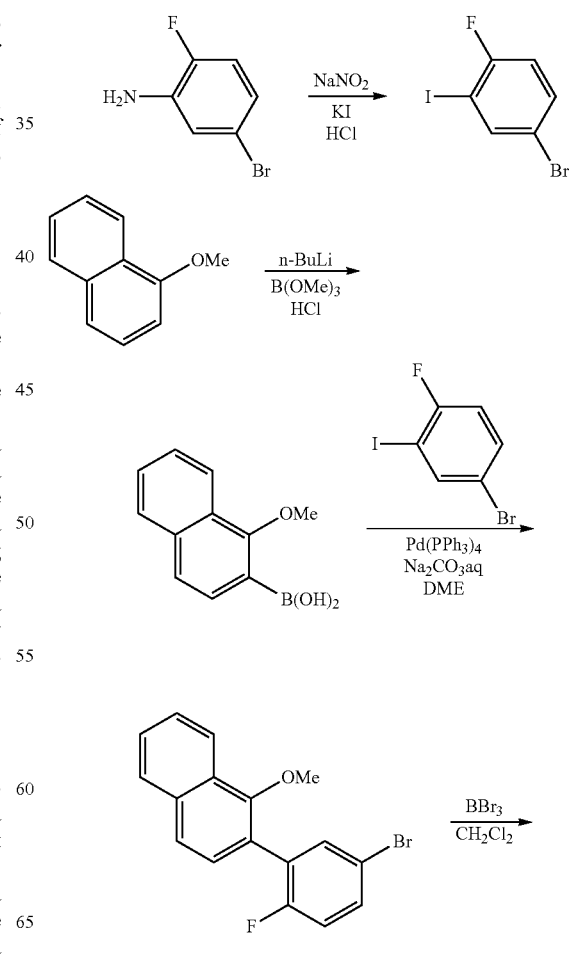

233

-continued

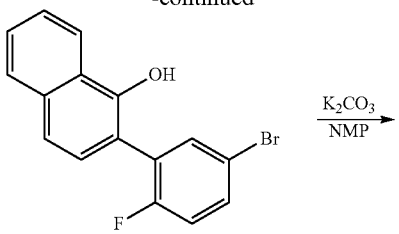

Chemical Formula: C₁₆H₁₀BrFO
Molecular Weight: 317.15

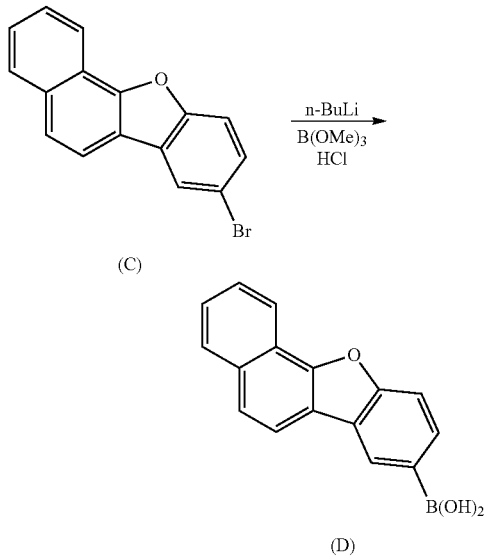

Intermediates (C) and (D) were synthesized in the same manner as in the synthesis of intermediates (A) and (B) in accordance with the above-mentioned scheme, except that 1-methoxynaphthalene was used instead of 2-methoxynaphthalene as the starting material.

(8) Synthesis of Intermediate (E)

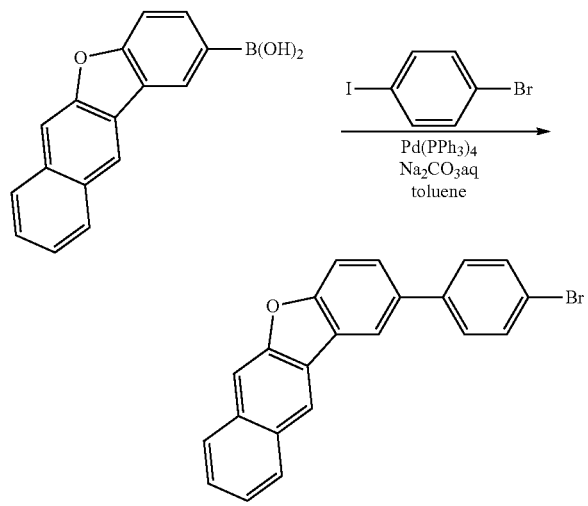

234

In an atmosphere of argon, 2.88 g of the intermediate (B), 2.81 g of 4-bromoiodobenzene, 0.231 g of tetrakistriphenylphosphine palladium (0), 40 mL of toluene and 20 mL of a 2M aqueous sodium carbonate solution were put in a flask, and the resultant was stirred for 8 hours while heating under reflux. After cooling to room temperature, the reaction solution was extracted with toluene. After removing an aqueous layer, an organic layer was washed with saturated saline. After drying with magnesium sulfate, the organic layer was concentrated, and the residues were purified by means of silica gel column chromatography, whereby 3.16 g (yield: 85%) of intermediate (E) was obtained.

(9) Synthesis of Intermediate (F)

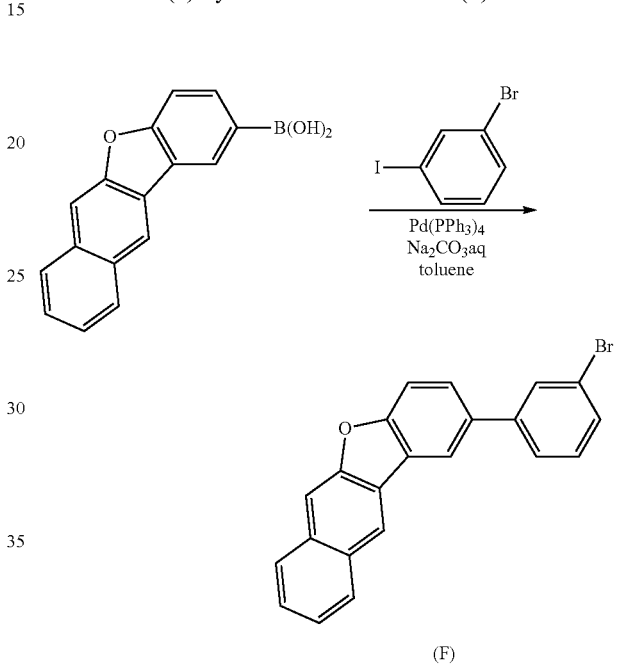

Intermediate (F) was synthesized in the same manner as in the synthesis of intermediate (E), except that 3-bromoiodobenzene was used instead of 4-bromoiodobenzene.

(10) Synthesis of Intermediate (G)

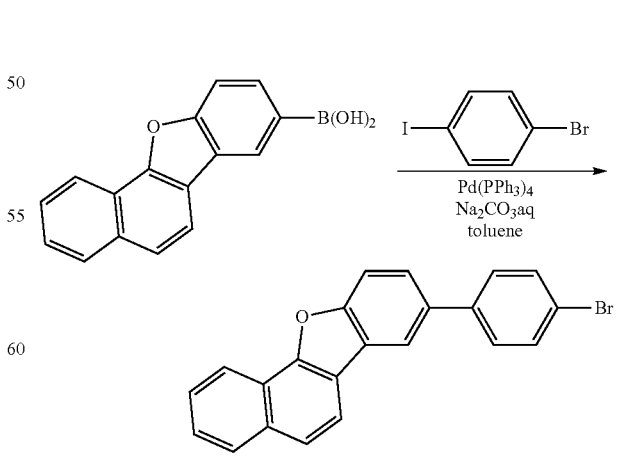

Intermediate (G) was synthesized in the same manner as in the synthesis of intermediate (E), except that intermediate (D) was used instead of intermediate (B).

(11) Synthesis of Intermediate (H)

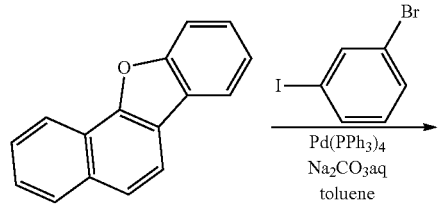

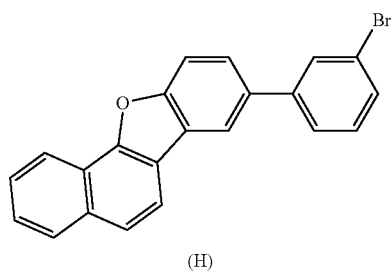

(H)

Intermediate (H) was synthesized in the same manner as in the synthesis of intermediate (E), except that intermediate (D) was used instead of intermediate (B) and 3-bromoiodobenzene was used instead of 4-bromoiodobenzene.

(12) Synthesis of Intermediates (I) and (J)

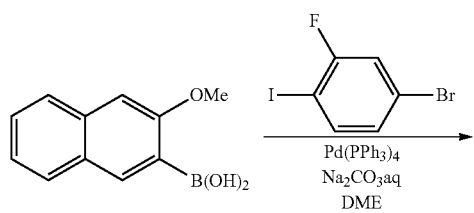

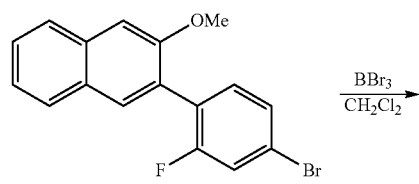

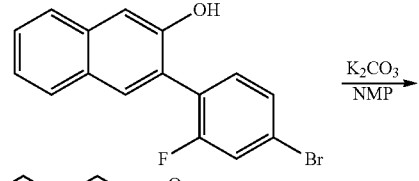

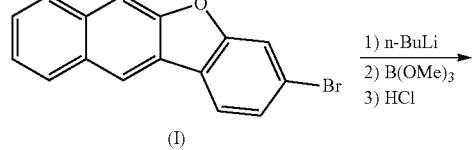

(I)

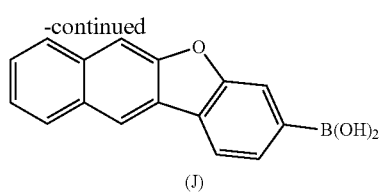

(J)

Intermediates (I) and (J) were synthesized in the same manner as in the synthesis of intermediates (A) and (B) in accordance with the above-mentioned scheme, except that 2-fluoro-4-bromoiodobenzene was used instead of 2-fluoro-5-bromoiodobenzene.

(13) Synthesis of Intermediates (K) and (L)

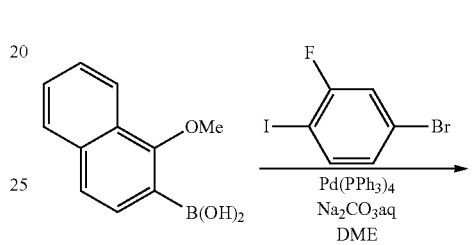

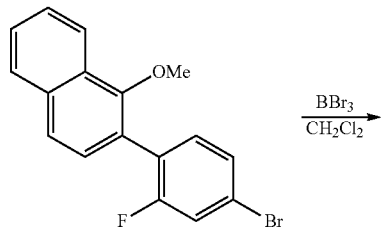

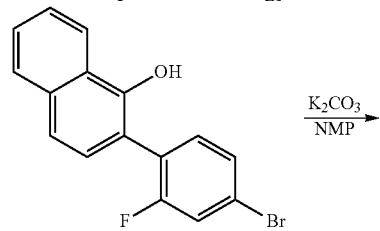

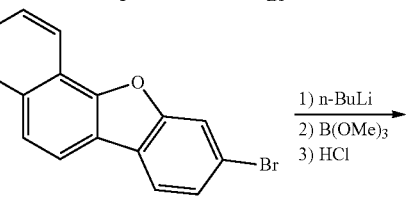

(K)

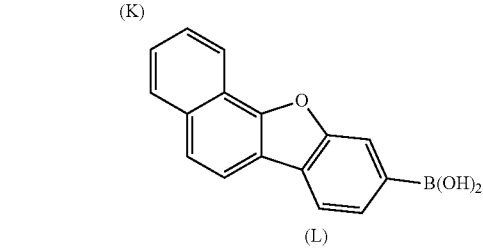

(L)

Intermediates (K) and (L) were synthesized in the same manner as in the synthesis of intermediates (A) and (B) in accordance with the above-mentioned scheme, except that 1-methoxynaphthalene was used instead of 2-methoxynaphthalene and 2-fluoro-4-bromoiodobenzene was used instead of 2-fluoro-5-bromoiodobenzene.

(14) Synthesis of Intermediate (M)

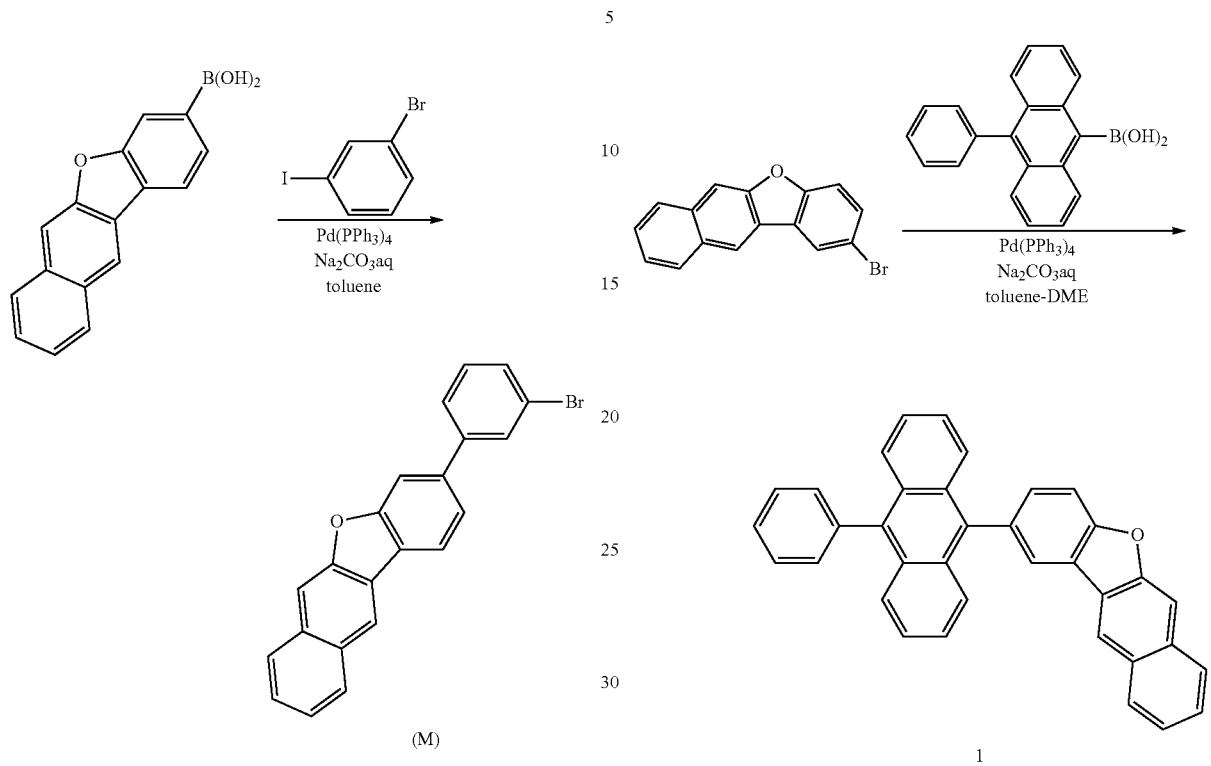

(M)

Intermediate (M) was synthesized in the same manner as in the synthesis of intermediate (E), except that intermediate (J) was used instead of intermediate (B).

(15) Synthesis of Intermediate (N)

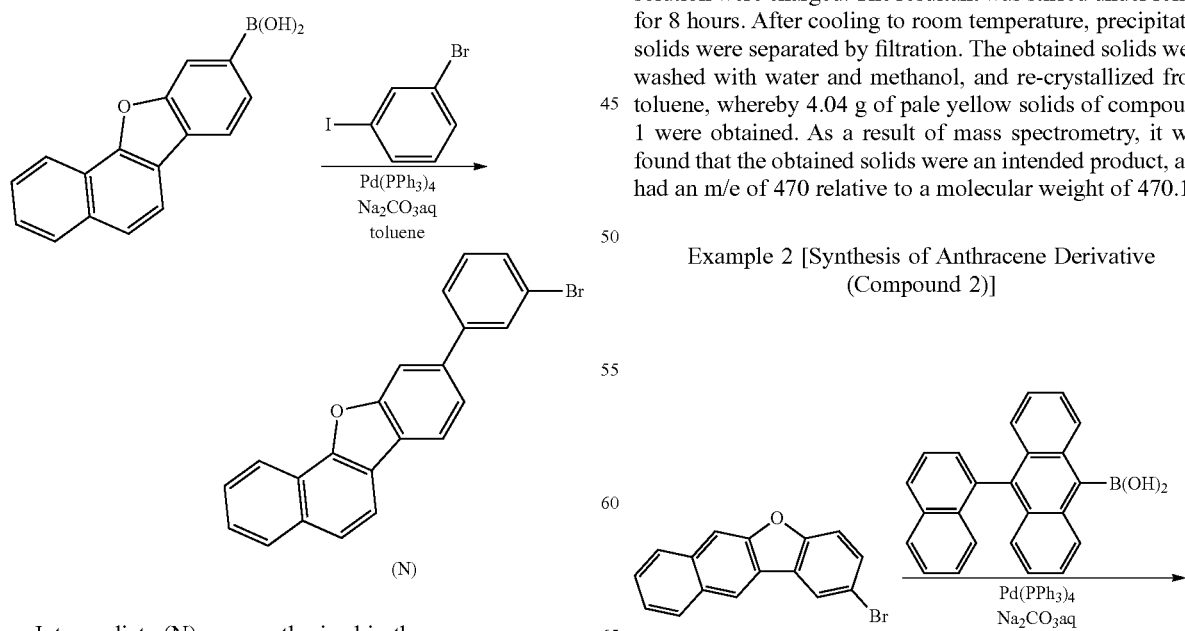

(N)

Intermediate (N) was synthesized in the same manner as in the synthesis of intermediate (E), except that intermediate (L) was used instead of intermediate (B).

Example 1 [Synthesis of Anthracene Derivative (Compound 1)]

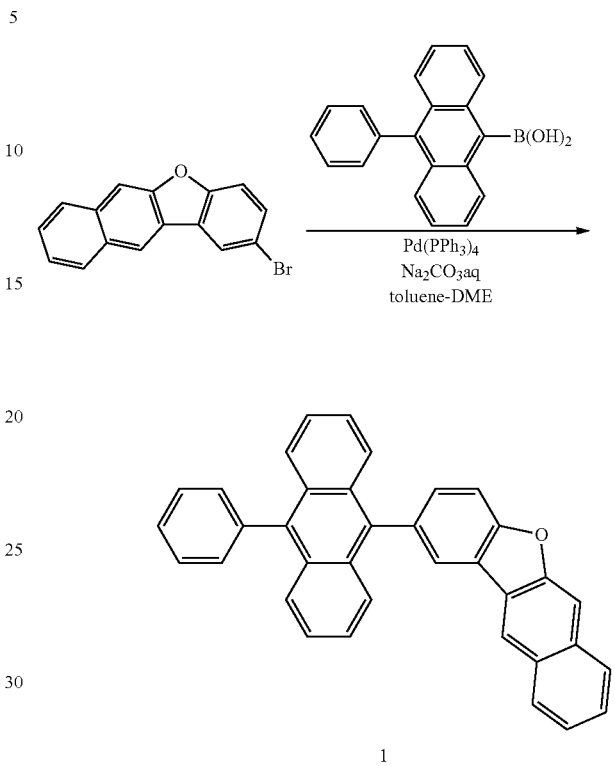

1

In an argon atmosphere, 2.96 g of intermediate (A), 3.28 g of 10-phenylanthracene-9-boronic acid, that had been prepared by a known method, 0.231 g of tetrakis(triphenylphosphine)palladium (0), 20 mL of 1,2-dimethoxyethane, 20 mL of toluene and 20 mL of a 2M aqueous sodium carbonate solution were charged. The resultant was stirred under reflux for 8 hours. After cooling to room temperature, precipitated solids were separated by filtration. The obtained solids were washed with water and methanol, and re-crystallized from toluene, whereby 4.04 g of pale yellow solids of compound 1 were obtained. As a result of mass spectrometry, it was found that the obtained solids were an intended product, and had an m/e of 470 relative to a molecular weight of 470.17.

Example 2 [Synthesis of Anthracene Derivative (Compound 2)]

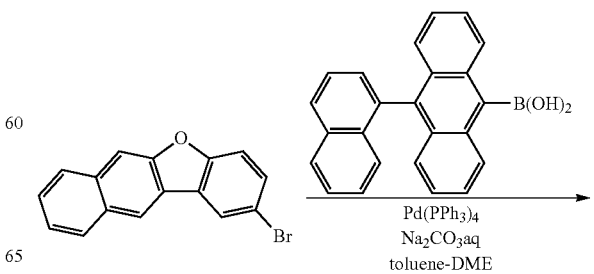

-continued

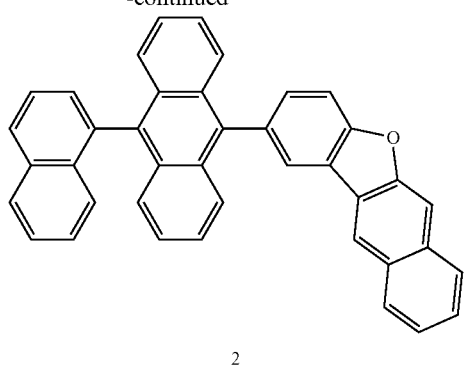

2

Synthesis was conducted in the same manner as in the synthesis of compound 1 in Example 1, except that 10-(1-naphthyl)anthracene-9-boronic acid, that was synthesized by a known method, was used instead of 10-phenylanthracene-9-boronic acid, whereby compound 2 was obtained. As a result of mass spectrometry, it was found that the compound was an intended product, and had an m/e of 520 relative to a molecular weight of 520.18.

Example 3 [Synthesis of Anthracene Derivative (Compound 3)]

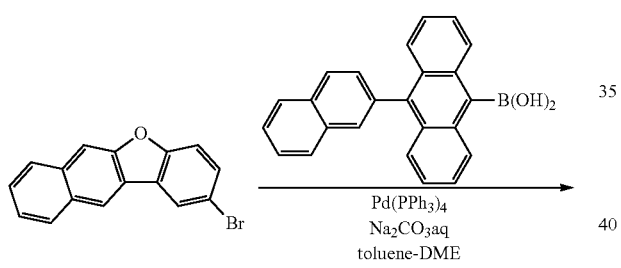

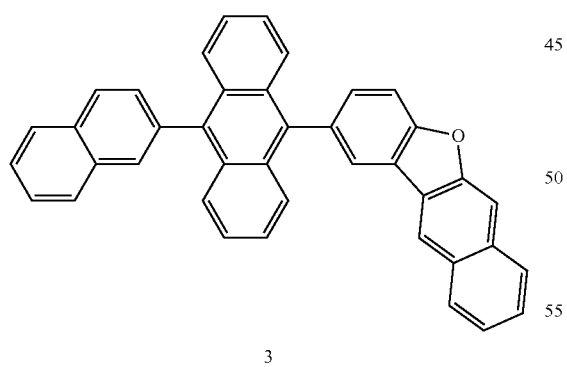

3

Synthesis was conducted in the same manner as in the synthesis of compound 1 in Example 1, except that 10-(2-naphthyl)anthracene-9-boronic acid, that was synthesized by a known method, was used instead of 10-phenylanthracene-9-boronic acid, whereby compound 3 was obtained. As a result of mass spectrometry, it was found that the compound was an intended product, and had an m/e of 520 relative to a molecular weight of 520.18.

Example 4 [Synthesis of Anthracene Derivative (Compound 4)]

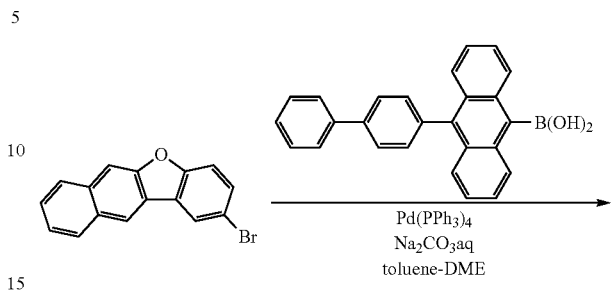

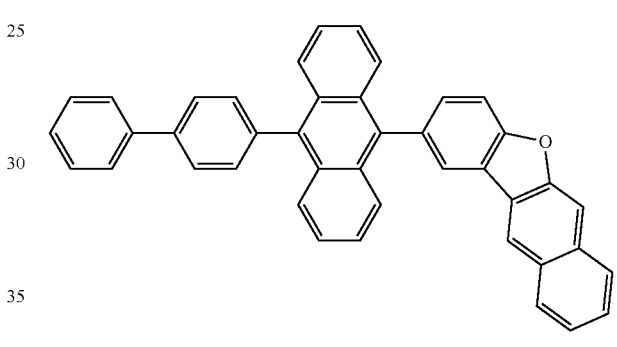

4

Synthesis was conducted in the same manner as in the synthesis of compound 1 in Example 1, except that 10-(4-biphenyl)anthracene-9-boronic acid, that was synthesized by a known method, was used instead of 10-phenylanthracene-9-boronic acid, whereby compound 4 was obtained. As a result of mass spectrometry, it was found that the compound was an intended product, and had an m/e of 546 relative to a molecular weight of 546.20.

Example 5 [Synthesis of Anthracene Derivative (Compound 5)]

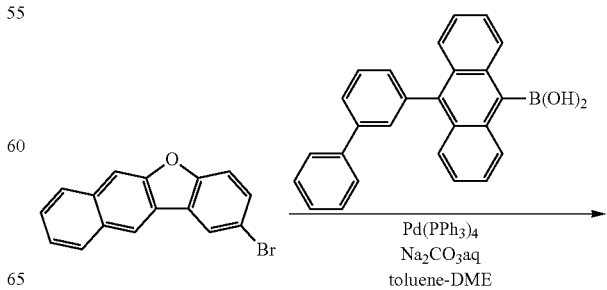

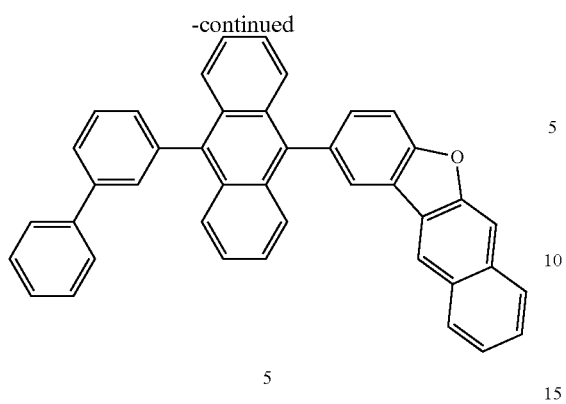

5

Synthesis was conducted in the same manner as in the synthesis of compound 1 in Example 1, except that 10-(3-biphenyl)anthracene-9-boronic acid, that was synthesized by a known method, was used instead of 10-phenylanthracene-9-boronic acid, whereby compound 5 was obtained. As a result of mass spectrometry, it was found that the compound was an intended product, and had an m/e of 546 relative to a molecular weight of 546.20.

Example 6 [Synthesis of Anthracene Derivative (Compound 6)]

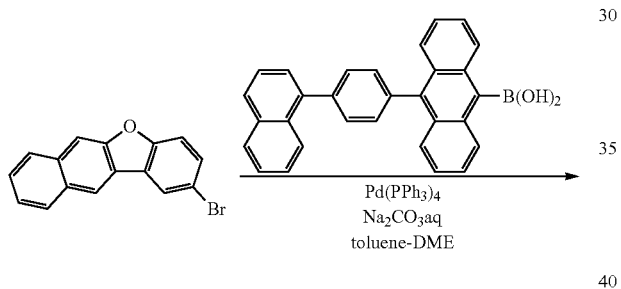

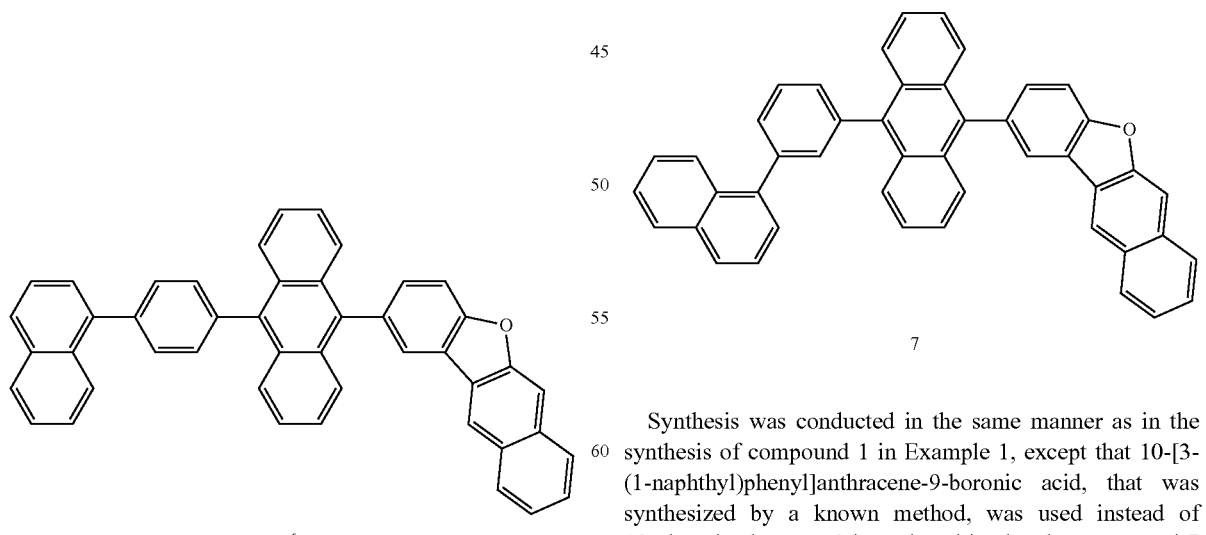

6

Synthesis was conducted in the same manner as in the synthesis of compound 1 in Example 1, except that 10-[4-(1-naphthyl)phenyl]anthracene-9-boronic acid, that was synthesized by a known method, was used instead of 10-phenylanthracene-9-boronic acid, whereby compound 6 was obtained. As a result of mass spectrometry, it was found that the compound was an intended product, and had an m/e of 596 relative to a molecular weight of 596.21.

Example 7 [Synthesis of Anthracene Derivative (Compound 7)]

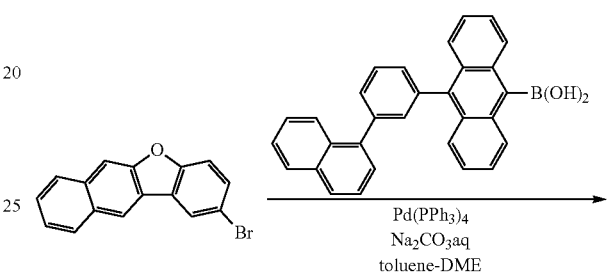

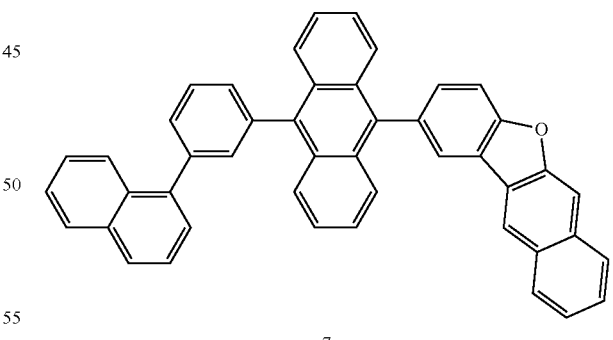

7

Synthesis was conducted in the same manner as in the synthesis of compound 1 in Example 1, except that 10-[3-(1-naphthyl)phenyl]anthracene-9-boronic acid, that was synthesized by a known method, was used instead of 10-phenylanthracene-9-boronic acid, whereby compound 7 was obtained. As a result of mass spectrometry, it was found that the compound was an intended product, and had an m/e of 596 relative to a molecular weight of 596.21.

Example 8 [Synthesis of Anthracene Derivative (Compound 8)]

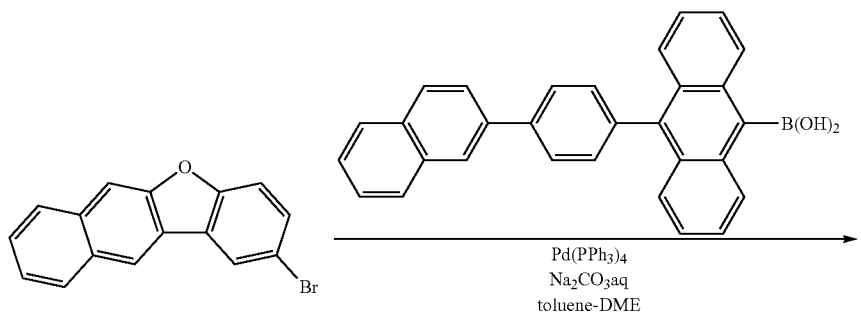

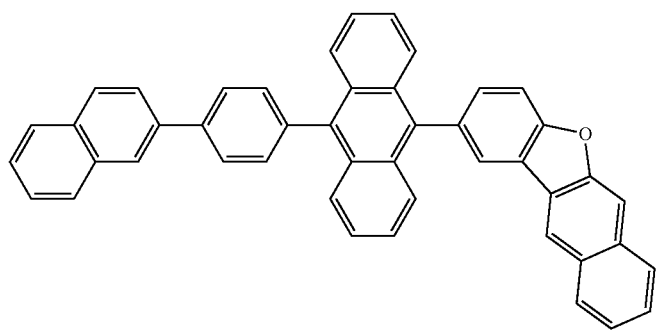

8

Synthesis was conducted in the same manner as in the synthesis of compound 1 in Example 1, except that 10-[4-(2-naphthyl)phenyl]anthracene-9-boronic acid, that was synthesized by a known method, was used instead of 10-phenylanthracene-9-boronic acid, whereby compound 8 was obtained. As a result of mass spectrometry, it was found that the compound was an intended product, and had an m/e of 596 relative to a molecular weight of 596.21.

Example 9 [Synthesis of Anthracene Derivative (Compound 9)]

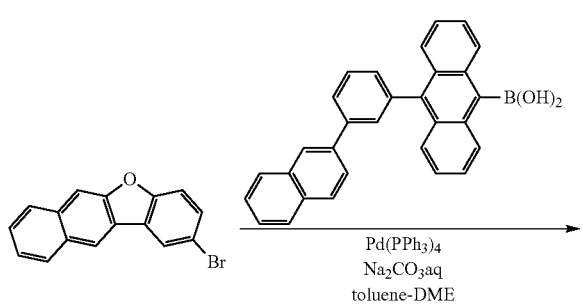

-continued

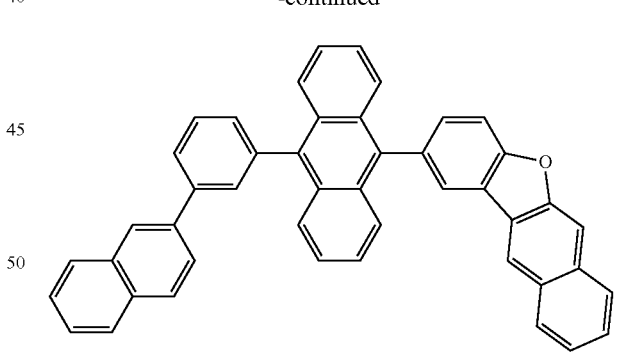

9

Synthesis was conducted in the same manner as in the synthesis of compound 1 in Example 1, except that 10-[3-(2-naphthyl)phenyl]anthracene-9-boronic acid, that was synthesized by a known method, was used instead of 10-phenylanthracene-9-boronic acid, whereby compound 9 was obtained. As a result of mass spectrometry, it was found that the compound was an intended product, and had an m/e of 596 relative to a molecular weight of 596.21.

Example 10 [Synthesis of Anthracene Derivative (Compound 10)]

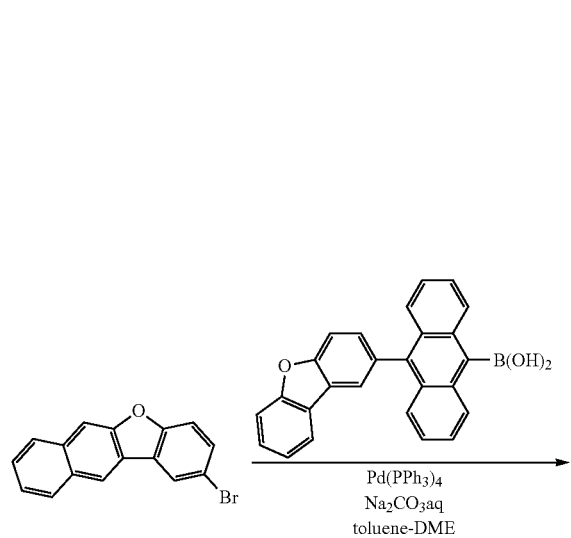

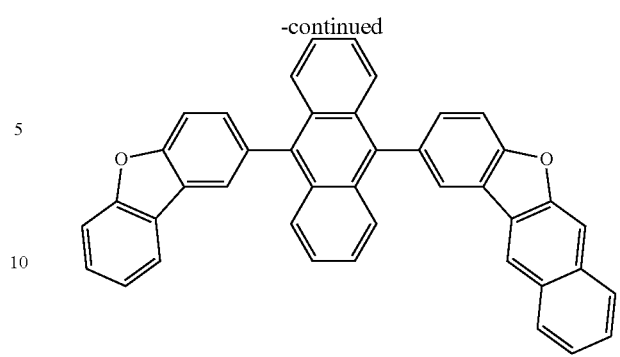

10

Synthesis was conducted in the same manner as in the synthesis of compound 1 in Example 1, except that 10-(2-dibenzofuranyl)anthracene-9-boronic acid, that was synthesized by a known method, was used instead of 10-phenylanthracene-9-boronic acid, whereby compound 10 was obtained. As a result of mass spectrometry, it was found that the compound was an intended product, and had an m/e of 560 relative to a molecular weight of 560.64.

Example 11 [Synthesis of Anthracene Derivative (Compound 11)]

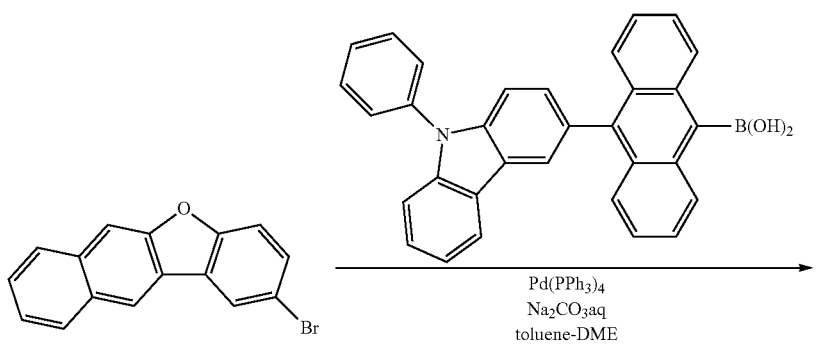

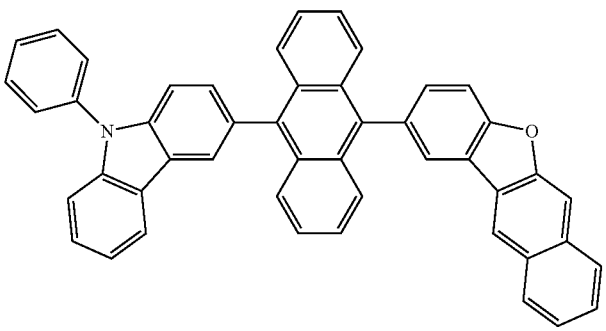

11

Synthesis was conducted in the same manner as in the synthesis of compound 1 in Example 1, except that 10-[3-(9-phenyl)carbazolyl]anthracene-9-boronic acid, that was synthesized by a known method, was used instead of 10-phenylanthracene-9-boronic acid, whereby compound 11 was obtained. As a result of mass spectrometry, it was found that the compound was an intended product, and had an m/e of 635 relative to a molecular weight of 635.22.

Example 12 [Synthesis of Anthracene Derivative (Compound 12)]

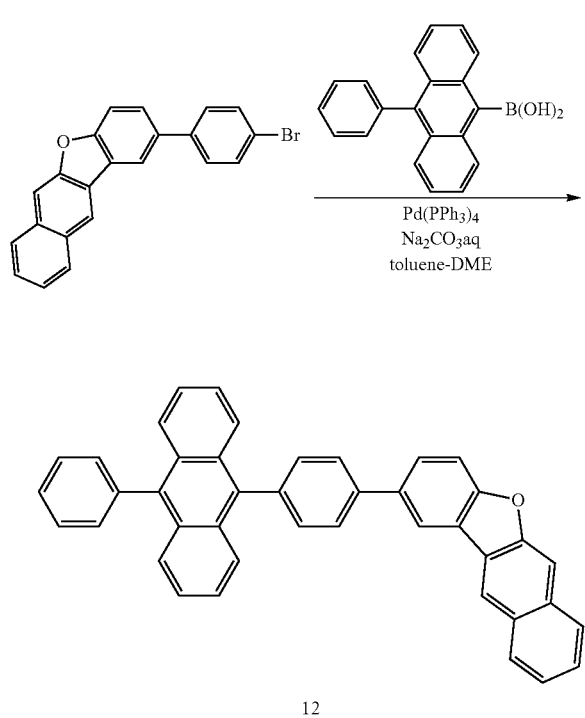

12

Synthesis was conducted in the same manner as in the synthesis of compound 1 in Example 1, except that intermediate (E) was used instead of intermediate (A), whereby compound 12 was obtained. As a result of mass spectrometry, it was found that the compound was an intended product, and had an m/e of 546 relative to a molecular weight of 546.20.

Example 13 [Synthesis of Anthracene Derivative (Compound 13)]

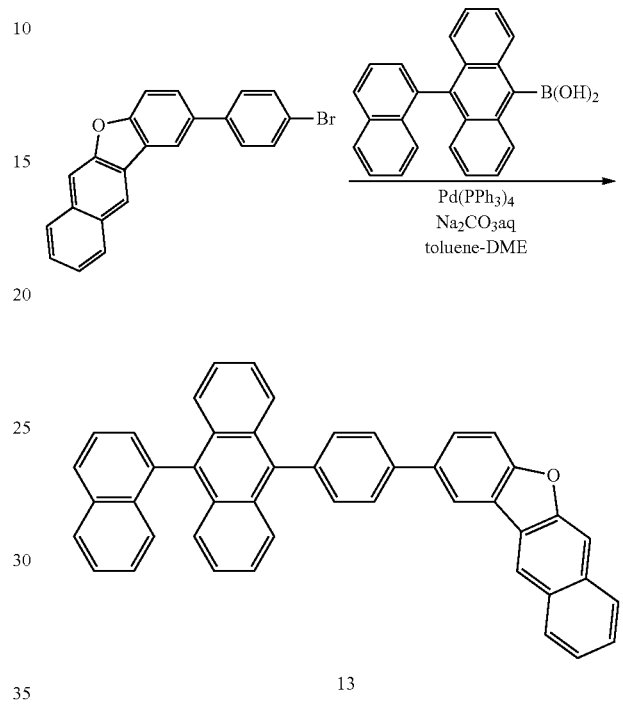

13

Synthesis was conducted in the same manner as in the synthesis of compound 1 in Example 1, except that intermediate (E) was used instead of intermediate (A), and 10-(1-naphthyl)anthracene-9-boronic acid, that was synthesized by a known method, was used instead of 10-phenylanthracene-9-boronic acid, whereby compound 13 was obtained. As a result of mass spectrometry, it was found that the compound was an intended product, and had an m/e of 596 relative to a molecular weight of 596.21.

Example 14 [Synthesis of Anthracene Derivative (Compound 14)]

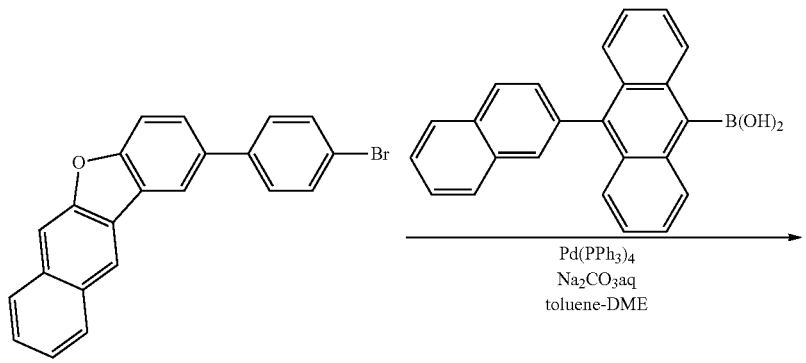

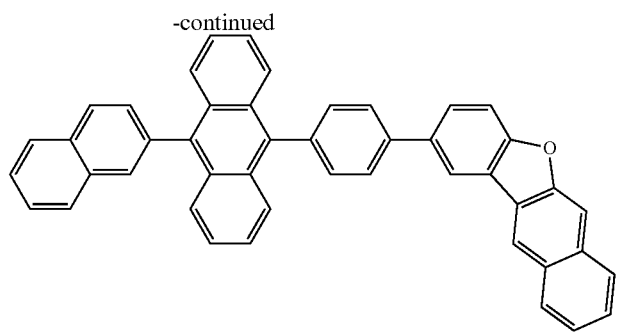

14

Synthesis was conducted in the same manner as in the synthesis of compound 1 in Example 1, except that intermediate (E) was used instead of intermediate (A), and 10-(2-naphthyl)anthracene-9-boronic acid, that was synthesized by a known method, was used instead of 10-phenylanthracene-9-boronic acid, whereby compound 14 was obtained. As a result of mass spectrometry, it was found that the compound was an intended product, and had an m/e of 596 relative to a molecular weight of 596.21.

Example 15 [Synthesis of Anthracene Derivative (Compound 15)]

Synthesis was conducted in the same manner as in the synthesis of compound 1 in Example 1, except that intermediate (E) was used instead of intermediate (A), and 10-(4-biphenyl)anthracene-9-boronic acid, that was synthesized by a known method, was used instead of 10-phenylanthracene-9-boronic acid, whereby compound 15 was obtained. As a result of mass spectrometry, it was found that the compound was an intended product, and had an m/e of 622 relative to a molecular weight of 622.23.

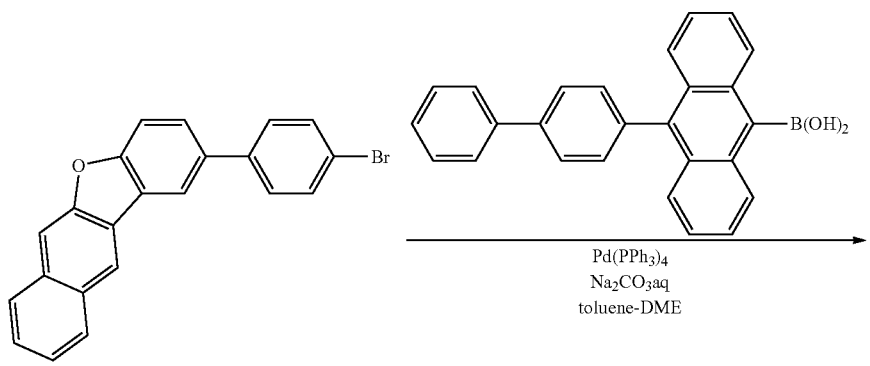

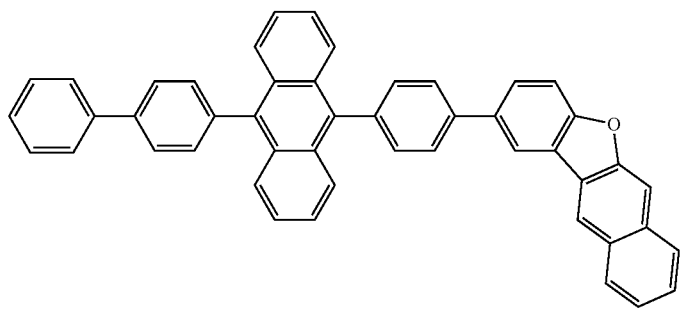

15

Example 16 [Synthesis of Anthracene Derivative (Compound 16)]

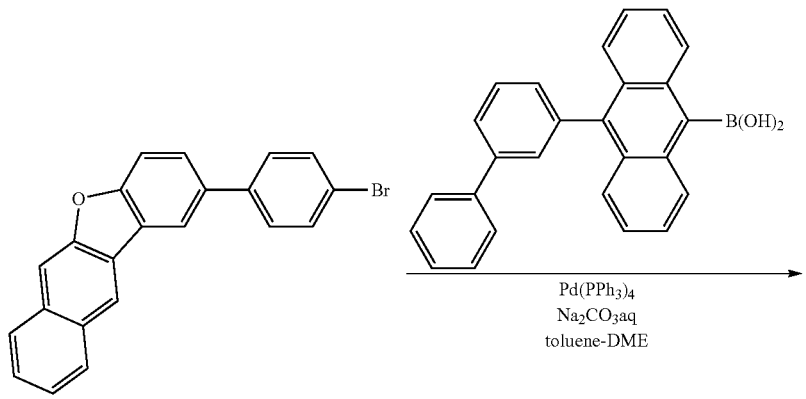

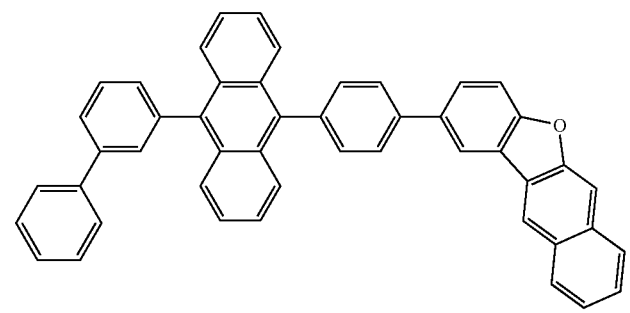

16

Synthesis was conducted in the same manner as in the synthesis of compound 1 in Example 1, except that intermediate (E) was used instead of intermediate (A), and 10-(3-biphenyl)anthracene-9-boronic acid, that was synthesized by a known method, was used instead of 10-phenylanthracene-9-boronic acid, whereby compound 16 was obtained. As a result of mass spectrometry, it was found that the compound was an intended product, and had an m/e of 622 relative to a molecular weight of 622.23.

Example 17 [Synthesis of Anthracene Derivative (Compound 17)]

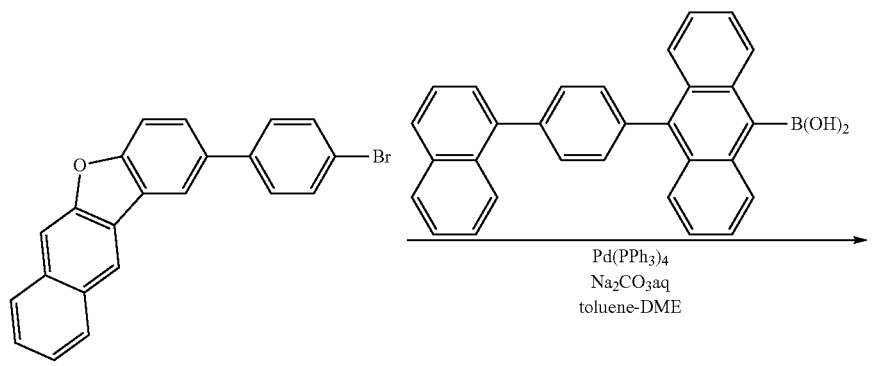

-continued

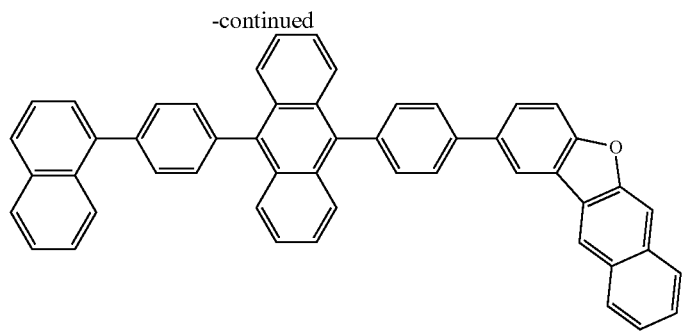

17

Synthesis was conducted in the same manner as in the synthesis of compound 1 in Example 1, except that intermediate (E) was used instead of intermediate (A), and 10-[4-(1-naphthyl)phenyl]anthracene-9-boronic acid, that was synthesized by a known method, was used instead of 10-phenylanthracene-9-boronic acid, whereby compound 17 was obtained. As a result of mass spectrometry, it was found that the compound was an intended product, and had an m/e of 672 relative to a molecular weight of 672.25.

Example 18 [Synthesis of Anthracene Derivative (Compound 18)]

Synthesis was conducted in the same manner as in the synthesis of compound 1 in Example 1, except that intermediate (E) was used instead of intermediate (A), and 10-[3-(1-naphthyl)phenyl]anthracene-9-boronic acid, that was synthesized by a known method, was used instead of 10-phenylanthracene-9-boronic acid, whereby compound 18 was obtained. As a result of mass spectrometry, it was found that the compound was an intended product, and had an m/e of 672 relative to a molecular weight of 672.25.

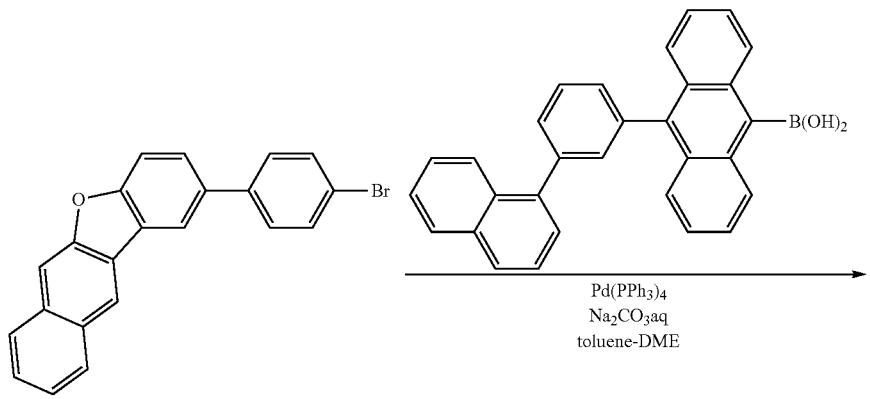

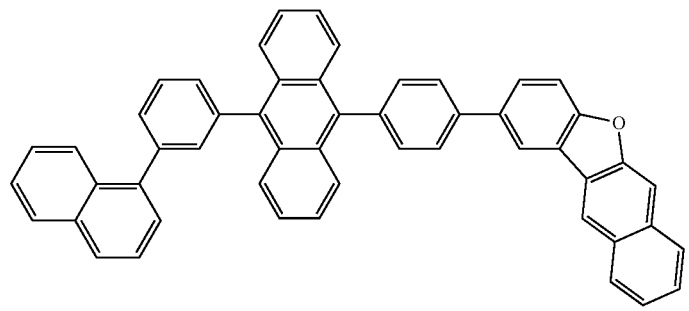

18

Example 19 [Synthesis of Anthracene Derivative (Compound 19)]

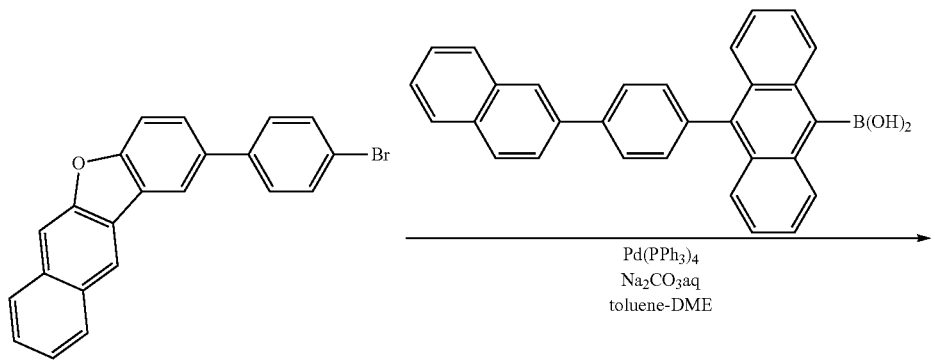

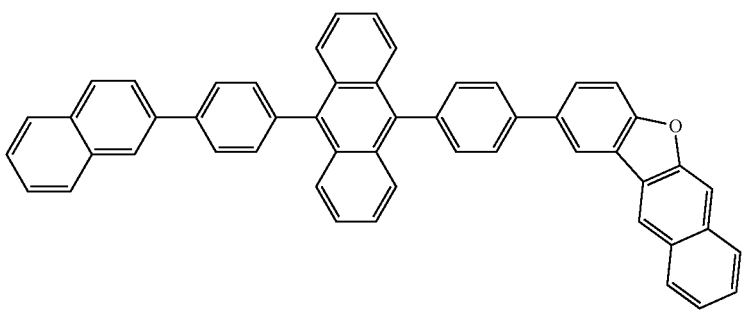

19

Synthesis was conducted in the same manner as in the synthesis of compound 1 in Example 1, except that intermediate (E) was used instead of intermediate (A), and 10-[4-(2-naphthyl)phenyl]anthracene-9-boronic acid, that was synthesized by a known method, was used instead of 10-phenylanthracene-9-boronic acid, whereby compound 19 was obtained. As a result of mass spectrometry, it was found that the compound was an intended product, and had an m/e of 672 relative to a molecular weight of 672.25.

Example 20 [Synthesis of Anthracene Derivative (Compound 20)]

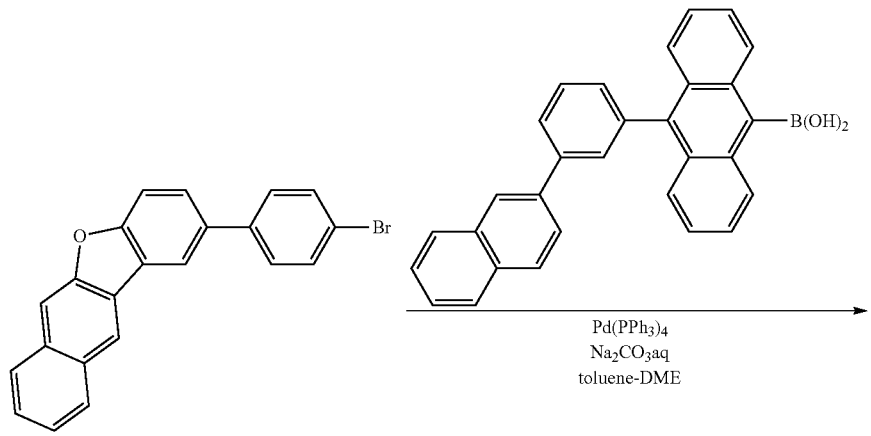

-continued

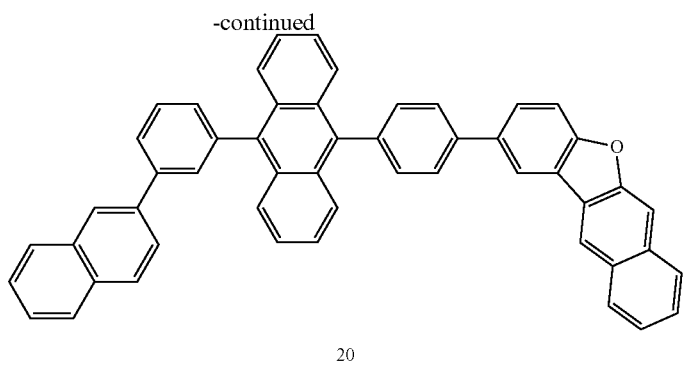

20

Synthesis was conducted in the same manner as in the synthesis of compound 1 in Example 1, except that intermediate (E) was used instead of intermediate (A), and 10-[3-(2-naphthyl)phenyl]anthracene-9-boronic acid, that was synthesized by a known method, was used instead of 10-phenylanthracene-9-boronic acid, whereby compound 20 was obtained. As a result of mass spectrometry, it was found that the compound was an intended product, and had an m/e of 672 relative to a molecular weight of 672.25.

Example 21 [Synthesis of Anthracene Derivative (Compound 21)]

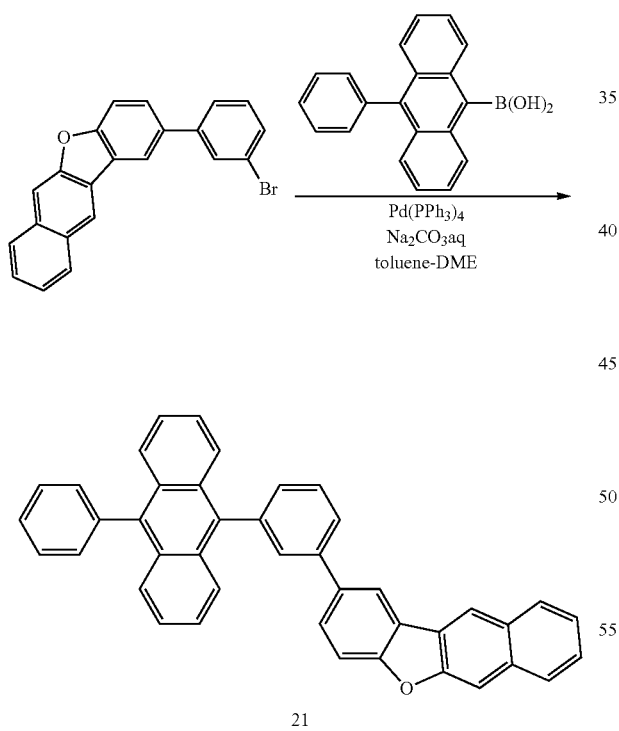

21

Synthesis was conducted in the same manner as in the synthesis of compound 1 in Example 1, except that intermediate (F) was used instead of intermediate (A), whereby compound 21 was obtained. As a result of mass spectrometry, it was found that the compound was an intended product, and had an m/e of 546 relative to a molecular weight of 546.20.

Example 22 [Synthesis of Anthracene Derivative (Compound 22)]

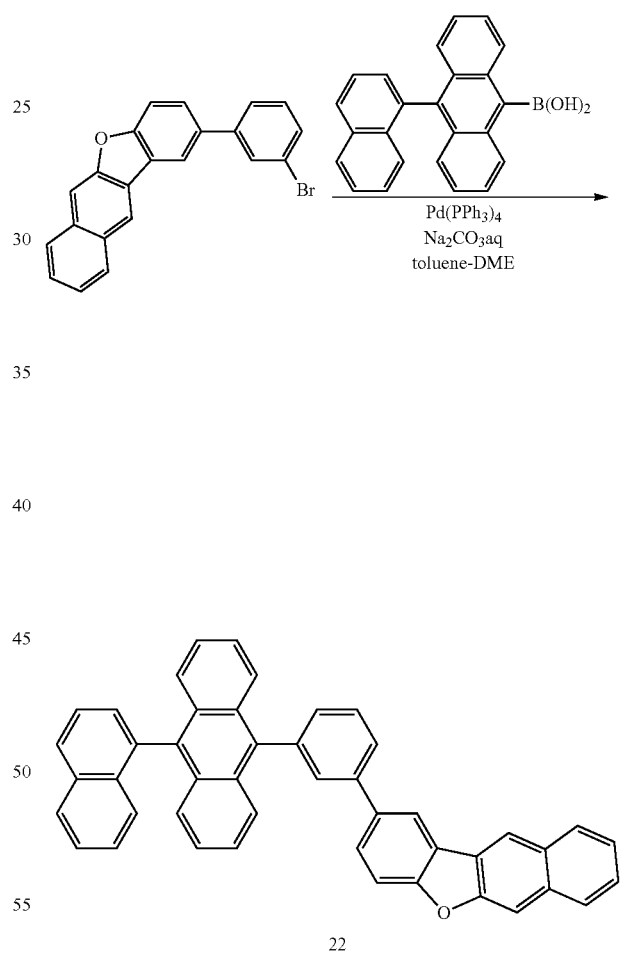

22

Synthesis was conducted in the same manner as in the synthesis of compound 1 in Example 1, except that intermediate (F) was used instead of intermediate (A), and 10-(1-naphthyl)phenyl]anthracene-9-boronic acid, that was synthesized by a known method, was used instead of 10-phenylanthracene-9-boronic acid, whereby compound 22 was obtained. As a result of mass spectrometry, it was found that the compound was an intended product, and had an m/e of 596 relative to a molecular weight of 596.21.

Example 23 [Synthesis of Anthracene Derivative (Compound 23)]

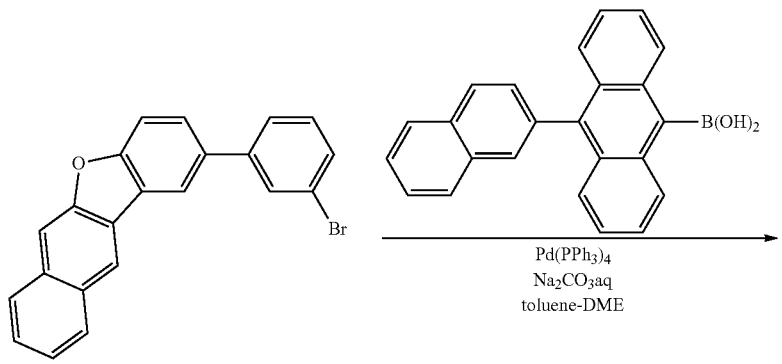

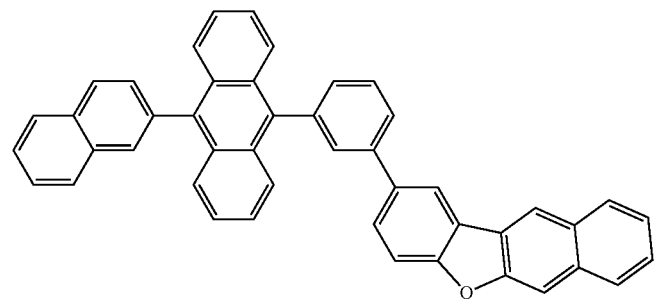
23

Synthesis was conducted in the same manner as in the synthesis of compound 1 in Example 1, except that intermediate (F) was used instead of intermediate (A), and 10-(2-naphthyl)anthracene-9-boronic acid, that was synthesized by a known method, was used instead of 10-phenylanthracene-9-boronic acid, whereby compound 23 was obtained. As a result of mass spectrometry, it was found that the compound was an intended product, and had an m/e of 596 relative to a molecular weight of 596.21.

Example 24 [Synthesis of Anthracene Derivative (Compound 24)]

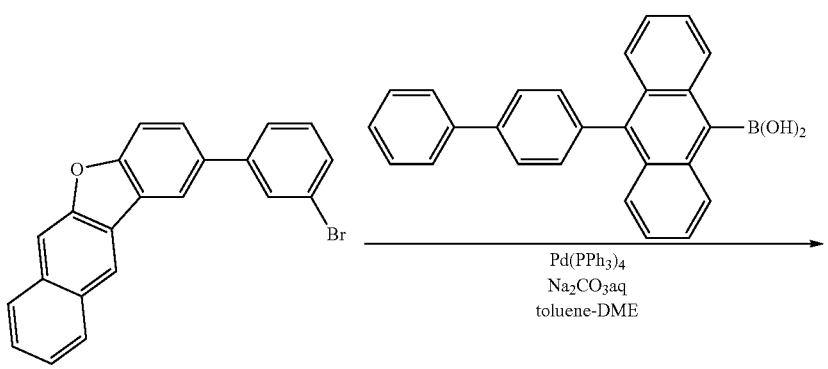

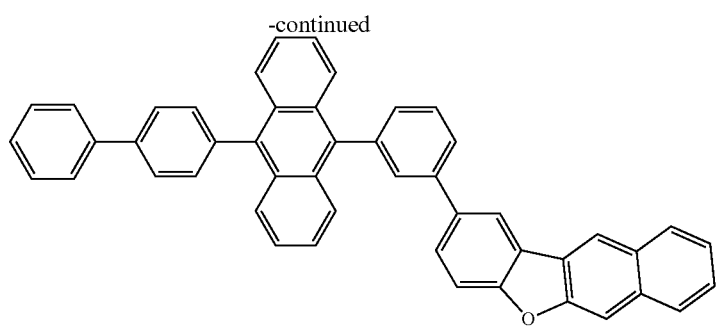

24

Synthesis was conducted in the same manner as in the synthesis of compound 1 in Example 1, except that intermediate (F) was used instead of intermediate (A), and 10-(4-biphenyl)anthracene-9-boronic acid, that was synthesized by a known method, was used instead of 10-phenylanthracene-9-boronic acid, whereby compound 24 was obtained. As a result of mass spectrometry, it was found that the compound was an intended product, and had an m/e of 622 relative to a molecular weight of 622.23.

Example 25 [Synthesis of Anthracene Derivative (Compound 25)]

Synthesis was conducted in the same manner as in the synthesis of compound 1 in Example 1, except that intermediate (F) was used instead of intermediate (A), and 10-(3-biphenyl)anthracene-9-boronic acid, that was synthesized by a known method, was used instead of 10-phenylanthracene-9-boronic acid, whereby compound 25 was obtained. As a result of mass spectrometry, it was found that the compound was an intended product, and had an m/e of 622 relative to a molecular weight of 622.23.

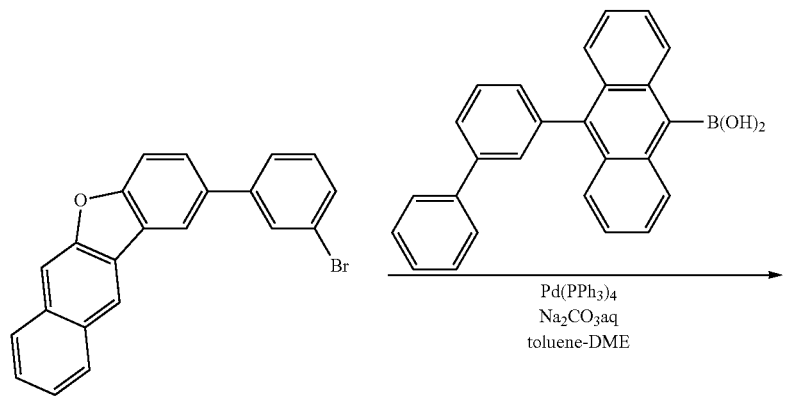

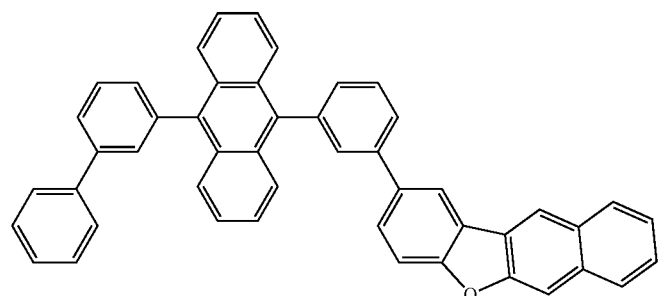

25

Example 26 [Synthesis of Anthracene Derivative (Compound 26)]

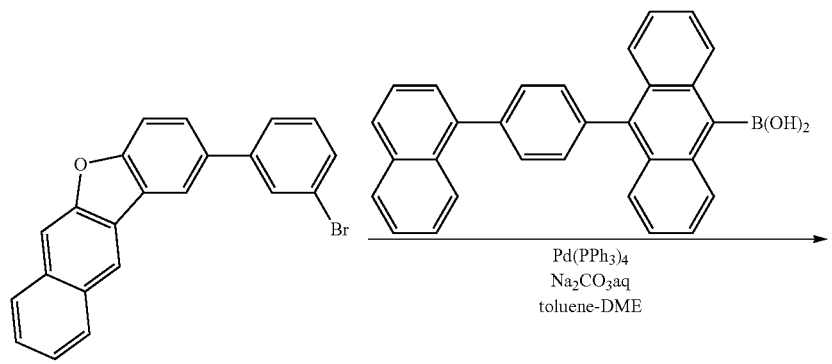

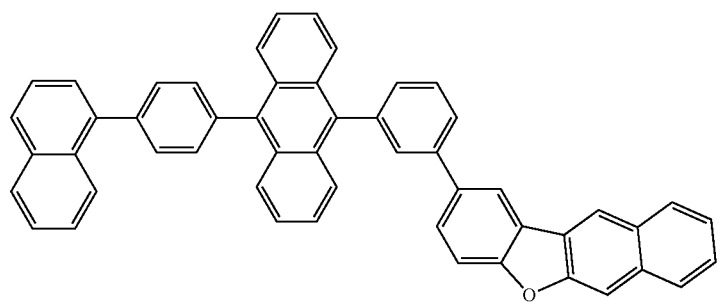

26

Synthesis was conducted in the same manner as in the synthesis of compound 1 in Example 1, except that intermediate (F) was used instead of intermediate (A), and 10-[4-(1-naphthyl)phenyl]anthracene-9-boronic acid, that was synthesized by a known method, was used instead of 10-phenylanthracene-9-boronic acid, whereby compound 26 was obtained. As a result of mass spectrometry, it was found that the compound was an intended product, and had an m/e of 672 relative to a molecular weight of 672.25.

Example 27 [Synthesis of Anthracene Derivative (Compound 27)]

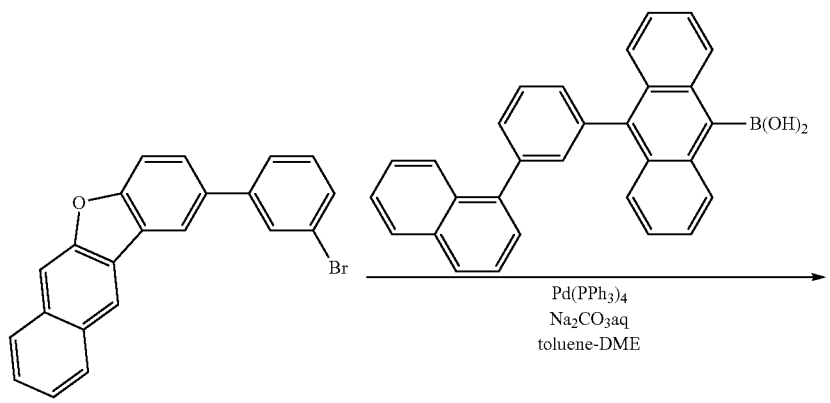

-continued

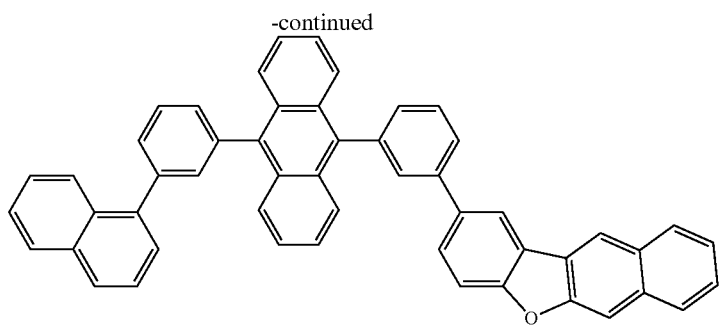

27

Synthesis was conducted in the same manner as in the synthesis of compound 1 in Example 1, except that intermediate (F) was used instead of intermediate (A), and 10-[3-(1-naphthyl)phenyl]anthracene-9-boronic acid, that was synthesized by a known method, was used instead of 10-phenylanthracene-9-boronic acid, whereby compound 27 was obtained. As a result of mass spectrometry, it was found that the compound was an intended product, and had an m/e of 672 relative to a molecular weight of 672.25.

Example 28 [Synthesis of Anthracene Derivative (Compound 28)]

Synthesis was conducted in the same manner as in the synthesis of compound 1 in Example 1, except that intermediate (F) was used instead of intermediate (A), and 10-[4-(2-naphthyl)phenyl]anthracene-9-boronic acid, that was synthesized by a known method, was used instead of 10-phenylanthracene-9-boronic acid, whereby compound 28 was obtained. As a result of mass spectrometry, the compound was an intended product, and had an m/e of 672 relative to a molecular weight of 672.25.

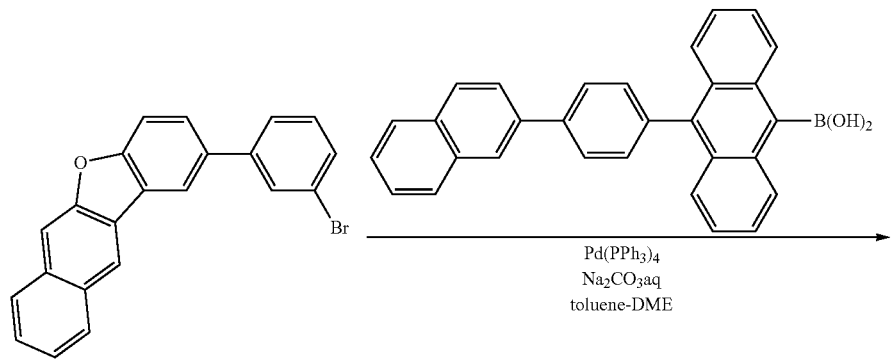

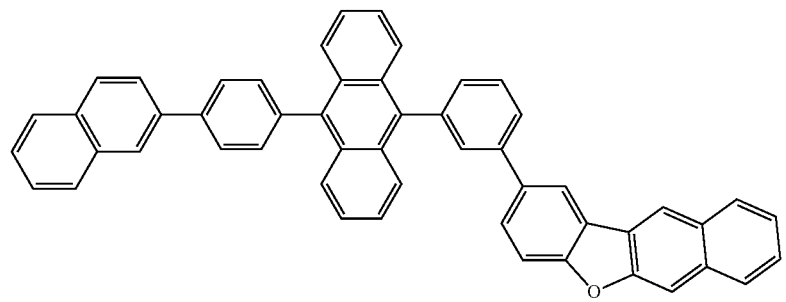

28

Example 29 [Synthesis of Anthracene Derivative (Compound 29)]

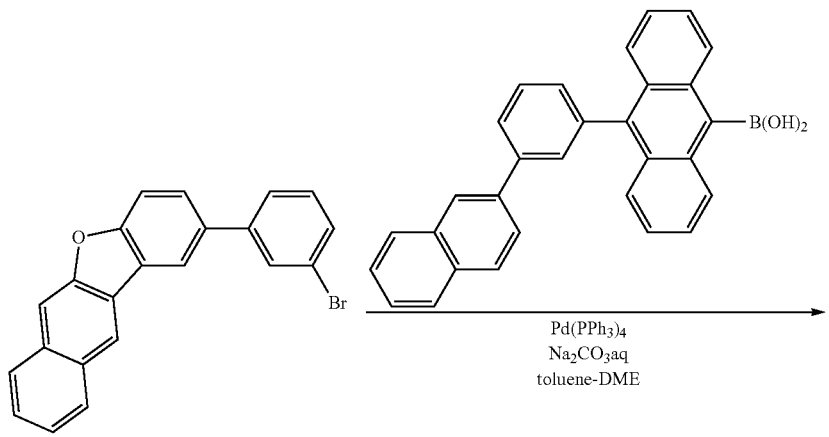

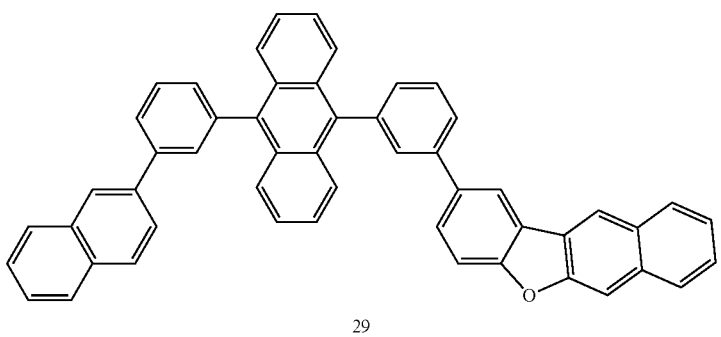

29

Synthesis was conducted in the same manner as in the synthesis of compound 1 in Example 1, except that intermediate (F) was used instead of intermediate (A), and 10-[3-(2-naphthyl)phenyl]anthracene-9-boronic acid, that was synthesized by a known method, was used instead of 10-phenylanthracene-9-boronic acid, whereby compound 29 was obtained. As a result of mass spectrometry, it was found that the compound was an intended product, and had an m/e of 672 relative to a molecular weight of 672.25.

Example 30 [Synthesis of Anthracene Derivative (Compound 30)]

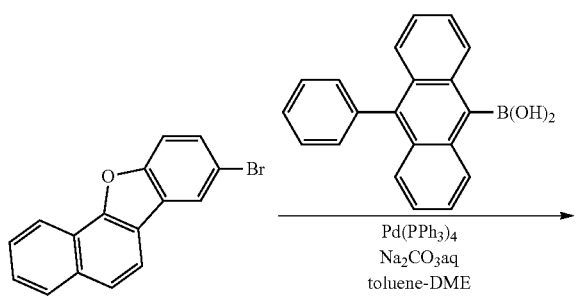

-continued

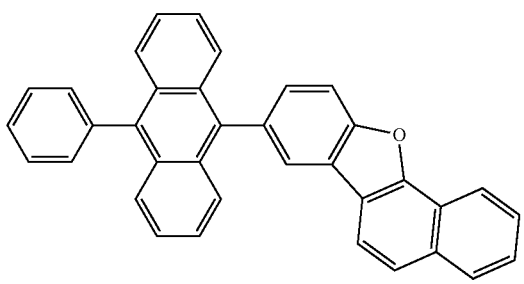

30

Synthesis was conducted in the same manner as in the synthesis of compound 1 in Example 1, except that intermediate (C) was used instead of intermediate (A), whereby compound 30 was obtained. As a result of mass spectrometry, it was found that the compound was an intended product, and had an m/e of 470 relative to a molecular weight of 470.17.

Example 31 [Synthesis of Anthracene Derivative (Compound 31)]

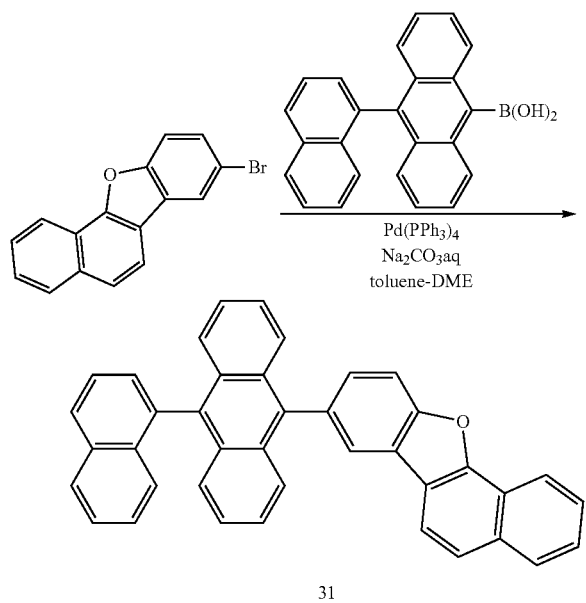

31

Synthesis was conducted in the same manner as in the synthesis of compound 1 in Example 1, except that intermediate (C) was used instead of intermediate (A), and 10-(1-naphthyl)anthracene-9-boronic acid, that was synthesized by a known method, was used instead of 10-phenylanthracene-9-boronic acid, whereby compound 31 was obtained. As a result of mass spectrometry, it was found that the compound was an intended product, and had an m/e of 520 relative to a molecular weight of 520.18.

Example 32 [Synthesis of Anthracene Derivative (Compound 32)]

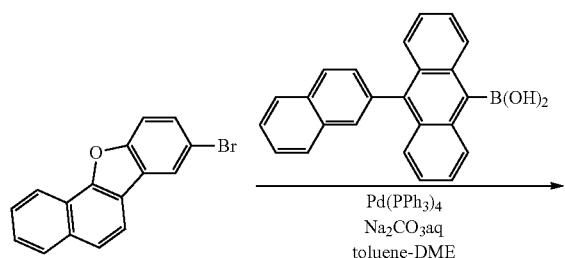

32

Synthesis was conducted in the same manner as in the synthesis of compound 1 in Example 1, except that intermediate (C) was used instead of intermediate (A), and 10-(2-naphthyl)anthracene-9-boronic acid, that was synthesized by a known method, was used instead of 10-phenylanthracene-9-boronic acid, whereby compound 32 was obtained. As a result of mass spectrometry, it was found that the compound was an intended product, and had an m/e of 520 relative to a molecular weight of 520.18.

Example 33 [Synthesis of Anthracene Derivative (Compound 33)]

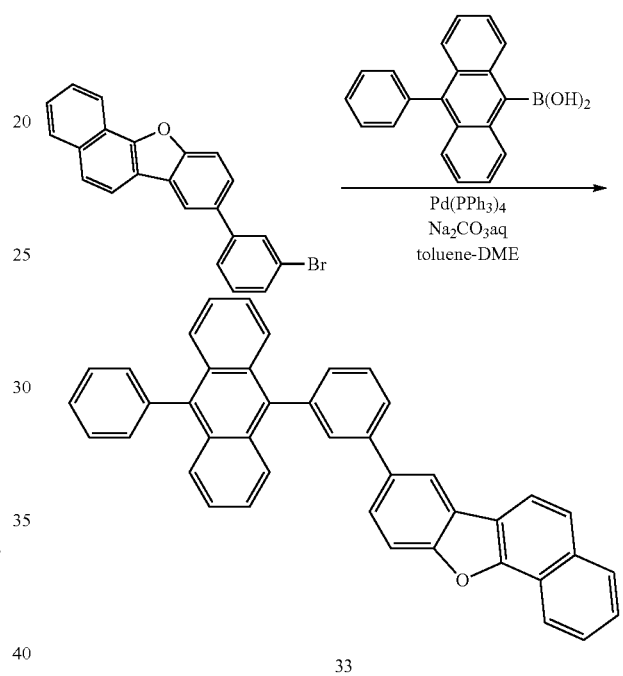

33

Synthesis was conducted in the same manner as in the synthesis of compound 1 in Example 1, except that intermediate (H) was used instead of intermediate (A), whereby compound 33 was obtained. As a result of mass spectrometry, it was found that the compound was an intended product, and had an m/e of 546 relative to a molecular weight of 546.20.

Example 34 [Synthesis of Anthracene Derivative (Compound 34)]

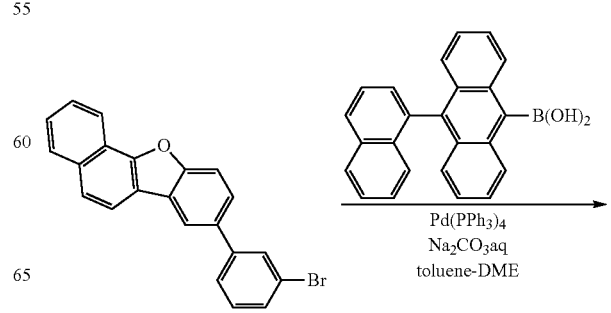

-continued

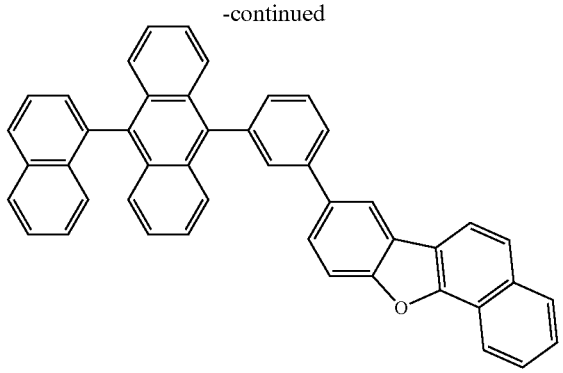

34

Synthesis was conducted in the same manner as in the synthesis of compound 1 in Example 1, except that intermediate (H) was used instead of intermediate (A), and 10-(1-naphthyl)anthracene-9-boronic acid, that was synthesized by a known method, was used instead of 10-phenylanthracene-9-boronic acid, whereby compound 34 was obtained. As a result of mass spectrometry, it was found that the compound was an intended product, and had an m/e of 596 relative to a molecular weight of 596.21.

Example 35 [Synthesis of Anthracene Derivative (Compound 35)]

Synthesis was conducted in the same manner as in the synthesis of compound 1 in Example 1, except that intermediate (H) was used instead of intermediate (A), and 10-(2-naphthyl)anthracene-9-boronic acid, that was synthesized by a known method, was used instead of 10-phenylanthracene-9-boronic acid, whereby compound 35 was obtained. As a result of mass spectrometry, it was found that the compound was an intended product, and had an m/e of 596 relative to a molecular weight of 596.21.

Example 36 [Synthesis of Anthracene Derivative (Compound 36)]

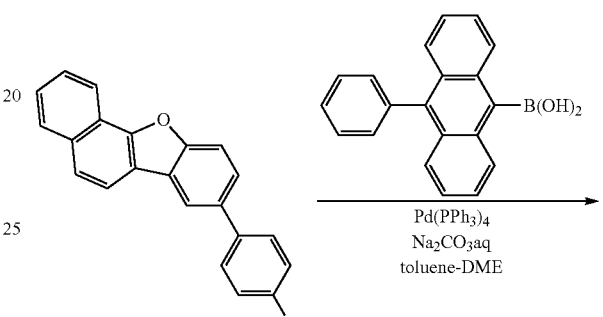

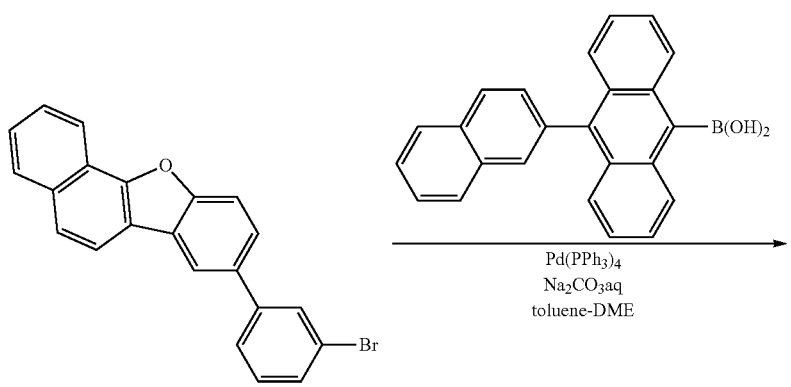

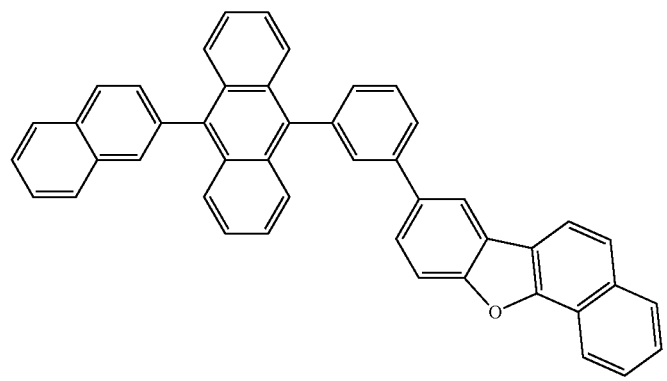

35

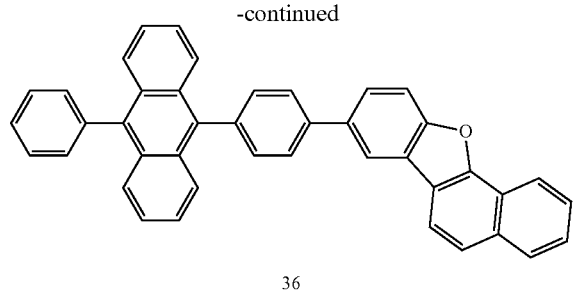

36

Synthesis was conducted in the same manner as in the synthesis of compound 1 in Example 1, except that intermediate (G) was used instead of intermediate (A), whereby compound 36 was obtained. As a result of mass spectrometry, it was found that the compound was an intended product, and had an m/e of 546 relative to a molecular weight of 546.20.

Example 37 [Synthesis of Anthracene Derivative (Compound 37)]

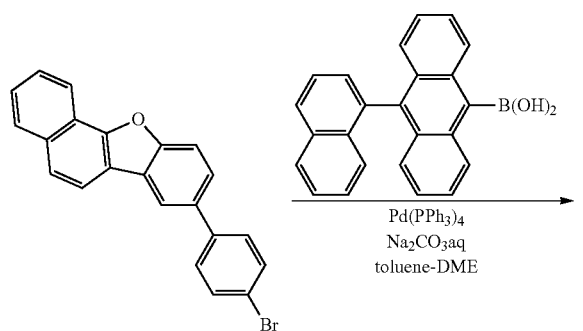

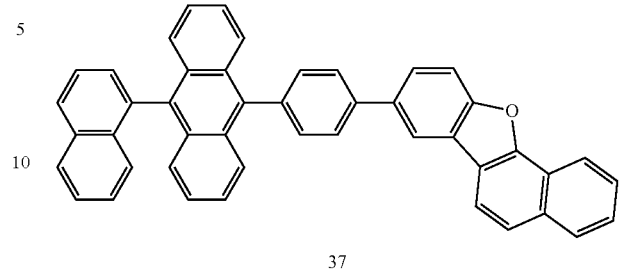

37

Synthesis was conducted in the same manner as in the synthesis of compound 1 in Example 1, except that intermediate (G) was used instead of intermediate (A), and 10-(1-naphthyl)anthracene-9-boronic acid, that was synthesized by a known method, was used instead of 10-phenylanthracene-9-boronic acid, whereby compound 37 was obtained. As a result of mass spectrometry, it was found that the compound was an intended product, and had an m/e of 596 relative to a molecular weight of 596.21.

Example 38 [Synthesis of Anthracene Derivative (Compound 38)]

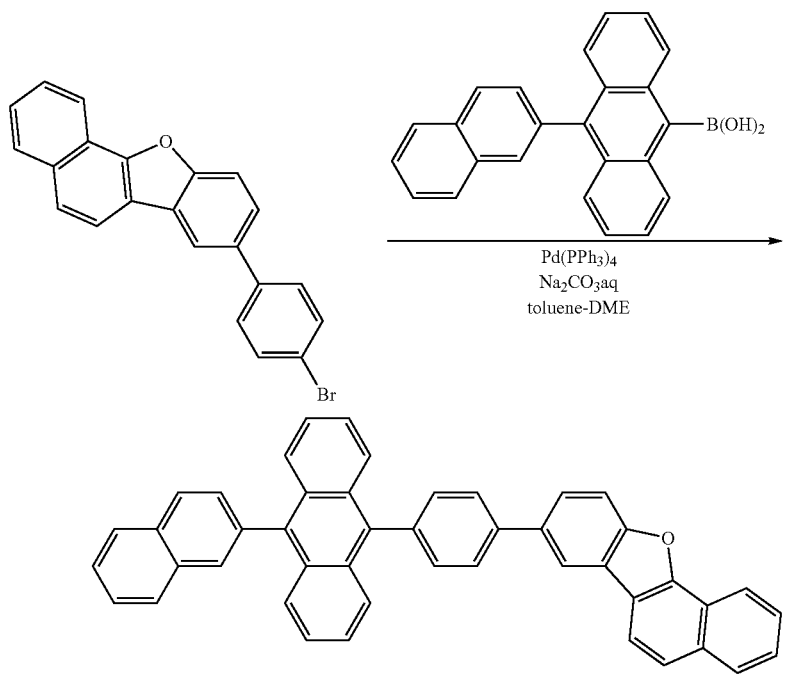

38

Synthesis was conducted in the same manner as in the synthesis of compound 1 in Example 1, except that intermediate (G) was used instead of intermediate (A), and 10-(2-naphthyl)anthracene-9-boronic acid, that was synthesized by a known method, was used instead of 10-phenylanthracene-9-boronic acid, whereby compound 38 was obtained. As a result of mass spectrometry, it was found that the compound was an intended product, and had an m/e of 596 relative to a molecular weight of 596.21.

Example 39 [Synthesis of Anthracene Derivative (Compound 39)]

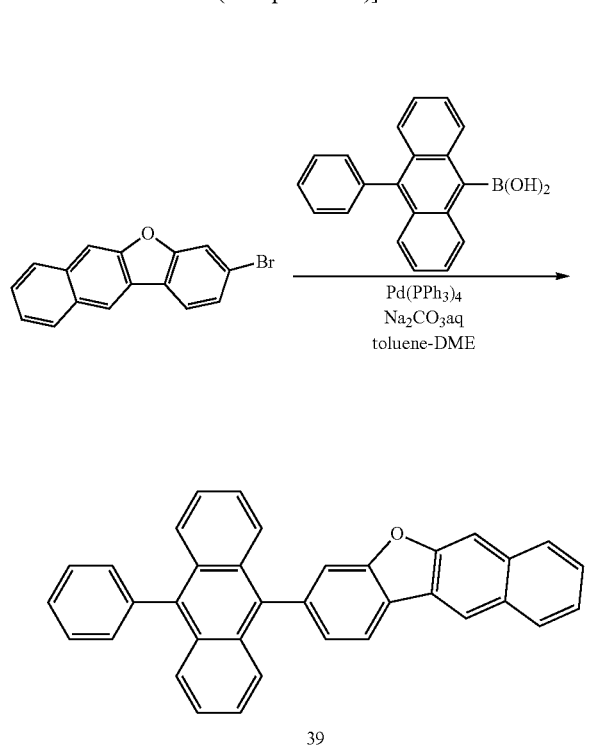

39

Synthesis was conducted in the same manner as in the synthesis of compound 1 in Example 1, except that intermediate (I) was used instead of intermediate (A), whereby compound 39 was obtained. As a result of mass spectrometry, it was found that the compound was an intended product, and had an m/e of 470 relative to a molecular weight of 470.17.

Example 40 [Synthesis of Anthracene Derivative (Compound 40)]

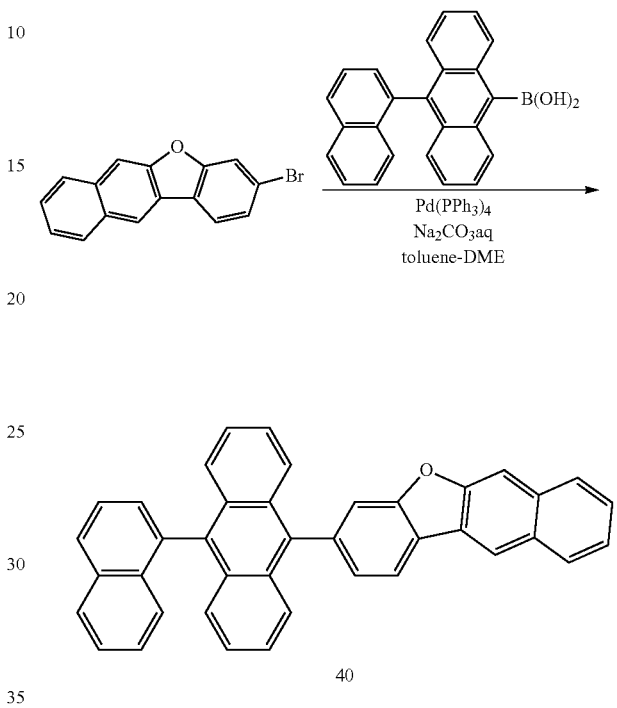

40

Synthesis was conducted in the same manner as in the synthesis of compound 1 in Example 1, except that intermediate (I) was used instead of intermediate (A), and 10-(1-naphthyl)anthracene-9-boronic acid, that was synthesized by a known method, was used instead of 10-phenylanthracene-9-boronic acid, whereby compound 40 was obtained. As a result of mass spectrometry, it was found that the compound was an intended product, and had an m/e of 520 relative to a molecular weight of 520.62.

Example 41 [Synthesis of Anthracene Derivative (Compound 41)]

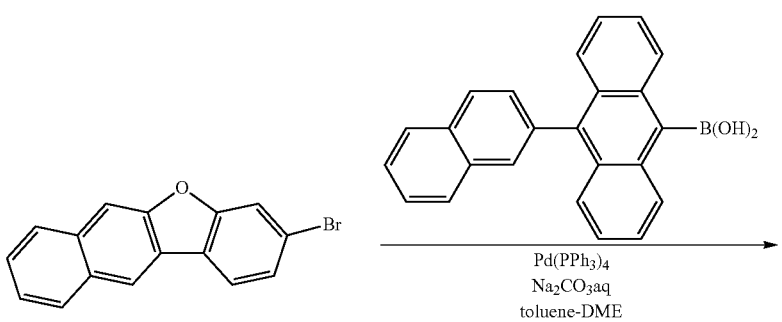

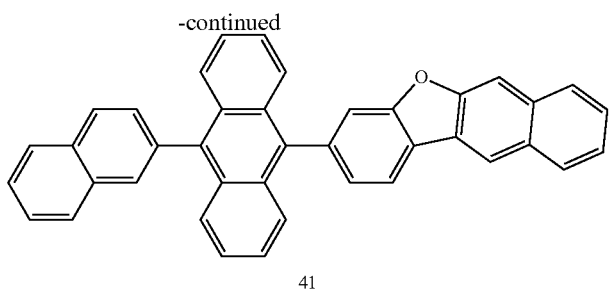

41

Synthesis was conducted in the same manner as in the synthesis of compound 1 in Example 1, except that intermediate (I) was used instead of intermediate (A), and 10-(2-naphthyl)anthracene-9-boronic acid, that was synthesized by a known method, was used instead of 10-phenylanthracene-9-boronic acid, whereby compound 41 was obtained. As a result of mass spectrometry, it was found that the compound was an intended product, and had an m/e of 520 relative to a molecular weight of 520.62.

Example 42 [Synthesis of Anthracene Derivative (Compound 42)]

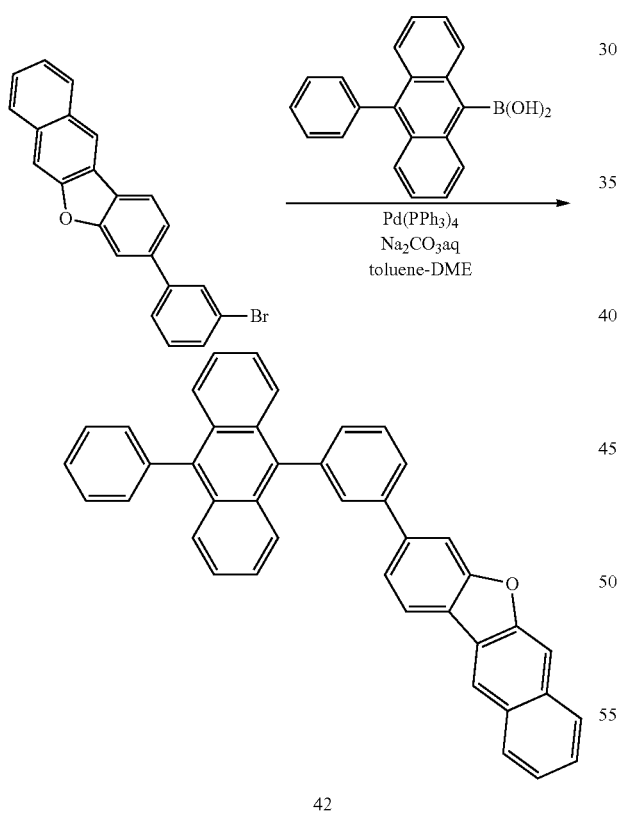

42

Synthesis was conducted in the same manner as in the synthesis of compound 1 in Example 1, except that intermediate (M) was used instead of intermediate (A), whereby compound 42 was obtained. As a result of mass spectrometry, it was found that the compound was an intended product, and had an m/e of 546 relative to a molecular weight of 546.20.

Example 43 [Synthesis of Anthracene Derivative (Compound 43)]

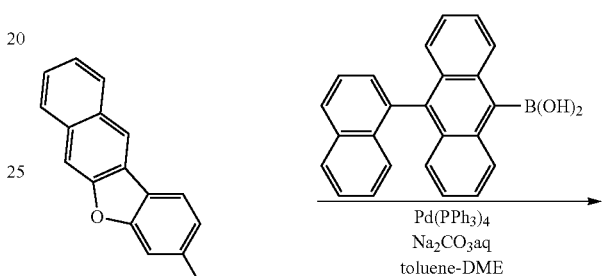

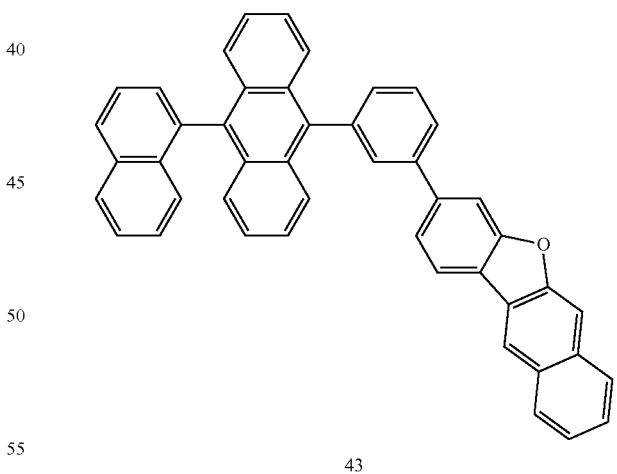

43

Synthesis was conducted in the same manner as in the synthesis of compound 1 in Example 1, except that intermediate (M) was used instead of intermediate (A), and 10-(1-naphthyl)anthracene-9-boronic acid, that was synthesized by a known method, was used instead of 10-phenylanthracene-9-boronic acid, whereby compound 43 was obtained. As a result of mass spectrometry, it was found that the compound was an intended product, and had an m/e of 596 relative to a molecular weight of 596.21.

Example 44 [Synthesis of Anthracene Derivative (Compound 44)]

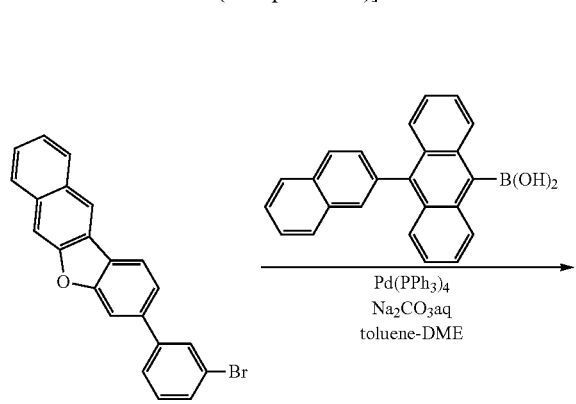

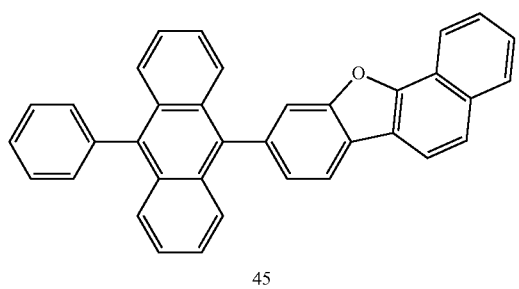

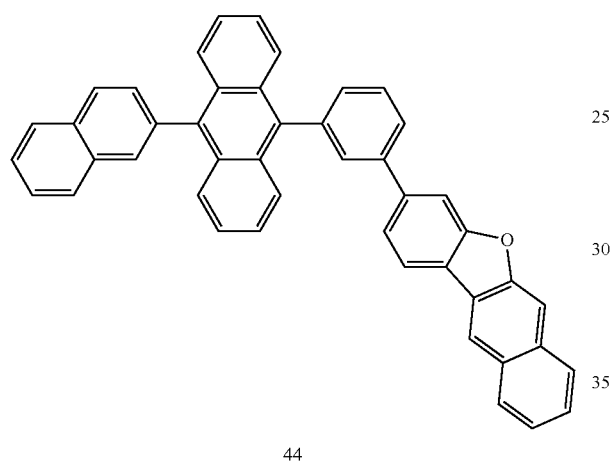

44

Synthesis was conducted in the same manner as in the synthesis of compound 1 in Example 1, except that intermediate (M) was used instead of intermediate (A), and 10-(2-naphthyl)anthracene-9-boronic acid, that was synthesized by a known method, was used instead of 10-phenylanthracene-9-boronic acid, whereby compound 44 was obtained. As a result of mass spectrometry, it was found that the compound was an intended product, and had an m/e of 596 relative to a molecular weight of 596.21.

Example 45 [Synthesis of Anthracene Derivative (Compound 45)]

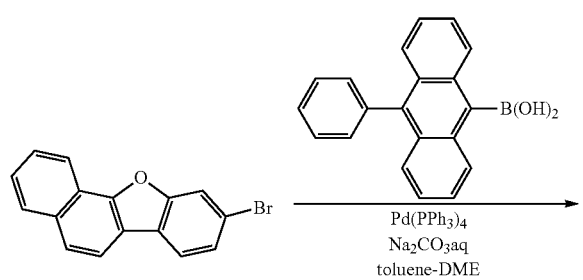

45

Synthesis was conducted in the same manner as in the synthesis of compound 1 in Example 1, except that intermediate (K) was used instead of intermediate (A), whereby compound 45 was obtained. As a result of mass spectrometry, it was found that the compound was an intended product, and had an m/e of 470 relative to a molecular weight of 470.17.

Example 46 [Synthesis of Anthracene Derivative (Compound 46)]

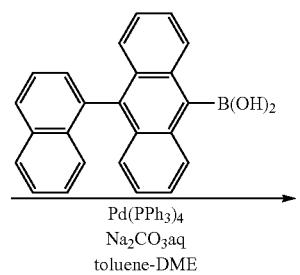

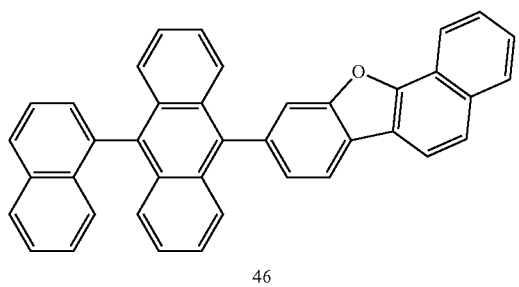

46

Synthesis was conducted in the same manner as in the synthesis of compound 1 in Example 1, except that intermediate (K) was used instead of intermediate (A), and 10-(1-naphthyl)anthracene-9-boronic acid, that was synthesized by a known method, was used instead of 10-phenylanthracene-9-boronic acid, whereby compound 46 was obtained. As a result of mass spectrometry, it was found that the compound was an intended product, and had an m/e of 520 relative to a molecular weight of 520.18.

Example 47 [Synthesis of Anthracene Derivative (Compound 47)]

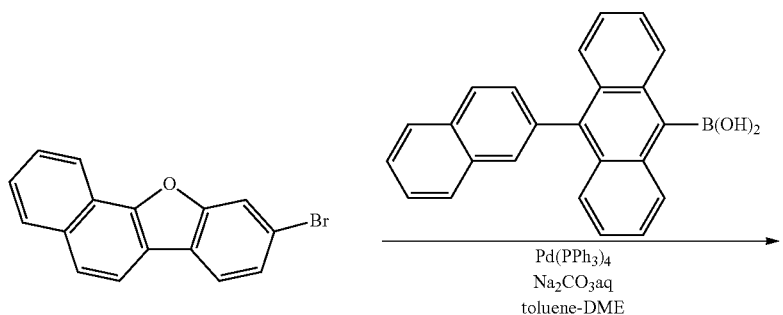

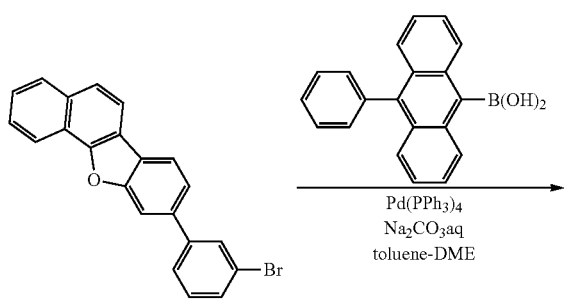

Synthesis was conducted in the same manner as in the synthesis of compound 1 in Example 1, except that intermediate (K) was used instead of intermediate (A), and 10-(2-naphthyl)anthracene-9-boronic acid, that was synthesized by a known method, was used instead of 10-phenylanthracene-9-boronic acid, whereby compound 47 was obtained. As a result of mass spectrometry, it was found that the compound was an intended product, and had an m/e of 520 relative to a molecular weight of 520.18.

Example 48 [Synthesis of Anthracene Derivative (Compound 48)]

-continued

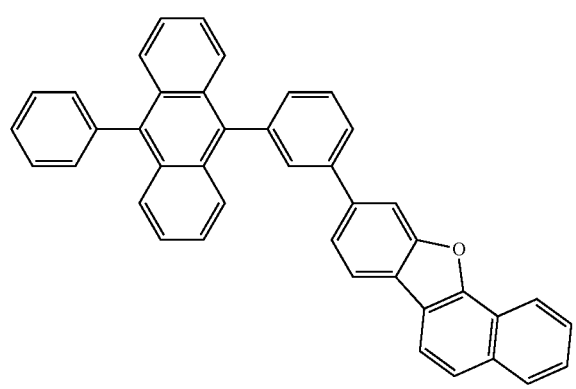

Synthesis was conducted in the same manner as in the synthesis of compound 1 in Example 1, except that intermediate (N) was used instead of intermediate (A), whereby compound 48 was obtained. As a result of mass spectrometry, it was found that the compound was an intended product, and had an m/e of 546 relative to a molecular weight of 546.20.

Example 49 [Synthesis of Anthracene Derivative (Compound 49)]

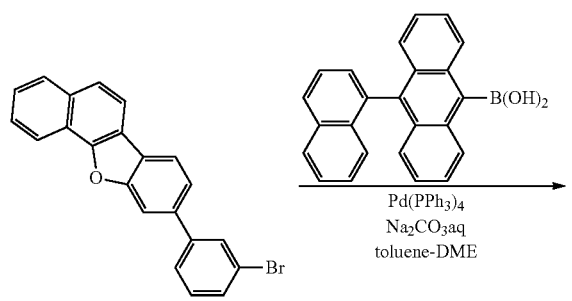

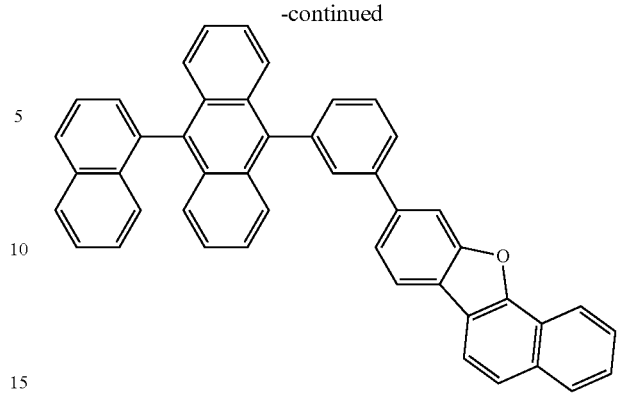

49

Synthesis was conducted in the same manner as in the synthesis of compound 1 in Example 1, except that intermediate (N) was used instead of intermediate (A), and 10-(1-naphthyl)anthracene-9-boronic acid, that was synthesized by a known method, was used instead of 10-phenylanthracene-9-boronic acid, whereby compound 49 was obtained. As a result of mass spectrometry, it was found that the compound was an intended product, and had an m/e of 596 relative to a molecular weight of 596.21.

Example 50 [Synthesis of Anthracene Derivative (Compound 50)]

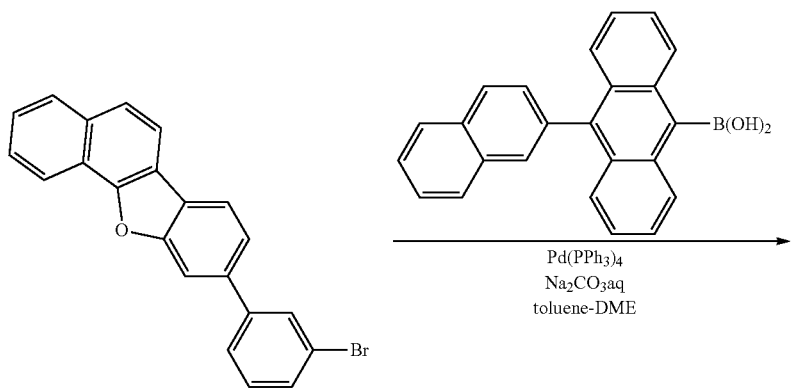

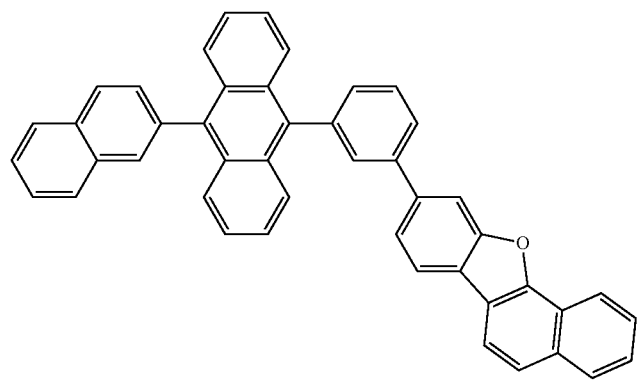

50

Synthesis was conducted in the same manner as in the synthesis of compound 1 in Example 1, except that intermediate (N) was used instead of intermediate (A), and 10-(2-naphthyl)anthracene-9-boronic acid, that was synthesized by a known method, was used instead of 10-phenylanthracene-9-boronic acid, whereby compound 50 was obtained. As a result of mass spectrometry, it was found that the compound was an intended product, and had an m/e of 596 relative to a molecular weight of 596.21.

Production Example 2 [Synthesis of Intermediate]

(1) Synthesis of Intermediates (O) and (P)

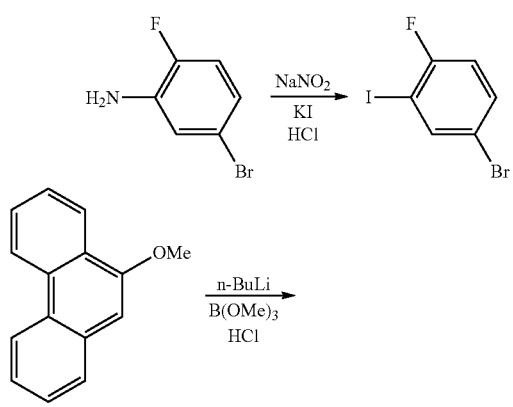

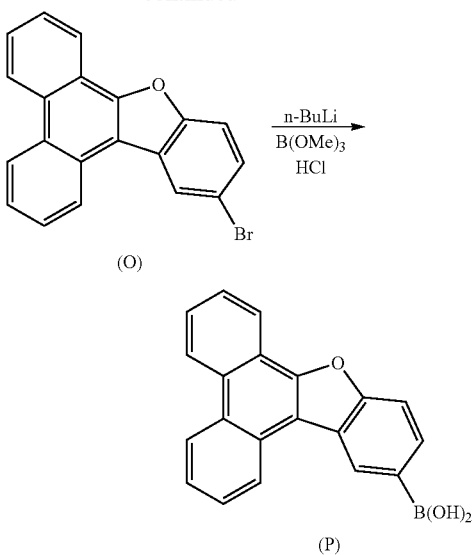

Intermediates (O) and (P) were synthesized in the same manner as in the synthesis of intermediates (A) and (B) in accordance with the above-mentioned scheme, except that 9-methoxyphenathrene was used instead of 2-methoxynaphthalene as the starting material.

(2) Synthesis of Intermediate (Q)

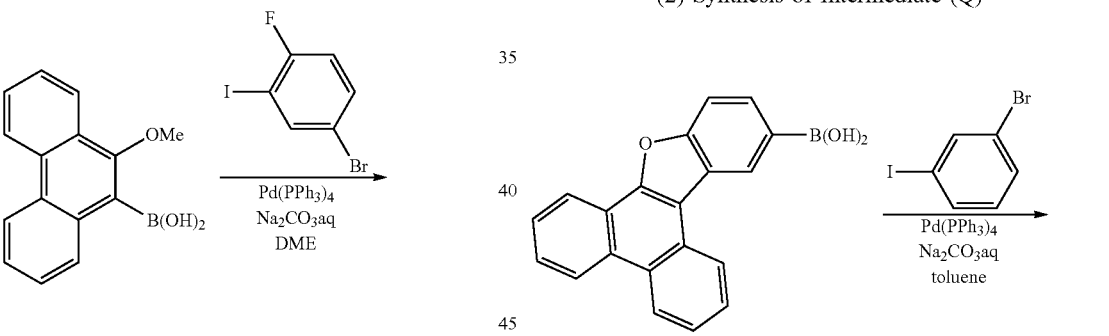

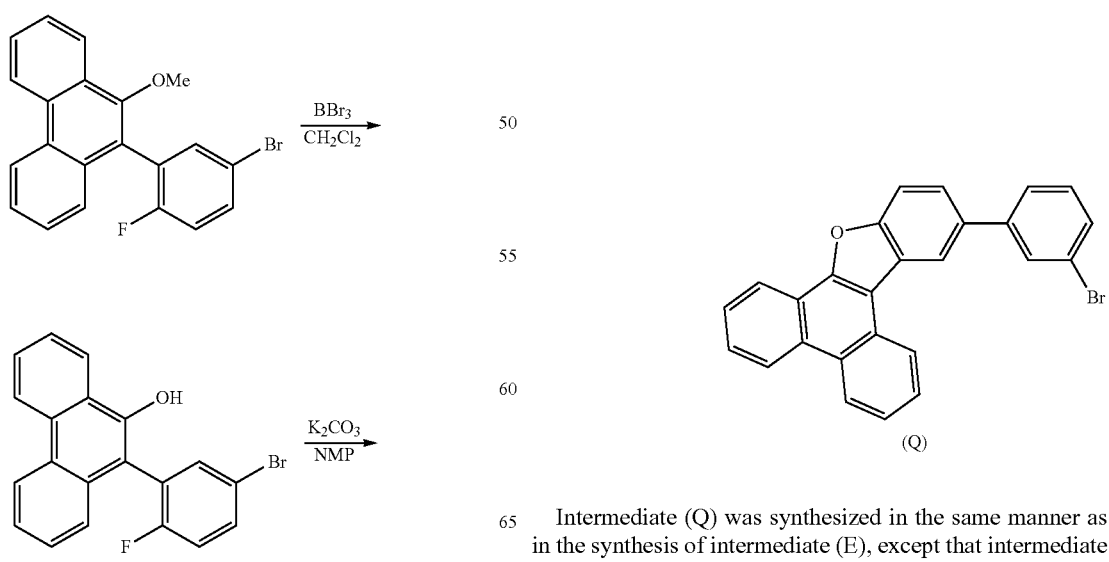

Intermediate (Q) was synthesized in the same manner as in the synthesis of intermediate (E), except that intermediate (P) was used instead of intermediate (B).

Example 51 [Synthesis of Anthracene Derivative (Compound 51)]

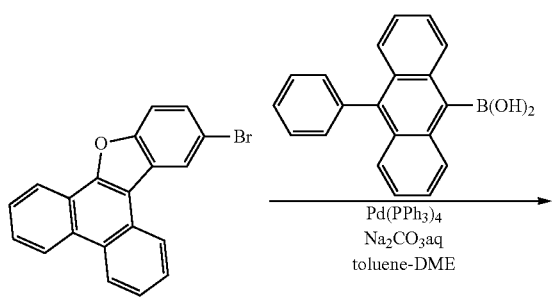

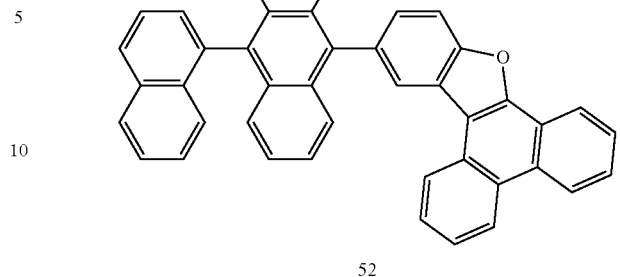

52

Synthesis was conducted in the same manner as in the synthesis of compound 1 in Example 1, except that intermediate (O) was used instead of intermediate (A), and 10-(1-naphthyl)anthracene-9-boronic acid, that was synthesized by a known method, was used instead of 10-phenylanthracene-9-boronic acid, whereby compound 52 was obtained. As a result of mass spectrometry, it was found that the compound was an intended product, and had an m/e of 570 relative to a molecular weight of 570.20.

Example 53 [Synthesis of Anthracene Derivative (Compound 53)]

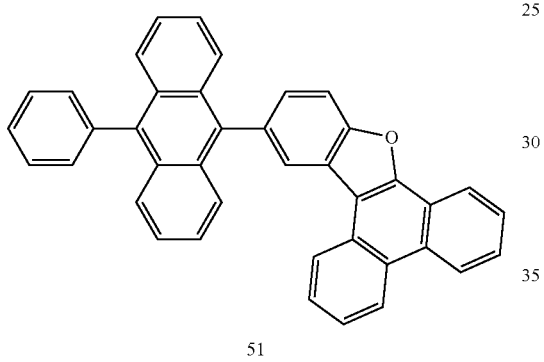

51

Synthesis was conducted in the same manner as in the synthesis of compound 1 in Example 1, except that intermediate (O) was used instead of intermediate (A), whereby compound 51 was obtained. As a result of mass spectrometry, it was found that the compound was an intended product, and had an m/e of 520 relative to a molecular weight of 520.18.

Example 52 [Synthesis of Anthracene Derivative (Compound 52)]

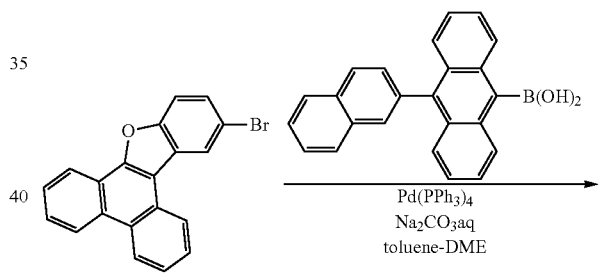

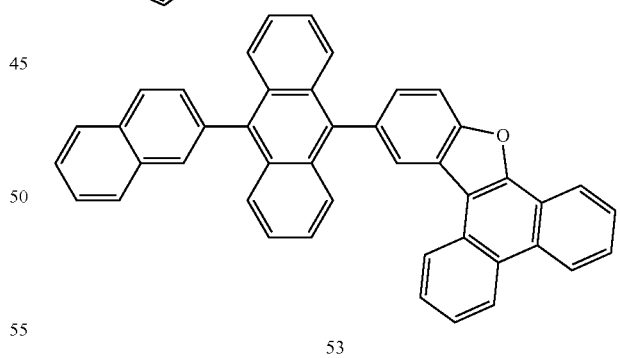

53

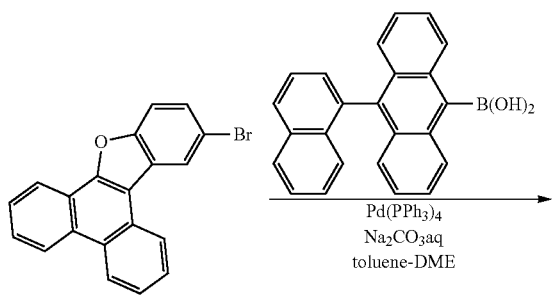

Synthesis was conducted in the same manner as in the synthesis of compound 1 in Example 1, except that intermediate (O) was used instead of intermediate (A), and 10-(2-naphthyl)anthracene-9-boronic acid, that was synthesized by a known method, was used instead of 10-phenylanthracene-9-boronic acid, whereby compound 53 was obtained. As a result of mass spectrometry, it was found that the compound was an intended product, and had an m/e of 570 relative to a molecular weight of 570.20.

Example 54 [Synthesis of Anthracene Derivative (Compound 54)]

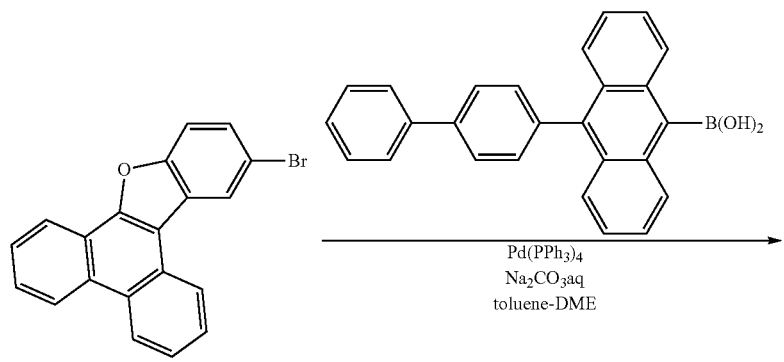

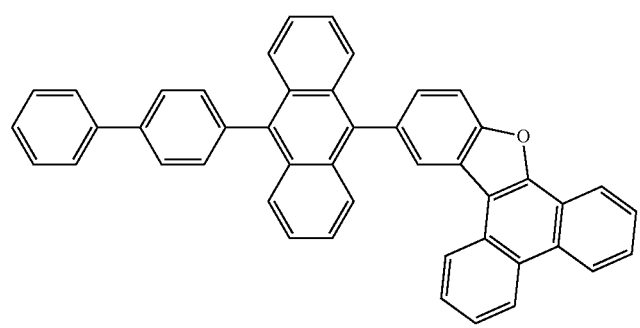

54

Synthesis was conducted in the same manner as in the synthesis of compound 1 in Example 1, except that intermediate (O) was used instead of intermediate (A), and 10-(4-biphenyl)anthracene-9-boronic acid, that was synthesized by a known method, was used instead of 10-phenylanthracene-9-boronic acid, whereby compound 54 was obtained. As a result of mass spectrometry, it was found that the compound was an intended product, and had an m/e of 570 relative to a molecular weight of 596.21.

Example 55 [Synthesis of Anthracene Derivative (Compound 55)]

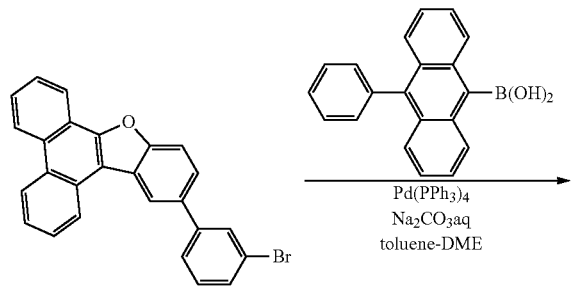

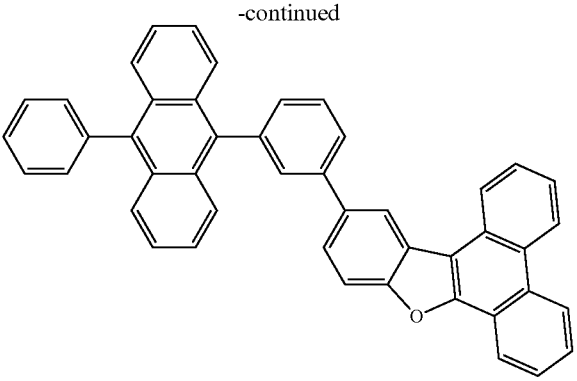

55

Synthesis was conducted in the same manner as in the synthesis of compound 1 in Example 1, except that intermediate (Q) was used instead of intermediate (A), whereby compound 55 was obtained. As a result of mass spectrometry, it was found that the compound was an intended product, and had an m/e of 596 relative to a molecular weight of 596.21.

Example 56 [Synthesis of Anthracene Derivative (Compound 56)]

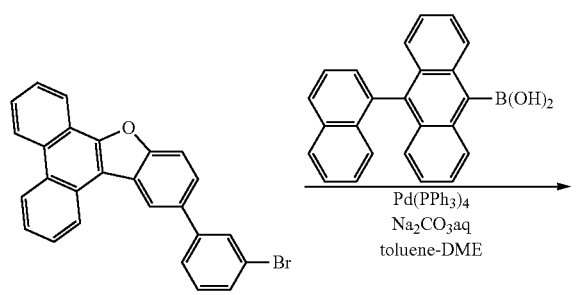
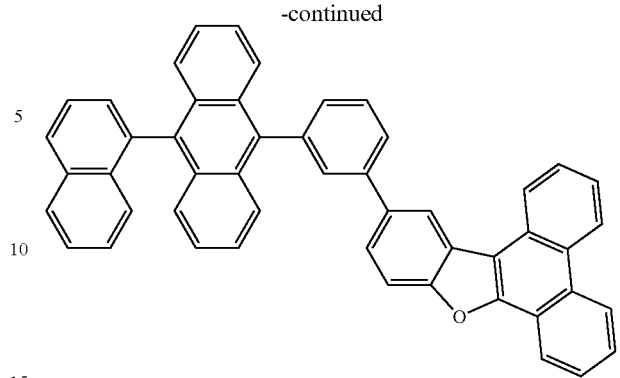

Synthesis was conducted in the same manner as in the synthesis of compound 1 in Example 1, except that intermediate (Q) was used instead of intermediate (A), and 10-(1-naphthyl)anthracene-9-boronic acid, that was synthesized by a known method, was used instead of 10-phenylanthracene-9-boronic acid, whereby compound 56 was obtained. As a result of mass spectrometry, it was found that the compound was an intended product, and had an m/e of 646 relative to a molecular weight of 646.23.

Example 57 [Synthesis of Anthracene Derivative (Compound 57)]

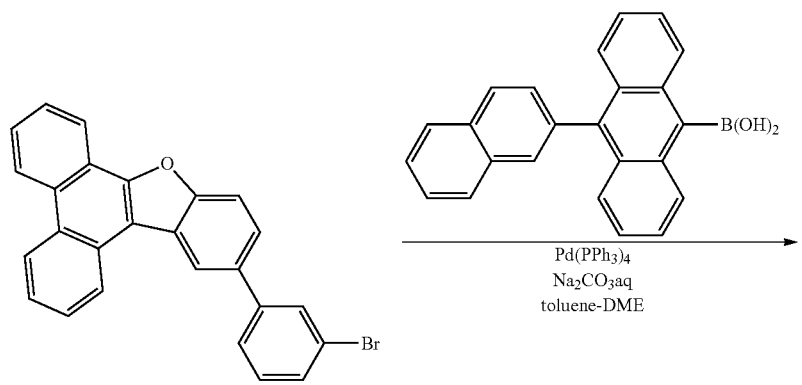
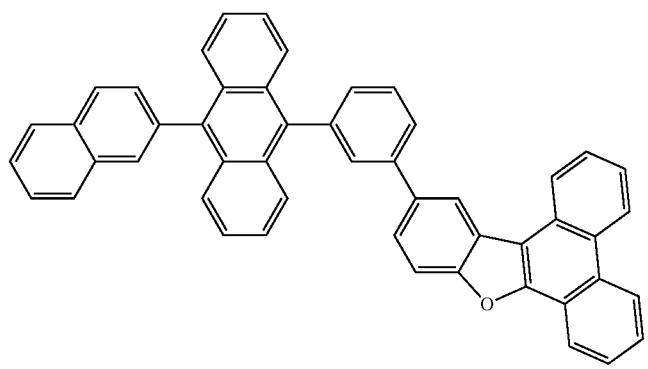

Synthesis was conducted in the same manner as in the synthesis of compound 1 in Example 1, except that intermediate (Q) was used instead of intermediate (A), and 10-(2-naphthyl)anthracene-9-boronic acid, that was synthesized by a known method, was used instead of 10-phenylanthracene-9-boronic acid, whereby compound 57 was obtained. As a result of mass spectrometry, it was found that the compound was an intended product, and had an m/e of 646 relative to a molecular weight of 646.23.

Example 58 [Synthesis of Anthracene Derivative (Compound 58)]

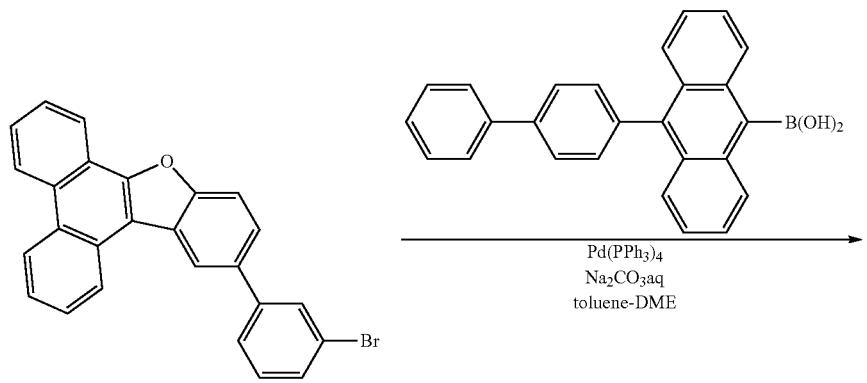

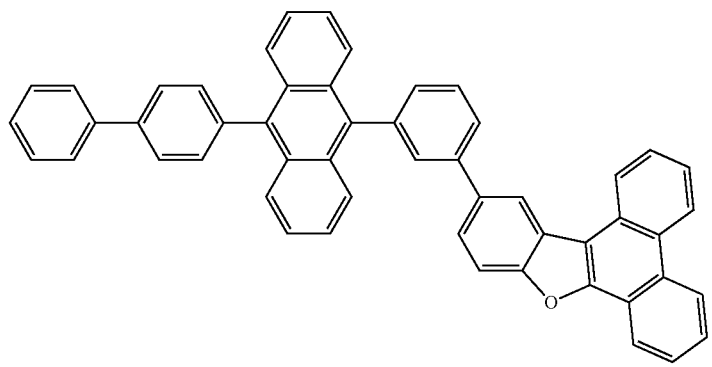

58

Synthesis was conducted in the same manner as in the synthesis of compound 1 in Example 1, except that intermediate (Q) was used instead of intermediate (A), and 10-(4-biphenyl)anthracene-9-boronic acid, that was synthesized by a known method, was used instead of 10-phenylanthracene-9-boronic acid, whereby compound 58 was obtained. As a result of mass spectrometry, it was found that the compound was an intended product, and had an m/e of 672 relative to a molecular weight of 672.25.

Production Example 3 [Synthesis of Intermediate]

(1) Synthesis of Intermediates (R) and (S)

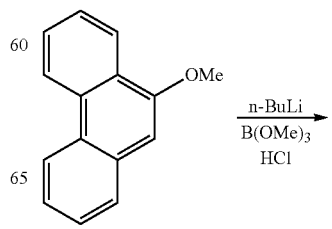

-continued

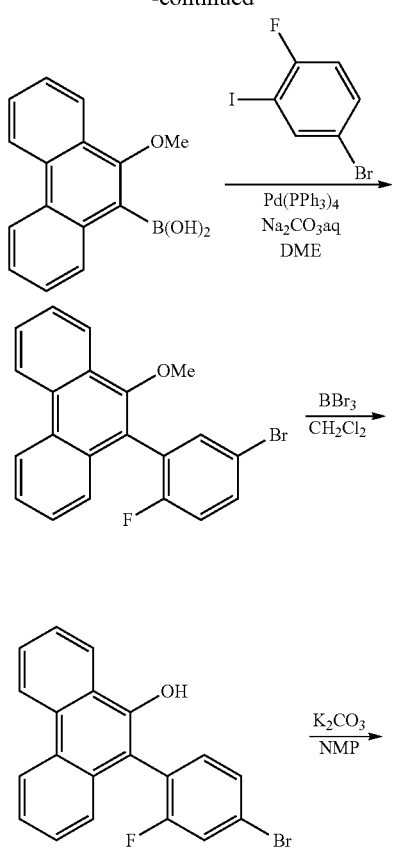

(R)

(S)

Intermediates (R) and (S) were synthesized in the same manner as in the synthesis of intermediates (A) and (B) in accordance with the above-mentioned scheme, except that 9-methoxyphenanthrene was used instead of 2-methoxynaphthalene and 2-fluoro-4-bromoiodobenzene was used instead of 2-fluoro-5-bromoiodobenzene.

(2) Synthesis of Intermediate (T)

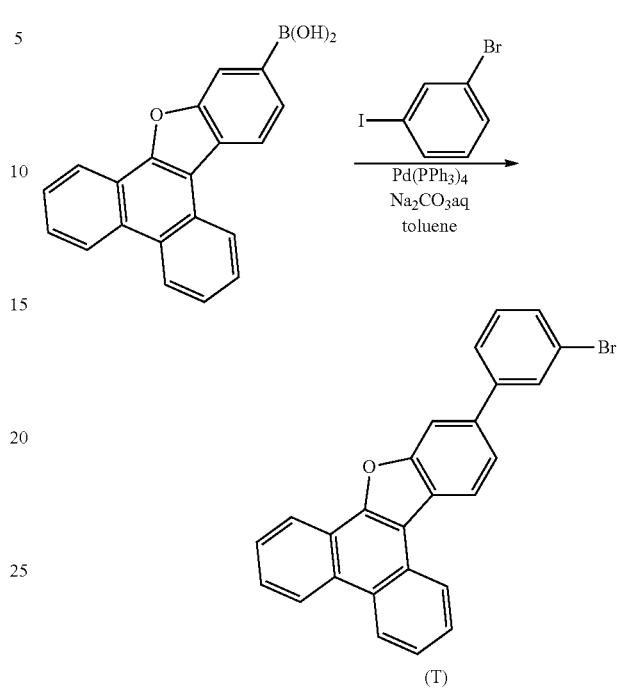

(T)

Synthesis was conducted in the same manner as in the synthesis of intermediate (E), except that intermediate (S) was used instead of the intermediate (B), whereby intermediate (T) was obtained.

Example 59 [Synthesis of Anthracene Derivative (Compound 59)]

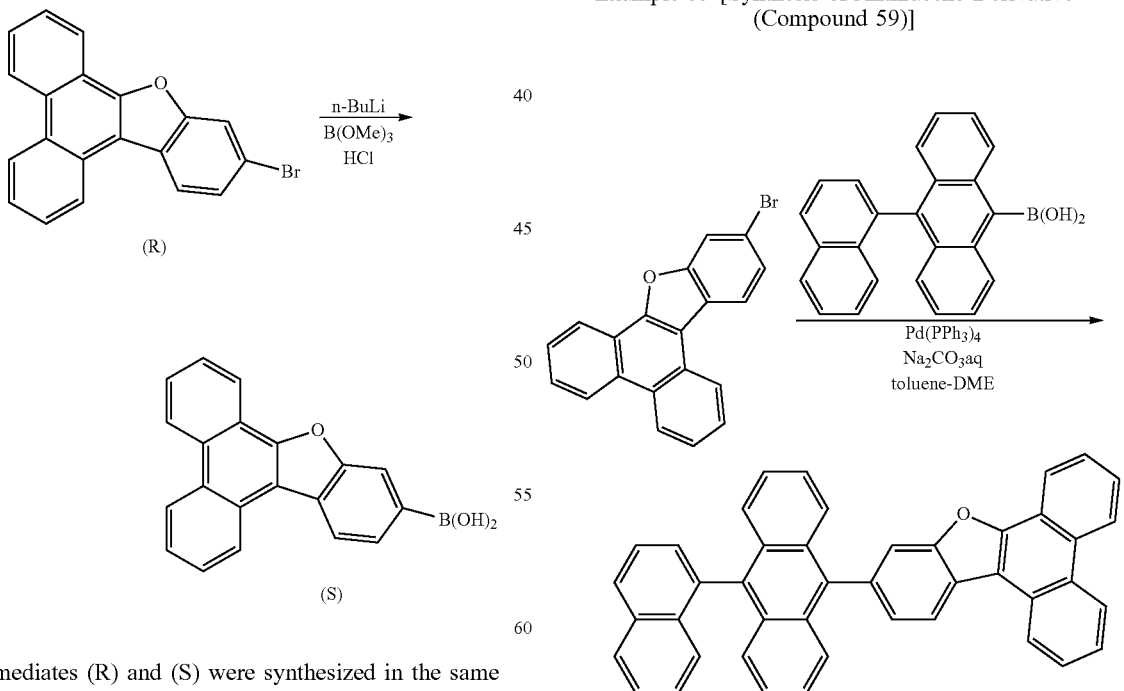

59

Synthesis was conducted in the same manner as in the synthesis of compound 1 in Example 1, except that intermediate (R) was used instead of intermediate (A), and 10-(1-naphthyl)anthracene-9-boronic acid, that was synthesized by a known method, was used instead of 10-phenylanthracene-9-boronic acid, whereby compound 59 was obtained. As a result of mass spectrometry, it was found that the compound was an intended product, and had an m/e of 570 relative to a molecular weight of 570.20.

Example 60 [Synthesis of Anthracene Derivative (Compound 60)]

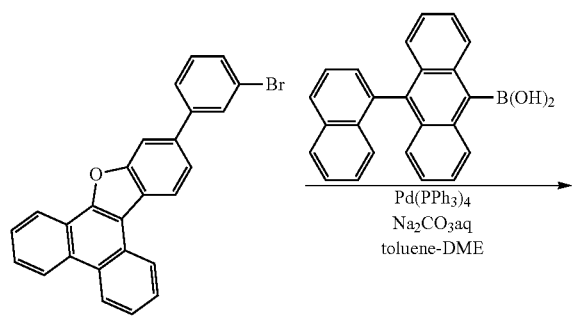

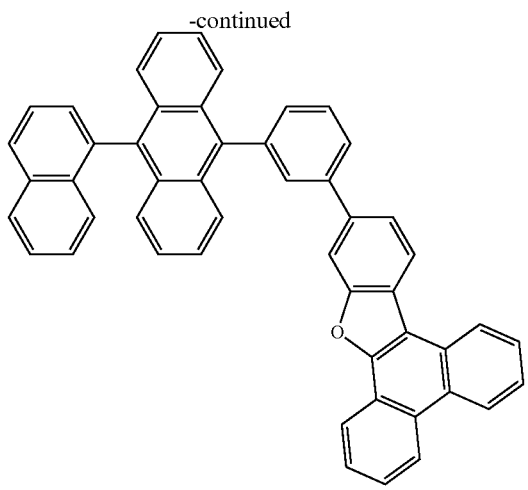

60

Synthesis was conducted in the same manner as in the synthesis of compound 1 in Example 1, except that intermediate (T) was used instead of intermediate (A), and 10-(1-naphthyl)anthracene-9-boronic acid, that was synthesized by a known method, was used instead of 10-phenylanthracene-9-boronic acid, whereby compound 60 was obtained. As a result of mass spectrometry, it was found that the compound was an intended product, and had an m/e of 646 relative to a molecular weight of 646.23.

Example 61 [Synthesis of Anthracene Derivative (Compound 61)]

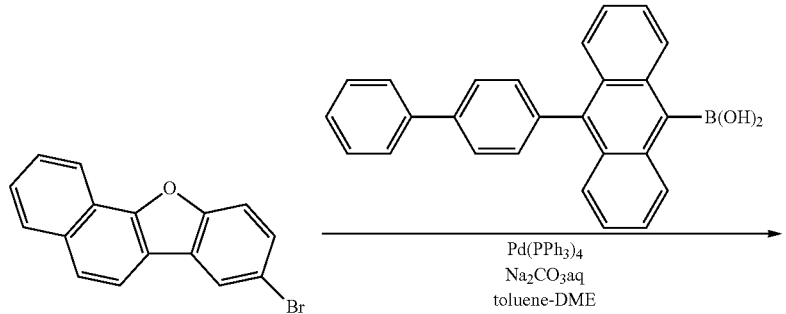

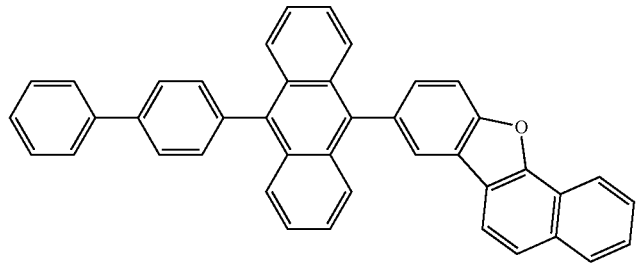

61

Synthesis was conducted in the same manner as in the synthesis of compound 1 in Example 1, except that intermediate (C) was used instead of intermediate (A), and 10-(4-biphenyl)anthracene-9-boronic acid, that was synthesized by a known method, was used instead of 10-phenylanthracene-9-boronic acid, whereby compound 61 was obtained. As a result of mass spectrometry, it was found that the compound was an intended product, and had an m/e of 546 relative to a molecular weight of 546.20.

Example 62 [Synthesis of Anthracene Derivative (Compound 62)]

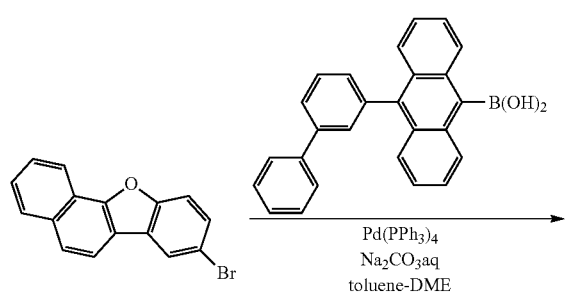

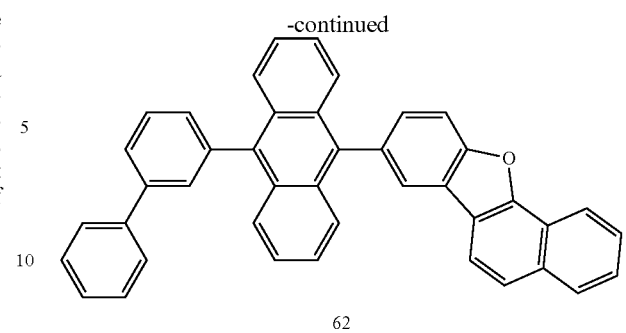

62

Synthesis was conducted in the same manner as in the synthesis of compound 1 in Example 1, except that intermediate (C) was used instead of intermediate (A), and 10-(3-biphenyl)anthracene-9-boronic acid, that was synthesized by a known method, was used instead of 10-phenylanthracene-9-boronic acid, whereby compound 62 was obtained. As a result of mass spectrometry, it was found that the compound was an intended product, and had an m/e of 546 relative to a molecular weight of 546.20.

Example 63 [Synthesis of Anthracene Derivative (Compound 63)]

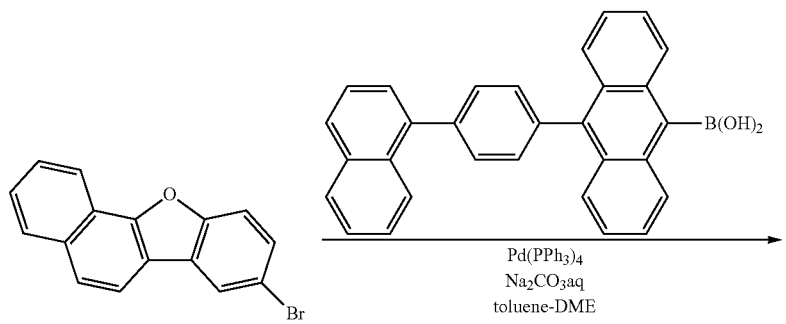

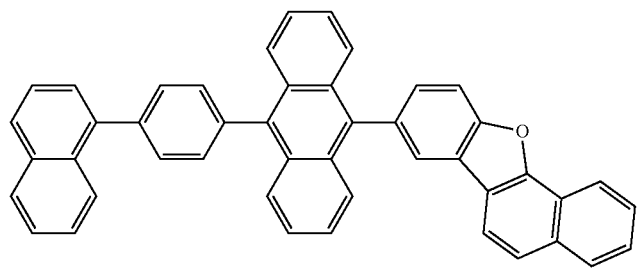

63

Synthesis was conducted in the same manner as in the synthesis of compound 1 in Example 1, except that intermediate (C) was used instead of intermediate (A), and 10-[4-(1-naphthyl)phenyl]anthracene-9-boronic acid, that was synthesized by a known method, was used instead of 10-phenylanthracene-9-boronic acid, whereby compound 63 was obtained. As a result of mass spectrometry, it was found that the compound was an intended product, and had an m/e of 596 relative to a molecular weight of 596.21.

Example 64 [Synthesis of Anthracene Derivative (Compound 64)]

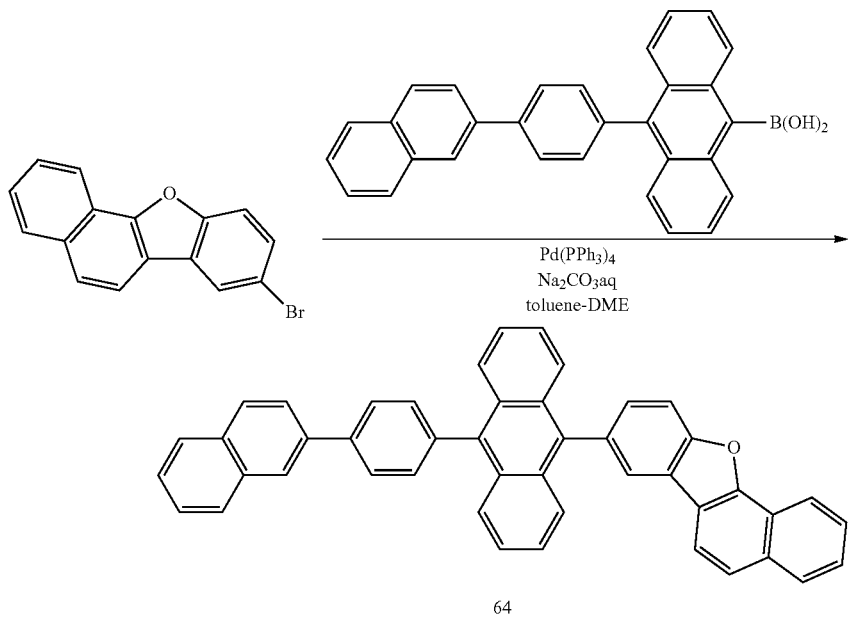

Synthesis was conducted in the same manner as in the synthesis of compound 1 in Example 1, except that intermediate (C) was used instead of intermediate (A), and 10-[4-(2-naphthyl)phenyl]anthracene-9-boronic acid, that was synthesized by a known method, was used instead of 10-phenylanthracene-9-boronic acid, whereby compound 64 was obtained. As a result of mass spectrometry, it was found that the compound was an intended product, and had an m/e of 596 relative to a molecular weight of 596.21.

Example 65 [Synthesis of Anthracene Derivative (Compound 65)]

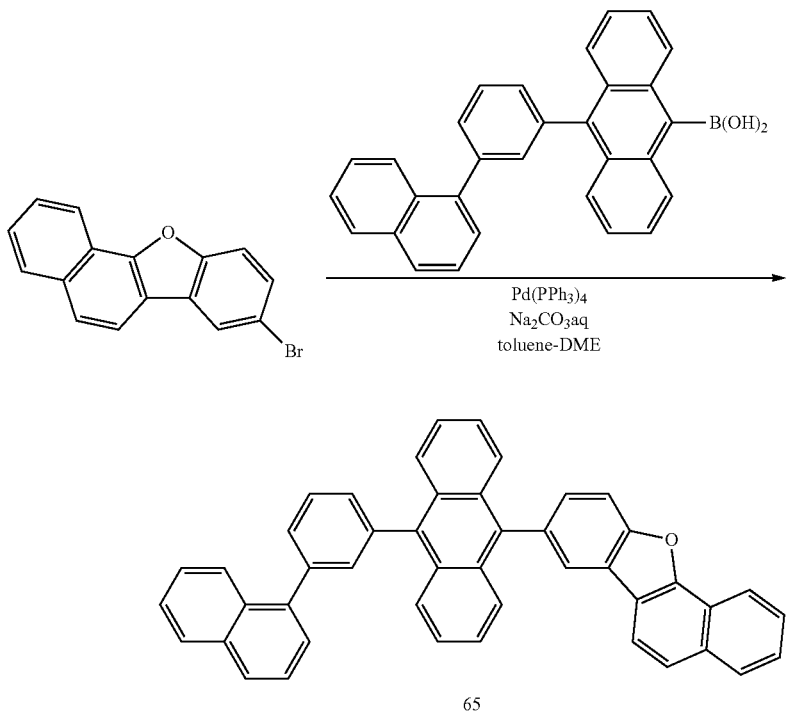

Synthesis was conducted in the same manner as in the synthesis of compound 1 in Example 1, except that intermediate (C) was used instead of intermediate (A), and 10-[3-(1-naphthyl)phenyl]anthracene-9-boronic acid, that was synthesized by a known method, was used instead of 10-phenylanthracene-9-boronic acid, whereby compound 65 was obtained. As a result of mass spectrometry, it was found that the compound was an intended product, and had an m/e of 596 relative to a molecular weight of 596.21.

Example 66 [Synthesis of Anthracene Derivative (Compound 66)]

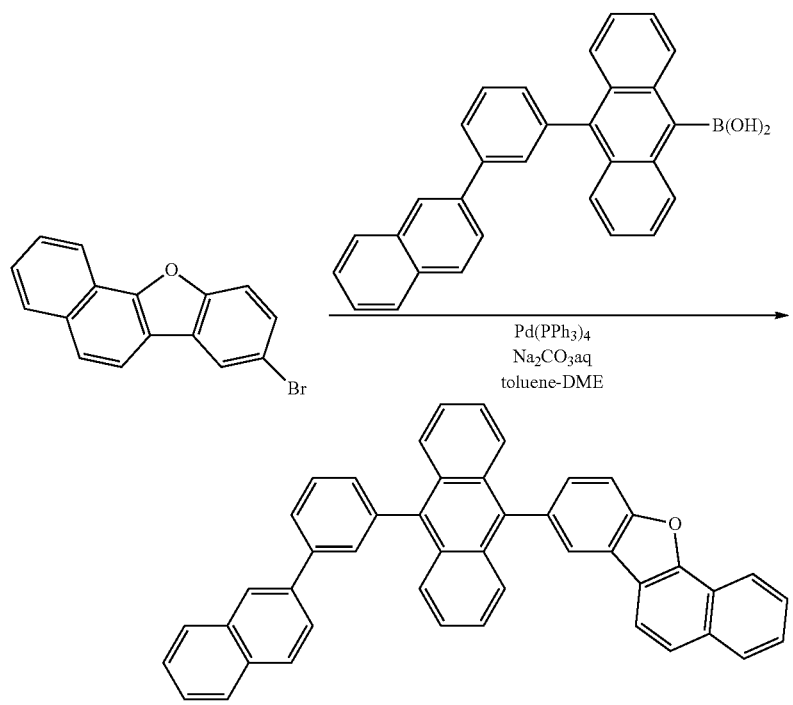

66

Synthesis was conducted in the same manner as in the synthesis of compound 1 in Example 1, except that intermediate (C) was used instead of intermediate (A), and 10-[3-(2-naphthyl)phenyl]anthracene-9-boronic acid, that was synthesized by a known method, was used instead of 10-phenylanthracene-9-boronic acid, whereby compound 66 was obtained. As a result of mass spectrometry, it was found that the compound was an intended product, and had an m/e of 596 relative to a molecular weight of 596.21.

Example 67

A glass substrate (25 mm×75 mm×1.1 mm) with ITO transparent electrode lines (manufactured by GEOMATEC Co., Ltd.) was subjected to ultrasonic cleaning in isopropyl alcohol for 5 minutes and then UV ozone cleaning for 30 minutes. The cleaned glass substrate with ITO transparent electrode lines was mounted on a substrate holder in a vacuum deposition apparatus. First, on the surface of the side on which the ITO transparent electrode lines had been formed, compound HAT was deposited so as to cover the ITO transparent electrode lines to form a 5 nm-thick film.

Subsequent to the formation of the HAT film, an 80 nm-thick HT1 film was formed on this HAT film. Subsequent to the formation of the HT1 film, a 15 nm-thick HT2 film was formed on this HT1 film.

On the HT2 film, BH1 (compound 4) produced in Example 4 and dopant BD1 were formed into films in a thickness ratio of 19:1, whereby a 25 nm-thick blue-emitting layer was formed.

On the emitting layer, ET1 was formed into a 20 nm-thick film by deposition as an electron-transporting layer. Subsequent to the formation of the ET1 film, ET2 was formed into a 5 nm-thick film on this ET1 film. Thereafter, LiF was formed into a 1 nm-thick film. Metal Al was deposited on this LiF film in a thickness of 80 nm to form a metal electrode, whereby an organic EL device was formed.

For the organic EL device fabricated above, the voltage and the external quantum efficiency (EQE) were measured. Specifically, they were measured by the following methods. The results are shown in Table 1.

Driving Voltage

A voltage (unit: V) when electric current was flown between the ITO transparent electrode and the metal Al cathode such that the current density became 10 mA/cm$^2$ was measured.

External Quantum Yield Efficiency EQE

Assuming that Lambertian irradiation was conducted, an external quantum yield efficiency EQE (unit: %) was calculated from the spectral radiance.

Comparative Example 1

An organic EL device was fabricated and evaluated in the same manner as in Example 67, except that BH2 was used instead of BH1 in the formation of the emitting layer. The results are shown in Table 1.

The compounds used in the Examples and the Comparative Examples are shown below.

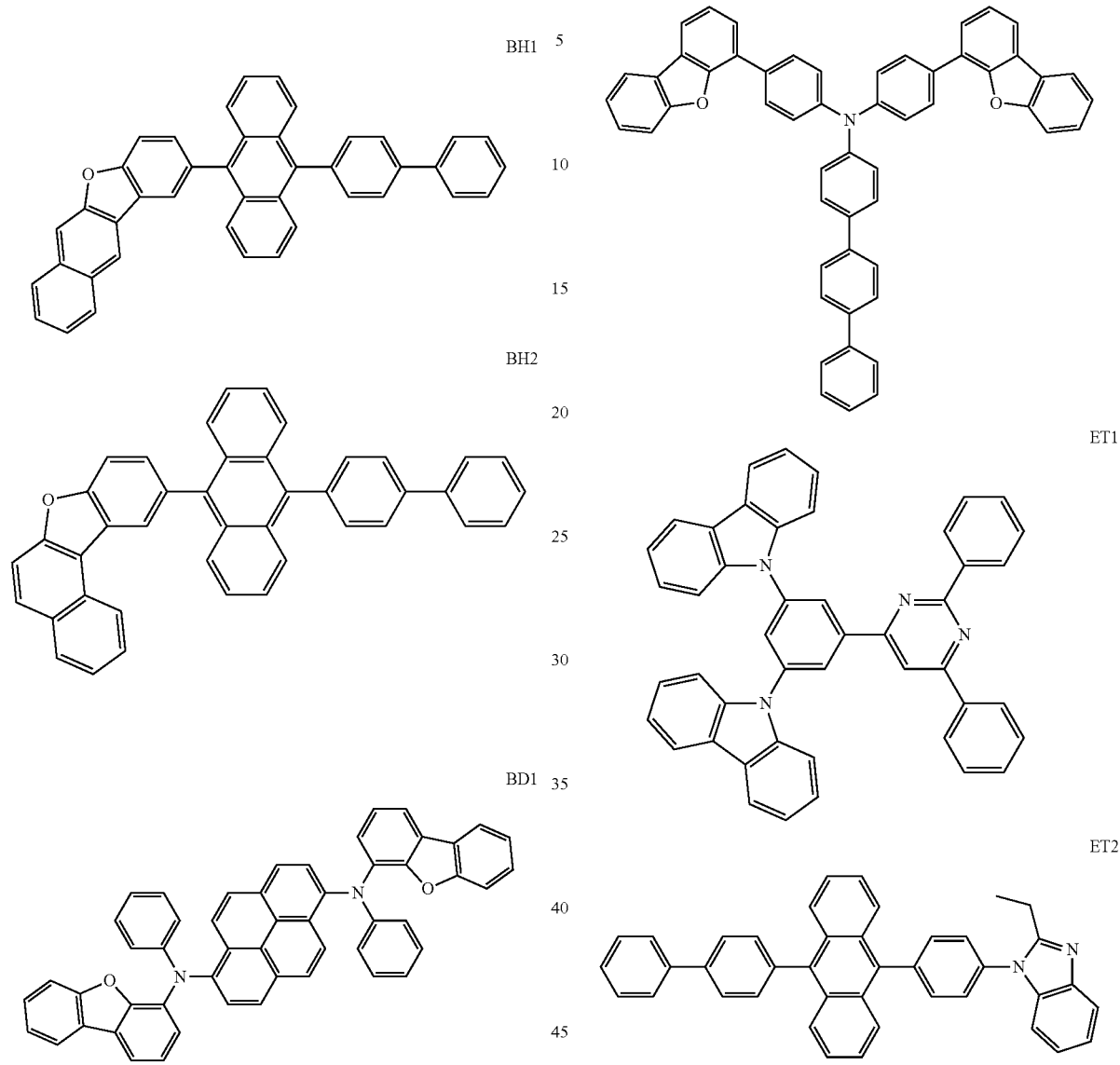

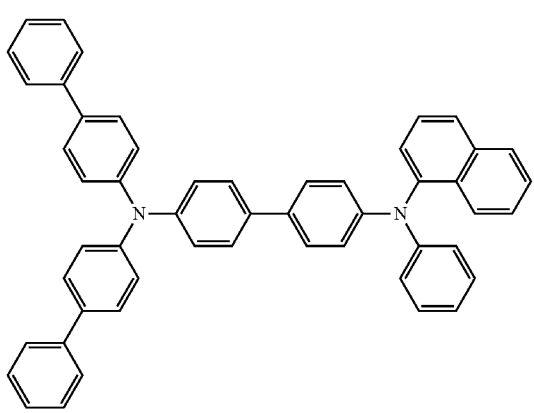

TABLE 1

| Host compound of Emitting layer | Voltage (V) | EQE (%) |
|---|---|---|
| Example 67 | BH1 | 3.4 | 9.26 |
| Comp. Ex. 1 | BH2 | 3.6 | 8.96 |

From the above results, as compared with Comparative Example 1 in which compound BH2 was used, in Example 67 where the compound BH1 of the invention was used, by bonding of the group represented by the formula (2) with an anthracene skeleton at a specific position, the device could be driven at a low voltage and exhibited a high efficiency. The reason therefor is assumed that, intermolecular packing is increased due to the widening of the planarity of molecules, leading to an improvement in electron-injecting and transporting properties.

Example 68

A glass substrate (25 mm×75 mm×1.1 mm) with ITO transparent electrode lines (manufactured by GEOMATEC Co., Ltd.) was subjected to ultrasonic cleaning in isopropyl alcohol for 5 minutes and then UV ozone cleaning for 30 minutes. The cleaned glass substrate with ITO transparent electrode lines was mounted on a substrate holder in a vacuum deposition apparatus. First, on the surface of the side on which the ITO transparent electrode lines had been formed, compound HAT was deposited so as to cover the ITO electrode lines to form a 5 nm-thick film. Subsequent to the formation of the HAT film, an 80 nm-thick HT3 film was formed on this HAT film. Subsequent to the formation of the HT3 film, a 15 nm-thick HT4 film was formed on this HT3 film.

On the HT4 film, compound 1 produced in Example 1 and dopant BD1 were formed into films in a thickness ratio of 19:1, whereby a 25 nm-thick blue-emitting layer was formed.

On the emitting layer, ET1 was formed into a 20 nm-thick film by deposition as an electron-transporting layer. Subsequent to the formation of the ET1 film, ET3 was formed into a 5 nm-thick film on this ET-1 film. Thereafter, LiF was formed into a 1 nm-thick film. Metal Al was deposited on this LiF film in a thickness of 80 nm to form a metal electrode, whereby an organic EL device was fabricated.

The obtained organic EL device was evaluated in the same manner as in Example 67. The results are shown in Table 2.

Examples 69 to 88 and Comparative Examples 2 and 3

Organic EL devices were fabricated and evaluated in the same manner as in Example 68, except that, in the formation of an emitting layer, compounds shown in Table 2 were used instead of compound 1. The results are shown in Table 2.

The compounds used in Examples and Comparative Examples are shown below.

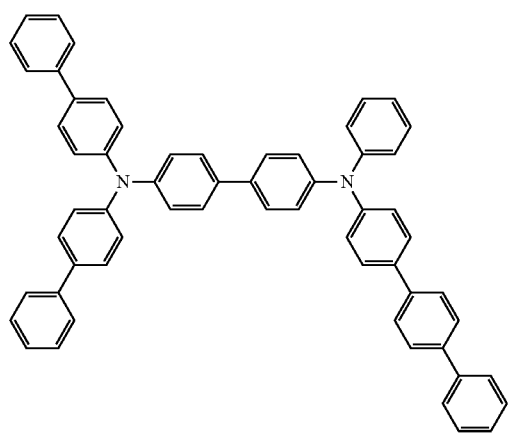

HT3

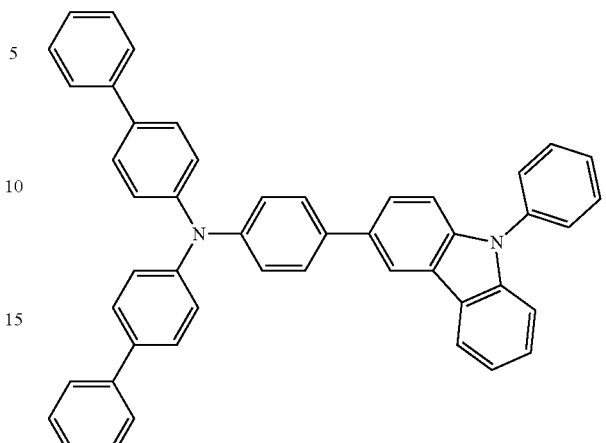

HT4

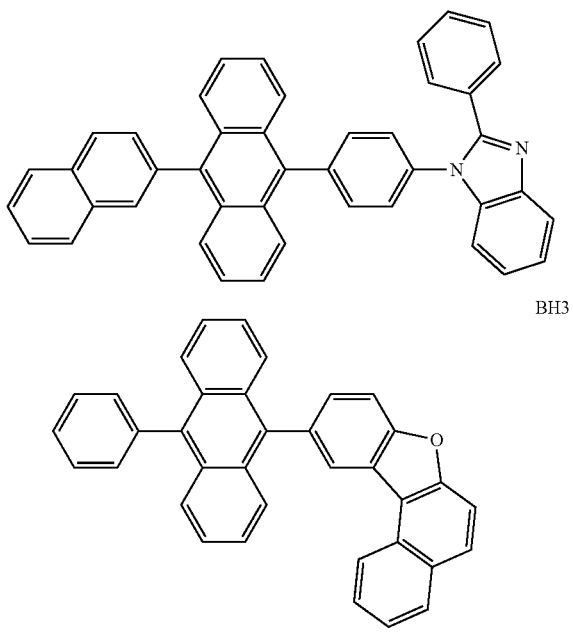

ET3

BH3

BH4

TABLE 2

|  | Host compound | Voltage (V) | EQE (%) |
| --- | --- | --- | --- |
| Example 68 | Compound 1 | 3.9 | 9.1 |
| Example 69 | Compound 2 | 3.8 | 9.2 |
| Example 70 | Compound 3 | 3.8 | 9.2 |
| Example 71 | Compound 4 | 3.8 | 9.0 |
| Example 72 | Compound 5 | 3.9 | 9.2 |
| Example 73 | Compound 6 | 3.8 | 9.0 |
| Example 74 | Compound 7 | 3.9 | 8.9 |
| Example 75 | Compound 8 | 3.8 | 9.0 |
| Example 76 | Compound 9 | 3.9 | 8.9 |
| Example 77 | Compound 10 | 4.0 | 9.2 |
| Example 78 | Compound 23 | 4.0 | 8.9 |
| Example 79 | Compound 30 | 4.1 | 8.9 |
| Example 80 | Compound 31 | 4.0 | 8.8 |
| Example 81 | Compound 32 | 4.0 | 8.9 |
| Example 82 | Compound 52 | 4.1 | 8.6 |
| Example 83 | Compound 61 | 4.0 | 8.9 |
| Example 84 | Compound 62 | 4.1 | 8.9 |
| Example 85 | Compound 63 | 4.0 | 8.8 |
| Example 86 | Compound 64 | 4.0 | 8.9 |
| Example 87 | Compound 65 | 4.1 | 8.8 |
| Example 88 | Compound 66 | 4.1 | 8.9 |
| Com. Ex. 2 | BH3 | 4.4 | 8.1 |
| Com. Ex. 3 | BH4 | 4.4 | 4.9 |

It can be understood that the devices of Examples 68 to 88, in which the compounds of the invention were used, could be driven at a lower voltage and had a high efficiency as compared with the device of Comparative Example 2 in which compound BH3 was used. As mentioned above, the reason therefor is assumed that intermolecular packing is increased due to the widening of the planarity of molecules, leading to improvement in electron-injecting and transporting properties.

Further, the devices of Examples 68 to 88 could be driven at a lower voltage, and had a significantly high efficiency as compared with the device of Comparative Example 3 in which compound BH4 was used. The reason therefor is that the planarity of molecules is widened due to the specific bonding position on the anthracene skeleton, leading to improvement in electron-injecting and transporting properties, as mentioned above.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The specification of a Japanese application on the basis of which the present application claims Paris Convention priority is incorporated herein by reference in its entirety.

The invention claimed is:

1. An anthracene derivative that is represented by any of the following formulas (4) to (7):

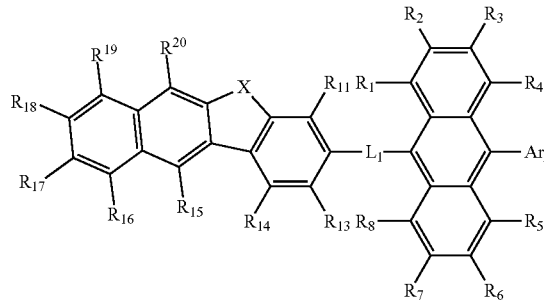

(4)

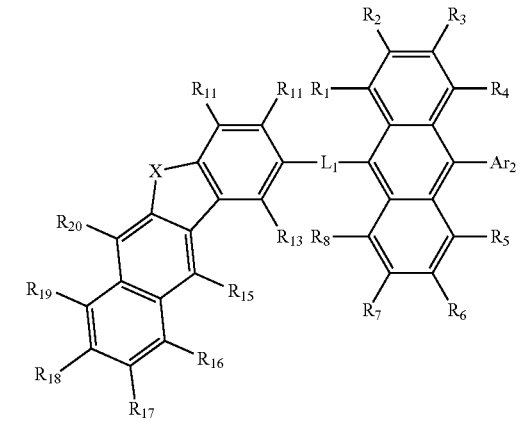

(5)

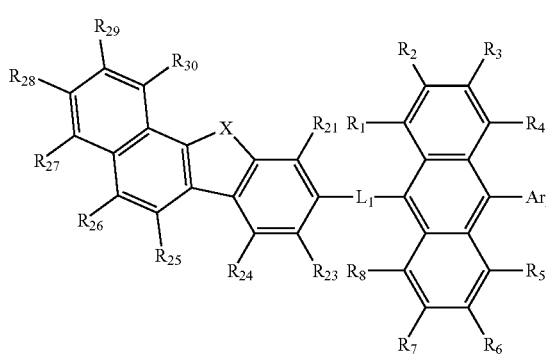

(6)

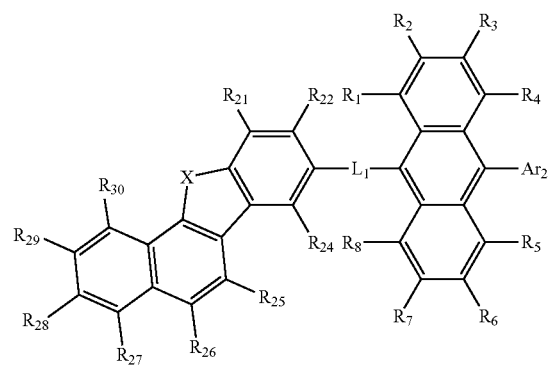

(7)

wherein in the formulas (4) to (7), $R_1$ to $R_8$ are independently selected from a hydrogen atom, a halogen atom, a hydroxyl group, a cyano group, a substituted or unsubstituted amino group, a substituted or unsubstituted alkyl group including 1 to 20 carbon atoms, a substituted or unsubstituted alkoxy group including 1 to 20 carbon atoms, a substituted or unsubstituted aryloxy group including 6 to 30 ring carbon atoms, a substituted or unsubstituted arylthio group including 6 to 30 ring carbon atoms, a substituted or unsubstituted aryl group including 6 to 30 ring carbon atoms and a substituted or unsubstituted heterocyclic group including 5 to 30 ring atoms;

$L_1$ is selected from a single bond and a linking group, and the linking group is selected from a divalent arylene group and a divalent heterocyclic group;

X is selected from an oxygen atom and a sulfur atom;

$R_{11}$ to $R_{20}$ and $R_{21}$ to $R_{30}$ are the same as $R_1$ to $R_8$;

$Ar_2$ is selected from a substituted or unsubstituted aryl group including 6 to 50 ring carbon atoms and a substituted or unsubstituted heterocyclic group including 5 to 50 ring atoms; and adjacent groups of $R_1$ to $R_8$, $R_{11}$ to $R_{20}$, $R_{21}$ to $R_{30}$, $L_1$ and $Ar_2$ may be bonded with each other to form a ring.

2. The anthracene derivative according to claim 1, that is represented by any one of the following formulas (8) to (11):

(8)
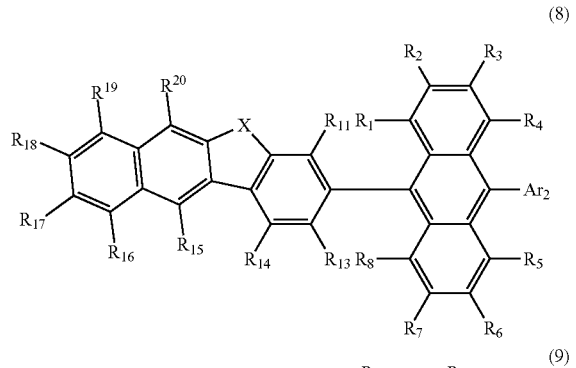

(9)
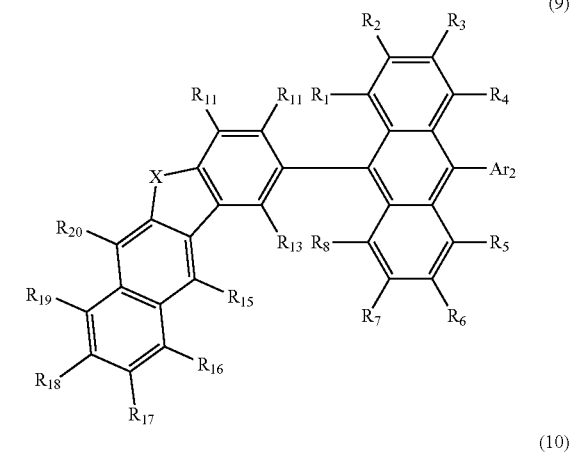

(10)
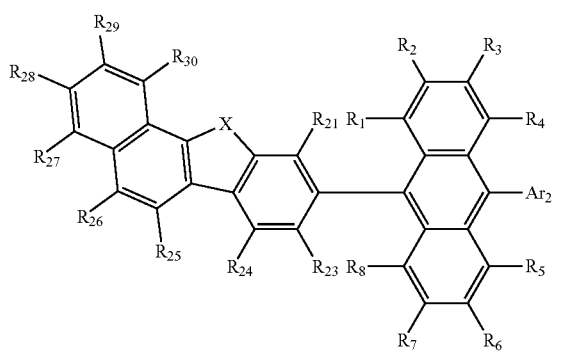

(11)
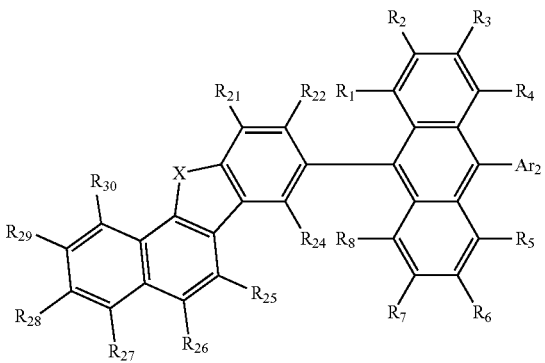

wherein in the formulas (8) to (11), $R_1$ to $R_8$, X, $R_{11}$ to $R_{20}$, $R_{21}$ to $R_{30}$ and $Ar_2$ are as defined in the formulas (4) to (7).

3. The anthracene derivative according to claim 1, that is represented by any of the following formulas (12) to (15):

(12)
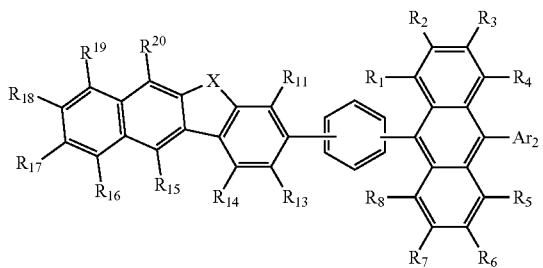

(13)
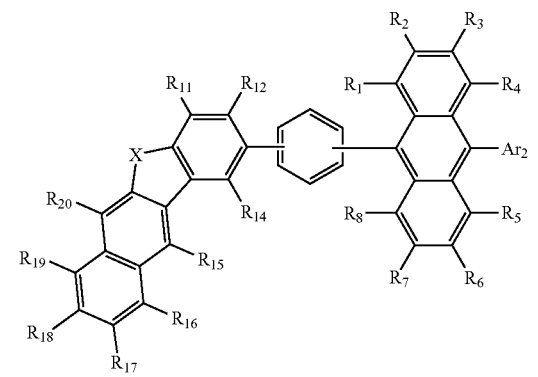

(14)
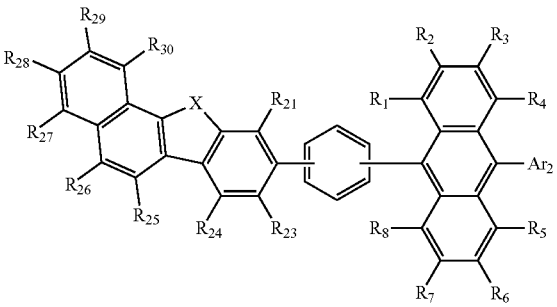

(15)

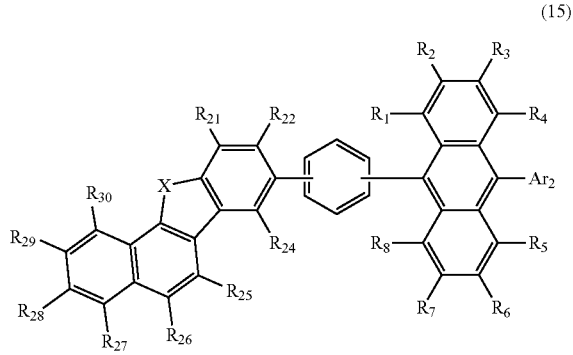

(20)

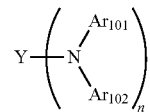

wherein in the formulas (12) to (15), $R_1$ to $R_8$, X, $R_{11}$ to $R_{20}$, $R_{21}$ to $R_{30}$ and $Ar_2$ are as defined in the formulas (4) to (7).

4. The anthracene derivative according to claim 1, wherein $Ar_2$ is selected from a substituted or unsubstituted phenyl group, a substituted or unsubstituted naphthyl group, a substituted or unsubstituted phenanthryl group, a substituted or unsubstituted benzanthryl group, a substituted or unsubstituted 9,9-dimethylfluorenyl group and a substituted or unsubstituted dibenzofuranyl group.

5. The anthracene derivative according to claim 1, wherein $R_1$ to $R_8$ are a hydrogen atom.

6. The anthracene derivative according to claim 1, wherein $R_{11}$ to $R_{14}$ that are not used for bonding to $L_1$ and $R_{15}$ to $R_{20}$, and $R_{21}$ to $R_{24}$ that are not used for bonding to $L_1$ and $R_{25}$ to $R_{30}$ are a hydrogen atom.

7. The anthracene derivative according to claim 1, wherein X is an oxygen atom.

8. The anthracene derivative according to claim 1, that is a material for an organic electroluminescence device.

9. The anthracene derivative according to claim 1, that is an emitting material for an organic electroluminescence device.

10. An organic electroluminescence device comprising:
a cathode and an anode; and
one or more organic thin film layers including an emitting layer being disposed between the cathode and the anode;
wherein at least one of the organic thin film layers comprises the anthracene derivative according to claim 1 singly or as a mixture component.

11. The organic electroluminescence device according to claim 10, wherein the emitting layer comprises the anthracene derivative.

12. The organic electroluminescence device according to claim 11, wherein the anthracene derivative is a host material.

13. The organic electroluminescence device according to claim 11, wherein the emitting layer further comprises a dopant material.

14. The organic electroluminescence device according to claim 13, wherein the dopant material is an arylamine compound.

15. The organic electroluminescence device according to claim 13, wherein the dopant material is a styrylamine compound.

16. The organic electroluminescence device according to claim 14, wherein the dopant material is a fused polycyclic amine derivative represented by the following formula (20):

wherein in the formula (20), Y is a substituted or unsubstituted fused aromatic hydrocarbon group including 10 to 50 ring carbon atoms;

$Ar_{101}$ and $Ar_{102}$ are independently selected from a substituted or unsubstituted aryl group including 6 to 50 ring carbon atoms and a substituted or unsubstituted heterocyclic group including 5 to 50 ring atoms; and n is an integer of 1 to 4.

17. The organic electroluminescence device according to claim 14, wherein the dopant material is a fused polycyclic amine derivative represented by the following formula (21):

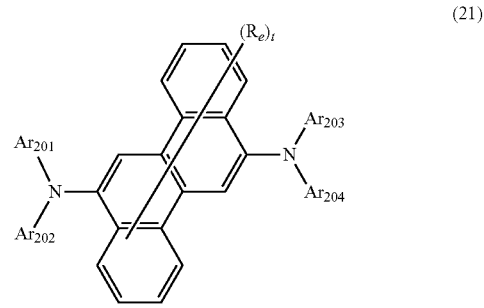

(21)

wherein in the formula (21), $R_e$ is independently selected from a substituted or unsubstituted alkyl group including 1 to 20 carbon atoms, a substituted or unsubstituted alkenyl group including 2 to 50 carbon atoms, a substituted or unsubstituted alkynyl group including 2 to 50 carbon atoms, a substituted or unsubstituted aralkyl group including 7 to 20 carbon atoms, a substituted or unsubstituted cycloalkyl group including 3 to 20 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 50 ring carbon atoms, a substituted or unsubstituted silyl group, a substituted or unsubstituted alkyl germanium group including 1 to 50 carbon atoms and a substituted or unsubstituted aryl germanium group including 6 to 50 ring carbon atoms; $R_e$ may be bonded to any of bonding positions of the four benzene rings of the fused polycyclic ring;

t is an integer of 0 to 10; and $Ar_{201}$ to $Ar_{204}$ are independently selected from a substituted or unsubstituted aryl group including 6 to 50 ring carbon atoms and a substituted or unsubstituted heterocyclic group including 5 to 50 ring atoms.

18. The organic electroluminescence device according to claim 14, wherein the dopant material is a fused polycyclic amine derivative represented by the following formula (22):

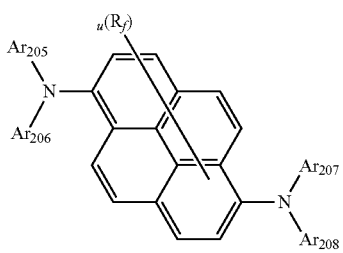

(22)

wherein in the formula (22), $R_f$ is independently selected from a substituted or unsubstituted alkyl group including 1 to 20 carbon atoms, a substituted or unsubstituted alkenyl group including 2 to 50 carbon atoms, a substituted or unsubstituted alkynyl group including 2 to 50 carbon atoms, a substituted or unsubstituted aralkyl group including 7 to 20 carbon atoms, a substituted or unsubstituted cycloalkyl group including 3 to 20 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 50 ring carbon atoms, a substituted or unsubstituted silyl group, a substituted or unsubstituted alkyl germanium group including 1 to 50 carbon atoms, and a substituted or unsubstituted aryl germanium group including 6 to 50 ring carbon atoms; $R_f$ may be bonded to any of bonding positions of the four benzene rings of the fused polycyclic ring;

u is an integer of 0 to 8; and $Ar_{205}$ to $Ar_{208}$ are independently selected from a substituted or unsubstituted aryl group including 6 to 50 ring carbon atoms and a substituted or unsubstituted heterocyclic group including 5 to 50 ring atoms.

19. The organic electroluminescence device according to claim 14, wherein the dopant material is a fused polycyclic amine derivative represented by the following formula (23):

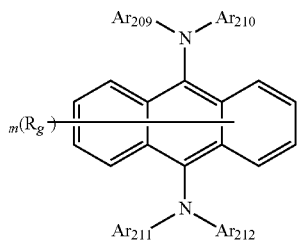

(23)

wherein in the formula (23), $R_g$ is independently selected from a substituted or unsubstituted alkyl group including 1 to 20 carbon atoms, a substituted or unsubstituted alkenyl group including 2 to 50 carbon atoms, a substituted or unsubstituted alkynyl group including 2 to 50 carbon atoms, a substituted or unsubstituted aralkyl group including 7 to 20 carbon atoms, a substituted or unsubstituted cycloalkyl group including 3 to 20 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 50 ring carbon atoms, a substituted or unsubstituted silyl group, a substituted or unsubstituted alkyl germanium group including 1 to 50 carbon atoms and a substituted or unsubstituted aryl germanium group including 6 to 50 ring carbon atoms; $R_g$ may be bonded to any of bonding positions of the three benzene rings of the fused polycyclic ring;

m is an integer of 0 to 8; and $Ar_{209}$ to $Ar_{212}$ are independently selected from a substituted or unsubstituted aryl group including 6 to 50 ring carbon atoms and a substituted or unsubstituted heterocyclic group including 5 to 50 ring atoms.

20. The organic electroluminescence device according to claim 14, wherein the dopant material is a fused polycyclic amine derivative represented by the following formula (24):

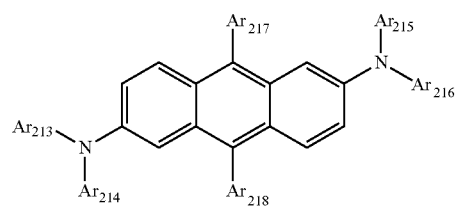

(24)

wherein in the formula (24), $Ar_{213}$ to $Ar_{218}$ are independently selected from a substituted or unsubstituted aryl group including 6 to 50 ring carbon atoms and a substituted or unsubstituted heterocyclic group including 5 to 50 ring atoms.

21. An electronic appliance comprising the organic electroluminescence device according to claim 10.

22. An anthracene derivative that is represented by any one of the following formulas (10'), (11'), (14'), and (15'):

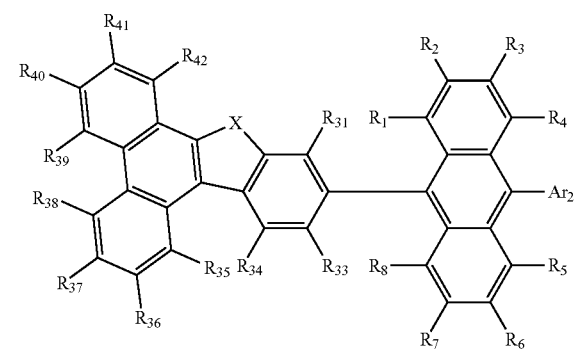

(10')

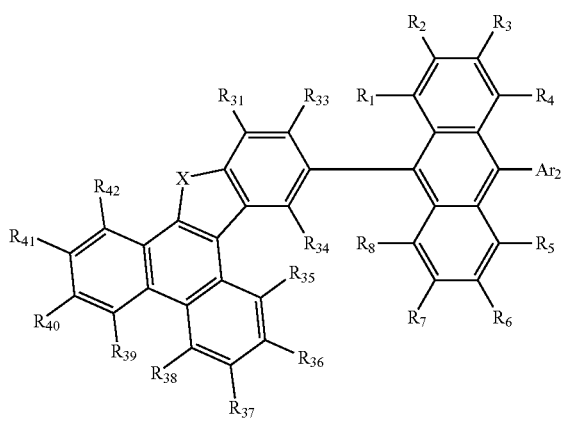

(11')

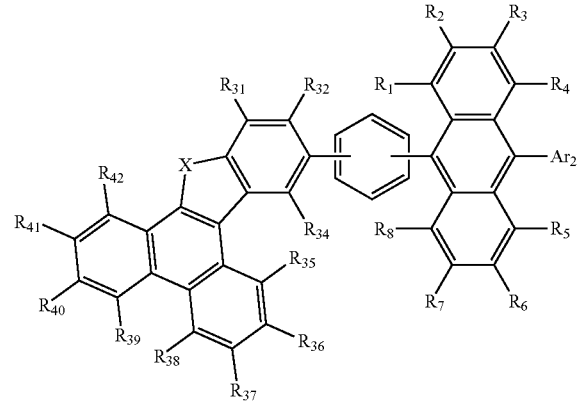

(15')

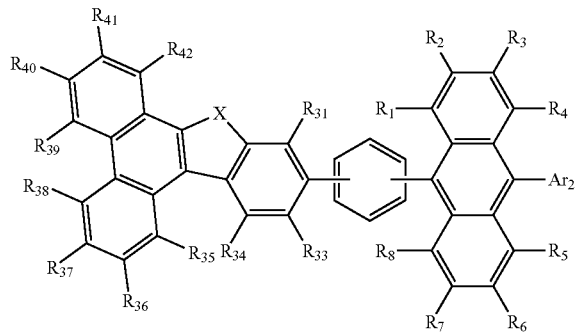

(14')

wherein in the formulas (10'), (11'), (14'), and (15'), $R_1$ to $R_8$ and $R_{31}$ to $R_{42}$ are independently selected from a hydrogen atom, a halogen atom, a hydroxyl group, a cyano group, a substituted or unsubstituted amino group, a substituted or unsubstituted alkyl group including 1 to 20 carbon atoms, a substituted or unsubstituted alkoxy group including 1 to 20 carbon atoms, a substituted or unsubstituted aryloxy group including 6 to 30 ring carbon atoms, a substituted or unsubstituted arylthio group including 6 to 30 ring carbon atoms, a substituted or unsubstituted aryl group including 6 to 30 ring carbon atoms and a substituted or unsubstituted heterocyclic group including 5 to 30 ring atoms;

X is selected from an oxygen atom and a sulfur atom;

$Ar_2$ is selected from a substituted or unsubstituted aryl group including 6 to 50 ring carbon atoms and a substituted or unsubstituted heterocyclic group including 5 to 50 ring atoms; and adjacent groups of $R_1$ to $R_8$, $R_{31}$ to $R_{42}$ and $Ar_2$ may be bonded with each other to form a ring.

23. The anthracene derivative according to claim 16, wherein Y in the formula (20) is a substituted or unsubstituted anthryl group, a substituted or unsubstituted pyrenyl group or a substituted or unsubstituted chrysenyl group.

* * * * *